US012723083B2

(12) United States Patent
Bruenker et al.

(10) Patent No.: US 12,723,083 B2
(45) Date of Patent: Sep. 1, 2026

(54) ANTI-CD3/ANTI-CD28 BISPECIFIC ANTIGEN BINDING MOLECULES

(71) Applicant: Hoffmann-La Roche Inc., Little Falls, NJ (US)

(72) Inventors: Peter Bruenker, Hittnau (CH); Martina Geiger, Obfelden (CH); Thomas Hofer, Zurich (CH); Christian Klein, Bonsetten (CH); Pablo Umaña, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 753 days.

(21) Appl. No.: 18/069,847

(22) Filed: Dec. 21, 2022

(65) Prior Publication Data

US 2023/0416366 A1 Dec. 28, 2023

Related U.S. Application Data

(63) Continuation of application No. PCT/EP2021/067244, filed on Jun. 23, 2021.

(30) Foreign Application Priority Data

Jun. 25, 2020 (EP) .................................... 20182307

(51) Int. Cl.
*C07K 16/28* (2006.01)

(52) U.S. Cl.
CPC ...... *C07K 16/2818* (2013.01); *C07K 16/2809* (2013.01); *C07K 2317/31* (2013.01); *C07K 2317/92* (2013.01)

(58) Field of Classification Search
CPC ............ C07K 16/2818; C07K 16/2809; C07K 2317/31; C07K 2319/70; A61K 51/1042; A61K 39/0011
USPC ....................................................... 424/136.1
See application file for complete search history.

(56) References Cited

U.S. PATENT DOCUMENTS

| | | | |
|---|---|---|---|
| 5,731,168 A | 3/1998 | Carter et al. | |
| 5,821,333 A | 10/1998 | Carter et al. | |
| 6,171,586 B1 | 1/2001 | Lam et al. | |
| 6,267,958 B1 | 7/2001 | Andya et al. | |
| 6,737,056 B1 | 5/2004 | Presta et al. | |
| 7,332,581 B2 | 2/2008 | Presta et al. | |
| 7,695,936 B2 | 4/2010 | Carter et al. | |
| 11,608,376 B2 * | 3/2023 | Georges | A61P 35/00 |
| 12,600,781 B2 * | 4/2026 | Georges | A61P 35/00 |
| 2004/0132066 A1 | 7/2004 | Balint et al. | |
| 2005/0260186 A1 | 11/2005 | Bookbinder et al. | |
| 2006/0104968 A1 | 5/2006 | Bookbinder et al. | |
| 2023/0172923 A1 * | 6/2023 | Jeyaraju | A61K 39/3955 514/326 |
| 2023/0416365 A1 * | 12/2023 | Georges | A61P 35/00 |
| 2024/0043535 A1 * | 2/2024 | Amann | C07K 16/2818 |
| 2024/0368309 A1 * | 11/2024 | Gasser | C07K 16/2818 |

FOREIGN PATENT DOCUMENTS

| | | | |
|---|---|---|---|
| CN | 108264560 | A | 7/2018 |
| EP | 3 575 319 | A1 | 12/2019 |
| JP | 2019-141066 | A | 8/2019 |
| JP | 2020-33376 | A | 3/2020 |
| JP | 2020-515256 | A | 5/2020 |
| WO | 02/020565 | A2 | 2/2002 |
| WO | 2006/044908 | A2 | 4/2006 |
| WO | 2006/050949 | A2 | 5/2006 |
| WO | 2009/080252 | A1 | 7/2009 |
| WO | 2009/089004 | A1 | 7/2009 |
| WO | 2012/020006 | A2 | 2/2012 |
| WO | 2012/130831 | A1 | 10/2012 |
| WO | 2014/131712 | A1 | 9/2014 |
| WO | 2015/091738 | A1 | 6/2015 |
| WO | 2015/150447 | A1 | 10/2015 |
| WO | 2016/020309 | A1 | 2/2016 |
| WO | 2017011580 | * | 7/2016 |
| WO | 2017/055388 | A2 | 4/2017 |
| WO | 2017/162587 | A1 | 9/2017 |
| WO | 2018/177966 | A1 | 10/2018 |
| WO | 2018/177967 | A1 | 10/2018 |
| WO | 2019/115659 | A1 | 6/2019 |
| WO | 2020/007817 | A1 | 1/2020 |
| WO | 2020/023553 | A1 | 1/2020 |
| WO | 2020/027330 | A1 | 2/2020 |

OTHER PUBLICATIONS

Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., "Computational design of antibody-affinity improvement beyond in vivo maturation," Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*
Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, Mar. 16, 2021).*
Lo et al., BMC Genomics vol. 22, Article No. 116 (2021).*

(Continued)

*Primary Examiner* — Lynn A Bristol

(74) *Attorney, Agent, or Firm* — Lawrence S. Graham; Hoffmann-La Roche Inc.

(57) ABSTRACT

The present invention relates to anti-CD3/anti-CD28 bispecific antigen binding molecules and masked protease activated forms thereof, methods for their production, pharmaceutical compositions containing these molecules, and their use as immunomodulators and/or costiumulators in the treatment of cancer.

21 Claims, 15 Drawing Sheets

Specification includes a Sequence Listing.

(56) References Cited

OTHER PUBLICATIONS

Acuto et al., "CD28-mediated co-stimulation: a quantitative support for TCR signalling." Nat. Rev. Immunol. 3:939-951 (2003).
Armour, K. et al., "Recombinant human IgG molecules lacking Fcÿreceptor I binding and monocyte triggering activities" Eur J Immunol 29(8):2613-2624 (Aug. 1, 1999).
Bahlis et al., "CD28-mediated regulation of multiple myeloma cell proliferation and survival" Blood 109(11):5002-5010 (2007).
Boomer and Green et al., "An Enigmatic Tail of CD28 Signaling" Herb Perspect Biol. 2(a002436):1-20 (2010).
Bowie, J. et al., "Deciphering the message in protein sequences: tolerance to amino acid substitutions" Science 247(4948):1306-1310 (Mar. 16, 1990).
Burton, D.R., "Immunoglobulin G: Functional Sites" Mol Immunol 22(3):161-206 (Mar. 1, 1985).
Capel, P., et al., "Heterogeneity of human IgG Fc receptors" Immunomethods 4(1):25-34 (Feb. 1, 1994).
Carter, P., et al., "Bispecific human IgG by design" J Immunol Methods 248(1-2):7-15 (Feb. 1, 2001).
Chothia et al., "Canonical structures for the hypervariable regions of immunoglobulins" J Mol Biol 196:901-917 ( 1987).
De Haas, M., et al., "Fcγ receptors of phagocytes" J Lab Clin Med 126(4):330-341 (Oct. 1, 1995).
Esensten et al., "CD28 costimulation: from mechanism to therapy" Immunity 44(5):973-988 ( 2016).
Fraser et al., "Regulation of interleukin-2 gene enhancer activity by the T cell accessory molecule CD28" Science 251:313-316 ( 1991).
Gessner, J., et al., "The IgG Fc Receptor Family" Ann Hematol 76(6):231-248 (Jun. 1, 1998).
Hui et al., "T cell costimulatory receptor CD28 is a primary target for PD-I—mediated inhibition" Science 355:1428-1433 (2017).
Hunig et al., "The storm has cleared: lessons from the CD28 superagomst TGN1412 trial" Nat. Rev. Immunol. 12:317-318 (2012).
International Preliminary Report on Patentability—PCT/EP2021/067244 issued Dec. 13, 2022, pp. 1-10.
International Search Report with Written Opinion—PCT/EP2021/067244 mailed Sep. 22, 2021, pp. 1-18.
Isaacs et al., "T cell immunomodulation—the Holy Grail of therapeutic tolerance" Curr. Opin Pharmacol 7:418-425 (2007).
June et al., "T-Cell Proliferation Involving the CD28 Pathway Is Associated with Cyclosporine-Resistant Interleukin 2 Gene Expression" Mol. Cell .Biol. 7(12):4472-4481 (1987).
Kabat, E., et al. Sequences of Proteins of Immunological Interest 5th edition, Washington, D.C.-USA:U.S. Dept. of Health and Human Services, NIH, vol. 1:103-108, 324-331 (1991).
Kamphorst et al., "Rescue of exhausted CD8 T cells by PD-1-targeted therapies is CD28-dependent" Science 355:1423-1427 (2017).
Kindt et al. Antigens and Antibodies "4" (14 pages), 6th ed edition, N.Y.:W.H. Freeman and Co,:p. 91 (2007).
Linsley at al., "T-cell antigen CD28 mediates adhesion with B cells by interacting with activation antigen B7/BB-1" Proc. Natl. Acad. Sci. USA 87:5031-5035 (1990).
Lu, Y.C. et al., "Specific activation of pro-Infliximab enhances selectivity and safety of rheumatoid arthritis therapy" PLOS BIOL 17(e3000286):1-18 (Jul. 13, 2019).
Maccallum, R., et al., "Antibody-antigen Interactions: Contact Analysis and Binding Site Topography" J Mol Biol 262:732-745 (Oct. 11, 1996).
Murray et al., "CD28-mediated pro-survival signaling induces chemotherapeutic resistance in multiple myeloma" Blood 123(24):3770-3779.
Otz, T., et al., "A bispecific single-chain antibody that mediates target cell-restricted, supra-agonistic CD28 stimulation and killing of lymphoma cells" Leukemia 23(1):71-77 (Oct. 2, 2008).
Ravetch, J., et al., "Fc receptors" Annu Rev Immunol 9:457-492 (Apr. 1, 1991).
Ridgway, J., et al., "Knobs-into-holes' engineeiing of antibody CH3 domains for heavy chain heterodimerization" Protein Eng 9(7):617-621 (Jul. 1, 1996).
Romer et al., "Preculture of PBMCs at high cell desity increases sensitivity of T-Cell responses, revealing cytokine release by CD28 superagonist TGN1412" Blood 118(26):6772-6782 (2011).
Roux, K.H., et al., "Comparisos of the ability of human IgG3 hinge mutants, IgM, IgE, and IgA2, to form small immune complexes: a role of flexibility and geometry" J Immunol 161(8):4083-4090 (Oct. 15, 1998).
Schaefer, W., et al., "Immunoglobulin domain crossover as a generic approach for the production of bispecific IgG antibodies" PNAS USA 108(27):11187-11192 (Jul. 5, 2011).
Shields, R., et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Tai et al., "Induction of autoimmune disease in CTLA-4-/-mice depends on a specific CD28 motif that is required for in vivo costimulation" Proc. Natl. Acad. Sci. USA 104:13756-13761 (2007).
Thompson et al., "CD28 activation pathway regulates the production of multiple T-cell-derived lymphokines/cytokines" P Natl Acad Sci USA 86(4):1333-1337 (Feb. 1989).
Trickett, A. et al., "T cell stimulation and expansion using anti-CD3/CD28 beads" J Immunol Methods 275:251-255 ( 2003).
Van De Winkel, J.G., et al., "Biology of human immunoglobulin G Fc receptors" J Leukocyte Biol 49(5):511-524 (May 1, 1991).
Wang, X.B. et al., "A new recombinant single chain trispecific antibody recruits T lymphocytes to kill CEA (carcinoma embryonic antigen) positive tumor cells in vitro efficiently" J Biochemistry 135(4):555-565 (Apr. 1, 2004).

* cited by examiner

CDR1
CDR2
CDR3
CDR1
CDR2
CDR3

ANTI-CD3/ANTI-CD28 BISPECIFIC ANTIGEN BINDING MOLECULES

CROSS-REFERENCE TO RELATED APPLICATIONS

This application is a Continuation of International Application No. PCT/EP2021/067244, filed Jun. 23, 2021, which claims benefit of priority to European Application No. 20182307.7 filed Jun. 25, 2020, the contents of each of which are incorporated herein by reference in their entirety.

SEQUENCE LISTING

This application contains a Sequence Listing which has been submitted electronically in XML format and is hereby incorporated by reference in its entirety. Said XML copy, created on Jan. 29, 2026, is named Sequence-Listing-P36198-US.xml and is 291,653 bytes in size.

FIELD OF THE INVENTION

The present invention relates to anti-CD3/anti-CD28 bispecific antigen binding molecules and protease activated forms thereof, methods for their production, pharmaceutical compositions containing these molecules, and their use as immunomodulators and/or costiumulators in the treatment of a disease, in particular cancer.

BACKGROUND

Cancer immunotherapy is becoming an increasingly effective therapy option that can result in dramatic and durable responses in cancer types such as melanoma, non-small cell lung cancer and renal cell carcinoma. This is mostly driven by the success of several immune checkpoint blockades including anti-PD-1 (e.g. KEYTRUDA®, Merck; OPDIVO®, BMS), anti-CTLA-4 (e.g. YERVOY®, BMS) and anti-PD-L1 (e.g. TECENTRIQ®, Roche). These agents are likely to serve as standard of care for many cancer types, or as the backbone of combination therapies, however, only a fraction of patients (<25%) benefits from such therapies. Furthermore, various cancers (prostate cancer, colorectal cancer, pancreatic cancer, sarcomas, non-triple negative breast cancer etc.) present primary resistance to these immunomodulators. A number of reports indicate that the absence of pre-existing anti-tumor T cells contributes to the absence or poor response of some patients. In summary, despite impressive anti-cancer effects of existing immunotherapies, there is a clear medical need for addressing a large cancer patient population and for developing therapies that aim to induce and enhance novel tumor-specific T cell responses.

CD28 is the founding member of a subfamily of costimulatory molecules characterized by paired V-set immunoglobulin superfamily (IgSF) domains attached to single transmembrane domains and cytoplasmic domains that contain critical signaling motifs (Carreno and Collins, 2002). Other members of the subfamily include ICOS, CTLA-4, PD1, PD1H, TIGIT, and BTLA (Chen and Flies, 2013). CD28 expression is restricted to T cells and prevalent on all naïve and a majority of antigen-experienced subsets, including those that express PD-1 or CTLA-4. CD28 and CTLA-4 are highly homologous and compete for binding to the same B7 molecules CD80 and CD86, which are expressed on dendritic cells, B cells, macrophages, and tumor cells (Linsley et al., 1990). The higher affinity of CTLA-4 for the B7 family of ligands allows CTLA-4 to outcompete CD28 for ligand binding and suppress effector T cells responses (Engelhardt et al., 2006). In contrast, PD-1 was shown to inhibit CD28 signaling by in part dephosphorylating the cytoplasmic domain of CD28 (Hui et al., 2017). Ligation of CD28 by CD80 or CD86 on the surface of professional antigen-presenting cells is strictly required for functional de novo priming of naïve T cells, subsequent clonal expansion, cytokine production, target cell lysis, and formation of long-lived memory. Binding of CD28 ligands also promotes the expression of inducible co-stimulatory receptors such as OX-40, ICOS, and 4-1BB (reviewed in Acuto and Michel, 2003). Upon ligation of CD28, a disulfide-linked homodimer, the membrane proximal YMNM (SEQ ID NO: 216) motif and the distal PYAP (SEQ ID NO: 217) motif have been shown to complex with several kinases and adaptor proteins (Boomer and Green, 2010). These motifs are important for the induction of IL2 transcription, which is mediated by the CD28-dependent activation of NFAT, AP-1, and NFκB family transcription factors (Fraser et al., 1991) (June et al., 1987) (Thompson et al., 1989). However, additional poorly characterized sites for phosphorylation and ubiquitination are found within the cytoplasmic domain of CD28. As reviewed by (Esensten et al., 2016), CD28-initiated pathways have critical roles in promoting the proliferation and effector function of conventional T cells. CD28 ligation also promotes the anti-inflammatory function of regulatory T cells. CD28 co-stimulates T cells by in part augmenting signals from the T cell receptor, but was also shown to mediate unique signaling events (Acuto and Michel, 2003; Boomer and Green, 2010; June et al., 1987). Signals specifically triggered by CD28 control many important aspects of T cell function, including phosphorylation and other post-translational modifications of downstream proteins (e.g., PI3K mediated phosphorylation), transcriptional changes (eg. Bcl-xL expression), epigenetic changes (e.g. IL-2 promoter), cytoskeletal remodeling (e.g. orientation of the microtubule-organizing center) and changes in the glycolytic rate (e.g. glycolytic flux). CD28-deficient mice have reduced responses to infectious pathogens, allograft antigens, graft-versus-host disease, contact hypersensitivity and asthma (Acuto and Michel, 2003). Lack of CD28-mediated co-stimulation results in reduced T cell proliferation in vitro and in vivo, in severe inhibition of germinal-centre formation and immunoglobulin isotype-class switching, reduced T helper (Th)-cell differentiation and the expression of Th2-type cytokines. CD4-dependent cytotoxic CD8+ T-cell responses are also affected. Importantly, CD28-deficient naïve T cells showed a reduced proliferative response particularly at lower antigen concentrations. A growing body of literature supports the idea that engaging CD28 on T cells has anti-tumor potential. Recent evidence demonstrates that the anti-cancer effects of PD-L1/PD-1 and CTLA-4 checkpoint inhibitors depend on CD28 (Kamphorst et al., 2017; Tai et al., 2007). Clinical studies investigating the therapeutic effects of CTLA-4 and PD-1 blockade have shown exceptionally promising results in patients with advanced melanoma and other cancers. In addition, infusion of genetically engineered T cells expressing artificial chimeric T cell receptors comprising an extracellular antigen recognition domain fused to the intracellular TCR signaling domains (CD3z) and intracellular co-stimulatory domains (CD28 and/or 4-1BB domains) has shown high rates and durability of response in B cell cancers and other cancers.

CD28 agonistic antibodies can be divided into two categories: (i) CD28 superagonistic antibodies and (ii) CD28 conventional agonistic antibodies. Normally, for the activation of naïve T cells both engagement of the T cell antigen receptor (TCR, signal 1) and costimulatory signaling by CD28 (signal 2) is required. CD28 Superagonists (CD28SA) are CD28-specific monoclonal antibodies, which are able to autonomously activate T cells without overt T cell receptor engagement (Hunig, 2012). In rodents, CD28SA activates conventional and regulatory T cells. CD28SA antibodies are therapeutically effective in multiple models of autoimmunity, inflammation and transplantation. However, a phase I study of the human CD28SA antibody TGN1412 resulted in a life-threatening cytokine storm in 2006. Follow-up studies have suggested that the toxicity was caused by dosing errors due to differences in the CD28 responsiveness of human T cells and T cells of preclinical animal models. TGN1412 is currently being re-evaluated in an open-label, multi-center dose escalation study in RA patients and patients with metastatic or unresectable advanced solid malignancies. CD28 conventional agonistic antibodies, such as clone 9.3, mimic CD28 natural ligands and are only able to enhance T cell activation in presence of a T cell receptor signal (signal 1). Published insights indicate that the binding epitope of the antibody has a major impact on whether the agonistic antibody is a superagonist or a conventional agonist (Beyersdorf et al., 2005). The superagonistic TGN1412 binds to a lateral motif of CD28, while the conventional agonistic molecule 9.3 binds close to the ligand binding epitope. As a consequence of the different binding epitopes, superagonistic and conventional agonistic antibodies differ in their ability to form linear complexes of CD28 molecules on the surface of T cells. Precisely, TGN1412 is able to efficiently form linear arrays of CD28, which presumably leads to aggregated signaling components which are sufficient to surpass the threshold for T cell activation. The conventional agonist 9.3, on the other hand, leads to complexes which are not linear in structure. An attempt to convert conventional agonistic binders based on the 9.3 clone has been previously published (Otz et al., 2009) using a recombinant bi-specific single-chain antibody directed to a melanoma-associated proteoglycan and CD28. The reported bispecific single chain antibody was reported to exert "supra-agonistic" activity despite the use of a conventional CD28 agonistic binder 9.3, based in the intrinsic tendency of bispecific single chain antibodies to form multimeric constructs.

CD3 (cluster of differentiation 3) is a protein complex composed of four subunits, the CD3γ chain, the CD3δ chain, and two CD3ε chains. CD3 associates with the T-cell receptor and the ζ chain to generate an activation signal in T lymphocytes. CD3 has been extensively explored as drug target. Monoclonal antibodies targeting CD3 have been used as immunosuppressant therapies in autoimmune diseases such as type I diabetes, or in the treatment of transplant rejection. The CD3 antibody muromonab-CD3 (OKT3) was the first monoclonal antibody ever approved for clinical use in humans, in 1985.

A more recent application of CD3 antibodies is in the form of bispecific antibodies, binding CD3 on the one hand and a tumor cell antigen on the other hand. The simultaneous binding of such an antibody to both of its targets will force a temporary interaction between target cell and T cell, causing activation of any cytotoxic T cell and subsequent lysis of the target cell. For therapeutic purposes, an important requirement that antibodies have to fulfill is sufficient stability both in vitro (for storage of the drug) an in vivo (after administration to the patient). Modifications like asparagine deamidation are typical degradations for recombinant antibodies and can affect both in vitro stability and in vivo biological functions. Given the tremendous therapeutic potential of antibodies, particularly bispecific antibodies for the activation of T cells, there is a need for enhanced CD3 antibodies with optimized properties.

SUMMARY

The present invention describes anti-CD3/anti-CD28 bispecific antigen binding molecules and masked protease activated forms thereof which achieve a tumor-dependent T cell activation and tumor cell killing without the necessity to form multimers. The bispecific CD28 antigen binding molecules of the present invention are characterized by monovalent binding to CD28 and in that they comprise a second antigen binding domain capable of specific binding to CD3 that can be masked. Specifically, the invention relates to anti-CD3/anti-CD28 bispecific antigen binding molecules having an anti-idiotype-binding moiety that masks the CD3 antigen binding domain until cleaved by a protease. This allows the CD3 antigen binding domain to be inaccessible or "masked" until it is in proximity to a target tissue, such as a tumor, e.g., tumor-infiltrating T cells. Furthermore, the anti-CD3/anti-CD28 bispecific antigen binding molecules possess an Fc domain composed of a first and a second subunit capable of stable association comprising one or more amino acid substitution that reduces the binding affinity of the antigen binding molecule to an Fc receptor and/or effector function. Fc receptor-mediated cross-linking is thereby abrogated and tumor-specific activation is achieved by cross-linking through binding of the second antigen binding domain capable of specific binding to CD3.

Thus, the invention provides a bispecific agonistic CD28 antigen binding molecule characterized by monovalent binding to CD28, comprising (a) a first antigen binding domain capable of specific binding to CD28, (b) a second antigen binding domain capable of specific binding to CD3, and (c) a Fc domain composed of a first and a second subunit capable of stable association comprising one or more amino acid substitution that reduces the binding affinity of the antigen binding molecule to an Fc receptor and/or effector function, wherein said second antigen binding domain capable of specific binding to CD3 comprises (i) a heavy chain variable region ($V_H$CD3) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$CD3) comprising a light chain complementary determining region CDR-L1 of SEQ ID NO: 5, a CDR-L2 of SEQ ID NO: 6 and a CDR-L3 of SEQ ID NO: 7; or (ii) a heavy chain variable region ($V_H$CD3) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$CD3) comprising a light chain complementary determining region CDR-L1 of SEQ ID NO: 13, a CDR-L2 of SEQ ID NO: 14 and a CDR-L3 of SEQ ID NO: 15.

In one aspect, a bispecific agonistic CD28 antigen binding molecule as defined below is provided, wherein the Fc domain is an IgG, particularly an IgG1 Fc domain or an IgG4 Fc domain. In one particular aspect, the Fc domain composed of a first and a second subunit capable of stable association is an IgG1 Fc domain. In one aspect, the Fc domain comprises the amino acid substitutions L234A and L235A (numbering according to Kabat EU index). In one aspect, the Fc domain is of human IgG1 subclass and comprises the amino acid mutations L234A, L235A and P329G (numbering according to Kabat EU index).

In one aspect, provided is a bispecific agonistic CD28 antigen binding molecule as defined herein before, wherein the first antigen binding domain capable of specific binding to CD28 comprises (i) a heavy chain variable region ($V_H$CD28) comprising a heavy chain complementary determining region CDR-H1 of SEQ ID NO: 26, a CDR-H2 of SEQ ID NO: 27, and a CDR-H3 of SEQ ID NO: 28, and a light chain variable region ($V_L$CD28) comprising a light chain complementary determining region CDR-L1 of SEQ ID NO: 29, a CDR-L2 of SEQ ID NO: 30 and a CDR-L3 of SEQ ID NO: 31; or (ii) a heavy chain variable region ($V_H$CD28) comprising a CDR-H1 of SEQ ID NO: 18, a CDR-H2 of SEQ ID NO: 19, and a CDR-H3 of SEQ ID NO: 20, and a light chain variable region ($V_L$CD28) comprising a CDR-L1 of SEQ ID NO: 21, a CDR-L2 of SEQ ID NO: 22 and a CDR-L3 of SEQ ID NO: 23.

In one aspect, the antigen binding domain capable of specific binding to CD28 of the bispecific agonistic CD28 antigen binding molecule comprises a heavy chain variable region ($V_H$CD28) comprising a CDR-H1 of SEQ ID NO: 26, a CDR-H2 of SEQ ID NO: 27, and a CDR-H3 of SEQ ID NO: 28, and a light chain variable region ($V_L$CD28) comprising a CDR-L1 of SEQ ID NO: 29, a CDR-L2 of SEQ ID NO: 30 and a CDR-L3 of SEQ ID NO: 31.

In another aspect, the antigen binding domains capable of specific binding to CD28 of the bispecific agonistic CD28 antigen binding molecule comprises a heavy chain variable region ($V_H$CD28) comprising a CDR-H1 of SEQ ID NO: 18, a CDR-H2 of SEQ ID NO: 19, and a CDR-H3 of SEQ ID NO: 20, and a light chain variable region ($V_L$CD28) comprising a CDR-L1 of SEQ ID NO: 21, a CDR-L2 of SEQ ID NO: 22 and a CDR-L3 of SEQ ID NO: 23.

Furthermore, provided is a bispecific agonistic CD28 antigen binding molecule as defined herein before, wherein the first antigen binding domain capable of specific binding to CD28 comprises a heavy chain variable region ($V_H$CD28) comprising an amino acid sequence that is at least about 95%, 96%, 97%, 98%, 99% or 100% identical to the amino acid sequence of SEQ ID NO: 24, and a light chain variable region ($V_L$CD28) comprising an amino acid sequence that is at least about 95%, 96%, 97%, 98%, 99% or 100% identical to the amino acid sequence of SEQ ID NO: 25.

In a further aspect, a bispecific agonistic CD28 antigen binding molecule is provided, wherein the first antigen binding domain capable of specific binding to CD28 comprises a heavy chain variable region ($V_H$CD28) comprising an amino acid sequence selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 and SEQ ID NO:41, and a light chain variable region ($V_L$CD28) comprising an amino acid sequence selected from the group consisting of SEQ ID NO:25, SEQ ID NO:42, SEQ ID NO:43, SEQ ID NO:44, SEQ ID NO: 45, SEQ ID NO:46, SEQ ID NO:47, SEQ ID NO:48, SEQ ID NO:49, SEQ ID NO:50 and SEQ ID NO:51.

In another aspect, provided is a bispecific agonistic CD28 antigen binding molecule, wherein the first antigen binding domain capable of specific binding to CD28 comprises (a) a heavy chain variable region ($V_H$CD28) comprising the amino acid sequence of SEQ ID NO: 37 and a light chain variable region ($V_L$CD28) comprising the amino acid sequence of SEQ ID NO:44, or (b) a heavy chain variable region ($V_H$CD28) comprising the amino acid sequence of SEQ ID NO: 37 and a light chain variable region ($V_L$CD28) comprising the amino acid sequence of SEQ ID NO:25, or (c) a heavy chain variable region ($V_H$CD28) comprising the amino acid sequence of SEQ ID NO: 41 and a light chain variable region ($V_L$CD28) comprising the amino acid sequence of SEQ ID NO:51, or (d) a heavy chain variable region ($V_H$CD28) comprising the amino acid sequence of SEQ ID NO: 36 and a light chain variable region ($V_L$CD28) comprising the amino acid sequence of SEQ ID NO:43, or (e) a heavy chain variable region ($V_H$CD28) comprising the amino acid sequence of SEQ ID NO: 36 and a light chain variable region ($V_L$CD28) comprising the amino acid sequence of SEQ ID NO:44, or (f) a heavy chain variable region ($V_H$CD28) comprising the amino acid sequence of SEQ ID NO: 36 and a light chain variable region ($V_L$CD28) comprising the amino acid sequence of SEQ ID NO:49, or (g) a heavy chain variable region ($V_H$CD28) comprising the amino acid sequence of SEQ ID NO: 36 and a light chain variable region ($V_L$CD28) comprising the amino acid sequence of SEQ ID NO:25, or (h) a heavy chain variable region ($V_H$CD28) comprising the amino acid sequence of SEQ ID NO: 33 and a light chain variable region ($V_L$CD28) comprising the amino acid sequence of SEQ ID NO:25, or (i) a heavy chain variable region ($V_H$CD28) comprising the amino acid sequence of SEQ ID NO: 32 and a light chain variable region ($V_L$CD28) comprising the amino acid sequence of SEQ ID NO:43, or (j) a heavy chain variable region ($V_H$CD28) comprising the amino acid sequence of SEQ ID NO: 32 and a light chain variable region ($V_L$CD28) comprising the amino acid sequence of SEQ ID NO:49, or (k) a heavy chain variable region ($V_H$CD28) comprising the amino acid sequence of SEQ ID NO: 32 and a light chain variable region ($V_L$CD28) comprising the amino acid sequence of SEQ ID NO:25.

In one particular aspect, a bispecific agonistic CD28 antigen binding molecule is provided, wherein the first antigen binding domain capable of specific binding to CD28 comprises (i) a heavy chain variable region ($V_H$CD28) comprising a heavy chain complementary determining region CDR-H1 of SEQ ID NO: 52, a CDR-H2 of SEQ ID NO: 53, and a CDR-H3 of SEQ ID NO: 54, and a light chain variable region ($V_L$CD28) comprising a light chain complementary determining region CDR-L1 of SEQ ID NO: 55, a CDR-L2 of SEQ ID NO: 56 and a CDR-L3 of SEQ ID NO: 57. In one aspect, the first antigen binding domain capable of specific binding to CD28 comprises the CDRs of the heavy chain variable region ($V_H$CD28) comprising the amino acid sequence of SEQ ID NO:37 and the CDRs of the light chain variable region ($V_L$CD28) comprising the amino acid sequence of SEQ ID NO:44.

In another particular aspect, a bispecific agonistic CD28 antigen binding molecule is provided, wherein the antigen binding domain capable of specific binding to CD28 comprises a heavy chain variable region ($V_H$CD28) comprising the amino acid sequence of SEQ ID NO:36 and a light chain variable region ($V_L$CD28) comprising the amino acid sequence of SEQ ID NO: 43. In a further particular aspect, a bispecific agonistic CD28 antigen binding molecule is provided, wherein the antigen binding domain capable of specific binding to CD28 comprises a heavy chain variable region ($V_H$CD28) comprising the amino acid sequence of SEQ ID NO:32 and a light chain variable region ($V_L$CD28) comprising the amino acid sequence of SEQ ID NO: 25.

In one aspect, a bispecific agonistic CD28 antigen binding molecule is provided, wherein the antigen binding domain capable of specific binding to CD3 comprises a heavy chain variable region ($V_H$CD3) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$CD3) comprising a light chain complementary determining region CDR-L1 of SEQ ID NO: 5, a CDR-L2 of SEQ ID NO: 6 and a CDR-L3 of SEQ ID NO: 7. In one aspect, the antigen binding domain capable of specific binding to CD3 comprises the CDRs of the heavy chain variable region ($V_H$CD3) comprising the amino acid sequence of SEQ ID NO:8 and the CDRs of the light chain variable region ($V_L$CD3) comprising the amino acid sequence of SEQ ID NO: 9. In one particular aspect, the antigen binding domain capable of specific binding to CD3 comprises a heavy chain variable region ($V_H$CD3) comprising the amino acid sequence of SEQ ID NO:8, and a light chain variable region ($V_L$CD3) comprising the amino acid sequence of SEQ ID NO:9.

In another aspect, provided is a bispecific agonistic CD28 antigen binding molecule as described herein, wherein the antigen binding domain capable of specific binding to CD3 comprises a heavy chain variable region ($V_H$CD3) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$CD3) comprising a light chain complementary determining region CDR-L1 of SEQ ID NO: 13, a CDR-L2 of SEQ ID NO: 14 and a CDR-L3 of SEQ ID NO: 15. In one aspect, the antigen binding domain capable of specific binding to CD3 comprises the CDRs of the heavy chain variable region ($V_H$CD3) comprising the amino acid sequence of SEQ ID NO:16 and the CDRs of the light chain variable region ($V_L$CD3) comprising the amino acid sequence of SEQ ID NO:17. In one particular aspect, the antigen binding domain capable of specific binding to CD3 comprises a heavy chain variable region ($V_H$CD3) comprising the amino acid sequence of SEQ ID NO:16, and a light chain variable region ($V_L$CD3) comprising the amino acid sequence of SEQ ID NO:17.

In a further aspect, provided is a bispecific agonistic CD28 antigen binding molecule as defined herein before, wherein the first antigen binding domain capable of specific binding to CD28 and/or the second antigen binding domain capable of specific binding to CD3 is a Fab fragment or a crossFab fragment. In one aspect, provided is a bispecific agonistic CD28 antigen binding molecule as described herein, comprising (a) a Fab fragment capable of specific binding to CD28, (b) a crossFab fragment capable of specific binding to CD3, and (c) a Fc domain composed of a first and a second subunit capable of stable association comprising one or more amino acid substitution that reduces the binding affinity of the antigen binding molecule to an Fc receptor and/or effector function. In another aspect, provided is a bispecific agonistic CD28 antigen binding molecule as described herein, comprising (a) a crossFab fragment capable of specific binding to CD28, (b) a Fab fragment capable of specific binding to CD3, and (c) a Fc domain composed of a first and a second subunit capable of stable association comprising one or more amino acid substitution that reduces the binding affinity of the antigen binding molecule to an Fc receptor and/or effector function.

In one aspect, the first antigen binding domain capable of specific binding to CD28 is a Fab fragment wherein the variable domains VL and VH or the constant domains CL and CH1, particularly the variable domains VL and VH, of the Fab light chain and the Fab heavy chain are replaced by each other. In one aspect, the second antigen binding domain capable of specific binding to CD3 is a conventional Fab fragment. In one aspect, the second antigen binding domain capable of specific binding to CD3 is a Fab molecule wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In a further aspect, provided is a bispecific agonistic CD28 antigen binding molecule as described herein, wherein the second antigen binding domain capable of specific binding to CD3 is a Fab molecule wherein the variable domains VL and VH or the constant domains CL and CH1, particularly the constant domains CL and CH1, of the Fab light chain and the Fab heavy chain are replaced by each other. In one aspect, the first antigen binding domain capable of specific binding to CD28 is a conventional Fab molecule. In one aspect, the first antigen binding domain capable of specific binding to CD28 is a Fab molecule wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In another aspect, a bispecific agonistic CD28 antigen binding molecule as disclosed herein is provided, wherein the first and the second antigen binding domain are each a Fab molecule and the Fc domain is composed of a first and a second subunit capable of stable association; and wherein (i) the first antigen binding domain is fused at the C-terminus of the Fab heavy chain to the N-terminus of the first subunit of the Fc domain and the second antigen binding domain is fused at the C-terminus of the Fab heavy chain to the N-terminus of the second subunit of the Fc domain, or (ii) the second antigen binding domain is fused at the C-terminus of the Fab heavy chain to the N-terminus of the first subunit of the Fc domain and the first antigen binding domain is fused at the C-terminus of the Fab heavy chain to the N-terminus of the second subunit of the Fc domain. In one aspect, the Fc domain comprises a modification promoting the association of the first and the second subunit of the Fc domain. In one aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In a further aspect, provided a bispecific agonistic CD28 antigen binding molecule characterized by monovalent binding to CD28, comprising (a) a first antigen binding domain capable of specific binding to CD28, (b) a second antigen binding domain capable of specific binding to CD3, (c) a Fc domain composed of a first and a second subunit capable of stable association comprising one or more amino acid substitution that reduces the binding affinity of the antigen binding molecule to an Fc receptor and/or effector function, wherein said second antigen binding domain capable of specific binding to CD3 comprises (i) a heavy chain variable region ($V_H$CD3) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$CD3) comprising a light chain complementary determining region CDR-L1 of SEQ ID NO: 5, a CDR-L2 of SEQ ID NO: 6 and a CDR-L3 of SEQ ID NO: 7; or (ii) a heavy chain variable region ($V_H$CD3) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$CD3) comprising a light chain complementary determining region CDR-L1 of SEQ ID NO: 13, a CDR-L2 of SEQ ID NO: 14 and a CDR-L3 of SEQ ID NO: 15, and further comprising (d) a masking moiety covalently attached to the bispecific agonistic CD28 antigen binding molecule through a protease-cleavable linker, wherein the masking moiety is capable of binding to the idiotype of the second antigen binding domain capable of specific binding to CD3 thereby reversibly concealing the antigen binding domain capable of specific binding to CD3.

In one aspect, the masking moiety is covalently attached to the heavy chain variable region ($V_H$CD3) of the second antigen binding domain capable of specific binding to CD3, particularly via a peptide linker, more particularly via a protease cleavable linker. In one aspect, the masking moiety is an scFv.

In a further aspect, the masking moiety comprises (i) a heavy chain variable region (VH) comprising a CDR-H1 amino acid sequence of DYSMN (SEQ ID NO:123), a CDR H2 amino acid sequence selected from the group consisting of WINTETGEPRYTDDFKG (SEQ ID NO:124), WINTETGEPRYTDDFTG (SEQ ID NO:130) and WINTETGEPRYTQGFKG (SEQ ID NO:131), and a CDR H3 amino acid sequence of EGDYDVFDY (SEQ ID NO:125), and a light chain variable region (VL) comprising a light chain complementary determining region CDR-L1 amino acid sequence selected from the group consisting of RASKSVSTSSYSYMH (SEQ ID NO:126) and KSSKSVSTSSYSYMH (SEQ ID NO: 129), a CDR-L2 amino acid sequence of YVSYLES (SEQ ID NO:127) and a CDR-L3 amino acid sequence selected from the group consisting of QHSREFPYT (SEQ ID NO:128) and QQSREFPYT (SEQ ID NO:132); or (ii) a heavy chain variable region (VH) comprising a CDR-H1 amino acid sequence of DYSMN (SEQ ID NO:123), a CDR-H2 amino acid sequence of WINTETGEPRYTDDFKG (SEQ ID NO:124), and a CDR-H3 amino acid sequence of EGDYDVFDY (SEQ ID NO:125), and a light chain variable region (VL) comprising a CDR-L1 amino acid sequence of RASKSVSTSSYSYMH (SEQ ID NO:126), a CDR-L2 amino acid sequence of YVSYLES (SEQ ID NO:127) and a CDR-L3 amino acid sequence of QHSREFPYT (SEQ ID NO:128), or (iii) a heavy chain variable region (VH) comprising a CDR-H1 amino acid sequence of SYGVS (SEQ ID NO:123), a CDR-H2 amino acid sequence of IIWGDGSTNYHSALIS (SEQ ID NO: 124), and a CDR-H3 amino acid sequence of GITTVVDDYYAMDY (SEQ ID NO:125), and a light chain variable region (VL) comprising a CDR-L1 amino acid sequence of KSSKSVSTSSYSYMH (SEQ ID NO:129), a CDR-L2 amino acid sequence of AATFLAD (SEQ ID NO:127) and a CDR-L3 amino acid sequence of QHYYSTPYT (SEQ ID NO:128), or (iv) a heavy chain variable region (VH) comprising a CDR-H1 amino acid sequence of SYGVS (SEQ ID NO:123), a CDR-H2 amino acid sequence of WINTETGEPRYTDDFTG (SEQ ID NO:130), and a CDR-H3 amino acid sequence of GITTVVDDYYAMDY (SEQ ID NO: 125), and a light chain variable region (VL) comprising a CDR-L1 amino acid sequence of KSSKSVSTSSYSYMH (SEQ ID NO:129), a CDR-L2 amino acid sequence of AATFLAD (SEQ ID NO:127) and a CDR-L3 amino acid sequence of QHYYSTPYT (SEQ ID NO:128), or (v) a heavy chain variable region (VH) comprising a CDR-H1 amino acid sequence of SYGVS (SEQ ID NO:123), a CDR-H2 amino acid sequence of WINTETGEPRYTQGFKG (SEQ ID NO:131), and a CDR-H3 amino acid sequence of GITTVVDDYYAMDY (SEQ ID NO: 125), and a light chain variable region (VL) comprising a CDR-L1 amino acid sequence of KSSKSVSTSSYSYMH (SEQ ID NO:129), a CDR-L2 amino acid sequence of AATFLAD (SEQ ID NO:127) and a CDR-L3 amino acid sequence of QHYYSTPYT (SEQ ID NO:128).

In one particular aspect, the masking moiety comprises a heavy chain variable region (VH) comprising a CDR-H1 amino acid sequence of SYGVS (SEQ ID NO:115), a CDR-H2 amino acid sequence of IIWGDGSTNYHSALIS (SEQ ID NO:116), and a CDR-H3 amino acid sequence of GITTVVDDYYAMDY (SEQ ID NO:117), and a light chain variable region (VL) comprising a CDR-L1 amino acid sequence of RASENIDSYLA (SEQ ID NO:118), a CDR-L2 amino acid sequence of AATFLAD (SEQ ID NO:119) and a CDR-L3 amino acid sequence of QHYYSTPYT (SEQ ID NO:120).

In another aspect, provided is a bispecific agonistic CD28 antigen binding molecule as described herein before, wherein the protease cleavable linker comprises at least one protease recognition sequence. In one aspect, the protease recognition sequence is selected from the group consisting of:

(a)
(SEQ ID NO: 148)
RQARVVNG;

-continued

```
(b)
                               (SEQ ID NO: 149)
VHMPLGFLGPGRSRGSFP;

(c)
                               (SEQ ID NO: 150)
RQARVVNGXXXXXVPLSLYSG,

wherein X is any amino acid;

(d)
                               (SEQ ID NO: 151)
RQARVVNGVPLSLYSG;

(e)
                               (SEQ ID NO: 152)
PLGLWSQ;

(f)
                               (SEQ ID NO: 153)
VHMPLGFLGPRQARVVNG;

(g)
                               (SEQ ID NO: 154)
FVGGTG;

(h)
                               (SEQ ID NO: 155)
KKAAPVNG;

(i)
                               (SEQ ID NO: 156)
PMAKKVNG;

(j)
                               (SEQ ID NO: 157)
QARAKVNG;

(k)
                               (SEQ ID NO: 158)
VHMPLGFLGP;

(l)
                               (SEQ ID NO: 159)
QARAK;

(m)
                               (SEQ ID NO: 160)
VHMPLGFLGPPMAKK;

(n)
                               (SEQ ID NO: 161)
KKAAP;
and

(o)
                               (SEQ ID NO: 162)
PMAKK.
```

In one aspect, the protease cleavable linker comprises the protease recognition sequence RQARVVNG (SEQ ID NO:148). In another aspect, the protease cleavable linker comprises the protease recognition sequence PMAKK (SEQ ID NO:162).

According to another aspect of the invention, there is provided one or more isolated polynucleotide(s) encoding the bispecific agonistic CD28 antigen binding molecule of the invention. The invention further provides one or more vector(s), particularly expression vector(s), comprising the isolated polynucleotide(s) of the invention, and a host cell comprising the isolated polynucleotide(s) or the expression vector(s) of the invention. In some aspects, the host cell is a eukaryotic cell, particularly a mammalian cell. In another aspect, provided is a method of producing a bispecific agonistic CD28 antigen binding molecule as described herein comprising culturing the host cell of the invention under conditions suitable for the expression of the bispecific agonistic CD28 antigen binding molecule. Optionally, the method also comprises recovering the bispecific agonistic CD28 antigen binding molecule. The invention also encompasses a bispecific agonistic CD28 antigen binding molecule produced by the method of the invention.

The invention further provides a pharmaceutical composition comprising a bispecific agonistic CD28 antigen binding molecule of the invention and at least one pharmaceutically acceptable excipient. In one aspect, the pharmaceutical composition is for use in the treatment of a disease, particularly cancer.

Also encompassed by the invention are methods of using the bispecific agonistic CD28 antigen binding molecule or the pharmaceutical composition of the invention. In one aspect, the invention provides a bispecific agonistic CD28 antigen binding molecule or a pharmaceutical composition according to the invention for use as a medicament. In one aspect, provided is a bispecific agonistic CD28 antigen binding molecule as described herein for use in (a) enhancing cell activation or (b) enhancing T cell effector functions. In one aspect, provided is a bispecific agonistic CD28 antigen binding molecule or a pharmaceutical composition according to the invention for use in the treatment of a disease. In a specific aspect, the disease is cancer. In another aspect is provided a bispecific agonistic CD28 antigen binding molecule or pharmaceutical composition according to the invention is for use in the treatment of cancer, wherein the bispecific agonistic CD28 antigen binding molecule is for administration in combination with a chemotherapeutic agent, radiation therapy and/or other agents for use in cancer immunotherapy.

Also provided is the use of a bispecific agonistic CD28 antigen binding molecule or the pharmaceutical composition according to the invention in the manufacture of a medicament for the treatment of a disease; as well as a method of treating a disease in an individual, comprising administering to said individual a therapeutically effective amount of a bispecific agonistic CD28 antigen binding molecule according to the invention or a composition comprising the bispecific agonistic CD28 antigen binding molecule according to the invention in a pharmaceutically acceptable form. In a specific aspect, the disease is cancer. In one aspect, provided is a method (a) enhancing cell activation or (b) enhancing T cell effector functions in an individual, comprising administering a bispecific agonistic CD28 antigen binding molecule according to the invention or a composition comprising the bispecific agonistic CD28 antigen binding molecule according to the invention in a pharmaceutically acceptable form to said individual. In another aspect, provided is the use of a bispecific agonistic CD28 antigen binding molecule according to the invention in the manufacture of a medicament for the treatment of a disease, wherein the treatment comprises co-administration with a chemotherapeutic agent, radiation therapy and/or other agents for use in cancer immunotherapy. In a further aspect, provided is a method of treating a disease in an individual, comprising administering to said individual a therapeutically effective amount of a bispecific agonistic CD28 antigen binding molecule according to the invention or a composition comprising the bispecific agonistic CD28 antigen binding molecule according to the invention in a pharmaceutically acceptable form, wherein the method comprises co-administration with a chemotherapeutic agent, radiation therapy and/or other agents for use in cancer immunotherapy. Also provided is a method of inhibiting the growth of tumor cells in an individual comprising administering to the individual an effective amount of the bispecific agonistic CD28 antigen binding molecule according to the invention, or a composition comprising the bispecific agonistic CD28 antigen binding molecule according to the invention in a pharmaceutically acceptable form, to inhibit the growth of the tumor cells. In any of the above aspects, the individual preferably is a mammal, particularly a human.

BRIEF DESCRIPTION OF THE DRAWINGS

FIG. 1A shows a schematic illustration of the CD28 agonistic antibody variants as monovalent hu IgG1 PGLALA isotype ("Fc silent"). FIG. 1B shows a bispecific CD3-CD28 antigen binding molecule in 1+1 format, wherein in the Fab molecule comprising the CD3 antigen binding domain the CH1 and CL domains are exchanged with each other (CH1/CL crossfab) and wherein in the Fab molecule comprising the CD28 antigen binding domain certain amino acids in the CH1 and CL domain are exchanged (Charged variants) to allow better pairing with the light chain. FIG. 1C shows a schematic illustration of the CD28 agonistic antibody variants as monovalent hu IgG1 PGLALA isotype ("Fc silent") and FIG. 1D shows the CD3 antibody as monovalent hu IgG1 PGLALA isotype ("Fc silent"). FIG. 1E illustrates a bispecific CD3-CD28 antigen binding molecule in 1+1 format as huIgG1 PG-LALA CrossFab molecule, wherein in the CD3 (CH2527) Fab fragment (knob) the CH1 and CK domain are exchanged and wherein the CD3 is masked with anti-idiotypic CD3 scFv 4.24.72 and a cleavable linker (MK062 Matriptase site). FIG. 1F illustrates a bispecific CD3-CD28 antigen binding molecule in 1+1 format as huIgG1 PG-LALA CrossFab molecule, wherein in the CD3 (CH2527) Fab fragment (knob) the CH1 and CL domain are exchanged with each other (CL/CH1 crossfab) and wherein the CD3 is masked with anti-idiotypic CD3 scFv 4.24.72 and a non-cleavable linker.

FIG. 1G shows a bispecific CD3-CD28 antigen binding molecule in 1+1 format, wherein in the Fab molecule comprising the CD28 antigen binding domain the VH and VL domains are exchanged with each other (VH/VL crossfab) and wherein in the Fab molecule comprising the CD3 antigen binding domain certain amino acids in the CH1 and CL domain are exchanged (Charged variants) to allow better pairing with the light chain. FIG. 1H illustrates a bispecific CD3-CD28 antigen binding molecule in 1+1 format as huIgG1 PG-LALA CrossFab molecule, wherein in the CD28 Fab fragment (hole) the VH and CL domains are exchanged and wherein the CD3 is masked with anti-idiotypic CD3 scFv 4.72.24 and a cleavable linker (MK062 Matriptase site). FIG. 1I illustrates a bispecific CD3-CD28 antigen binding molecule in 1+1 format as huIgG1 PG-LALA CrossFab molecule, wherein in the CD28 Fab fragment (hole) the VH and CL domains are exchanged and wherein the CD3 is masked with anti-idiotypic CD3 scFv 4.72.24 and a non-cleavable linker.

The alignment of the variable domains of CD28 (SA) and variants thereof is shown in FIG. 2A to 2D. Alignment of the CD28 (SA) VH domain and variants thereof in order to remove cysteine 50 and to reduce the affinity of the resulting anti-CD28 binders to different degrees is shown in FIG. 2A. Of note, in VH variants i and j, the CDRs of CD28 (SA) were grafted from an IGHV1-2 framework into an IGHV3-23 framework (FIG. 2B).

FIG. 4A shows Jurkat NFAT activation mediated by bispecific CD28 mAb9.3-CD3 IgG. Jurkat NFAT effector cells were incubated with bispecific CD28 (9.3)-CD3 IgG or monovalent control IgGs. Luminescence was measured after 5 h of incubation after addition of One Glo substrate. Each point represents the mean value of triplicates (n=2). In FIG. 4B is shown Jurkat NFAT activation mediated by bispecific CD28 (SA)-CD3 IgG. Jurkat NFAT effector cells were incubated with bispecific CD28 (SA)-CD3 IgG or monovalent control IgGs. Luminescence was measured after 5 h of incubation after addition of One Glo substrate. Each point represents the mean value of triplicates (n=2).

In FIG. 5A dose-dependent T cell activation (measured by IFN gamma release) is shown for the bispecific CD3-CD28 (9.3) IgG when huFc coating is used for crosslinking, whereas in FIG. 5B dose-dependent T cell activation (measured by IFN gamma release) without huFc coating is shown. FIG. 5C shows dose-dependent T cell activation (measured by IFN gamma release) for the bispecific CD3-CD28 (SA) IgG when huFc coating is used for crosslinking, whereas in FIG. 5D dose-dependent T cell activation (measured by IFN gamma release) without huFc coating is shown.

In FIG. 6A dose-dependent T cell activation (measured by IFN gamma release) is shown for the bispecific CD3-CD28 (9.3) IgG constructs when huFc coating is used for crosslinking, whereas in FIG. 6B dose-dependent T cell activation (measured by quantification of CD69 on CD8 positive T cells) with huFc coating is shown. FIG. 6C shows dose-dependent T cell activation (measured by IFN gamma release) for the bispecific CD3-CD28 (SA) IgG without huFc coating, whereas in FIG. 6D dose-dependent T cell activation (measured by quantification of CD69 on CD8 positive T cells) without huFc coating is shown.

In FIG. 7A dose-dependent T cell activation (measured by IFN gamma release) is shown for the bispecific CD3-CD28 (SA) IgG constructs when huFc coating is used for crosslinking. FIG. 7B shows dose-dependent T cell activation (measured by quantification of CD69 on CD8 positive T cells) when huFc coating is used for crosslinking. FIG. 7C shows dose-dependent T cell activation (measured by IFN gamma release) for the bispecific CD3-CD28 (SA) IgG constructs without huFc coating. In FIG. 7D dose-dependent T cell activation (measured by quantification of CD69 on CD8 positive T cells) without huFc coating is shown.

DETAILED DESCRIPTION OF THE INVENTION

Definitions

Figure 1A:
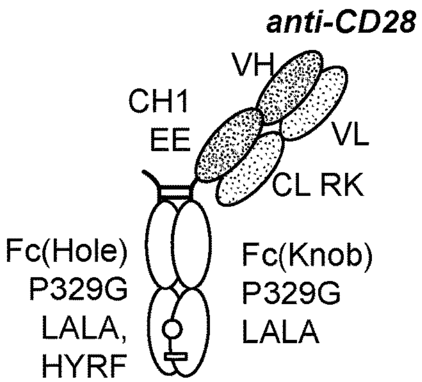
In FIG. 1A to 1I schematic illustrations of exemplary molecules as described herein are shown.
Figure 1B:
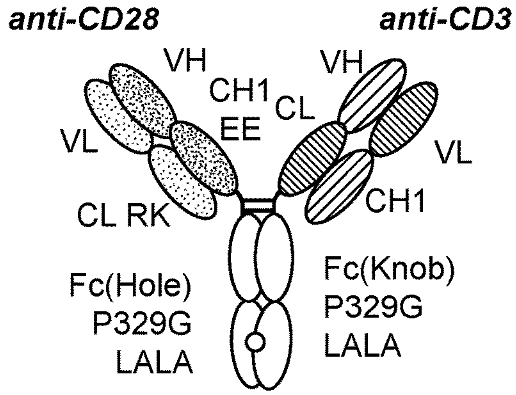

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, multispecific antibodies (e.g., bispecific antibodies), antibody fragments and scaffold antigen binding proteins.

As used herein, the term "antigen binding domain that binds to antigen expressed on T cells" or "moiety capable of specific binding to an antigen expressed on T cells" refers to a polypeptide molecule that specifically binds to the antigen CD3. In one aspect, the antigen binding domain is able to activate signaling through CD3. In a particular aspect, the antigen binding domain is able to direct the entity to which it is attached (e.g. the CD28 antibody) to a CD3-expressing cell, for example to a specific type of T cell. Antigen binding domains capable of specific binding to CD3 include antibodies and fragments thereof as further defined herein. In addition, antigen binding domains capable of specific binding to an antigen include scaffold antigen binding proteins as further defined herein, e.g. binding domains which are based on designed repeat proteins or designed repeat domains (see e.g. WO 2002/020565).

In relation to an antigen binding molecule, i.e. an antibody or fragment thereof, the term "antigen binding domain" refers to the part of the molecule that comprises the area which specifically binds to and is complementary to part or all of an antigen. An antigen binding domain capable of specific antigen binding may be provided, for example, by one or more antibody variable domains (also called antibody variable regions). Particularly, an antigen binding domain capable of specific antigen binding comprises an antibody light chain variable region (VL) and an antibody heavy chain variable region (VH). In another aspect, the "antigen binding domain capable of specific binding to a tumor-associated antigen" can also be a Fab fragment or a crossFab fragment. As used herein, the terms "first", "second" or "third" with respect to antigen binding domains etc., are used for convenience of distinguishing when there is more than one of each type of moiety. Use of these terms is not intended to confer a specific order or orientation of the moiety unless explicitly so stated.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. However, a bispecific antigen binding molecule may also comprise additional antigen binding sites which bind to further antigenic determinants. In certain aspects, the bispecific antigen binding molecule is capable of simultaneously binding two antigenic determinants, particularly two antigenic determinants expressed on two distinct cells or on the same cell. The term "bispecific" in accordance with the present invention thus may also include a trispecific molecule, e.g. a bispecific molecule comprising a CD28 antibody and two antigen binding domains directed to two different target cell antigens.

The term "valent" as used within the current application denotes the presence of a specified number of binding sites specific for one distinct antigenic determinant in an antigen binding molecule that are specific for one distinct antigenic determinant. As such, the terms "bivalent", "tetravalent", and "hexavalent" denote the presence of two binding sites, four binding sites, and six binding sites specific for a certain antigenic determinant, respectively, in an antigen binding molecule. In particular aspects of the invention, the bispecific antigen binding molecules according to the invention can be monovalent for a certain antigenic determinant, meaning that they have only one binding site for said antigenic determinant or they can be bivalent or tetravalent for a certain antigenic determinant, meaning that they have two binding sites or four binding sites, respectively, for said antigenic determinant.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies, triabodies, tetrabodies, crossFab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab') 2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" or "Fab molecule" refers to an antibody fragment comprising a light chain fragment comprising a variable light chain (VL) domain and a constant domain of a light chain (CL), and a variable heavy chain (VH) domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an F(ab') 2 fragment that has two antigen-combining sites (two Fab fragments) and a part of the Fc region. A "conventional Fab fragment" is comprised of a VL-CL light chain and a VH-CH1 heavy chain.

The term "crossFab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable (VL) domain and the heavy chain constant domain (CH1), and a peptide chain composed of the heavy chain variable domain (VH) and the light chain constant domain (CL). This crossover Fab molecule is also referred to as $CrossFab_{(VLVH)}$. On the other hand, when the constant regions of the Fab heavy and light chain are exchanged, the crossover Fab molecule comprises a peptide chain composed of the heavy chain variable domain (VH) and the light chain constant domain (CL), and a peptide chain composed of the light chain variable domain (VL) and the heavy chain constant domain (CH1). This crossover Fab molecule is also referred to as $CrossFab_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins®) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13:695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin®), a variable domain of antibody light chain or heavy chain (single-domain antibody, sdAb), a variable domain of antibody heavy chain (NANOBODY®, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (AFFILIN® molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly $CD4^+$ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details, see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details, see Biochim Biophys Acta 1482:337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details, see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details, see Nature Biotechnology 23 (12), 1556-1561 (2005) and Expert Opinion on Investigational Drugs 16 (6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details, see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details, see J. Mol. Biol. 332, 489-503 (2003), PNAS 100 (4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or $V_HH$ fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the beta-sandwich can be engineered to enable an Adnectin to specifically recognize a therapeutic target of interest. For further details, see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details, see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can beengineered to include upto 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable domain (VL) and an antibody heavy chain variable domain (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIACORE™ instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

A "T-cell antigen" as used herein refers to an antigenic determinant presented on the surface of a T lymphocyte, particularly a cytotoxic T lymphocyte.

A "T cell activating therapeutic agent" as used herein refers to a therapeutic agent capable of inducing T cell activation in a subject, particularly a therapeutic agent designed for inducing T-cell activation in a subject. Examples of T cell activating therapeutic agents include bispecific antibodies that specifically bind an activating T cell antigen, such as CD3, and another antigen, such as CD28.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3.

The term "CD3" refers to any native CD3 from any vertebrate source, including mammals such as primates (e.g. humans), non-human primates (e.g. cynomolgus monkeys) and rodents (e.g. mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UNIPROT® (www(dot)uniprot(dot)org) accession no. P07766 (version 144), or NCBI® (www(dot)ncbi(dot)nlm(dot)nih(dot)gov/) RefSeq NP_000724.1. See also SEQ ID NO: 70. The amino acid sequence of cynomolgus [*Macaca fascicularis*] CD3ε is shown in NCBI® GENBANK℠ no. BAB71849.1. See also SEQ ID NO: 71.

The term "CD28" (Cluster of differentiation 28, Tp44) refers to any CD28 protein from any vertebrate source, including mammals such as primates (e.g. humans) non-human primates (e.g. cynomolgus monkeys) and rodents (e.g. mice and rats), unless otherwise indicated. CD28 is expressed on T cells and provides co-stimulatory signals required for T cell activation and survival. T cell stimulation through CD28 in addition to the T-cell receptor (TCR) can provide a potent signal for the production of various interleukins. CD28 is the receptor for CD80 (B7.1) and CD86 (B7.2) proteins and is the only B7 receptor constitutively expressed on naive T cells. The amino acid sequence of human CD28 is shown in UNIPROT® (www(dot)uniprot(dot)org) accession no. P10747 (SEQ ID NO:1).

An "agonistic antibody" refers to an antibody that comprises an agonistic function against a given receptor. In general, when an agonist ligand (factor) binds to a receptor, the tertiary structure of the receptor protein changes, and the receptor is activated (when the receptor is a membrane protein, a cell growth signal or such is usually transduced). If the receptor is a dimer-forming type, an agonistic antibody can dimerize the receptor at an appropriate distance and angle, thus acting similarly to a ligand. An appropriate anti-receptor antibody can mimic dimerization of receptors performed by ligands, and thus can become an agonistic antibody.

A "CD28 agonistic antigen binding molecule" or "CD28 conventional agonistic antigen binding molecule" is an antigen binding molecule that mimicks CD28 natural ligands (CD80 or CD86) in their role to enhance T cell activation in presence of a T cell receptor signal ("signal 2"). A T cell needs two signals to become fully activated. Under physiological conditions "signal 1" arises form the interaction of T cell receptor (TCR) molecules with peptide/major histocompatibility complex (MHC) complexes on antigen presenting cells (APCs) and "signal 2" is provided by engagement of a costimulatory receptor, e.g. CD28. A CD28 agonistic antigen binding molecule is able to costimulate T cells (signal 2). It is also able to induce T cell proliferation and cytokine secretion in combination with a molecule with specificity for the TCR complex, however the CD28 agonistic antigen binding molecule is not capable of fully activating T cells without additional stimulation of the TCR. There is however a subclass of CD28 specific antigen binding molecules, the so-called CD28 superagonistic antigen binding molecules. A "CD28 superagonistic antigen binding molecule" is a CD28 antigen binding molecule which is capable of fully activating T cells without additional stimulation of the TCR. A CD28 superagonistic antigen binding molecule is capable to induce T cell proliferation and cytokine secretion without prior T cell activation (signal 1).

An "idiotype-specific polypeptide" as used herein refers to a polypeptide that recognizes the idiotype of an antigen-binding domain, e.g., an antigen-binding domain specific for CD3. The idiotype-specific polypeptide is capable of specifically binding to the variable region of the antigen-binding domain and thereby reducing or preventing specific binding of the antigen-binding domain to its cognate antigen. When associated with a molecule that comprises the antigen binding domain, the idiotype-specific polypeptide can function as a masking moiety of the molecule. Specifically disclosed herein are anti-idiotype antibodies or anti-idiotype-binding antibody fragments specific for the idiotype of anti-CD3 binding molecules.

"Protease" or "proteolytic enzyme" as used herein refers to any proteolytic enzyme that cleaves the linker at a recognition site and that is expressed by a target cell. Such proteases might be secreted by the target cell or remain associated with the target cell, e.g., on the target cell surface. Examples of proteases include but are not limited to metalloproteinases, e.g., matrix metalloproteinase 1-28 and A Disintegrin And Metalloproteinase (ADAM) 2, 7-12, 15, 17-23, 28-30 and 33, serine proteases, e.g., urokinase-type plasminogen activator and Matriptase, cysteine protease, aspartic proteases, and members of the cathepsin family. A particular example is human Matriptase comprising an amino acid sequence of SEQ ID NO:164.

"Protease activatable" as used herein, with respect to the bispecific agonistic CD28 antigen binding molecule, refers to a bispecific agonistic CD28 antigen binding molecule having reduced or abrogated ability to activate T cells due to a masking moiety that reduces or abrogates the bispecific agonistic CD28 antigen binding molecule's ability to bind to CD3. Upon dissociation of the masking moiety by proteolytic cleavage, e.g., by proteolytic cleavage of a linker connecting the masking moiety to the bispecific agonistic CD28 antigen binding molecule, binding to CD3 is restored and the T cell activating bispecific molecule is thereby activated.

"Reversibly concealing" as used herein refers to the binding of a masking moiety or idiotype-specific polypeptide to an antigen binding domain or molecule such as to prevent binding of the antigen binding domain or molecule to its antigen, e.g., CD3. This concealing is reversible in that the idiotype-specific polypeptide can be released from the antigen binding domain or molecule, e.g. by protease cleavage, and thereby freeing the antigen binding domain or molecule to bind to its antigen.

The term "variable domain" or "variable region" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR" as used herein refers to each of the regions of an antigen binding variable domain which are hypervariable in sequence and which determine antigen binding specificity, for example "complementarity determining regions" ("CDRs"). Generally, antigen binding domains comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262:732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature. Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2 (L2)-FR3-H3 (L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgG1, IgG2, IgG3, IgG4, IgA1, and IgA2. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "CH1 domain" denotes the part of an antibody heavy chain polypeptide that extends approximately from EU position 118 to EU position 215 (EU numbering system according to Kabat). In one aspect, a CH1 domain has the amino acid sequence of ASTKGP SVFP LAPSSKSTSG GTAALGCLVK DYFPEPVTVS WNSGALTSGV HTFPAVLQSS GLYSLSSVVT VPSSSLGTQT YICNVNHKPS NTKVDKKV (SEQ ID NO: 165). Usually, a segment having the amino acid sequence of EPKSC (SEQ ID NO:168) is following to link the CH1 domain to the hinge region, The term "hinge region" denotes the part of an antibody heavy chain polypeptide that joins in a wild-type antibody heavy chain the CH1 domain and the CH2 domain, e. g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence. The hinge region is normally a dimeric molecule consisting of two polypeptides with identical amino acid sequence. The hinge region generally comprises up to 25 amino acid residues and is flexible allowing the associated target binding sites to move independently. The hinge region can be subdivided into three domains: the upper, the middle, and the lower hinge domain (see e.g. Roux, et al., J. Immunol. 161 (1998) 4083).

In one aspect, the hinge region has the amino acid sequence DKTHTCPXCP (SEQ ID NO: 169), wherein X is either S or P. In one aspect, the hinge region has the amino acid sequence HTCPXCP (SEQ ID NO: 170), wherein X is either S or P. In one aspect, the hinge region has the amino acid sequence CPXCP (SEQ ID NO:171), wherein X is either S or P.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain.

The "CH2 domain" of a human IgG Fc region usually extends from an amino acid residue at about EU position 231 to an amino acid residue at about EU position 340 (EU numbering system according to Kabat). In one aspect, a CH2 domain has the amino acid sequence of APELLGGPSV FLFPPKPKDT LMISRTPEVT CVVVDVSHEDP EVKFNWYVDG VEVHNAKTKP REEQYSTYRW SVLTVLHQDW LNGKEYKCKV SNKALPAPIE KTISKAK (SEQ ID NO: 166). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206. In one embodiment, a carbohydrate chain is attached to the CH2 domain. The CH2 domain herein may be a native sequence CH2 domain or variant CH2 domain.

The "CH3 domain" comprises the stretch of residues C-terminal to a CH2 domain in an Fc region denotes the part of an antibody heavy chain polypeptide that extends approximately from EU position 341 to EU position 446 (EU numbering system according to Kabat). In one aspect, the CH3 domain has the amino acid sequence of GQPREPQVYT LPPSRDELTK NQVSLTCLVK GFYPS- DIAVE WESNGOPENN YKTTPPVLDS DGSFFLYSKL TVDKSRWOQG NVFSCSVMHE ALHNHYTQKS LSLSPG (SEQ ID NO: 167). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "wild-type Fc domain" denotes an amino acid sequence identical to the amino acid sequence of an Fc domain found in nature. Wild-type human Fc domains include a native human IgG1 Fc-region (non-A and A allotypes), native human IgG2 Fc-region, native human IgG3 Fc-region, and native human IgG4 Fc-region as well as naturally occurring variants thereof. Wild-type Fc-regions are denoted in SEQ ID NO: 172 (IgG1, caucasian allotype), SEQ ID NO: 173 (IgG1, afroamerican allotype), SEQ ID NO: 174 (IgG2), SEQ ID NO: 175 (IgG3) and SEQ ID NO:176 (IgG4).

The term "variant (human) Fc domain" denotes an amino acid sequence which differs from that of a "wild-type" (human) Fc domain amino acid sequence by virtue of at least one "amino acid mutation". In one aspect, the variant Fc-region has at least one amino acid mutation compared to a native Fc-region, e.g. from about one to about ten amino acid mutations, and in one aspect from about one to about five amino acid mutations in a native Fc-region. In one aspect, the (variant) Fc-region has at least about 95% homology with a wild-type Fc-region.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by 103-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "ADCC" or "antibody-dependent cellular cytotoxicity" is an immune mechanism leading to lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example, the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831). For example, the capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In particular, binding to FcγR on NK cells is measured.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (SEQ ID NO:177, UNIPROT® accession no. P08637, version 141).

An "ectodomain" is the domain of a membrane protein that extends into the extracellular space (i.e. the space outside the target cell). Ectodomains are usually the parts of proteins that initiate contact with surfaces, which leads to signal transduction.

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$ (SEQ ID NO:213), $(SG_4)_n$ (SEQ ID NO:214) or $G_4(SG_4)_n$ (SEQ ID NO:215) peptide linkers, wherein "n" is generally a number between 1 and 5, typically between 2 and 4, in particular 2, i.e. the peptides selected from the group consisting of GGGGS (SEQ ID NO:178) GGGGSGGGGS (SEQ ID NO:179), SGGGGSGGGG (SEQ ID NO:180) and GGGGSGGGGSGGGG (SEQ ID NO:183), but also include the sequences GSPGSSSSGS (SEQ ID NO:182), (G4S) 3 (SEQ ID NO:183), (G4S) 4 (SEQ ID NO: 184), GSGSGSGS (SEQ ID NO:185), GSGSGNGS (SEQ ID NO:186), GGSGSGSG (SEQ ID NO:187), GGSGSG (SEQ ID NO:188), GGSG (SEQ ID NO:189), GGSGNGSG (SEQ ID NO: 190), GGNGSGSG (SEQ ID NO:191) and GGNGSG (SEQ ID NO:192). Peptide linkers of particular interest are (G4S) (SEQ ID NO:178), (G4S) 2 or GGGGSGGGGS (SEQ ID NO:179), (G4S) 3 (SEQ ID NO:183) and (G4S) 4 (SEQ ID NO:184). A particular group of peptide linkers are the protease cleavable linkers described herein.

The term "amino acid" as used within this application denotes the group of naturally occurring carboxy a-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a polypeptide and an ectodomain of said TNF ligand family member) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or MEGALIGN® (DNASTAR®) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX® operating system, including digital UNIX® V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the CD28 antigen binding molecules provided herein are contemplated. For example, it may be desirable to improve the binding affinity and/or other biological properties of the CD28 antigen binding molecules.

Amino acid sequence variants of the CD28 antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |

TABLE A-continued

| Original Residue | Exemplary Substitutions | Preferred Substitutions |
|---|---|---|
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of insertions include CD28 antigen binding molecules with a fusion to the N- or C-terminus to a polypeptide which increases the serum half-life of the CD28 antigen binding molecules.

In certain embodiments, the CD28 antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the agonistic ICOS-binding molecule comprises an Fc domain, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in agonistic ICOS-binding molecules may be made in order to create variants with certain improved properties. In one aspect, variants of agonistic ICOS-binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the CD28 antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the CD28 antigen binding molecules of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the CD28 antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the CD28 antigen binding molecules provided herein maybe obtained. An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al. (2017) Nature Medicine 23:815-817, or EP 2 101 823 B1).

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

In some embodiments, the molecules of the invention are used to delay development of a disease or to slow the progression of a disease.

The term "combination treatment" or "co-administration" as noted herein encompasses combined administration (where two or more therapeutic agents are included in the same or separate formulations), and separate administration, in which case, administration of an antibody as reported herein can occur prior to, simultaneously, and/or following, administration of the additional therapeutic agent or agents, preferably an antibody or antibodies.

The term "cancer" refers to or describes the physiological condition in mammals that is typically characterized by unregulated cell growth/proliferation. Thus, the term cancer as used herein refers to proliferative diseases, such as carcinoma, lymphomas (e.g., Hodgkin's and non-Hodgkin's lymphoma), blastoma, sarcoma, and leukemia. In particular, the term cancer includes lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers. In one aspect, the cancer is a solid tumor. In another aspect, the cancer is a haematological cancer, particularly leukemia, most particularly acute lymphoblastic leukemia (ALL) or acute myelogenous leukemia (AML).

Bispecific Agonistic CD28 Antigen Binding Molecules of the Invention

The invention provides novel bispecific agonistic CD28 antigen binding molecules with particularly advantageous properties such as producibility, stability, binding affinity, biological activity, targeting efficiency, reduced toxicity, an extended dosage range that can be given to a patient and thereby a possibly enhanced efficacy. The novel bispecific agonistic CD28 antigen binding molecules comprise an Fc domain composed of a first and a second subunit capable of stable association comprising one or more amino acid substitution that reduces the binding affinity of the antigen binding molecule to an Fc receptor and/or effector function (Fc silent) and thus unspecific cross-linking via Fc receptors is avoided. Instead, they comprise at least one antigen binding domain capable of specific binding to CD3 which causes cross-linking at the tumor site. Thus, tumor-specific T cell activation is achieved. In one particular aspect, provided are bispecific agonistic CD28 antigen binding molecules with a masked CD3 antigen binding domain. Masking the CD3 binder with an anti-idiotypic CD3 scFv N-terminally linked to the HC of the CD3 binder by a linker containing a protease site is aimed to reduce potential toxicity. The protease is active in the tumor microenvironment causing a cleavage of the protease site in the linker thereby recovering the CD3 binding. CD3 binding will thus be possible in the presence of tumor cells but not in healthy tissue.

Herein provided is a bispecific agonistic CD28 antigen binding molecule with monovalent binding to CD28, comprising (a) a first antigen binding domain capable of specific binding to CD28, (b) a second antigen binding domain capable of specific binding to CD3, and (c) a Fc domain composed of a first and a second subunit capable of stable association comprising one or more amino acid substitution that reduces the binding affinity of the antigen binding molecule to an Fc receptor and/or effector function, wherein said second antigen binding domain capable of specific binding to CD3 comprises (i) a heavy chain variable region ($V_H$CD3) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$CD3) comprising a light chain complementary determining region CDR-L1 of SEQ ID NO: 5, a CDR-L2 of SEQ ID NO: 6 and a CDR-L3 of SEQ ID NO: 7; or (ii) a heavy chain variable region ($V_H$CD3) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$CD3) comprising a light chain complementary determining region CDR-L1 of SEQ ID NO: 13, a CDR-L2 of SEQ ID NO: 14 and a CDR-L3 of SEQ ID NO: 15.

In one aspect, a bispecific agonistic CD28 antigen binding molecule as defined herein before is provided, wherein the Fc domain is an IgG, particularly an IgG1 Fc domain or an IgG4 Fc domain. In one particular aspect, the Fc domain composed of a first and a second subunit capable of stable association is an IgG1 Fc domain. The Fc domain comprises one or more amino acid substitution that reduces the binding affinity of the antigen binding molecule to an Fc receptor and/or reduces or abolishes effector function. In one aspect, the Fc domain comprises the amino acid substitutions L234A and L235A (numbering according to Kabat EU index). In one aspect, the Fc domain is of human IgG1 subclass and comprises the amino acid mutations L234A, L235A and P329G (numbering according to Kabat EU index). In one aspect, a bispecific agonistic CD28 antigen binding molecule is provided, wherein the antigen binding molecule comprises an Fc domain composed of a first and a second subunit capable of stable association, wherein the first subunit comprises the amino acid sequence of SEQ ID NO:96 (Fc hole PGLALA) and the second subunit comprise the amino acid sequence of SEQ ID NO:95 (Fc knob PGLALA).

In one aspect, provided is a bispecific agonistic CD28 antigen binding molecule as defined herein before, wherein the first antigen binding domain capable of specific binding to CD28 comprises (i) a heavy chain variable region ($V_H$CD28) comprising a heavy chain complementary determining region CDR-H1 of SEQ ID NO: 26, a CDR-H2 of SEQ ID NO: 27, and a CDR-H3 of SEQ ID NO: 28, and a light chain variable region ($V_L$CD28) comprising a light chain complementary determining region CDR-L1 of SEQ ID NO: 29, a CDR-L2 of SEQ ID NO: 30 and a CDR-L3 of SEQ ID NO: 31; or (ii) a heavy chain variable region ($V_H$CD28) comprising a CDR-H1 of SEQ ID NO: 18, a CDR-H2 of SEQ ID NO: 19, and a CDR-H3 of SEQ ID NO: 20, and a light chain variable region ($V_L$CD28) comprising a CDR-L1 of SEQ ID NO: 21, a CDR-L2 of SEQ ID NO: 22 and a CDR-L3 of SEQ ID NO: 23.

In one aspect, the antigen binding domain capable of specific binding to CD28 of the bispecific agonistic CD28 antigen binding molecule comprises a heavy chain variable region ($V_H$CD28) comprising a CDR-H1 of SEQ ID NO: 26, a CDR-H2 of SEQ ID NO: 27, and a CDR-H3 of SEQ ID NO: 28, and a light chain variable region ($V_L$CD28) comprising a CDR-L1 of SEQ ID NO: 29, a CDR-L2 of SEQ ID NO: 30 and a CDR-L3 of SEQ ID NO: 31.

In another aspect, the antigen binding domain capable of specific binding to CD28 of the bispecific agonistic CD28 antigen binding molecule comprises a heavy chain variable region ($V_H$CD28) comprising a CDR-H1 of SEQ ID NO: 18, a CDR-H2 of SEQ ID NO: 19, and a CDR-H3 of SEQ ID NO: 20, and a light chain variable region ($V_L$CD28) comprising a CDR-L1 of SEQ ID NO: 21, a CDR-L2 of SEQ ID NO: 22 and a CDR-L3 of SEQ ID NO: 23.

Furthermore, provided is a bispecific agonistic CD28 antigen binding molecule as defined herein before, wherein the antigen binding domain capable of specific binding to CD28 comprises a heavy chain variable region ($V_H$CD28) comprising an amino acid sequence that is at least about 95%, 96%, 97%, 98%, 99% or 100% identical to the amino acid sequence of SEQ ID NO: 24, and a light chain variable region ($V_L$CD28) comprising an amino acid sequence that is at least about 95%, 96%, 97%, 98%, 99% or 100% identical to the amino acid sequence of SEQ ID NO: 25. In one aspect, the first antigen binding domain capable of specific binding to CD28 comprises a heavy chain variable region ($V_H$CD28) comprising an amino acid sequence selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40 and SEQ ID NO: 41, and a light chain variable region ($V_L$CD28) comprising an amino acid sequence selected from the group consisting of SEQ ID NO:25, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO: 50 and SEQ ID NO:51.

In another aspect, provided is bispecific agonistic CD28 antigen binding molecule, wherein the first antigen binding domain capable of specific binding to CD28 comprises (a) a heavy chain variable region ($V_H$CD28) comprising the amino acid sequence of SEQ ID NO: 37 and a light chain variable region ($V_L$CD28) comprising the amino acid sequence of SEQ ID NO:44, or (b) a heavy chain variable region ($V_H$CD28) comprising the amino acid sequence of SEQ ID NO: 37 and a light chain variable region ($V_L$CD28) comprising the amino acid sequence of SEQ ID NO:25, or (c) a heavy chain variable region ($V_H$CD28) comprising the amino acid sequence of SEQ ID NO: 41 and a light chain variable region ($V_L$CD28) comprising the amino acid sequence of SEQ ID NO:51, or (d) a heavy chain variable region ($V_H$CD28) comprising the amino acid sequence of SEQ ID NO: 36 and a light chain variable region ($V_L$CD28) comprising the amino acid sequence of SEQ ID NO:43, or (e) a heavy chain variable region ($V_H$CD28) comprising the amino acid sequence of SEQ ID NO: 36 and a light chain variable region ($V_L$CD28) comprising the amino acid sequence of SEQ ID NO:44, or (f) a heavy chain variable region ($V_H$CD28) comprising the amino acid sequence of SEQ ID NO: 36 and a light chain variable region ($V_L$CD28) comprising the amino acid sequence of SEQ ID NO:49, or (g) a heavy chain variable region ($V_H$CD28) comprising the amino acid sequence of SEQ ID NO: 36 and a light chain variable region ($V_L$CD28) comprising the amino acid sequence of SEQ ID NO:25, or (h) a heavy chain variable region ($V_H$CD28) comprising the amino acid sequence of SEQ ID NO: 33 and a light chain variable region ($V_L$CD28) comprising the amino acid sequence of SEQ ID NO:25, or (i) a heavy chain variable region ($V_H$CD28) comprising the amino acid sequence of SEQ ID NO: 32 and a light chain variable region ($V_L$CD28) comprising the amino acid sequence of SEQ ID NO:43, or (j) a heavy chain variable region ($V_H$CD28) comprising the amino acid sequence of SEQ ID NO: 32 and a light chain variable region ($V_L$CD28) comprising the amino acid sequence of SEQ ID NO:49, or (k) a heavy chain variable region ($V_H$CD28) comprising the amino acid sequence of SEQ ID NO: 32 and a light chain variable region ($V_L$CD28) comprising the amino acid sequence of SEQ ID NO:25.

In one aspect, provided is a bispecific agonistic CD28 antigen binding molecule, wherein the first antigen binding domain capable of specific binding to CD28 comprises the CDRs of the heavy chain variable region ($V_H$CD28) comprising the amino acid sequence of SEQ ID NO:37 and the CDRs of the light chain variable region ($V_L$CD28) comprising the amino acid sequence of SEQ ID NO:44. In another aspect, the first antigen binding domain capable of specific binding to CD28 of the bispecific agonistic CD28 antigen binding molecule comprises a heavy chain variable region ($V_H$CD28) comprising a CDR-H1 of SEQ ID NO: 52, a CDR-H2 of SEQ ID NO: 53, and a CDR-H3 of SEQ ID NO: 54, and a light chain variable region ($V_L$CD28) comprising a CDR-L1 of SEQ ID NO: 55, a CDR-L2 of SEQ ID NO: 56 and a CDR-L3 of SEQ ID NO: 57.

In another aspect, provided is a bispecific agonistic CD28 antigen binding molecule, wherein the antigen binding domain capable of specific binding to CD28 comprises the CDRs of the heavy chain variable region ($V_H$CD28) comprising the amino acid sequence of SEQ ID NO: 36 and the CDRs of the light chain variable region ($V_L$CD28) comprising the amino acid sequence of SEQ ID NO:43. In another aspect, the antigen binding domain capable of specific binding to CD28 of the bispecific agonistic CD28 antigen binding molecule comprises a heavy chain variable region ($V_H$CD28) comprising a CDR-H1 of SEQ ID NO: 58, a CDR-H2 of SEQ ID NO: 59, and a CDR-H3 of SEQ ID NO: 60, and a light chain variable region ($V_L$CD28) comprising a CDR-L1 of SEQ ID NO: 61, a CDR-L2 of SEQ ID NO: 62 and a CDR-L3 of SEQ ID NO: 63.

In another aspect, provided is a bispecific agonistic CD28 antigen binding molecule, wherein the antigen binding domain capable of specific binding to CD28 comprises the CDRs of the heavy chain variable region ($V_H$CD28) comprising the amino acid sequence of SEQ ID NO: 32 and the CDRs of the light chain variable region ($V_L$CD28) comprising the amino acid sequence of SEQ ID NO:25. In another aspect, the antigen binding domain capable of specific binding to CD28 of the bispecific agonistic CD28 antigen binding molecule comprises a heavy chain variable region ($V_H$CD28) comprising a CDR-H1 of SEQ ID NO: 64, a CDR-H2 of SEQ ID NO: 65, and a CDR-H3 of SEQ ID NO: 66, and a light chain variable region ($V_L$CD28) comprising a CDR-L1 of SEQ ID NO: 67, a CDR-L2 of SEQ ID NO: 68 and a CDR-L3 of SEQ ID NO: 69.

In one aspect, a bispecific agonistic CD28 antigen binding molecule is provided, wherein the antigen binding domain capable of specific binding to CD28 binds to CD28 with an reduced affinity compared to an antigen binding domain comprising a heavy chain variable region ($V_H$CD28) comprising the amino acid sequence of SEQ ID NO:24 and a light chain variable region ($V_L$CD28) comprising the amino acid sequence of SEQ ID NO:25. The affinity is measured by flow cytometry as binding to CHO cells expressing CD28. In one aspect, the antigen binding domain capable of specific binding to CD28 binds to CD28 with an reduced affinity compared to an antigen binding domain comprising a heavy chain variable region ($V_H$CD28) comprising the amino acid sequence of SEQ ID NO:24 and a light chain variable region ($V_L$CD28) comprising the amino acid sequence of SEQ ID NO:25 and comprises the CDR-H1, CDR-H2 and CDR-H3 of the heavy chain variable region ($V_H$CD28) comprising the amino acid sequence of SEQ ID NO:37 and the CDR-L1, CDR-L2 and CDR-L3 of the light chain variable region ($V_L$CD28) comprising the amino acid sequence of SEQ ID NO:44. In one aspect, the antigen binding domain capable of specific binding to CD28 with reduced affinity compared to an antigen binding domain comprising a heavy chain variable region ($V_H$CD28) comprising the amino acid sequence of SEQ ID NO:24 and a light chain variable region ($V_L$CD28) comprising the amino acid sequence of SEQ ID NO:25 comprises a heavy chain variable region ($V_H$CD28) comprising an amino acid sequence that is at least about 95%, 96%, 97%, 98%, 99% or 100% identical to the amino acid sequence of SEQ ID NO:37, and a light chain variable region ($V_L$CD28) comprising an amino acid sequence that is at least about 95%, 96%, 97%, 98%, 99% or 100% identical to the amino acid sequence of SEQ ID NO:44.

In one particular aspect, a bispecific agonistic CD28 antigen binding molecule is provided, wherein the antigen binding domain capable of specific binding to CD28 comprises a heavy chain variable region ($V_H$CD28) comprising the amino acid sequence of SEQ ID NO:37 and a light chain variable region ($V_L$CD28) comprising the amino acid sequence of SEQ ID NO:44.

In another particular aspect, a bispecific agonistic CD28 antigen binding molecule is provided, wherein the antigen binding domain capable of specific binding to CD28 comprises a heavy chain variable region ($V_H$CD28) comprising the amino acid sequence of SEQ ID NO:36 and a light chain variable region ($V_L$CD28) comprising the amino acid sequence of SEQ ID NO: 43.

In further particular aspect, a bispecific agonistic CD28 antigen binding molecule is provided, wherein the antigen binding domain capable of specific binding to CD28 comprises a heavy chain variable region ($V_H$CD28) comprising the amino acid sequence of SEQ ID NO:32 and a light chain variable region ($V_L$CD28) comprising the amino acid sequence of SEQ ID NO: 25.

CD3-Targeting Bispecific Agonistic CD28 Antigen Binding Molecules

A bispecific agonistic CD28 antigen binding molecule is provided herein, wherein the antigen binding domain capable of specific binding to a tumor-associated antigen is an antigen binding domain capable of specific binding to CD3.

In one aspect, provided is a bispecific agonistic CD28 antigen binding molecule as described herein, wherein the antigen binding domain capable of specific binding to CD3 comprises a heavy chain variable region ($V_H$CD3) comprising a CDR-H1 comprising the amino acid sequence of SEQ ID NO:2, a CDR-H2 comprising the amino acid sequence of SEQ ID NO: 3, and a CDR-H3 comprising the amino acid sequence of SEQ ID NO:4, and a light chain variable region ($V_L$CD3) comprising a CDR-L1 comprising the amino acid sequence of SEQ ID NO: 5, a CDR-L2 comprising the amino acid sequence of SEQ ID NO:6, and a CDR-L3 comprising the amino acid sequence of SEQ ID NO:7. In one aspect, the antigen binding domain capable of specific binding to CD3 comprises the CDRs of the heavy chain variable region ($V_H$CD3) comprising the amino acid sequence of SEQ ID NO:8 and the CDRs of the light chain variable region ($V_L$CD3) comprising the amino acid sequence of SEQ ID NO:9. In one aspect, a bispecific agonistic CD28 antigen binding molecule is provided, wherein the antigen binding domain capable of specific binding to CD3 comprises a heavy chain variable region ($V_H$CD3) comprising an amino acid sequence that is at least about 95%, 96%, 97%, 98%, 99% or 100% identical to the amino acid sequence of SEQ ID NO:8, and a light chain variable region ($V_L$CD3) comprising an amino acid sequence that is at least about 95%, 96%, 97%, 98%, 99% or 100% identical to the amino acid sequence of SEQ ID NO:9. Particularly, the antigen binding domain capable of specific binding to CD3 comprises a heavy chain variable region ($V_H$CD3) comprising the amino acid sequence of SEQ ID NO:8 and a light chain variable region ($V_L$CD3) comprising the amino acid sequence of SEQ ID NO:9.

In another aspect, provided is a bispecific agonistic CD28 antigen binding molecule as described herein, wherein the antigen binding domain capable of specific binding to CD3 comprises a heavy chain variable region ($V_H$CD3) comprising a CDR-H1 comprising the amino acid sequence of SEQ ID NO:10, a CDR-H2 comprising the amino acid sequence of SEQ ID NO: 11, and a CDR-H3 comprising the amino acid sequence of SEQ ID NO:12, and a light chain variable region ($V_L$CD3) comprising a CDR-L1 comprising the amino acid sequence of SEQ ID NO: 13, a CDR-L2 comprising the amino acid sequence of SEQ ID NO:14, and a CDR-L3 comprising the amino acid sequence of SEQ ID NO:15. In one aspect, the antigen binding domain capable of specific binding to CD3 comprises the CDRs of the heavy chain variable region ($V_H$CD3) comprising the amino acid sequence of SEQ ID NO:16 and the CDRs of the light chain variable region ($V_L$CD3) comprising the amino acid sequence of SEQ ID NO:17. In one aspect, a bispecific agonistic CD28 antigen binding molecule is provided, wherein the antigen binding domain capable of specific binding to CD3 comprises a heavy chain variable region ($V_H$CD3) comprising an amino acid sequence that is at least about 95%, 96%, 97%, 98%, 99% or 100% identical to the amino acid sequence of SEQ ID NO:16, and a light chain variable region ($V_L$CD3) comprising an amino acid sequence that is at least about 95%, 96%, 97%, 98%, 99% or 100% identical to the amino acid sequence of SEQ ID NO:17. Particularly, the antigen binding domain capable of specific binding to CD3 comprises a heavy chain variable region ($V_H$CD3) comprising the amino acid sequence of SEQ ID NO:16 and a light chain variable region ($V_L$CD3) comprising the amino acid sequence of SEQ ID NO:17.

Bispecific Agonistic CD28 Antigen Binding Molecules Monovalent for Binding to CD28 and Monovalent for Binding to CD3 (1+1 Format)

In one aspect, a bispecific agonistic CD28 antigen binding molecule is provided, wherein the first antigen binding domain capable of specific binding to CD28 and/or the second antigen binding domain capable of specific binding to CD3 is a Fab fragment. In one particular aspect, both the first antigen binding domain capable of specific binding to CD28 and the second antigen binding domain capable of specific binding to CD3 are Fab fragments.

In one aspect, provided is a bispecific agonistic CD28 antigen binding molecule as described herein, comprising (a) a crossFab fragment capable of specific binding to CD28, (b) a conventional Fab fragment capable of specific binding to CD3, and (c) a Fc domain composed of a first and a second subunit capable of stable association comprising one or more amino acid substitution that reduces the binding affinity of the antigen binding molecule to an Fc receptor and/or effector function. In another aspect, provided is a bispecific agonistic CD28 antigen binding molecule as described herein, comprising (a) a conventional Fab fragment capable of specific binding to CD28, (b) a crossFab fragment capable of specific binding to CD3, and (c) a Fc domain composed of a first and a second subunit capable of stable association comprising one or more amino acid substitution that reduces the binding affinity of the antigen binding molecule to an Fc receptor and/or effector function.

In one aspect, provided is a bispecific agonistic CD28 antigen binding molecule as described herein, wherein the first antigen binding domain capable of specific binding to CD28 is a Fab fragment wherein the variable domains VL and VH or the constant domains CL and CH1, particularly the variable domains VL and VH, of the Fab light chain and the Fab heavy chain are replaced by each other (crossfab fragment). In one aspect, the first antigen binding domain capable of specific binding to CD28 is a Fab fragment wherein the variable domains VL and VH or the constant domains CL and CH1, particularly the variable domains VL and VH, of the Fab light chain and the Fab heavy chain are replaced by each other and the second antigen binding domain capable of specific binding to CD3 is a conventional Fab fragment. In one aspect, the second antigen binding domain capable of specific binding to CD3 is a Fab fragment wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In one particular aspect, provided is a bispecific agonistic CD28 antigen binding molecule comprising a first light chain comprising the amino acid sequence of SEQ ID NO:102, a first heavy chain comprising the amino acid sequence of SEQ ID NO:101, a second heavy chain comprising the amino acid sequence of SEQ ID NO:103 and a second light chain comprising the amino acid sequence of SEQ ID NO:104 (Molecule 10).

In one aspect, provided is a bispecific agonistic CD28 antigen binding molecule as described herein, wherein the second antigen binding domain capable of specific binding to CD3 is a Fab fragment and wherein the variable domains VL and VH or the constant domains CL and CH1, particularly the variable domains CL and CH1, of the Fab light chain and the Fab heavy chain are replaced by each other (crossfab fragment). In one aspect, the second antigen binding domain capable of specific binding to CD3 is a Fab fragment wherein the variable domains VL and VH or the constant domains CL and CH1, particularly the variable domains CL and CH1, of the Fab light chain and the Fab heavy chain are replaced by each other and the first antigen binding domain capable of specific binding to CD28 is a conventional Fab fragment. In one aspect, the antigen binding domain capable of specific binding to CD28 is a Fab fragment wherein in the constant domain CL the amino acid at position 123 (numbering according to Kabat EU index) is substituted by an amino acid selected from lysine (K), arginine (R) or histidine (H) and the amino acid at position 124 (numbering according to Kabat EU index) is substituted independently by lysine (K), arginine (R) or histidine (H), and wherein in the constant domain CH1 the amino acid at position 147 (numbering according to Kabat EU index) is substituted independently by glutamic acid (E) or aspartic acid (D) and the amino acid at position 213 (numbering according to Kabat EU index) is substituted independently by glutamic acid (E), or aspartic acid (D) (numbering according to Kabat EU index).

In one particular aspect, provided is a bispecific agonistic CD28 antigen binding molecule comprising a first light chain comprising the amino acid sequence of SEQ ID NO:90, a first heavy chain comprising the amino acid sequence of SEQ ID NO:89, a second heavy chain comprising the amino acid sequence of SEQ ID NO:91 and a second light chain comprising the amino acid sequence of SEQ ID NO:92 (Molecule 1).

In one particular aspect, provided is a bispecific agonistic CD28 antigen binding molecule comprising a first light chain comprising the amino acid sequence of SEQ ID NO:90, a first heavy chain comprising the amino acid sequence of SEQ ID NO:89, a second heavy chain comprising the amino acid sequence of SEQ ID NO:93 and a second light chain comprising the amino acid sequence of SEQ ID NO:94 (Molecule 2).

In another particular aspect, provided is a bispecific agonistic CD28 antigen binding molecule comprising a first light chain comprising the amino acid sequence of SEQ ID NO:102, a first heavy chain comprising the amino acid sequence of SEQ ID NO:101, a second heavy chain comprising the amino acid sequence of SEQ ID NO:103 and a second light chain comprising the amino acid sequence of SEQ ID NO:104 (Molecule 10).

Fc Domain Modifications Reducing Fc Receptor Binding and/or Effector Function

The Fc domain of the bispecific agonistic CD28 antigen binding molecule of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. The Fc domain confers favorable pharmacokinetic properties to the antigen binding molecules of the invention, including a long serum half-life which contributes to good accumulation in the target tissue and a favorable tissue-blood distribution ratio. On the other side, it may, however, lead to undesirable targeting of the bispecific antibodies of the invention to cells expressing Fc receptors rather than to the preferred antigen-bearing cells.

Accordingly, the Fc domain of the bispecific agonistic CD28 antigen binding molecule of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In one particular aspect, the invention provides an antigen binding molecule, wherein the Fc region comprises one or more amino acid substitution that reduces binding to an Fc receptor, in particular towards Fcγ receptor. In one aspect, the invention provides an antibody, wherein the Fc region comprises one or more amino acid substitution and wherein the ADCC induced by the antibody is reduced to 0-20% of the ADCC induced by an antibody comprising the wild-type human IgG1 Fc region.

In one aspect, the Fc domain of the antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antigen binding molecule according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIACORE™ instrument (GE Healthcare), and Fc receptors such as may be obtained by recombinant expression. Alternatively, binding affinity of Fc domains or cell activating antibodies comprising an Fc domain for Fc receptors may be evaluated using cell lines known to express particular Fc receptors, such as human NK cells expressing FcγIIIa receptor.

Effector function of an Fc domain, or antigen binding molecules of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998).

In some aspects, binding of the Fc domain to a complement component, specifically to C1q, is reduced. Accordingly, in some aspects wherein the Fc domain is engineered to have reduced effector function, said reduced effector function includes reduced CDC. Clq binding assays may be carried out to determine whether the bispecific antibodies of the invention are able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In one particular aspect, the Fc domain exhibiting reduced binding affinity to an Fc receptor and/or reduced effector function, as compared to a native IgG1 Fc domain, is a human IgG1 Fc domain comprising the amino acid substitutions L234A, L235A and optionally P329G, or a human IgG4 Fc domain comprising the amino acid substitutions S228P, L235E and optionally P329G (numberings according to Kabat EU index). More particularly, it is a human IgG1 Fc domain comprising the amino acid substitutions L234A, L235A and P329G (numbering according to Kabat EU index).

Fc Domain Modifications Promoting Heterodimerization

The bispecific agonistic CD28 antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antigen binding molecules of the invention in recombinant production, it will thus be advantageous to introduce in the Fc domain of the bispecific antigen binding molecules of the invention a modification promoting the association of the desired polypeptides.

Accordingly, in particular aspects the invention relates to the bispecific agonistic CD28 antigen binding molecule with monovalent binding to CD28 comprising (a) one antigen binding domain capable of specific binding to CD28, (b) at least one antigen binding domain capable of specific binding to CD3, and (c) a Fc domain composed of a first and a second subunit capable of stable association comprising one or more amino acid substitution that reduces the binding affinity of the antigen binding molecule to an Fc receptor and/or effector function, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to the bispecific agonistic CD28 antigen binding molecule with monovalent binding to CD28 comprising (a) one antigen binding domain capable of specific binding to CD28, (b) at least one antigen binding domain capable of specific binding to a tumor-associated antigen, and (c) a Fc domain composed of a first and a second subunit capable of stable association comprising one or more amino acid substitution that reduces the binding affinity of the antigen binding molecule to an Fc receptor and/or effector function, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

The C-terminus of the heavy chain of the bispecific agonistic CD28 antigen binding molecule as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending P. In one preferred aspect, the C-terminus of the heavy chain is a shortened C-terminus ending PG. In one aspect of all aspects as reported herein, a CD28 antigen binding molecule comprising a heavy chain including a C-terminal CH3 domain as specified herein, comprises the C-terminal glycine-lysine dipeptide (G446 and K447, numbering according to Kabat EU index). In one aspect of all aspects as reported herein, a CD28 antigen binding molecule comprising a heavy chain including a C-terminal CH3 domain, as specified herein, comprises a C-terminal glycine residue (G446, numbering according to Kabat EU index).

Modifications in the Fab domains

In one aspect, the invention relates to a bispecific agonistic CD28 antigen binding molecule characterized by monovalent binding to CD28 comprising (a) a first antigen binding domain capable of specific binding to CD28, (b) a second antigen binding domain capable of specific binding to CD3, and (c) a Fc domain composed of a first and a second subunit capable of stable association comprising one or more amino acid substitution that reduces the binding affinity of the antigen binding molecule to an Fc receptor and/or effector function, wherein the second antigen binding domain capable of specific binding to CD3 is a Fab fragment and in the Fab fragment either the variable domains VH and VL or the constant domains CH1 and CL are exchanged according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific agonistic CD28 antigen binding molecule characterized by monovalent binding to CD28 comprising (a) a first antigen binding domain capable of specific binding to CD28, (b) a second antigen binding domain capable of specific binding to CD3, and (c) a Fc domain composed of a first and a second subunit capable of stable association comprising one or more amino acid substitution that reduces the binding affinity of the antigen binding molecule to an Fc receptor and/or effector function, wherein in the Fab fragment capable of specific binding to CD28 the variable domains VL and VH are replaced by each other so that the VH domain is part of the light chain and the VL domain is part of the heavy chain.

In another aspect, and to further improve correct pairing, the bispecific agonistic CD28 antigen binding molecule characterized by monovalent binding to CD28 comprising (a) a first antigen binding domain capable of specific binding to CD28, (b) a second antigen binding domains capable of specific binding to a CD3, and (c) a Fc domain composed of a first and a second subunit capable of stable association comprising one or more amino acid substitution that reduces the binding affinity of the antigen binding molecule to an Fc receptor and/or effector function, can contain different charged amino acid substitutions (so-called "charged residues"). These modifications are introduced in the crossed or non-crossed CH1 and CL domains. In a particular aspect, the invention relates to a bispecific agonistic CD28 antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E). In one particular aspect, in the CL domain of the Fab fragment capable of specific binding to CD28 the amino acid at position 123 (EU numbering) has been replaced by arginine (R) and the amino acid at position 124 (EU numbering) has been substituted by lysine (K) and in the CH1 domain of the Fab fragment capable of specific binding to CD28 the amino acids at position 147 (EU numbering) and at position 213 (EU numbering) have been substituted by glutamic acid (E).

Protease Activatable Bispecific Agonistic CD28 Antigen Binding Molecules

In another aspect, provided is a bispecific agonistic CD28 antigen binding molecule characterized by monovalent binding to CD28, comprising (a) a first antigen binding domain capable of specific binding to CD28, (b) a second antigen binding domain capable of specific binding to CD3, (c) a Fc domain composed of a first and a second subunit capable of stable association comprising one or more amino acid substitution that reduces the binding affinity of the antigen binding molecule to an Fc receptor and/or effector function, wherein said second antigen binding domain capable of specific binding to CD3 comprises (i) a heavy chain variable region ($V_H$CD3) comprising a heavy chain complementary determining region CDR-H1 of SEQ ID NO: 2, a CDR-H2 of SEQ ID NO: 3, and a CDR-H3 of SEQ ID NO: 4, and a light chain variable region ($V_L$CD3) comprising a light chain complementary determining region CDR-L1 of SEQ ID NO: 5, a CDR-L2 of SEQ ID NO: 6 and a CDR-L3 of SEQ ID NO: 7; or (ii) a heavy chain variable region ($V_H$CD3) comprising a heavy chain complementary determining region CDR-H1 of SEQ ID NO: 10, a CDR-H2 of SEQ ID NO: 11, and a CDR-H3 of SEQ ID NO: 12, and a light chain variable region ($V_L$CD3) comprising a light chain complementary determining region CDR-L1 of SEQ ID NO: 13, a CDR-L2 of SEQ ID NO: 14 and a CDR-L3 of SEQ ID NO: 15, and further comprising (d) a masking moiety covalently attached to the bispecific agonistic CD28 antigen binding molecule through a protease-cleavable linker, wherein the masking moiety is capable of binding to the idiotype of the second antigen binding domain capable of specific binding to CD3 thereby reversibly concealing the antigen binding domain capable of specific binding to CD3.

In one aspect, the masking moiety is capable of binding to the idiotype of antigen binding domain capable of specific binding to CD3 thereby reversibly concealing the antigen binding domain. In one aspect, the masking moiety of the protease-activatable bispecific agonistic CD28 antigen binding molecule is covalently attached to the first antigen binding moiety. In one aspect, the masking moiety is covalently attached to the heavy chain variable region of the first antigen binding moiety. In one aspect, the masking moiety is covalently attached to the light chain variable region of the first antigen binding moiety. This covalent bond is separate from the specific binding, which is preferably non-covalent, of the masking moiety to the idiotype first antigen binding site. The idiotype of the first antigen binding moiety comprises its variable region. In one aspect, the masking moiety binds to amino acid residues that make contact with CD3 when the first antigen binding domain is bound to CD3. In a preferred aspect, the masking moiety is not the cognate antigen or fragments thereof of the first antigen binding domain, i.e., the masking moiety is not a CD3 or fragments thereof. In one aspect, the masking moiety is an anti-idiotypic antibody or fragment thereof. In one aspect, the masking moiety is an anti-idiotypic scFv. Exemplary masking moieties which are anti-idiotypic scFv, and protease activatable CD28 antigen binding molecules comprising such masking moieties, are described in detail in the examples.

The components of the protease-activatable bispecific agonistic CD28 antigen binding molecule can be fused to each other in a variety of configurations. In particular aspects, the protease-activatable T cell activating bispecific molecule comprises an Fc domain composed of a first and a second subunit capable of stable association. In some aspects, the first antigen binding domain is fused at the C-terminus of the Fab heavy chain to the N-terminus of the first or the second subunit of the Fc domain and the second antigen binding domain is fused at the C-terminus of the Fab heavy chain to the N-terminus of the other subunit of the Fc domain, respectively. The antigen binding moieties may be fused to the Fc domain directly or through a peptide linker, comprising one or more amino acids, typically about 2-20 amino acids. Peptide linkers are known in the art and are described herein. Suitable, non-immunogenic peptide linkers include, for example, (G4S) n (SEQ ID NO: 213), (SG4) n (SEQ ID NO: 214), or G4 (SG4) n (SEQ ID NO: 215) peptide linkers. "n" is generally a number between 1 and 10, typically between 2 and 4. An exemplary peptide linker suitable for connecting the Fab heavy chains of the first and the second antigen binding moiety is EPKSC (D)-(G4S) 2 (SEQ ID NOs 193 and 194).

Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

Masking moiety The bispecific agonistic CD28 antigen binding molecule of the invention may comprise at least one masking moiety. It has been tried to mask binding of an antibody by capping the binding moiety with a fragment of the antigen recognized by the binding moiety (e.g., WO2013128194). This approach has several limitations. For example, using the antigen allows for less flexibility in reducing the affinity of the binding moiety. This is because the affinity has to be high enough to be reliably masked by the antigen mask. Also, dissociated antigen may potentially bind to and interact with its cognate receptor(s) in vivo and cause undesirable signals to the cell expressing such receptor. In contrast, the approach described herein uses an anti-idiotype antibody or fragment thereof as a mask. Two countervailing considerations for designing an effective masking moiety are 1. effectiveness of the masking and 2. reversibility of the masking. If the affinity is too low, masking would be inefficient. However, if the affinity is too high, the masking process might not be readily reversible. It was not predictable whether a high affinity anti-idiotype mask or a low affinity anti-idiotype mask would work better. As described herein, higher affinity masking moieties performed overall better in masking the antigen binding side and, at the same time, could be effectively removed for activation of the molecule. In one aspect, the anti-idiotype mask has a Kp of 1-8 nM. In one aspect, the anti-idiotype mask has a Kp of 2 nM at 37° C. In one specific embodiment, the masking moiety recognizes the idiotype of the first antigen binding moiety capable of binding to a CD3, e.g., a human CD3. In one specific embodiment, the masking moiety recognizes the idiotype of the second antigen binding moiety capable of binding to a target cell antigen.

In one aspect, the masking moiety masks a CD3 antigen binding domain and comprises (i) a heavy chain variable region (VH) comprising a CDR-H1 amino acid sequence of DYSMN (SEQ ID NO:123), a CDR H2 amino acid sequence selected from the group consisting of WINTETGEPRYTDDFKG (SEQ ID NO:124), WINTETGEPRYTDDFTG (SEQ ID NO:130) and WINTETGEPRYTQGFKG (SEQ ID NO:131), and a CDR H3 amino acid sequence of EGDYDVEDY (SEQ ID NO:125), and a light chain variable region (VL) comprising a light chain complementary determining region CDR-L1 amino acid sequence selected from the group consisting of RASKSVSTSSYSYMH (SEQ ID NO:126) and KSSKSVSTSSYSYMH (SEQ ID NO: 129), a CDR-L2 amino acid sequence of YVSYLES (SEQ ID NO:127) and a CDR-L3 amino acid sequence selected from the group consisting of QHSREFPYT (SEQ ID NO:128) and QQSREFPYT (SEQ ID NO:132); or (ii) a heavy chain variable region (VH) comprising a CDR-H1 amino acid sequence of DYSMN (SEQ ID NO:123), a CDR-H2 amino acid sequence of WINTETGEPRYTDDFKG (SEQ ID NO:124), and a CDR-H3 amino acid sequence of EGDYDVFDY (SEQ ID NO:125), and a light chain variable region (VL) comprising a CDR-L1 amino acid sequence of RASKSVSTSSYSYMH (SEQ ID NO:126), a CDR-L2 amino acid sequence of YVSYLES (SEQ ID NO:127) and a CDR-L3 amino acid sequence of QHSREFPYT (SEQ ID NO:128), or (iii) a heavy chain variable region (VH) comprising a CDR-H1 amino acid sequence of SYGVS (SEQ ID NO:123), a CDR-H2 amino acid sequence of IIWGDGSTNYHSALIS (SEQ ID NO: 124), and a CDR-H3 amino acid sequence of GITTVVDDYYAMDY (SEQ ID NO:125), and a light chain variable region (VL) comprising a CDR-L1 amino acid sequence of KSSKSVSTSSYSYMH (SEQ ID NO:129), a CDR-L2 amino acid sequence of AATFLAD (SEQ ID NO:127) and a CDR-L3 amino acid sequence of QHYYSTPYT (SEQ ID NO:128), or (iv) a heavy chain variable region (VH) comprising a CDR-H1 amino acid sequence of SYGVS (SEQ ID NO:123), a CDR-H2 amino acid sequence of WINTETGEPRYTDDFTG (SEQ ID NO:130), and a CDR- H3 amino acid sequence of GITTVVDDYYAMDY (SEQ ID NO: 125), and a light chain variable region (VL) comprising a CDR-L1 amino acid sequence of KSSKSVSTSSYSYMH (SEQ ID NO:129), a CDR-L2 amino acid sequence of AATFLAD (SEQ ID NO:127) and a CDR-L3 amino acid sequence of QHYYSTPYT (SEQ ID NO:128), or (v) a heavy chain variable region (VH) comprising a CDR-H1 amino acid sequence of SYGVS (SEQ ID NO:123), a CDR-H2 amino acid sequence of WINTETGEPRYTQGFKG (SEQ ID NO:131), and a CDR-H3 amino acid sequence of GITTVVDDYYAMDY (SEQ ID NO: 125), and a light chain variable region (VL) comprising a CDR-L1 amino acid sequence of KSSKSVSTSSYSYMH (SEQ ID NO:129), a CDR-L2 amino acid sequence of AATFLAD (SEQ ID NO:127) and a CDR-L3 amino acid sequence of QHYYSTPYT (SEQ ID NO:128).

In one aspect, the masking moiety masks a CD3 antigen binding domain and comprises a heavy chain variable region sequence that is at least about 95%, 96%, 97%, 98%, 99% or 100% identical to SEQ ID NO: 133 and a light chain variable region sequence that is at least about 95%, 96%, 97%, 98%, 99% or 100% identical to SEQ ID NO: 134, or variants thereof that retain functionality. In one aspect, the masking moiety comprises a heavy chain variable region sequence that is at least about 95%, 96%, 97%, 98%, 99% or 100% identical to SEQ ID NO: 135 and a light chain variable region sequence that is at least about 95%, 96%, 97%, 98%, 99% or 100% identical to SEQ ID NO: 136. In one aspect, the masking moiety comprises a heavy chain variable region sequence that is at least about 95%, 96%, 97%, 98%, 99% or 100% identical to SEQ ID NO: 135 and a light chain variable region sequence that is at least about 95%, 96%, 97%, 98%, 99% or 100% identical to SEQ ID NO: 137. In one aspect, the masking moiety comprises a heavy chain variable region sequence that is at least about 95%, 96%, 97%, 98%, 99% or 100% identical to SEQ ID NO: 138 and a light chain variable region sequence that is at least about 95%, 96%, 97%, 98%, 99% or 100% identical to SEQ ID NO: 137. In one aspect, the masking moiety comprises a heavy chain variable region sequence that is at least about 95%, 96%, 97%, 98%, 99% or 100% identical to SEQ ID NO: 139 and a light chain variable region sequence that is at least about 95%, 96%, 97%, 98%, 99% or 100% identical to SEQ ID NO: 140. In another aspect, the masking moiety comprises a heavy chain variable region sequence that is at least about 95%, 96%, 97%, 98%, 99% or 100% identical to SEQ ID NO: 141 and a light chain variable region sequence that is at least about 95%, 96%, 97%, 98%, 99% or 100% identical to SEQ ID NO: 142.

In one aspect, the masking moiety masks a CD3 binding domain and comprises the amino acid sequence of SEQ ID NO: 143. In another aspect, the masking moiety comprises the amino acid sequence of SEQ ID NO: 144. In yet another aspect, the masking moiety comprises the amino acid sequence of SEQ ID NO: 145. In one further aspect, the masking moiety comprises the amino acid sequence of SEQ ID NO: 146.

In another aspect, the masking moiety masks a CD3 antigen binding domain and comprises a heavy chain variable region (VH) comprising a CDR-H1 amino acid sequence of SYGVS (SEQ ID NO: 115), a CDR-H2 amino acid sequence of IIWGDGSTNYHSALIS (SEQ ID NO:116), and a CDR-H3 amino acid sequence of GITVVDDYYAMDY (SEQ ID NO:117), and a light chain variable region (VL) comprising a CDR-L1 amino acid sequence of RASENIDSYLA (SEQ ID NO:118), a CDR-L2 amino acid sequence of AATFLAD (SEQ ID NO:119) and a CDR-L3 amino acid sequence of QHYYSTPYT (SEQ ID NO:120).

In one aspect, the masking moiety masks a CD3 antigen binding domain and comprises a heavy chain variable region sequence that is at least about 95%, 96%, 97%, 98%, 99% or 100% identical to SEQ ID NO: 121 and a light chain variable region sequence that is at least about 95%, 96%, 97%, 98%, 99% or 100% identical to SEQ ID NO: 122, or variants thereof that retain functionality. In one aspect, the masking moiety masks a CD3 antigen binding domain and comprises a heavy chain variable region sequence of SEQ ID NO: 121 and a light chain variable region sequence of SEQ ID NO: 122. In one aspect, the masking moiety comprises the amino acid sequence of SEQ ID NO: 147.

In one particular aspect, the masking moiety is humanized. In one aspect, the idiotype-specific polypeptide for reversibly concealing an anti-CD3 antigen binding domain of a molecule is humanized. Methods to humanize immunoglobulins are well known in the art and herein described.

In one aspect, the masking moiety masks a CD3 antigen binding domain and comprises a heavy chain variable region sequence that is at least about 95%, 96%, 97%, 98%, 99% or 100% identical to SEQ ID NO: 133 and a light chain variable region sequence that is at least about 95%, 96%, 97%, 98%, 99% or 100% identical to SEQ ID NO: 134, or variants thereof that retain functionality. In one aspect, the masking moiety masks a CD3 antigen binding domain and comprises a heavy chain variable region sequence comprising the amino acid sequence of SEQ ID NO: 133 and a light chain variable region sequence comprising the amino acid sequence of SEQ ID NO: 134, or variants thereof that retain functionality. In one aspect, the masking moiety comprises the amino acid sequence of SEQ ID NO: 212.

In one particular aspect, the masking moiety is humanized. In one aspect, the idiotype-specific polypeptide for reversibly concealing an anti-CD3 antigen binding domain of a molecule is humanized. Methods to humanize immunoglobulins are well known in the art and herein described.

Linkers

In one aspect, provided is a bispecific agonistic CD28 antigen binding molecule comprising a masking moiety covalently attached to the bispecific agonistic CD28 antigen binding molecule through a protease-cleavable linker, wherein the masking moiety is capable of binding to the idiotype of the second antigen binding domain capable of specific binding to CD3 thereby reversibly concealing the antigen binding domain capable of specific binding to CD3. In one aspect, the masking moiety is covalently attached to the heavy chain variable region ($V_H$CD3) of the second antigen binding domain capable of specific binding to CD3. In one aspect, the masking moiety is an anti-idiotype scFv.

In one particular aspect, the protease-activatable bispecific agonistic CD28 antigen binding molecule comprises a linker having a protease recognition site comprising a polypeptide sequence that is at least about 95%, 96%, 97%, 98%, 99% or 100% identical to SEQ ID NO: 195, 196, 197, 198, 199, 200, 201, 202, 203, 204, 205, 206, 207, 208, 209, 210 or 211. In one aspect, the protease recognition site comprises the polypeptide sequence of SEQ ID NO: 148, 149, 150, 151, 152, 153, 154, 155, 156, 157, 158, 159, 160, 161 or 162. In a preferred embodiment, the protease recognition site comprises the polypeptide sequence of SEQ ID NO: 162.

In one aspect, the protease capable of cleaving the protease-cleavable linker is selected from the group consisting of a metalloproteinase, e.g., matrix metalloproteinase (MMP) 1-28, A Disintegrin AND Metalloproteinase (ADAM) 2, 7-12, 15, 17-23, 28-30 and 33, a serine protease, e.g., urokinase-type plasminogen activator and matriptase, a cysteine protease, an aspartic protease, and a cathepsin protease. In one specific aspect, the protease is MMP9 or MMP2. In a further specific aspect, the protease is human Matriptase. Matriptase, also called MT-SP1, ST14 (Suppression of tumorigenicity protein 14) or TADG-15 (tumor-associated differentially expressed gene 15 protein) is a trypsin-like serine protease expressed in most human epithelia and comprises the amino acid sequence of SEQ ID NO: 164 (UNIPROT® Q9Y5Y6). In one aspect, the protease cleavable linker comprises the protease recognition sequence RQARVVNG (SEQ ID NO:148). In another aspect, the protease cleavable linker comprises the protease recognition sequence PMAKK (SEQ ID NO:162).

In one particular aspect, provided is a bispecific agonistic CD28 antigen binding molecule comprising a first light chain comprising the amino acid sequence of SEQ ID NO:102, a first heavy chain comprising the amino acid sequence of SEQ ID NO:101, a second heavy chain comprising the amino acid sequence of SEQ ID NO:106 and a second light chain comprising the amino acid sequence of SEQ ID NO:104 (Molecule 11).

In another particular aspect, provided is a bispecific agonistic CD28 antigen binding molecule comprising a first light chain comprising the amino acid sequence of SEQ ID NO:90, a first heavy chain comprising the amino acid sequence of SEQ ID NO:98, a second heavy chain comprising the amino acid sequence of SEQ ID NO:97 and a second light chain comprising the amino acid sequence of SEQ ID NO:92 (Molecule 6).

In another particular aspect, provided is a bispecific agonistic CD28 antigen binding molecule comprising a first light chain comprising the amino acid sequence of SEQ ID NO:90, a first heavy chain comprising the amino acid sequence of SEQ ID NO:98, a second heavy chain comprising the amino acid sequence of SEQ ID NO:99 and a second light chain comprising the amino acid sequence of SEQ ID NO:94 (Molecule 7).

In another aspect, provided is a bispecific agonistic CD28 antigen binding molecule comprising a masking moiety covalently attached to the bispecific agonistic CD28 antigen binding molecule through a non-cleavable linker, wherein the masking moiety is capable of binding to the idiotype of the second antigen binding domain capable of specific binding to CD3 thereby reversibly concealing the antigen binding domain capable of specific binding to CD3. In one aspect, the masking moiety is covalently attached to the heavy chain variable region ($V_H$CD3) of the second antigen binding domain capable of specific binding to CD3. In one aspect, the masking moiety is an anti-idiotype scFv. In one aspect, the non-cleavable linker has the amino acid sequence of SEQ ID NO:163.

Polynucleotides

The invention further provides isolated polynucleotides encoding a bispecific agonistic CD28 antigen binding molecule as described herein or a fragment thereof. The one or more isolated polynucleotides encoding the bispecific agonistic CD28 antigen binding molecule of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin. In some aspects, the isolated polynucleotide encodes the entire bispecific agonistic CD28 antigen binding molecule according to the invention as described herein. In other aspects, the isolated polynucleotide encodes a polypeptide comprised in the bispecific agonistic CD28 antigen binding molecule according to the invention as described herein. In certain aspects the polynucleotide or nucleic acid is DNA. In other aspects, a polynucleotide of the present invention is RNA, for example, in the form of messenger RNA (mRNA). RNA of the present invention may be single stranded or double stranded.

Recombinant Methods

Bispecific agonistic CD28 antigen binding molecules of the invention may be obtained, for example, by solid-state peptide synthesis (e.g. Merrifield solid phase synthesis) or recombinant production. For recombinant production one or more polynucleotide encoding the bispecific agonistic CD28 antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N. Y. (1989). The expression vector can be part of a plasmid, virus, or may be a nucleic acid fragment. The expression vector includes an expression cassette into which the polynucleotide encoding the antibody or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or polypeptide fragments thereof is desired, DNA encoding a signal sequence may be placed upstream of the nucleic acid an antibody of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the bispecific agonistic CD28 antigen binding molecule may be included within or at the ends of the polynucleotide encoding an antibody of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) an antibody of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NSO, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NSO, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing a bispecific agonistic CD28 antigen binding molecule of the invention or polypeptide fragments thereof is provided, wherein the method comprises culturing a host cell comprising polynucleotides encoding the antibody of the invention or polypeptide fragments thereof, as provided herein, under conditions suitable for expression of the antibody of the invention or polypeptide fragments thereof, and recovering the antibody of the invention or polypeptide fragments thereof from the host cell (or host cell culture medium).

In certain aspects the antigen binding domain capable of specific binding to CD3 (e.g. a Fab fragment) forming part of the antigen binding molecule comprises at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31 (3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, NJ, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the antigen binding domains comprised in the bispecific agonistic CD28 antigen binding molecules are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, NJ). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch.14 (Cold Spring Harbor Laboratory, Cold Spring Harbor, NY).

Bispecific agonistic CD28 antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the antigen binding molecule binds.

For example, for affinity chromatography purification of antigen binding molecules of the invention, a matrix with protein A or protein G may be used. Sequential Protein A or G affinity chromatography and size exclusion chromatography can be used to isolate an antigen binding molecule essentially as described in the Examples. The purity of the CD28 antigen binding molecule or fragments thereof can be determined by any of a variety of well-known analytical methods including gel electrophoresis, high pressure liquid chromatography, and the like. For example, the CD28 antigen binding molecule expressed as described in the Examples were shown to be intact and properly assembled as demonstrated by reducing and non-reducing SDS-PAGE.

Assays

The bispecific agonistic CD28 antigen binding molecules provided herein may be identified, screened for, or characterized for their physical/chemical properties and/or biological activities by various assays known in the art.

1. Affinity Assays

The affinity of the antigen binding molecule provided herein for the corresponding target can be determined in accordance with the methods set forth in the Examples by surface plasmon resonance (SPR), using standard instrumentation such as a PROTEON™ instrument (Bio-rad), and receptors or target proteins such as may be obtained by recombinant expression. The affinity of the bispecific agonistic CD28 antigen binding molecule for its antigens can also be determined by surface plasmon resonance (SPR), using standard instrumentation such as a PROTEON™ instrument (Bio-rad), and receptors or target proteins such as may be obtained by recombinant expression. According to one aspect, Kp is measured by surface plasmon resonance using a PROTEON™ machine (Bio-Rad) at 25° C.

In one aspect, the binding activity to CD3 is determined by SPR as follows: SPR is performed on a BIACORE™ T200 instrument (GE Healthcare) at 25° C. with HBS-P+ (10 mM HEPES, 150 mM NaCl pH 7.4, 0.05% Surfactant P20) as running and dilution buffer. Biotinylated human CD3ε/δ (a heterodimer of CD3 delta and CD3 epsilon ectodomains fused to a human Fc domain with knob-into-hole modifications and a C-terminal Avi-tag; see SEQ ID NOs 41 and 42) as well as biotinylated anti-huIgG (Capture Select, Thermo Scientific, #7103262100) is immobilized on a Series S Sensor Chip SA (GE Healthcare, #29104992), resulting in surface densities of at least 1000 resonance units (RU). Anti-CD3 antibodies with a concentration of 2 μg/ml are injected for 30 s at a flow rate of 5 μl/min, and dissociation is monitored for 120 s. The surface is regenerated by injecting 10 mM glycine pH 1.5 for 60 s. Bulk refractive index differences are corrected by subtracting blank injections and by subtracting the response obtained from a blank control flow cell. For evaluation, the binding response 5 seconds after injection end is taken. To normalize the binding signal, the CD3 binding is divided by the anti-huIgG response (the signal (RU) obtained upon capture of the anti-CD3 antibody on the immobilized anti-huIgG antibody). The binding activity to CD3 of an antibody after a certain treatment, relative to the binding activity to CD3 of the antibody after a different treatment is calculated by referencing the binding activity of a sample of the antibody after the certain treatment to the binding activity of a corresponding sample of the antibody after the different treatment.

2. Binding Assays and Other Assays

Binding of the bispecific antigen binding molecule provided herein to the corresponding receptor expressing cells may be evaluated using cell lines expressing the particular receptor or target antigen, for example by flow cytometry (FACS). In one aspect, CHO cells expressing human CD28 (parental cell line CHO-k1 ATCC® #CCL-61, modified to stably overexpress human CD28) are used in the binding assay.

3. Activity Assays

In one aspect, assays are provided for identifying CD28 antigen binding molecules having biological activity. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival. In particular, T cell activation and cytokine secretion is measured with the methods as described in Example 2 to 4 or tumor cell killing. For instance Jurkat NFAT reporter cell assays are used to measure the T cell activation. Antigen binding molecules having such biological activity in vivo and/or in vitro are also provided.

Pharmaceutical Compositions, Formulations and Routes of Administation

In a further aspect, the invention provides pharmaceutical compositions comprising any of the bispecific agonistic CD28 antigen binding molecules provided herein, e.g., for use in any of the below therapeutic methods. In one embodiment, a pharmaceutical composition comprises a bispecific agonistic CD28 antigen binding molecule provided herein and at least one pharmaceutically acceptable excipient. In another aspect, a pharmaceutical composition comprises a bispecific agonistic CD28 antigen binding molecule provided herein and at least one additional therapeutic agent, e.g., as described below.

Pharmaceutical compositions of the present invention comprise a therapeutically effective amount of one or more bispecific antigen binding molecules dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific agonistic CD28 antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the TNF family ligand trimer-containing antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the bispecific agonistic CD28 antigen binding molecule may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof. Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer. In addition to the compositions described previously, the bispecific agonistic CD28 antigen binding molecule may also be formulated as a depot preparation. Such long acting formulations may be administered by implantation (for example subcutaneously or intramuscularly) or by intramuscular injection. Thus, for example, the bispecific agonistic CD28 antigen binding molecule may be formulated with suitable polymeric or hydrophobic materials (for example as emulsion in an acceptable oil) or ion exchange resins, or as sparingly soluble derivatives, for example, as a sparingly soluble salt.

Pharmaceutical compositions comprising the bispecific agonistic CD28 antigen binding molecule of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen. The bispecific agonistic CD28 antigen binding molecule of the invention may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms. The composition herein may also contain more than one active ingredients as necessary for the particular indication being treated, preferably those with complementary activities that do not adversely affect each other. Such active ingredients are suitably present in combination in amounts that are effective for the purpose intended. The formulations to be used for in vivo administration are generally sterile. Sterility may be readily accomplished, e.g., by filtration through sterile filtration membranes.

Therapeutic methods and compositions Any of the bispecific agonistic CD28 antigen binding molecules provided herein may be used in therapeutic methods, either alone or in combination.

In one aspect, a bispecific agonistic CD28 antigen binding molecule for use as a medicament is provided. In further aspects, a bispecific agonistic CD28 antigen binding molecule for use in treating cancer is provided. In certain aspects, a bispecific agonistic CD28 antigen binding molecule for use in a method of treatment is provided. In certain aspects, herein is provided a bispecific agonistic CD28 antigen binding molecule for use in a method of treating an individual having cancer comprising administering to the individual an effective amount of the bispecific agonistic CD28 antigen binding molecule. In one such embodiment, the method further comprises administering to the individual an effective amount of at least one additional therapeutic agent.

In one aspect, the bispecific agonistic CD28 antigen binding molecule is for use in inhibiting the growth of cancer cells. Thus, in particular aspects, the bispecific agonistic CD28 antigen binding molecule is for use in treating cancer. Such cancers include for example breast cancer, lung cancer, skin cancer, blood cancer, squamous cell carcinoma, bone cancer, kidney cancer, head and neck cancer, stomach cancer, prostate cancer, ovarian cancer, colorectal cancer, colon cancer, cervical cancer, esophageal cancer, tracheal cancer, gastric cancer, bladder cancer, uterine cancer, rectal cancer, or cancer of the small intestine, pancreatic cancer, or other epithelial cancer, or metastases associated therewith.

In certain aspects, a bispecific agonistic CD28 antigen binding molecule for use in a method of treatment is provided. In certain aspects, herein is provided a bispecific agonistic CD28 antigen binding molecule for use in a method of treating an individual having cancer comprising administering to the individual an effective amount of the bispecific agonistic CD28 antigen binding molecule. In another aspect, provided is a bispecific agonistic CD28 antigen binding molecule for use in a method of treating an individual having CD3-expressing cancer, in particular an epithelial or squamous cancer or a cancer selected from breast cancer, lung cancer, stomach cancer, prostate cancer, ovarian cancer, colorectal cancer, colon cancer, esophageal cancer, tracheal cancer, gastric cancer, bladder cancer, uterine cancer, rectal cancer, pancreatic cancer, or cancer of the small intestine, comprising administering to the individual an effective amount of the bispecific agonistic CD28 antigen binding molecule. In one such embodiment, the method further comprises administering to the individual an effective amount of at least one additional therapeutic agent.

In a further aspect, herein is provided for the use of a bispecific agonistic CD28 antigen binding molecule as described herein in the manufacture or preparation of a medicament. In one embodiment, the medicament is for treatment of cancer. In a further aspect, the medicament is for use in a method of treating cancer comprising administering to an individual having cancer an effective amount of the medicament. In one such aspect, the method further comprises administering to the individual an effective amount of at least one additional therapeutic agent, e.g., as described below. In another aspect, the medicament is for treatment of cancer. In a further aspect, the medicament is for use in a method of treating cancer, comprising administering to an individual having cancer an effective amount of the medicament. In a further aspect, herein is provided a method for treating a cancer. In one aspect, the method comprises administering to an individual having cancer an effective amount of a bispecific agonistic CD28 antigen binding molecule. In one such aspect, the method further comprises administering to the individual an effective amount of at least one additional therapeutic agent, as described below. An “individual” according to any of the above aspects may be a human.

In a further aspect, herein are provided pharmaceutical formulations comprising any of the bispecific agonistic CD28 antigen binding molecules as reported herein, e.g., for use in any of the above therapeutic methods. In one aspect, a pharmaceutical formulation comprises any of the bispecific agonistic CD28 antigen binding molecules as reported herein and a pharmaceutically acceptable carrier. In another aspect, a pharmaceutical formulation comprises any of the bispecific agonistic CD28 antigen binding molecules as reported herein and at least one additional therapeutic agent.

Bispecific agonistic CD28 antigen binding molecules as reported herein can be used either alone or in combination with other agents in a therapy. For instance, a bispecific agonistic CD28 antigen binding molecule as reported herein may be co-administered with at least one additional therapeutic agent. Thus, a bispecific agonistic CD28 antigen binding molecule as described herein for use in cancer immunotherapy is provided. In certain embodiments, a bispecific agonistic CD28 antigen binding molecule for use in a method of cancer immunotherapy is provided. An "individual" according to any of the above aspects is preferably a human.

Such combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one aspect, administration of the bispecific agonistic CD28 antigen binding molecule and administration of an additional therapeutic agent occur within about one month, or within about one, two or three weeks, or within about one, two, three, four, five, or six days, of each other.

An antigen binding molecule as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Bispecific agonistic CD28 antigen binding molecules as described herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The bispecific agonistic CD28 antigen binding molecule need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a bispecific agonistic CD28 antigen binding molecule as described herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The bispecific agonistic CD28 antigen binding molecule is suitably administered to the patient at one time or over a series of treatments. Depending on the type and severity of the disease, about 1 μg/kg to 15 mg/kg (e.g. 0.5 mg/kg-10 mg/kg) of bispecific agonistic CD28 antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Other Agents and Treatments

As described before, the bispecific agonistic CD28 antigen binding molecules of the invention may be administered in combination with one or more other agents in therapy. For instance, an antigen binding molecule of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. In certain aspects, an additional therapeutic agent is an immunomodulatory agent, a cytostatic agent, an inhibitor of cell adhesion, a cytotoxic or cytostatic agent, an activator of cell apoptosis, or an agent that increases the sensitivity of cells to apoptotic inducers.

Thus, provided are bispecific agonistic CD28 antigen binding molecules of the invention or pharmaceutical compositions comprising them for use in the treatment of cancer, wherein the bispecific antigen binding molecule is administered in combination with a chemotherapeutic agent, radiation and/or other agents for use in cancer immunotherapy.

Such other agents are suitably present in combination in amounts that are effective for the purpose intended. The effective amount of such other agents depends on the amount of fusion protein used, the type of disorder or treatment, and other factors discussed above. The bispecific antigen binding molecule or antibody of the invention are generally used in the same dosages and with administration routes as described herein, or about from 1 to 99% of the dosages described herein, or in any dosage and by any route that is empirically/clinically determined to be appropriate. Such combination therapies noted above encompass combined administration (where two or more therapeutic agents are included in the same or separate compositions), and separate administration, in which case, administration of the bispecific antigen binding molecule or antibody of the invention can occur prior to, simultaneously, and/or following, administration of the additional therapeutic agent and/or adjuvant.

In a further aspect, provided is the bispecific agonistic CD28 antigen binding molecule as described herein before for use in the treatment of cancer, wherein the bispecific antigen binding molecule is administered in combination with another immunomodulator. The term "immunomodulator" refers to any substance including a monoclonal antibody that effects the immune system. The molecules of the inventions can be considered immunomodulators. Immunomodulators can be used as anti-neoplastic agents for the treatment of cancer. In one aspect, immunomodulators include, but are not limited to anti-CTLA4 antibodies (e.g. ipilimumab), anti-PD1 antibodies (e.g. nivolumab or pembrolizumab), PD-L1 antibodies (e.g. atezolizumab, avelumab or durvalumab), OX40 agonists (in particular OX-40 antibodies), 4-1BB agonists (4-1BBL or 4-1BB antibodies) and GITR agonists (e.g. GITR antibodies). Such combination therapies noted above encompass combined administration (where two or more therapeutic agents are included in the same or separate compositions), and separate administration, in which case, administration of the bispecific antigen binding molecule can occur prior to, simultaneously, and/or following, administration of the additional therapeutic agent and/or adjuvant.

Such combination therapies noted above encompass combined administration (where two or more therapeutic agents are included in the same or separate formulations), and separate administration, in which case, administration of the therapeutic agent can occur prior to, simultaneously, and/or following, administration of an additional therapeutic agent or agents. In one embodiment, administration of the therapeutic agent and administration of an additional therapeutic agent occur within about one month, or within about one, two or three weeks, or within about one, two, three, four, five, or six days, of each other.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific agonistic CD28 antigen binding molecule of the invention. The label or package insert indicates that the composition is used for treating the condition of choice. Moreover, the article of manufacture may comprise (a) a first container with a composition contained therein, wherein the composition comprises a bispecific agonistic CD28 antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE B (Sequences):

| SEQ ID NO: | Name | Sequence |
|---|---|---|
| 1 | hu CD28<br>UniProt no. P10747,<br>version 1 | MLRLLLALNL FPSIQVTGNK ILVKQSPMLV<br>AYDNAVNLSC KYSYNLFSRE FRASLHKGLD<br>SAVEVCVVYG NYSQQLQVYS KTGFNCDGKL<br>GNESVTFYLQ NLYVNQTDIY FCKIEVMYPP<br>PYLDNEKSNG TIIHVKGKHL CPSPLFPGPS<br>KPFWVLVVVG GVLACYSLLV TVAFIIFWVR<br>SKRSRLLHSD YMNMTPRRPG PTRKHYQPYA<br>PPRDFAAYRS |
| 2 | CD3 (CH2527) CDR-H1 | TYAMN |
| 3 | CD3 (CH2527) CDR-H2 | RIRSKYNNYATYYADSVKG |
| 4 | CD3 (CH2527) CDR-H3 | HGNFGNSYVSWFAY |
| 5 | CD3 (CH2527) CDR-L1 | GSSTGAVTTSNYAN |
| 6 | CD3 (CH2527) CDR-L2 | GTNKRAP |
| 7 | CD3 (CH2527) CDR-L3 | ALWYSNLWV |
| 8 | heavy chain variable domain<br>VH, CD3 (CH2527) | EVQLLESGGGLVQPGGSLRLSCAASGFTFSTYAM<br>NWVRQAPGKGLEWVSRIRSKYNNYATYYADSVKG<br>RFTISRDDSKNTLYLQMNSLRAEDTAVYYCVRHG<br>NFGNSYVSWFAYWGQGTLVTVSS |
| 9 | light chain variable domain<br>VL, CD3 (CH2527) | QAVVTQEPSLTVSPGGTVTLTCGSSTGAVTTSNY<br>ANWVQEKPGQAFRGLIGGTNKRAPGTPARFSGSL<br>LGGKAALTLSGAQPEDEAEYYCALWYSNLWVFGG<br>GTKLTVL |
| 10 | CD3 (P035.093) CDR-H1 | SYAMN |
| 11 | CD3 (P035.093) CDR-H2 | RIRSKYNNYATYYADSVKG |

TABLE B-continued (Sequences):

| SEQ ID NO: | Name | Sequence |
|---|---|---|
| 12 | CD3 (P035.093) CDR-H3, | ASNFPASYVSYFAY |
| 13 | CD3 (P035.093) CDR-L1 | GSSTGAVTTSNYAN |
| 14 | CD3 (P035.093) CDR-L2 | GTNKRAP |
| 15 | CD3 (P035.093) CDR-L3 | ALWYSNLWV |
| 16 | heavy chain variable domain VH, CD3 (P035.093) | EVQLLESGGGLVQPGGSLRLSCAASGFTFSSYAM NWVRQAPGKGLEWVSRIRSKYNNYATYYADSVKG RFTISRDDSKNTLYLQMNSLRAEDTAVYYCVRAS NFPASYVSYFAYWGQGTLVTVSS |
| 17 | light chain variable domain VL, CD3 (P035.093) | QAVVTQEPSLTVSPGGTVTLTCGSSTGAVTTSNY ANWVQEKPGQAFRGLIGGTNKRAPGTPARFSGSL LGGKAALTLSGAQPEDEAEYYCALWYSNLWVFGG GTKLTVL |
| 18 | CD28(SA) CDR-H1 | SYYIH |
| 19 | CD28(SA) CDR-H2 | CIYPGNVNTNYNEKFKD |
| 20 | CD28(SA) CDR-H3 | SHYGLDWNFDV |
| 21 | CD28(SA) CDR-L1 | HASQNIYVWLN |
| 22 | CD28(SA) CDR-L2 | KASNLHT |
| 23 | CD28(SA) CDR-L3 | QQGQTYPYT |
| 24 | CD28(SA) VH | QVQLVQSGAEVKKPGASVKVSCKASGYTFTSYYI HWVRQAPGQGLEWIGCIYPGNVNTNYNEKFKDRA TLTVDTSISTAYMELSRLRSDDTAVYFCTRSHYG LDWNFDVWGQGTTVTVSS |
| 25 | CD28(SA) VL | DIQMTQSPSSLSASVGDRVTITCHASQNIYVWLN WYQQKPGKAPKLLIYKASNLHTGVPSRFSGSGSG TDFTLTISSLQPEDFATYYCQQGQTYPYTFGGGT KVEIK |
| 26 | CD28 CDR-H1 consensus | SYYIH |
| 27 | CD28 CDR-H2 consensus | SIYP$X_1X_2X_3X_4$TNYNEKFKD, wherein<br>$X_1$ is G or R<br>$X_2$ is N or D<br>$X_3$ is V or G<br>$X_4$ is N or Q or A |
| 28 | CD28 CDR-H3 consensus | SHYGX D$X_6$NFDV, wherein<br>$X_5$ is L or A<br>$X_6$ is W or H or Y or F |
| 29 | CD28 CDR-L1 consensus | $X_7$ASQ$X_8$I$X_9X_{10}X_{11}$LN, wherein<br>$X_7$ is H or R<br>$X_8$ is N or G<br>$X_9$ is Y or S<br>$X_{10}$ is V or N<br>$X_{11}$ is W or H or For Y |
| 30 | CD28 CDR-L2 consensus | $X_{12}X_{13}$S$X_{14}$L$X_{15}X_{16}$, wherein<br>$X_{12}$ is K or Y<br>$X_{13}$ is A or T<br>$X_{14}$ is N or S<br>$X_{15}$ is H or Y<br>$X_{16}$ is T or S |
| 31 | CD28 CDR-L3 consensus | QQ$X_{17}$QTYPYT, wherein<br>$X_{17}$ is G or A |
| 32 | CD28 VH variant a | QVQLVQSGAEVKKPGASVKVSCKASGYTFTSYYI HWVRQAPGQGLEWIGSIYPGNVNTNYNEKFKDRA TLTVDTSISTAYMELSRLRSDDTAVYFCTRSHYG LDWNFDVWGQGTTVTVSS |

TABLE B-continued (Sequences):

| SEQ ID NO: | Name | Sequence |
|---|---|---|
| 33 | CD28 VH variant b | QVQLVQSGAEVKKPGASVKVSCKASGYTFTSYYIHWVRQAPGQGLEWIGSIYPGNVQTNYNEKFKDRATLTVDTSISTAYMELSRLRSDDTAVYFCTRSHYGLDHNFDVWGQGTTVTVSS |
| 34 | CD28 VH variant c | QVQLVQSGAEVKKPGASVKVSCKASGYTFTSYYIHWVRQAPGQGLEWIGSIYPGNVQTNYNEKFKDRATLTVDTSISTAYMELSRLRSDDTAVYFCTRSHYGADHNFDVWGQGTTVTVSS |
| 35 | CD28 VH variant d | QVQLVQSGAEVKKPGASVKVSCKASGYTFTSYYIHWVRQAPGQGLEWIGSIYPRDGQTNYNEKFKDRATLTVDTSISTAYMELSRLRSDDTAVYFCTRSHYGLDYNFDVWGQGTTVTVSS |
| 36 | CD28 VH variant e | QVQLVQSGAEVKKPGASVKVSCKASGYTFTSYYIHWVRQAPGQGLEWIGSIYPGNVQTNYNEKFKDRATLTVDTSISTAYMELSRLRSDDTAVYFCTRSHYGLDWNFDVWGQGTTVTVSS |
| 37 | CD28 VH variant f | QVQLVQSGAEVKKPGASVKVSCKASGYTFTSYYIHWVRQAPGQGLEWIGSIYPGNVQTNYNEKFKDRATLTVDTSISTAYMELSRLRSDDTAVYFCTRSHYGLDFNFDVWGQGTTVTVSS |
| 38 | CD28 VH variant g | QVQLVQSGAEVKKPGASVKVSCKASGYTFTSYYIHWVRQAPGQGLEWIGSIYPRNVQTNYNEKFKDRATLTVDTSISTAYMELSRLRSDDTAVYFCTRSHYGLDHNFDVWGQGTTVTVSS |
| 39 | CD28 VH variant h | QVQLVQSGAEVKKPGASVKVSCKASGYTFTSYYIHWVRQAPGQGLEWIGSIYPRDVQTNYNEKFKDRATLTVDTSISTAYMELSRLRSDDTAVYFCTRSHYGLDHNFDVWGQGTTVTVSS |
| 40 | CD28 VH variant i | EVQLVESGGGLVQPGGSLRLSCAASGFTFTSYYIHWVRQAPGKGLEWVASIYPGNVNTRYADSVKGRFTISADTSKNTAYLQMNSLRAEDTAVYYCTRSHYGLDWNFDVWGQGTTVTVSS |
| 41 | CD28 VH variant j | EVQLVESGGGLVQPGGSLRLSCAASGFTFTSYYIHWVRQAPGKGLEWVASIYPGNVATRYADSVKGRFTISADTSKNTAYLQMNSLRAEDTAVYYCTRSHYGLDWNFDVWGQGTTVTVSS |
| 42 | CD28 VL variant k | DIQMTQSPSSLSASVGDRVTITCHASQNIYVHLNWYQQKPGKAPKLLIYKASNLHTGVPSRFSGSGSGTDFTLTISSLQPEDFATYYCQQAQTYPYTFGGGTKVEIK |
| 43 | CD28 VL variant l | DIQMTQSPSSLSASVGDRVTITCHASQNIYVFLNWYQQKPGKAPKLLIYKASNLHTGVPSRFSGSGSGTDFTLTISSLQPEDFATYYCQQGQTYPYTFGGGTKVEIK |
| 44 | CD28 VL variant m | DIQMTQSPSSLSASVGDRVTITCHASQNIYVYLNWYQQKPGKAPKLLIYKASNLHTGVPSRFSGSGSGTDFTLTISSLQPEDFATYYCQQGQTYPYTFGGGTKVEIK |
| 45 | CD28 VL variant n | DIQMTQSPSSLSASVGDRVTITCHASQGISNYLNWYQQKPGKAPKLLIYKASNLHTGVPSRFSGSGSGTDFTLTISSLQPEDFATYYCQQGQTYPYTFGGGTKVEIK |
| 46 | CD28 VL variant o | DIQMTQSPSSLSASVGDRVTITCHASQNIYVWLNWYQQKPGKAPKLLIYYTSSLHSGVPSRFSGSGSGTDFTLTISSLQPEDFATYYCQQGQTYPYTFGGGTKVEIK |
| 47 | CD28 VL variant p | DIQMTQSPSSLSASVGDRVTITCHASQGISNYLNWYQQKPGKAPKLLIYYTSSLHSGVPSRFSGSGSGTDFTLTISSLQPEDFATYYCQQGQTYPYTFGGGTKVEIK |

TABLE B-continued

| (Sequences): | | |
|---|---|---|
| SEQ ID NO: | Name | Sequence |
| 48 | CD28 VL variant q | DIQMTQSPSSLSASVGDRVTITCHASQGISNHLN WYQQKPGKAPKLLIYKASNLHTGVPSRFSGSGSG TDFTLTISSLQPEDFATYYCQQGQTYPYTFGGGT KVEIK |
| 49 | CD28 VL variant r | DIQMTQSPSSLSASVGDRVTITCHASQGIYVYLN WYQQKPGKAPKLLIYKASNLHTGVPSRFSGSGSG TDFTLTISSLQPEDFATYYCQQGQTYPYTFGGGT KVEIK |
| 50 | CD28 VL variant s | DIQMTQSPSSLSASVGDRVTITCHASQGISVYLN WYQQKPGKAPKLLIYKASNLHTGVPSRFSGSGSG TDFTLTISSLQPEDFATYYCQQGQTYPYTFGGGT KVEIK |
| 51 | CD28 VL variant t | DIQMTQSPSSLSASVGDRVTITCRASQNIYVWLN WYQQKPGKAPKLLIYKASNLYSGVPSRFSGSRSG TDFTLTISSLQPEDFATYYCQQGQTYPYTFGQGT KLEIK |
| 52 | CD28(variant 8) CDR-H1 | SYYIH |
| 53 | CD28(variant 8) CDR-H2 | SIYPGNVQTNYNEKFKD |
| 54 | CD28(variant 8) CDR-H3 | SHYGLDWNFDV |
| 55 | CD28(variant 8) CDR-L1 | HASQNIYVYLN |
| 56 | CD28(variant 8) CDR-L2 | KASNLHT |
| 57 | CD28(variant 8) CDR-L3 | QQGQTYPYT |
| 58 | CD28(variant 15) CDR-H1 | SYYIH |
| 59 | CD28(variant 15) CDR-H2 | SIYPGNVQTNYNEKFKD |
| 60 | CD28(variant 15) CDR-H3 | SHYGLDWNFDV |
| 61 | CD28(variant 15) CDR-L1 | HASQNIYVFLN |
| 62 | CD28(variant 15) CDR-L2 | KASNLHT |
| 63 | CD28(variant 15) CDR-L3 | QQGQTYPYT |
| 64 | CD28(variant 29) CDR-H1 | SYYIH |
| 65 | CD28(variant 29) CDR-H2 | SIYPGNVNTNYNEKFKD |
| 66 | CD28(variant 29) CDR-H3 | SHYGLDWNFDV |
| 67 | CD28(variant 29) CDR-L1 | HASQNIYVWLN |
| 68 | CD28(variant 29) CDR-L2 | KASNLHT |
| 69 | CD28(variant 29) CDR-L3 | QQGQTYPYT |
| 70 | human CD3ε Uniprot No. P07766 | MQSGTHWRVLGLCLLSVGVWGQDGNEEMGGITQT PYKVSISGTTVILTCPQYPGSEILWQHNDKNIGG DEDDKNIGSDEDHLSLKEFSELEQSGYYVCYPRG SKPEDANFYLYLRARVCENCMEMDVMSVATIVIV DICITGGLLLLVYYWSKNRKAKAKPVTRGAGAGG RQRGQNKERPPPVPNPDYEPIRKGQRDLYSGLNQ RRI |
| 71 | Cynomolgus CD3ε Uniprot No. Q95LI5 | MQSGTRWRVLGLCLLSIGVWGQDGNEEMGSITQT PYQVSISGTTVILTCSQHLGSEAQWQHNGKNKED SGDRLFLPEFSEMEQSGYYVCYPRGSNPEDASHH LYLKARVCENCMEMDVMAVATIVIVDICITLGLL LLVYYWSKNRKAKAKPVTRGAGAGGRQRGQNKER PPPVPNPDYEPIRKGQQDLYSGLNQRRI |
| 72 | VH (CD28 SA) CH1 (EE)- Fc knob PGLALA | QVQLVQSGAEVKKPGASVKVSCKASGYTFTSYYI HWVRQAPGQGLEWIGCIYPGNVNTNYNEKFKDRA TLTVDTSISTAYMELSRLRSDDTAVYFCTRSHYG LDWNFDVWGQGTTVTVSSASTKGPSVFPLAPSSK |

TABLE B-continued (Sequences):

| SEQ ID NO: | Name | Sequence |
| --- | --- | --- |
| | | STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 73 | VH (CD28 variant g) CH1 (EE) - Fc knob PGLALA | QVQLVQSGAEVKKPGASVKVSCKASGYTFTSYYI HWVRQAPGQGLEWIGSIYPRNVQTNYNEKFKDRA TLTVDTSISTAYMELSRLRSDDTAVYFCTRSHYG LDHNFDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 74 | VH (CD28 variant f) CH1 (EE) - Fc knob PGLALA | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDFNFDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 75 | VH (CD28 variant j) CH1 (EE) - Fc knob PGLALA | EVQLVESGGGLVQPGGSLRLSCAASGFTFTSYYI HWVRQAPGKGLEWVASIYPGNVATRYADSVKGRF TISADTSKNTAYLQMNSLRAEDTAVYYCTRSHYG LDWNFDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 76 | VH (CD28 variant e) CH1 (EE)- Fc knob PGLALA | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDWNFDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVYTLPPCRDELTKNQVSLWCLVKG FYPSDIAVEWESNGQPENNYKTTPPVLDSDGSFF LYSKLTVDKSRWQQGNVFSCSVMHEALHNHYTQK SLSLSP |
| 77 | VH (CD28 variant b) CH1 (EE) - Fc knob PGLALA | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDHNFDVWGQGTTVTVSSASTKGPSVFPLAPSSK |

TABLE B-continued (Sequences):

| SEQ ID NO: | Name | Sequence |
|---|---|---|
| | | STSGGTAALGCLVEDYFPEPVTVSWNSGALTSGV<br>HTFPAVLQSSGLYSLSSVVTVPSSSLGTQTYICN<br>VNHKPSNTKVDEKVEPKSCDKTHTCPPCPAPEAA<br>GGPSVFLFPPKPKDTLMISRTPEVTCVVVDVSHE<br>DPEVKFNWYVDGVEVHNAKTKPREEQYNSTYRVV<br>SVLTVLHQDWLNGKEYKCKVSNKALGAPIEKTIS<br>KAKGQPREPQVYTLPPCRDELTKNQVSLWCLVKG<br>FYPSDIAVEWESNGQPENNYKTTPPVLDSDGSFF<br>LYSKLTVDKSRWQQGNVFSCSVMHEALHNHYTQK<br>SLSLSP |
| 78 | VH (CD28 variant a) CH1 (EE) - Fc knob PGLALA | QVQLVQSGAEVKKPGASVKVSCKASGYTFTSYYI<br>HWVRQAPGQGLEWIGSIYPGNVNTNYNEKFKDRA<br>TLTVDTSISTAYMELSRLRSDDTAVYFCTRSHYG<br>LDWNFDVWGQGTTVTVSSASTKGPSVFPLAPSSK<br>STSGGTAALGCLVEDYFPEPVTVSWNSGALTSGV<br>HTFPAVLQSSGLYSLSSVVTVPSSSLGTQTYICN<br>VNHKPSNTKVDEKVEPKSCDKTHTCPPCPAPEAA<br>GGPSVFLFPPKPKDTLMISRTPEVTCVVVDVSHE<br>DPEVKFNWYVDGVEVHNAKTKPREEQYNSTYRVV<br>SVLTVLHQDWLNGKEYKCKVSNKALGAPIEKTIS<br>KAKGQPREPQVYTLPPCRDELTKNQVSLWCLVKG<br>FYPSDIAVEWESNGQPENNYKTTPPVLDSDGSFF<br>LYSKLTVDKSRWQQGNVFSCSVMHEALHNHYTQK<br>SLSLSP |
| 79 | VH (CD28 variant i) CH1 (EE) - Fc knob PGLALA | EVQLVESGGGLVQPGGSLRLSCAASGFTFTSYYI<br>HWVRQAPGKGLEWVASIYPGNVNTRYADSVKGRF<br>TISADTSKNTAYLQMNSLRAEDTAVYYCTRSHYG<br>LDWNFDVWGQGTTVTVSSASTKGPSVFPLAPSSK<br>STSGGTAALGCLVEDYFPEPVTVSWNSGALTSGV<br>HTFPAVLQSSGLYSLSSVVTVPSSSLGTQTYICN<br>VNHKPSNTKVDEKVEPKSCDKTHTCPPCPAPEAA<br>GGPSVFLFPPKPKDTLMISRTPEVTCVVVDVSHE<br>DPEVKFNWYVDGVEVHNAKTKPREEQYNSTYRVV<br>SVLTVLHQDWLNGKEYKCKVSNKALGAPIEKTIS<br>KAKGQPREPQVYTLPPCRDELTKNQVSLWCLVKG<br>FYPSDIAVEWESNGQPENNYKTTPPVLDSDGSFF<br>LYSKLTVDKSRWQQGNVFSCSVMHEALHNHYTQK<br>SLSLSP |
| 80 | VL-CD28(SA)-CL"RK" | DIQMTQSPSSLSASVGDRVTITCHASQNIYVWLN<br>WYQQKPGKAPKLLIYKASNLHTGVPSRFSGSGSG<br>TDFTLTISSLQPEDFATYYCQQGQTYPYTFGGGT<br>KVEIKRTVAAPSVFIFPPSDRKLKSGTASVVCLL<br>NNFYPREAKVQWKVDNALQSGNSQESVTEQDSKD<br>STYSLSSTLTLSKADYEKHKVYACEVTHQGLSSP<br>VTKSFNRGEC |
| 81 | VL (CD28 variant k)-CL(RK) | DIQMTQSPSSLSASVGDRVTITCHASQNIYVHLN<br>WYQQKPGKAPKLLIYKASNLHTGVPSRFSGSGSG<br>TDFTLTISSLQPEDFATYYCQQAQTYPYTFGGGT<br>KVEIKRTVAAPSVFIFPPSDRKLKSGTASVVCLL<br>NNFYPREAKVQWKVDNALQSGNSQESVTEQDSKD<br>STYSLSSTLTLSKADYEKHKVYACEVTHQGLSSP<br>VTKSFNRGEC |
| 82 | VL (CD28 variant l)-CL(RK) | DIQMTQSPSSLSASVGDRVTITCHASQNIYVFLN<br>WYQQKPGKAPKLLIYKASNLHTGVPSRFSGSGSG<br>TDFTLTISSLQPEDFATYYCQQGQTYPYTFGGGT<br>KVEIKRTVAAPSVFIFPPSDRKLKSGTASVVCLL<br>NNFYPREAKVQWKVDNALQSGNSQESVTEQDSKD<br>STYSLSSTLTLSKADYEKHKVYACEVTHQGLSSP<br>VTKSFNRGEC |
| 83 | VL (CD28 variant m)-CL(RK) | DIQMTQSPSSLSASVGDRVTITCHASQNIYVYLN<br>WYQQKPGKAPKLLIYKASNLHTGVPSRFSGSGSG<br>TDFTLTISSLQPEDFATYYCQQGQTYPYTFGGGT<br>KVEIKRTVAAPSVFIFPPSDRKLKSGTASVVCLL<br>NNFYPREAKVQWKVDNALQSGNSQESVTEQDSKD<br>STYSLSSTLTLSKADYEKHKVYACEVTHQGLSSP<br>VTKSFNRGEC |

TABLE B-continued

| SEQ ID NO: | Name | Sequence |
|---|---|---|
| | (Sequences): | |
| 84 | VL (CD28 variant r)-CL(RK) | DIQMTQSPSSLSASVGDRVTITCHASQGIYVYLN WYQQKPGKAPKLLIYKASNLHTGVPSRFSGSGSG TDFTLTISSLQPEDFATYYCQQGQTYPYTFGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 85 | VL (CD28 variant s)-CL(RK) | DIQMTQSPSSLSASVGDRVTITCHASQGISVYLN WYQQKPGKAPKLLIYKASNLHTGVPSRFSGSGSG TDFTLTISSLQPEDFATYYCQQGQTYPYTFGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 86 | VL (CD28 variant t)-CL(RK) | DIQMTQSPSSLSASVGDRVTITCRASQNIYVWLN WYQQKPGKAPKLLIYKASNLYSGVPSRFSGSRSG TDFTLTISSLQPEDFATYYCQQGQTYPYTFGQGT KLEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 87 | Fc hole PGLALA, HYRF | DKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVCTLPPSRD ELTKNQVSLSCAVKGFYPSDIAVEWESNGQPENN YKTTPPVLDSDGSFFLVSKLTVDKSRWQQGNVFS CSVMHEALHNRFTQKSLSLSP |
| 88 | Avi tag | GLNDIFEAQKIEWHE |
| 89 | CD3(CH2527) VH-CL hu IgG1 Fc knob PGLALA | EVQLLESGGGLVQPGGSLRLSCAASGFTFSTYAM NWVRQAPGKGLEWVSRIRSKYNNYATYYADSVKG RFTISRDDSKNTLYLQMNSLRAEDTAVYYCVRHG NFGNSYVSWFAYWGQGTLVTVSSASVAAPSVFIF PPSDEQLKSGTASVVCLLNNFYPREAKVQWKVDN ALQSGNSQESVTEQDSKDSTYSLSSTLTLSKADY EKHKVYACEVTHQGLSSPVTKSFNRGECDKTHTC PPCPAPEAAGGPSVFLFPPKPKDTLMISRTPEVT CVVVDVSHEDPEVKFNWYVDGVEVHNAKTKPREE QYNSTYRVVSVLTVLHQDWLNGKEYKCKVSNKAL GAPIEKTISKAKGQPREPQVYTLPPCRDELTKNQ VSLWCLVKGFYPSDIAVEWESNGQPENNYKTTPP VLDSDGSFFLYSKLTVDKSRWQQGNVFSCSVMHE ALHNHYTQKSLSLSP |
| 90 | CD3(CH2527) VL-CH1 | QAVVTQEPSLTVSPGGTVTLTCGSSTGAVTTSNY ANWVQEKPGQAFRGLIGGTNKRAPGTPARFSGSL LGGKAALTLSGAQPEDEAEYYCALWYSNLWVFGG GTKLTVLSSASTKGPSVFPLAPSSKSTSGGTAAL GCLVKDYFPEPVTVSWNSGALTSGVHTFPAVLQS SGLYSLSSVVTVPSSSLGTQTYICNVNHKPSNTK VDKKVEPKSC |
| 91 | CD28(9.3) VH-CH1 (EE) hu IgG1 Fc hole PGLALA | EVKLQQSGPGLVTPSQSLSITCTVSGFSLSDYGV HWVRQSPGQGLEWLGVIWAGGGTNYNSALMSRKS ISKDNSKSQVFLKMNSLQADDTAVYYCARDKGYS YYYSMDYWGQGTSVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVCTLPPSRDELTKNQVSLSCAVKG FYPSDIAVEWESNGQPENNYKTTPPVLDSDGSFF LVSKLTVDKSRWQQGNVFSCSVMHEALHNHYTQK SLSLSP |

TABLE B-continued (Sequences):

| SEQ ID NO: | Name | Sequence |
|---|---|---|
| 92 | CD28(9.3) VL-Ckappa (RK) | DIELTQSPASLAVSLGQRATISCRASESVEYYVT SLMQWYQQKPGQPPKLLIFAASNVESGVPARFSG SGSGTNFSLNIHPVDEDDVAMYFCQQSRKVPYTF GGGTKLEIKRTVAAPSVFIFPPSDRKLKSGTASV VCLLNNFYPREAKVQWKVDNALQSGNSQESVTEQ DSKDSTYSLSSTLTLSKADYEKHKVYACEVTHQG LSSPVTKSFNRGEC |
| 93 | CD28(SA) VH-CH1 (EE) hu IgG1 Fc hole PGLALA | QVQLVQSGAEVKKPGASVKVSCKASGYTFTSYYI HWVRQAPGQGLEWIGCIYPGNVNTNYNEKFKDRA TLTVDTSISTAYMELSRLRSDDTAVYFCTRSHYG LDWNFDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVCTLPPSRDELTKNQVSLSCAVKG FYPSDIAVEWESNGQPENNYKTTPPVLDSDGSFF LVSKLTVDKSRWQQGNVFSCSVMHEALHNHYTQK SLSLSP |
| 94 | CD28(SA) VL-Ckappa (RK) | DIQMTQSPSSLSASVGDRVTITCHASQNIYVWLN WYQQKPGKAPKLLIYKASNLHTGVPSRFSGSGSG TDFTLTISSLQPEDFATYYCQQGQTYPYTFGGGT KVEIKRTVAAPSVFIFPPSDRKLKSGTASVVCLL NNFYPREAKVQWKVDNALQSGNSQESVTEQDSKD STYSLSSTLTLSKADYEKHKVYACEVTHQGLSSP VTKSFNRGEC |
| 95 | Fc knob PGLALA | DKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVYTLPPCRD ELTKNQVSLWCLVKGFYPSDIAVEWESNGQPENN YKTTPPVLDSDGSFFLYSKLTVDKSRWQQGNVFS CSVMHEALHNHYTQKSLSLSP |
| 96 | Fc hole PGLALA | DKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVCTLPPSRD ELTKNQVSLSCAVKGFYPSDIAVEWESNGQPENN YKTTPPVLDSDGSFFLVSKLTVDKSRWQQGNVFS CSVMHEALHNHYTQKSLSLSP |
| 97 | CD28(9.3) VH-CH1 (EE) hu IgG1 Fc hole PGLALA | EVKLQQSGPGLVTPSQSLSITCTVSGFSLSDYGV HWVRQSPGQGLEWLGVIWAGGGTNYNSALMSRKS ISKDNSKSQVFLKMNSLQADDTAVYYCARDKGYS YYYSMDYWGQGTSVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVCTLPPSRDELTKNQVSLSCAVKG FYPSDIAVEWESNGQPENNYKTTPPVLDSDGSFF LVSKLTVDKSRWQQGNVFSCSVMHEALHNRFTQK SLSLSP |
| 98 | ScFv (4.24.72) VH-(G4S)4-VL-Matriptase linker-CD3 VH-CL hu IgG1 Fc knob PGLALA | QVQLKESGPGLVAPSQSLSITCTVSGFSLTSYGV SWVRQPPGKCLEWLGIIWGDGSTNYHSALISRLS ISKDNSKSQVFLKLNSLQTDDTATYYCAKGITTV VDDYYAMDYWGQGTSVTVSSGGGGSGGGGSGGGG SGGGGSDIQMTQSPASLSASVGETVTITCRASEN IDSYLAWYQQKQGKSPQLLVYAATFLADDVPSRF SGSGSGTQYSLKINSLQSEDVARYYCQHYYSTPY TFGCGTKLEIKGGGGSGGGGSRQARVVNGGGGGS GGGGSGGGGSEVQLLESGGGLVQPGGSLRLSCAA SGFTFSTYAMNWVRQAPGKGLEWVSRIRSKYNNY ATYYADSVKGRFTISRDDSKNTLYLQMNSLRAED TAVYYCVRHGNFGNSYVSWFAYWGQGTLVTVSSA |

TABLE B-continued

| SEQ ID NO: | Name | Sequence |
|---|---|---|
| | | SVAAPSVFIFPPSDEQLKSGTASVVCLLNNFYPR EAKVQWKVDNALQSGNSQESVTEQDSKDSTYSLS STLTLSKADYEKHKVYACEVTHQGLSSPVTKSFN RGECDKTHTCPPCPAPEAAGGPSVFLFPPKPKDT LMISRTPEVTCVVVDVSHEDPEVKFNWYVDGVEV HNAKTKPREEQYNSTYRVVSVLTVLHQDWLNGKE YKCKVSNKALGAPIEKTISKAKGQPREPQVYTLP PCRDELTKNQVSLWCLVKGFYPSDIAVEWESNGQ PENNYKTTPPVLDSDGSFFLYSKLTVDKSRWQQG NVFSCSVMHEALHNHYTQKSLSLSP |
| 99 | CD28(SA) VH-CH1 (EE) hu IgG1 Fc hole PGLALA | QVQLVQSGAEVKKPGASVKVSCKASGYTFTSYYI HWVRQAPGQGLEWIGCIYPGNVNTNYNEKFKDRA TLTVDTSISTAYMELSRLRSDDTAVYFCTRSHYG LDWNFDVWGQGTTVTVSSASTKGPSVFPLAPSSK STSGGTAALGCLVEDYFPEPVTVSWNSGALTSGV HTFPAVLQSSGLYSLSSVVTVPSSSLGTQTYICN VNHKPSNTKVDEKVEPKSCDKTHTCPPCPAPEAA GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALGAPIEKTIS KAKGQPREPQVCTLPPSRDELTKNQVSLSCAVKG FYPSDIAVEWESNGQPENNYKTTPPVLDSDGSFF LVSKLTVDKSRWQQGNVFSCSVMHEALHNRFTQK SLSLSP |
| 100 | ScFv (4.24.72) VH-(G4S)4-VL-uncleavable linker-CD3 VH-CL hu IgG1 Fc knob PGLALA | QVQLKESGPGLVAPSQSLSITCTVSGFSLTSYGV SWVRQPPGKCLEWLGIIWGDGSTNYHSALISRLS ISKDNSKSQVFLKLNSLQTDDTATYYCAKGITTV VDDYYAMDYWGQGTSVTVSSGGGGSGGGGSGGGG SGGGGSDIQMTQSPASLSASVGETVTITCRASEN IDSYLAWYQQKQGKSPQLLVYAATFLADDVPSRF SGSGSGTQYSLKINSLQSEDVARYYCQHYYSTPY TFGCGTKLEIKGGGGSGGGGSGGGGSGGGGGGGS GGGGSGGGGSEVQLLESGGGLVQPGGSLRLSCAA SGFTFSTYAMNWVRQAPGKGLEWVSRIRSKYNNY ATYYADSVKGRFTISRDDSKNTLYLQMNSLRAED TAVYYCVRHGNFGNSYVSWFAYWGQGTLVTVSSA SVAAPSVFIFPPSDEQLKSGTASVVCLLNNFYPR EAKVQWKVDNALQSGNSQESVTEQDSKDSTYSLS STLTLSKADYEKHKVYACEVTHQGLSSPVTKSFN RGECDKTHTCPPCPAPEAAGGPSVFLFPPKPKDT LMISRTPEVTCVVVDVSHEDPEVKFNWYVDGVEV HNAKTKPREEQYNSTYRVVSVLTVLHQDWLNGKE YKCKVSNKALGAPIEKTISKAKGQPREPQVYTLP PCRDELTKNQVSLWCLVKGFYPSDIAVEWESNGQ PENNYKTTPPVLDSDGSFFLYSKLTVDKSRWQQG NVFSCSVMHEALHNHYTQKSLSLSP |
| 101 | CD28(SA_variant 8) VL-CH hu IgG1 Fc hole PGLALA | DIQMTQSPSSLSASVGDRVTITCHASQNIYVYLN WYQQKPGKAPKLLIYKASNLHTGVPSRFSGSGSG TDFTLTISSLQPEDFATYYCQQGQTYPYTFGGGT KVEIKSSASTKGPSVFPLAPSSKSTSGGTAALGC LVKDYFPEPVTVSWNSGALTSGVHTFPAVLQSSG LYSLSSVVTVPSSSLGTQTYICNVNHKPSNTKVD KKVEPKSCDKTHTCPPCPAPEAAGGPSVFLFPPK PKDTLMISRTPEVTCVVVDVSHEDPEVKFNWYVD GVEVHNAKTKPREEQYNSTYRVVSVLTVLHQDWL NGKEYKCKVSNKALGAPIEKTISKAKGQPREPQV CTLPPSRDELTKNQVSLSCAVKGFYPSDIAVEWE SNGQPENNYKTTPPVLDSDGSFFLVSKLTVDKSR WQQGNVFSCSVMHEALHNHYTQKSLSLSP |
| 102 | CD28(SA_variant 8) VH-CL | QVQLVQSGAEVKKPGASVKVSCKASGYTFTSYYI HWVRQAPGQGLEWIGSIYPGNVQTNYNEKFKDRA TLTVDTSISTAYMELSRLRSDDTAVYFCTRSHYG LDFNFDVWGQGTTVTVSSASVAAPSVFIFPPSDE QLKSGTASVVCLLNNFYPREAKVQWKVDNALQSG NSQESVTEQDSKDSTYSLSSTLTLSKADYEKHKV YACEVTHQGLSSPVTKSFNRGEC |
| 103 | CD3 (P035.093) VH-CH1 (EE) Fc knob PGLALA | EVQLLESGGGLVQPGGSLRLSCAASGFTFSSYAM NWVRQAPGKGLEWVSRIRSKYNNYATYYADSVKG RFTISRDDSKNTLYLQMNSLRAEDTAVYYCVRAS NFPASYVSYFAYWGQGTLVTVSSASTKGPSVFPL |

TABLE B-continued (Sequences):

| SEQ ID NO: | Name | Sequence |
|---|---|---|
| | | APSSKSTSGGTAALGCLVEDYFPEPVTVSWNSGA LTSGVHTFPAVLQSSGLYSLSSVVTVPSSSLGTQ TYICNVNHKPSNTKVDEKVEPKSCDKTHTCPPCP APEAAGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALGAPI EKTISKAKGQPREPQVYTLPPCRDELTKNQVSLW CLVKGFYPSDIAVEWESNGQPENNYKTTPPVLDS DGSFFLYSKLTVDKSRWQQGNVFSCSVMHEALHN HYTQKSLSLSP |
| 104 | CD3 (P035.093) VL-Ckappa | QAVVTQEPSLTVSPGGTVTLTCGSSTGAVTTSNY ANWVQEKPGQAFRGLIGGTNKRAPGTPARFSGSL LGGKAALTLSGAQPEDEAEYYCALWYSNLWVFGG GTKLTVLGQPKAAPSVTLFPPSSKKLQANKATLV CLISDFYPGAVTVAWKADSSPVKAGVETTTPSKQ SNNKYAASSYLSLTPEQWKSHRSYSCQVTHEGST VEKTVAPTECS |
| 105 | ScFv (4.24.72) VH-(G4S)4-VL-non-cleavable linker-CD3 (P035.093) VH-CH1 hu IgG1 Fc knob PGLALA | QIQLVQSGPELKKPGETVKISCKASGYTVTDYSM NWVKQAPGKCLKWMGWINTETGEPRYTDDFKGRF AFSLETSASTAYLQINNLKNEDSATYFCAREGDY DVFDYWGHGTTLKVSSGGGGSGGGGSGGGGSGGG GSDIVLTQSPASLAVSLGQRATISCRASKSVSTS SYSYMHWYQQKPGQPPKLLIKYVSYLESGVPARF SGSGSGTDFTLNIHPVEEEDAATYYCQHSREFPY TFGCGTKLEIKGGGGSGGGGSGGGGSGGGGGGGS GGGGSGGGGSEVQLLESGGGLVQPGGSLRLSCAA SGFTFSSYAMNWVRQAPGKGLEWVSRIRSKYNNY ATYYADSVKGRFTISRDDSKNTLYLQMNSLRAED TAVYYCVRASNFPASYVSYFAYWGQGTLVTVSSA STKGPSVFPLAPSSKSTSGGTAALGCLVEDYFPE PVTVSWNSGALTSGVHTFPAVLQSSGLYSLSSVV TVPSSSLGTQTYICNVNHKPSNTKVDEKVEPKSC DKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVYTLPPCRD ELTKNQVSLWCLVKGFYPSDIAVEWESNGQPENN YKTTPPVLDSDGSFFLYSKLTVDKSRWQQGNVFS CSVMHEALHNHYTQKSLSLSP |
| 106 | ScFv (4.24.72) VH-(G4S)4-VL-PMAKK-CD3 (P035.093) VH-CH1 hu IgG1 Fc knob PGLALA | QIQLVQSGPELKKPGETVKISCKASGYTVTDYSM NWVKQAPGKCLKWMGWINTETGEPRYTDDFKGRF AFSLETSASTAYLQINNLKNEDSATYFCAREGDY DVFDYWGHGTTLKVSSGGGGSGGGGSGGGGSGGG GSDIVLTQSPASLAVSLGQRATISCRASKSVSTS SYSYMHWYQQKPGQPPKLLIKYVSYLESGVPARF SGSGSGTDFTLNIHPVEEEDAATYYCQHSREFPY TFGCGTKLEIKSGGGSGGGGSPMAKKGGGGSGGG GSGGGGSGGSEVQLLESGGGLVQPGGSLRLSCAA SGFTFSSYAMNWVRQAPGKGLEWVSRIRSKYNNY ATYYADSVKGRFTISRDDSKNTLYLQMNSLRAED TAVYYCVRASNFPASYVSYFAYWGQGTLVTVSSA STKGPSVFPLAPSSKSTSGGTAALGCLVEDYFPE PVTVSWNSGALTSGVHTFPAVLQSSGLYSLSSVV TVPSSSLGTQTYICNVNHKPSNTKVDEKVEPKSC DKTHTCPPCPAPEAAGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALGAPIEKTISKAKGQPREPQVYTLPPCRD ELTKNQVSLWCLVKGFYPSDIAVEWESNGQPENN YKTTPPVLDSDGSFFLYSKLTVDKSRWQQGNVFS CSVMHEALHNHYTQKSLSLSP |
| 107 | CD28(mAb 9.3) CDR-H1 | DYGVH |
| 108 | CD28(mAb 9.3) CDR-H2 | VIWAGGGTNYNSALMS |
| 109 | CD28(mAb 9.3) CDR-H3 | DKGYSYYYSMDY |
| 110 | CD28(mAb 9.3) CDR-L1 | RASESVEYYVTSLMQ |
| 111 | CD28(mAb 9.3) CDR-L2 | AASNVES |

TABLE B-continued (Sequences):

| SEQ ID NO: | Name | Sequence |
|---|---|---|
| 112 | CD28(mAb 9.3) CDR-L3 | QQSRKVPYT |
| 113 | CD28(mAb 9.3) VH | EVKLQQSGPGLVTPSQSLSITCTVSGFSLSDYGV HWVRQSPGQGLEWLGVIWAGGGTNYNSALMSRKS ISKDNSKSQVFLKMNSLQADDTAVYYCARDKGYS YYYSMDYWGQGTSVTVSS |
| 114 | CD28(mAb 9.3) VL | DIELTQSPASLAVSLGQRATISCRASESVEYYVT SLMQWYQQKPGQPPKLLIFAASNVESGVPARFSG SGSGTNFSLNIHPVDEDDVAMYFCQQSRKVPYTF GGGTKLEIK |
| 115 | CDR-H1 (ID_4.32.63) | SYGVS |
| 116 | CDR-H2 (ID_4.32.63) | IIWGDGSTNYHSALIS |
| 117 | CDR-H3 (ID_4.32.63) | GITTVVDDYYAMDY |
| 118 | CDR-L1 (ID_4.32.63) | RASENIDSYLA |
| 119 | CDR-L2 (ID_4.32.63) | AATFLAD |
| 120 | CDR-L3 (ID_4.32.63) | QHYYSTPYT |
| 121 | VH (ID_4.32.63) | QVQLKESGPGLVAPSQSLSITCTVSGFSLTSYGV SWVRQPPGKCLEWLGIIWGDGSTNYHSALISRLS ISKDNSKSQVFLKLNSLQTDDTATYYCAKGITTV VDDYYAMDYWGQGTSVTVSS |
| 122 | VL (ID_4.32.63) | DIQMTQSPASLSASVGETVTITCRASENIDSYLA WYQQKQGKSPQLLVYAATFLADDVPSRFSGSGSG TQYSLKINSLQSEDVARYYCQHYYSTPYTFGCGT KLEIK |
| 123 | CDR-H1 (ID_4.24.72, H1L1, H1L2, H2L2, H3L2, H3L3) | DYSMN |
| 124 | CDR-H2 (ID_4.24.72, H1L1, H1L2) | WINTETGEPRYTDDFKG |
| 125 | CDR-H3 (ID_4.24.72, H1L1, H1L2, H2L2, H3L2, H3L3) | EGDYDVFDY |
| 126 | CDR-L1 (ID_4.24.72, H1L1) | RASKSVSTSSYSYMH |
| 127 | CDR-L2 (ID_4.24.72, H1L1, H1L2, H2L2, H3L2, H3L3) | YVSYLES |
| 128 | CDR-L3 (ID_4.24.72, H1L1, H1L2, H2L2, H3L2) | QHSREFPYT |
| 129 | CDR-L1 (H1L2, H2L2, H3L3) | KSSKSVSTSSYSYMH |
| 130 | CDR-H2 (H2L2) | WINTETGEPRYTDDFTG |
| 131 | CDR-H2 (H3L2) | WINTETGEPRYTQGFKG |
| 132 | CDR-L3 (H3L3) | QQSREFPYT |
| 133 | ID_4.24.72 VH | QIQLVQSGPELKKPGETVKISCKASGYTVTDYSM NWVKQAPGKCLKWMGWINTETGEPRYTDDFKGRF AFSLETSASTAYLQINNLKNEDSATYFCAREGDY DVFDYWGHGTTLKVSS |
| 134 | ID_4.24.72 VL | DIVLTQSPASLAVSLGQRATISCRASKSVSTSSY SYMHWYQQKPGQPPKLLIKYVSYLESGVPARFSG SGSGTDFTLNIHPVEEEDAATYYCQHSREFPYTF GCGTKLEIK |
| 135 | H1L1, H1L2 VH | QVQLVQSGSELKKPGASVKVSCKASGYTVTDYSM NWVRQAPGQGLEWMGWINTETGEPRYTDDFKGRF VFSLDTSVSTAYLQISSLKAEDTAVYYCAREGDY DVFDYWGQGTLVTVSS |

TABLE B-continued

| SEQ ID NO: | Name | Sequence |
|---|---|---|
| | (Sequences): | |
| 136 | H1L1 VL | DIVMTQSPDSLAVSLGERATINCRASKSVSTSSY SYMHWYQQKPGQPPKLLIKYVSYLESGVPDRFSG SGSGTDFTLTISSLQAEDVAVYYCQHSREFPYTF GQGTKLEIK |
| 137 | H1L2, H2L2 VL | DIVMTQSPDSLAVSLGERATINCKSSKSVSTSSY SYMHWYQQKPGQPPKLLIKYVSYLESGVPDRFSG SGSGTDFTLTISSLQAEDVAVYYCQHSREFPYTF GQGTKLEIK |
| 138 | H2L2 VH | QVQLVQSGSELKKPGASVKVSCKASGYTVTDYSM NWVRQAPGQGLEWMGWINTETGEPRYTDDFTGRF VFSLDTSVSTAYLQISSLKAEDTAVYYCAREGDY DVFDYWGQGTLVTVSS |
| 139 | H3L3 VH | QVQLVQSGSELKKPGASVKVSCKASGYTVTDYSM NWVRQAPGQGLEWMGWINTETGEPRYTQGFKGRF VFSLDTSVSTAYLQISSLKAEDTAVYYCAREGDY DVFDYWGQGTLVTVSS |
| 140 | H3L3 VL | DIVMTQSPDSLAVSLGERATINCRASKSVSTSSY SYMHWYQQKPGQPPKLLIKYVSYLESGVPDRESG SGSGTDFTLTISSLQAEDVAVYYCQQSREFPYTF GQGTKLEIK |
| 141 | H7L5 VH | QVQLVQSGAEVKKPGASVKVSCKASGYTVTDYSM NWVRQAPGQGLEWMGWINTETGEPRYTDDFKGRV TMTRDTSISTAYMELSRLRSDDTAVYYCAREGDY DVFDYWGQGTLVTVSS |
| 142 | H7L5 VL | DIVMTQSPDSLAVSLGERATINCRASKSVSTSSY SYMHWYQQKPGQPPKLLIYYVSYLESGVPDRFSG SGSGTDFTLTISSLQAEDVAVYYCQHSREFPYTF GQGTKLEIK |
| 143 | H1L1 scFv | QVQLVQSGSELKKPGASVKVSCKASGYTVTDYSM NWVRQAPGQCLEWMGWINTETGEPRYTDDFKGRF VFSLDTSVSTAYLQISSLKAEDTAVYYCAREGDY DVFDYWGQGTLVTVSSGGGGSGGGGSGGGGSGGG GSDIVMTQSPDSLAVSLGERATINCRASKSVSTS SYSYMHWYQQKPGQPPKLLIKYVSYLESGVPDRF SGSGSGTDFTLTISSLQAEDVAVYYCQHSREFPY TFGCGTKLEIK |
| 144 | H1L2 scFv | QVQLVQSGSELKKPGASVKVSCKASGYTVTDYSM NWVRQAPGQCLEWMGWINTETGEPRYTDDFKGRF VFSLDTSVSTAYLQISSLKAEDTAVYYCAREGDY DVFDYWGQGTLVTVSSGGGGSGGGGSGGGGSGGG GSDIVMTQSPDSLAVSLGERATINCKSSKSVSTS SYSYMHWYQQKPGQPPKLLIKYVSYLESGVPDRF SGSGSGTDFTLTISSLQAEDVAVYYCQHSREFPY TFGCGTKLEIK |
| 145 | H2L2 scFv | QVQLVQSGSELKKPGASVKVSCKASGYTVTDYSM NWVRQAPGQCLEWMGWINTETGEPRYTDDFTGRF VFSLDTSVSTAYLQISSLKAEDTAVYYCAREGDY DVFDYWGQGTLVTVSSGGGGSGGGGSGGGGSGGG GSDIVMTQSPDSLAVSLGERATINCKSSKSVSTS SYSYMHWYQQKPGQPPKLLIKYVSYLESGVPDRF SGSGSGTDFTLTISSLQAEDVAVYYCQHSREFPY TFGCGTKLEIK |
| 146 | H3L2 scFv | QVQLVQSGSELKKPGASVKVSCKASGYTVTDYSM NWVRQAPGQCLEWMGWINTETGEPRYTQGFKGRF VFSLDTSVSTAYLQISSLKAEDTAVYYCAREGDY DVFDYWGQGTLVTVSSGGGGSGGGGSGGGGSGGG GSDIVMTQSPDSLAVSLGERATINCKSSKSVSTS SYSYMHWYQQKPGQPPKLLIKYVSYLESGVPDRF SGSGSGTDFTLTISSLQAEDVAVYYCQHSREFPY TFGCGTKLEIK |
| 147 | 4.32.63 scFv | QVQLKESGPGLVAPSQSLSITCTVSGFSLTSYGV SWVRQPPGKCLEWLGIIWGDGSTNYHSALISRLS ISKDNSKSQVFLKLNSLQTDDTATYYCAKGITTV |

TABLE B-continued

| (Sequences): | | |
|---|---|---|
| SEQ ID NO: | Name | Sequence |
| | | VDDYYAMDYWGQGTSVTVSSGGGGSGGGGSGGGG SGGGGSDIQMTQSPASLSASVGETVTITCRASEN IDSYLAWYQQKQGKSPQLLVYAATFLADDVPSRF SGSGSGTQYSLKINSLQSEDVARYYCQHYYSTPY TFGCGTKLEIK |
| 148 | Protease recognition site 1 | RQARVVNG |
| 149 | Protease recognition site 2 | VHMPLGFLGPGRSRGSFP |
| 150 | Protease recognition site 3 | RQARVVNGXXXXXVPLSLYSG |
| 151 | Protease recognition site 4 | RQARVVNGVPLSLYSG |
| 152 | Protease recognition site 5 | PLGLWSQ |
| 153 | Protease recognition site 6 | VHMPLGFLGPRQARVVNG |
| 154 | Protease recognition site 7 | FVGGTG |
| 155 | Protease recognition site 8 | KKAAPVNG |
| 156 | Protease recognition site 9 | PMAKKVNG |
| 157 | Protease recognition site 10 | QARAKVNG |
| 158 | Protease recognition site 11 | VHMPLGFLGP |
| 159 | Protease recognition site 12 | QARAK |
| 160 | Protease recognition site 13 | VHMPLGFLGPPMAKK |
| 161 | Protease recognition site 14 | KKAAP |
| 162 | Protease recognition site 15 | PMAKK |
| 163 | non-cleavable linker | GGGGSGGGGSGGGGSGGGGGGGSGGGGSGGGGS |
| 164 | human Matriptase UniProt Q9Y5Y6 | MGSDRARKGGGGPKDFGAGLKYNSRHEKVNGLEE GVEFLPVNNVKKVEKHGPGRWVVLAAVLIGLLLV LLGIGFLVWHLQYRDVRVQKVENGYMRITNENFV DAYENSNSTEFVSLASKVKDALKLLYSGVPFLGP YHKESAVTAFSEGSVIAYYWSEFSIPQHLVEEAE RVMAEERVVMLPPRARSLKSFVVTSVVAFPTDSK TVQRTQDNSCSFGLHARGVELMRFTTPGFPDSPY PAHARCQWALRGDADSVLSLTFRSFDLASCDERG SDLVTVYNTLSPMEPHALVQLCGTYPPSYNLTFH SSQNVLLITLITNTERRHPGFEATFFQLPRMSSC GGRLRKAQGTFNSPYYPGHYPPNIDCTWNIEVPN NQHVKVRFKFFYLLEPGVPAGTCPKDYVEINGEK YCGERSQFVVTSNSNKITVRFHSDQSYTDTGFLA EYLSYDSSDPCPGQFTCRTGRCIRKELRCDGWAD CTDHSDELNCSCDAGHQFTCKNKFCKPLFWVCDS VNDCGDNSDEQGCSCPAQTFRCSNGKCLSKSQQC NGKDDCGDGSDEASCPKVNVVTCTKHTYRCLNGL CLSKGNPECDGKEDCSDGSDEKDCDCGLRSFTRQ ARVVGGTDADEGEWPWQVSLHALGQGHICGASLI SPNWLVSAAHCYIDDRGFRYSDPTQWTAFLGLHD QSQRSAPGVQERRLKRIISHPFFNDFTFDYDIAL LELEKPAEYSSMVRPICLPDASHVFPAGKAIWVT GWGHTQYGGTGALILQKGEIRVINQTTCENLLPQ QITPRMMCVGFLSGGVDSCQGDSGGPLSSVEADG RIFQAGVVSWGDGCAQRNKPGVYTRLPLFRDWIK ENTGV |
| 165 | IgG CH1 domain | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKV |
| 166 | IgG CH2 domain | APELLGGPSVFLFPPKPKDTLMISRTPEVTCVWD VSHEDPEVKFNWYVDGVEVHNAKTPREEQESTY RWSVLTVLHQDWLNGKEYKCKVSNKALPAPIEKT ISKAK |

TABLE B-continued (Sequences):

| SEQ ID NO: | Name | Sequence |
|---|---|---|
| 167 | IgG CH3 domain | GQPREPQVYTLPPSRDELTKNQVSLTCLVKGFYP SDIAVEWESNGQPENNYKTTPPVLDSDGSFFLYS KLTVDKSRWQQGNVFSCSVMHEALHNHYTQKSLS LSPG |
| 168 | CH1 connector | EPKSC |
| 169 | Hinge full | DKTHTCPXCP with X being S or P |
| 170 | Hinge middle | HTCPXCP with X being S or P |
| 171 | Hinge short | CPXCP with X being S or P |
| 172 | IgG1, caucasian allotype | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR DELTKNQVSLTCLVKGFYPSDIAVEWESNGQPEN NYKTTPPVLDSDGSFFLYSKLTVDKSRWQQGNVF SCSVMHEALHNHYTQKSLSLSPGK |
| 173 | IgG1, afroamerican allotype | ASTKGPSVFPLAPSSKSTSGGTAALGCLVKDYFP EPVTVSWNSGALTSGVHTFPAVLQSSGLYSLSSV VTVPSSSLGTQTYICNVNHKPSNTKVDKKVEPKS CDKTHTCPPCPAPELLGGPSVFLFPPKPKDTLMI SRTPEVTCVVVDVSHEDPEVKFNWYVDGVEVHNA KTKPREEQYNSTYRVVSVLTVLHQDWLNGKEYKC KVSNKALPAPIEKTISKAKGQPREPQVYTLPPSR EEMTKNQVSLTCLVKGFYPSDIAVEWESNGQPEN NYKTTPPVLDSDGSFFLYSKLTVDKSRWQQGNVF SCSVMHEALHNHYTQKSLSLSPGK |
| 174 | IgG2 | ASTKGPSVFPLAPCSRSTSESTAALGCLVKDYFP EPVTVSWNSGALTSGVHTFPAVLQSSGLYSLSSV VTVPSSNFGTQTYTCNVDHKPSNTKVDKTVERKC CVECPPCPAPPVAGPSVFLFPPKPKDTLMISRTP EVTCVVVDVSHEDPEVQFNWYVDGVEVHNAKTKP REEQFNSTFRVVSVLTVVHQDWLNGKEYKCKVSN KGLPAPIEKTISKTKGQPREPQVYTLPPSREEMT KNQVSLTCLVKGFYPSDISVEWESNGQPENNYKT TPPMLDSDGSFFLYSKLTVDKSRWQQGNVFSCSV MHEALHNHYTQKSLSLSPGK |
| 175 | IgG3 | ASTKGPSVFPLAPCSRSTSGGTAALGCLVKDYFP EPVTVSWNSGALTSGVHTFPAVLQSSGLYSLSSV VTVPSSSLGTQTYTCNVNHKPSNTKVDKRVELKT PLGDTTHTCPRCPEPKSCDTPPPCPRCPEPKSCD TPPPCPRCPEPKSCDTPPPCPRCPAPELLGGPSV FLFPPKPKDTLMISRTPEVTCVVVDVSHEDPEVQ FKWYVDGVEVHNAKTKPREEQYNSTFRVVSVLTV LHQDWLNGKEYKCKVSNKALPAPIEKTISKTKGQ PREPQVYTLPPSREEMTKNQVSLTCLVKGFYPSD IAVEWESSGQPENNYNTTPPMLDSDGSFFLYSKL TVDKSRWQQGNIFSCSVMHEALHNRFTQKSLSLS PGK |
| 176 | IgG4 | ASTKGPSVFPLAPCSRSTSESTAALGCLVKDYFP EPVTVSWNSGALTSGVHTFPAVLQSSGLYSLSSV VTVPSSSLGTKTYTCNVDHKPSNTKVDKRVESKY GPPCPSCPAPEFLGGPSVFLFPPKPKDTLMISRT PEVTCVVVDVSQEDPEVQFNWYVDGVEVHNAKTK PREEQFNSTYRVVSVLTVLHQDWLNGKEYKCKVS NKGLPSSIEKTISKAKGQPREPQVYTLPPSQEEM TKNQVSLTCLVKGFYPSDIAVEWESNGQPENNYK TTPPVLDSDGSFFLYSRLTVDKSRWQEGNVFSCS VMHEALHNHYTQKSLSLSLGK |
| 177 | human FcγRIIIa UniProt accession no. P08637 | MWQLLLPTALLLLVSAGMRTEDLPKAVVFLEPQW YRVLEKDSVTLKCQGAYSPEDNSTQWFHNESLIS SQASSYFIDAATVDDSGEYRCQTNLSTLSDPVQL EVHIGWLLLQAPRWVFKEEDPIHLRCHSWKNTAL |

TABLE B-continued

| SEQ ID NO: | Name | Sequence |
|---|---|---|
| | | HKVTYLQNGKGRKYFHHNSDFYIPKATLKDSGSY FCRGLFGSKNVSSETVNITITQGLAVSTISSFFP PGYQVSFCLVMVLLFAVDTGLYFSVKTNIRSSTR DWKDHKFKWRKDPQDK |
| 178 | Peptide linker (G4S) | GGGGS |
| 179 | Peptide linker (G4S)2 | GGGGSGGGGS |
| 180 | Peptide linker (SG4)2 | SGGGGSGGGG |
| 181 | Peptide linker G4(SG4)2 | GGGGSGGGGSGGGG |
| 182 | peptide linker | GSPGSSSSGS |
| 183 | (G4S)3 peptide linker | GGGGSGGGGSGGGGS |
| 184 | (G4S)4 peptide linker | GGGGSGGGGSGGGGSGGGGS |
| 185 | peptide linker | GSGSGSGS |
| 186 | peptide linker | GSGSGNGS |
| 187 | peptide linker | GGSGSGSG |
| 188 | peptide linker | GGSGSG |
| 189 | peptide linker | GGSG |
| 190 | peptide linker | GGSGNGSG |
| 191 | peptide linker | GGNGSGSG |
| 192 | peptide linker | GGNGSG |
| 193 | peptide linker | EPKSCGGGGSGGGGS |
| 194 | peptide linker | EPKSCDGGGGSGGGGS |
| 195 | Matriptase linker | SGGGSGGGGSPMAKKGGGGSGGGGSGGGGSGGS |
| 196 | Linker 2 | GGGGSVHMPLGFLGPRQARVVNGGGGGSGGGGS |
| 197 | Linker 3 | GGGGSGGGGSRQARVVNGGGGGSGGGGSGGGGS |
| 198 | MMP Protease linker | GGGGSGGGGSGPLGLWSQGGGGSGGGGSGGGGSG G |
| 199 | Combined MMP9 MK062, 33 AA for CD3 | GGGGSVHMPLGFLGPRQARVVNGGGGGSGGGGS |
| 200 | Cathepsin S/B | GGGGSGGGGSGGGGSFVGGTGGGGSGGGGSGGS |
| 201 | KKAAPVNG | GGGGSGGGGSKKAAPVNGGGGGSGGGGSGGGGS |
| 202 | PMAKKVNG | GGGGSGGGGSPMAKKVNGGGGGSGGGGSGGGGS |
| 203 | QARAKVNG | GGGGSGGGGSQARAKVNGGGGGSGGGGSGGGGS |
| 204 | MMP9 | GGGGSGGGGSVHMPLGFLGPGGGGSGGGGSGGS |
| 205 | QARAK | GGGGSGGGGSQARAKGGGGSGGGGSGGGGSGGS |
| 206 | MMP9-PMAKK | GGGGSVHMPLGFLGPPMAKKGGGGSGGGGSGGS |
| 207 | KKAAP | GGGGSGGGGSKKAAPGGGGSGGGGSGGGGSGGS |
| 208 | PMAKK | GGGGSGGGGSPMAKKGGGGSGGGGSGGGGSGGS |
| 209 | Combined NF9/Mat5 linker | GGGGSVHMPLGFLGPGRSRGSFPGGGGS |
| 210 | Combined MK062 MMP9 | GGGGSGGGGSRQARVVNGGGGGSVPLSLYSGGGG GSGGGGS |

TABLE B-continued (Sequences):

| SEQ ID NO: | Name | Sequence |
|---|---|---|
| 211 | Combined MK062-MMP9 | GGGGSGGGGSRQARVVNGVPLSLYSGGGGGSGGGGS |
| 212 | 4.24.72 scFv | QIQLVQSGPELKKPGETVKISCKASGYTVTDYSMNWVKQAPGKCLKWMGWINTETGEPRYTDDFKGRFAFSLETSASTAYLQINNLKNEDSATYFCAREGDYDVFDYWGHGTTLKVSSGGGGSGGGGSGGGGSGGGGSDIVLTQSPASLAVSLGQRATISCRASKSVSTSSYSYMHWYQQKPGQPPKLLIKYVSYLESGVPARFSGSGSGTDFTLNIHPVEEEDAATYYCQHSREFPYTFGCGTKLEIK |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, MD (1991)) as defined above.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments, where required, were either generated by PCR using appropriate templates or were synthesized at GENEART™ AG (Regensburg, Germany) or Genscript® (New Jersey, USA) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A SEPHAROSE™ column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS™ Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel® G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or TRIS® buffer at 37° C. for up to 17 h at a protein concentration of 1 mg/ml. The plasmin or limited LysC (Roche) digestions were performed with 100 µg deglycosylated VH/VL CrossMabs in a TRIS® buffer pH 8 at room temperature for 120 hours and at 37° C. for 40 min, respectively. Prior to mass spectrometry the samples were desalted via HPLC on a SEPHADEX® G25 column (GE Healthcare). The total mass was determined via ESI-MS on a maXis™ 4G UHR-QTOF MS system (Bruker Daltonik) equipped with a TriVersa NanoMate source (Advion).

Determination of Binding and Binding Affinity of Multispecific Antibodies to the Respective Antigens Using Surface Plasmon Resonance (SPR) (BIACORE™)

Binding of the generated antibodies to the respective antigens is investigated by surface plasmon resonance using a BIACORE™ instrument (GE Healthcare Biosciences AB, Uppsala, Sweden). Briefly, for affinity measurements Goat-Anti-Human IgG, JIR 109-005-098 antibodies are immobilized on a CM5 chip via amine coupling for presentation of the antibodies against the respective antigen. Binding is measured in HBS buffer (HBS-P (10 mM HEPES, 150 mM NaCl, 0.005% TWEEN® 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective BIACORE™ Evaluation Software is used for analysis of sensorgrams and for calculation of affinity data.

Example 1

Generation and Production of Bispecific Antigen Binding Molecules Targeting CD28 and CD3

1.1 Generation of Anti-CD28 Antibodies

Cloning of the Antigen:

A DNA fragment encoding the extracellular domain (amino acids 1 to 134 of matured protein) of human CD28 (UNIPROT®: P10747) was inserted in frame into two different mammalian recipient vectors upstream of a fragment encoding a hum IgG1 Fc fragment which serves as solubility- and purification tag. One of the expression vectors contained the “hole” mutations in the Fc region, the other one the “knob” mutations as well as a C-terminal avi tag (GLNDIFEAQKIEWHE, SEQ ID NO:88) allowing specific biotinylation during co-expression with Bir A biotin ligase. In addition, both Fc fragments contained the PG-LALA mutations. Both vectors were co-transfected in combination with a plasmid coding for the BirA biotin ligase in order to get a dimeric CD28-Fc construct with a monovalent biotinylated avi-tag at the C-terminal end of the Fc-knob chain.

Generation and Characterization of CD28 (SA) Variants Devoid of Hotspots and Reduced in Affinity The CD28 superagonistic antibody (SA) with a VH comprising the amino acid sequence of SEQ ID NO:24 and a VL comprising the amino acid sequences of SEQ ID NO:25 is described in WO 2006/050949.

Removal of an Unpaired Cysteine Residue, Tryptophan Residues, a Deamidation Site and Generation of Affinity-Reduced CD28 (SA) Variants As part of our detailed binder characterization, a computational analysis of the CD28 (SA) variable domain sequences was performed. This analysis revealed an unpaired cysteine in the CDR2 region of VH (position 50, Kabat numbering), tryptophan residues in CDR3 of VH (position 100a, Kabat numbering) and CDR1 of VL (position 32, Kabat numbering), and a potential asparagine deamidation site in CDR2 of VH (position 56, Kabat numbering). While oxidation of tryptophan is a rather slow process and can be prevented by adding reducing compounds, the presence of unpaired cysteines in an antibody variable domain can be critical.

Figures 2A, 2B, 2C, 2D:
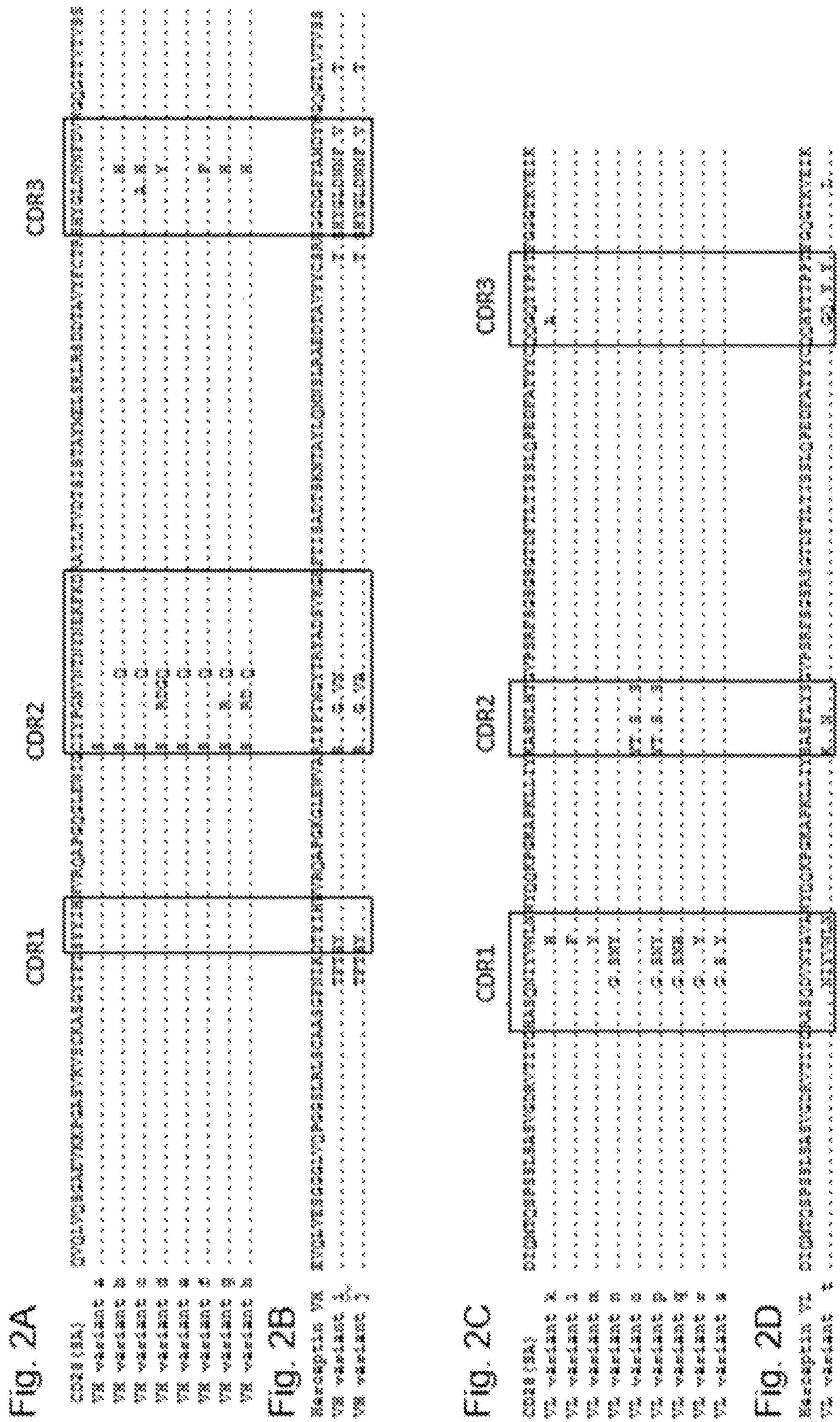
In FIG. 2C, alignment of the CD28 (SA) VL domain and variants thereof in order to reduce the affinity of the resulting anti-CD28 binders to different degrees is shown. In variant t, the CDRs were grafted into the framework sequence of the trastuzumab (Herceptin) VL sequence (FIG. 2D).

Free cysteines are reactive and can form stable bonds with other unpaired cysteines of other proteins or components of the cell or media. As a consequence, this can lead to a heterogeneous and instable product with unknown modifications which are potentially immunogenic and therefore may pose a risk for the patients. In addition, deamidation of asparagine and the resulting formation of iso-aspartate and succinimide can affect both in vitro stability and in vivo biological functions. A crystal structure analysis of the parental murine binder 5.11A revealed that C50 is not involved in binding to human CD28 and therefore can be replaced by a similar amino acid such as serine without affecting the affinity to CD28. Both tryptophan residues as well as asparagine at position 50, however, are close to or involved in the binding interface and a replacement by a similar amino acid can therefore lead to a reduction of the binding affinity. In this example, we particularly aimed at reducing the affinity of CD28 (SA) to human CD28 because of the following reason: The affinity of CD28 (SA) is in the range of 1-2 nM with a binding half-life of about 32 minutes. This strong affinity can lead to a sink effect in tissue containing large amounts of CD28-expressing cells such as blood and lymphatic tissue when injected intravenously into patients. As a consequence, site-specific targeting of the compound via the targeting component may be reduced and the efficacy of the construct can be diminished. In order to minimize such an effect, several VH and VL variants were generated in order to reduce to affinities to different degrees (FIGS. 2A and 2C). Besides the previously mentioned positions that represent potential stability hotspots, additional residues involved directly or indirectly in the binding to human CD28 were replaced either by the original murine germline amino acid or by a similar amino acid. In addition, the CDRs of both CD28 (SA) VL and VH were also grafted into the respective framework sequences of trastuzumab (FIGS. 2B and 2D).

Several combinations of VH and VL variants were then expressed as monovalent one-armed anti-CD28 IgG-like constructs and binding was characterized by SPR.

Analysis of the dissociation rate constants (koff) of reduced one-armed anti-CD28 variants by SPR In order to characterize the anti-CD28 binder variants in a first step, all binders were expressed as monovalent one-armed IgG-like constructs (FIG. 1A). This format was chosen in order to characterize the binding to CD28 in a 1:1 model. 5 days after transfection into HEK cells, the supernatant was harvested and the titer of the expressed constructs was determined.

The off-rate of the anti-CD28 binder variants was determined by surface plasmon resonance (SPR) using a PROTEON™ XPR36 instrument (Biorad) at 25° C. with biotinylated huCD28-Fc antigen immobilized on NLC chips by neutravidin capture. For the immobilization of recombinant antigen (ligand), huCD28-Fc was diluted with PBST (Phophate buffered saline with TWEEN® 20 consisting of 10 mM phosphate, 150 mM sodium chloride pH 7.4, 0.005% TWEEN® 20) to concentrations ranging from 100 to 500 nM, then injected at 25 µl/minute at varying contact times. This resulted in immobilization levels between 1000 to 3000 response units (RU) in vertical orientation.

For one-shot kinetics measurements, injection direction was changed to horizontal orientation. Based on the titer of the produced supernatants, the monovalent one-armed IgGs were diluted with PBST to get two-fold dilution series ranging from 100 nM to 6.25 nM. Injection was performed simultaneously at 50 µl/min along separate channels 1-5, with association times of 120s, and dissociation times of 300s. Buffer (PBST) was injected along the sixth channel to provide an "in-line" blank for referencing. Since the binding interaction was measured with monovalent one-armed IgGs from supernatant without purification and biochemical characterization, only the off-rates of the protein: protein interaction was used for further conclusions. Off-rates were calculated using a simple one-to-one Langmuir binding model in PROTEON™ Manager v3.1 software by fitting the dissociation sensorgrams. The dissociation rate constants (koff) values of all clones are summarized in Table 1. Comparison of the produced variants revealed koff values with an up to 30-fold decrease compared to the parental sequence.

TABLE 1

Summary of all expressed monovalent anti-CD28 variants with dissociation rate constants ($K_{off}$) values

| Binder variants | ID | SEQ ID NO: | SEQ ID NO: | SEQ ID NO: | $k_{off}$ ($10^{-4}$/M) |
|---|---|---|---|---|---|
| CD28(SA)_variant_1 (parental CD28) | P1AE4441 | 72 | 80 | 87 | 3.0 |
| CD28(SA)_variant_2 | P1AE3058 | 73 | 81 | 87 | N/A |
| CD28(SA)_variant_3 | P1AE3059 | 73 | 82 | 87 | N/A |
| CD28(SA)_variant_4 | P1AE3060 | 73 | 83 | 87 | N/A |
| CD28(SA)_variant_5 | P1AE3061 | 73 | 80 | 87 | N/A |
| CD28(SA)_variant_6 | P1AE3062 | 74 | 81 | 87 | N/A |
| CD28(SA)_variant_7 | P1AE3063 | 74 | 82 | 87 | 100 |
| CD28(SA)_variant_8 | P1AE3064 | 74 | 83 | 87 | 68 |
| CD28(SA)_variant_9 | P1AE3065 | 74 | 84 | 87 | 78 |
| CD28(SA)_variant_10 | P1AE3066 | 74 | 85 | 87 | N/A |
| CD28(SA)_variant_11 | P1AE3067 | 74 | 80 | 87 | 37 |
| CD28(SA)_variant_12 | P1AE3068 | 75 | 86 | 87 | 2.4 |
| CD28(SA)_variant_13 | P1AE3069 | 75 | 80 | 87 | 1.9 |
| CD28(SA)_variant_14 | P1AE3070 | 76 | 81 | 87 | 100 |
| CD28(SA)_variant_15 | P1AE3071 | 76 | 82 | 87 | 24 |
| CD28(SA)_variant_16 | P1AE3072 | 76 | 83 | 87 | 10 |
| CD28(SA)_variant_17 | P1AE3073 | 76 | 84 | 87 | 14 |
| CD28(SA)_variant_18 | P1AE3074 | 76 | 85 | 87 | 82 |
| CD28(SA)_variant_19 | P1AE3075 | 76 | 80 | 87 | 2.9 |
| CD28(SA)_variant_20 | P1AE3076 | 77 | 81 | 87 | N/A |
| CD28(SA)_variant_21 | P1AE3077 | 77 | 82 | 87 | N/A |
| CD28(SA)_variant_22 | P1AE3078 | 77 | 83 | 87 | 61 |
| CD28(SA)_variant_23 | P1AE3079 | 77 | 80 | 87 | 43 |
| CD28(SA)_variant_24 | P1AE3080 | 78 | 81 | 87 | 80 |
| CD28(SA)_variant_25 | P1AE3081 | 78 | 82 | 87 | 3.51 |
| CD28(SA)_variant_26 | P1AE3082 | 78 | 83 | 87 | 9.7 |
| CD28(SA)_variant_27 | P1AE3083 | 78 | 84 | 87 | 14 |
| CD28(SA)_variant_28 | P1AE3084 | 78 | 85 | 87 | 69 |
| CD28(SA)_variant_29 | P1AE3085 | 78 | 80 | 87 | 2.5 |
| CD28(SA)_variant_30 | P1AE3086 | 79 | 86 | 87 | 3.22 |
| CD28(SA)_variant_31 | P1AE3087 | 79 | 80 | 87 | 2.5 |

Figure 3B:
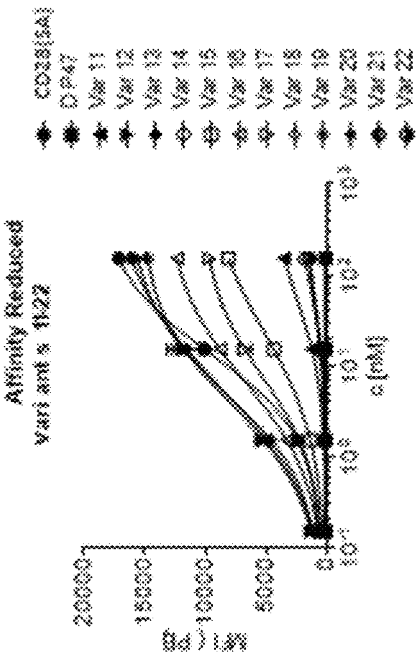
In FIG. 3A to 3C the binding of affinity-reduced CD28 agonistic antibody variants in monospecific, monovalent IgG formats from supernatants to human CD28 on cells is shown. Median fluorescence intensities of binding to CHO cells expressing human CD28 (parental cell line CHO-k1 ATCC® #CCL-61, modified to stably overexpress human CD28) compared to the negative control (anti-DP47) and the original CD28 antibody CD28 (SA), were assessed by flow cytometry. The binding curves of variants 1-10 are shown in FIG. 3A, those of variants 11 to 22 in FIG. 3B and those of variants 23 to 31 in FIG. 3C. Depicted are technical duplicates with SD.
Figure 3A:
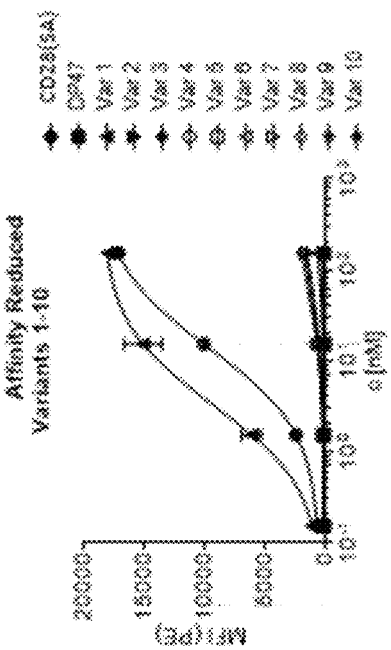
Figure 3C:
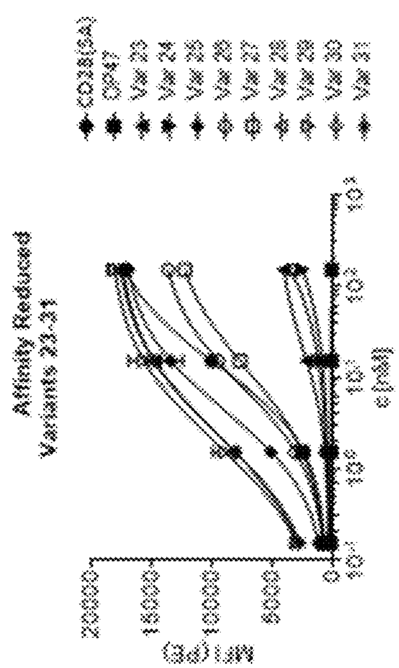

Binding to human CD28 was tested with CHO cells expressing human CD28 (parental cell line CHO-k1 ATCC® #CCL-61, modified to stably overexpress human CD28). To assess binding, cells were harvested, counted, checked for viability and re-suspended at $2.5\times10^5$/ml in FACS buffer (eBioscience, Cat No 00-4222-26). $5\times10^4$ cells were incubated in round-bottom 96-well plates for 2 h at 4° C. with increasing concentrations of the CD28 binders (1 µM-100 nM). Then, cells were washed three times with cold FACS buffer, incubated for further 60 min at 4° C. with PE-conjugated, goat-anti human PE (Jackson ImmunoReserach, Cat No 109-116-098), washed once with cold FACS buffer, centrifuged and resuspended in 100 µl FACS buffer. To monitor unspecific binding interactions between constructs and cells, an anti-DP47 IgG was included as negative control. Binding was assessed by flow cytometry with a FACS Fortessa (BD, Software FACSDiva™). Binding curves were obtained using GraphPadPrism6. The monovalent one-armed IgG-like CD28 variant constructs showed differences in binding as can be seen from FIG. 3A to 3C.

1.2 Preparation of Bispecific Antigen Binding Molecules Targeting CD3 and CD28

Cloning of Bispecific Antigen Binding Molecules Targeting CD3 and CD28

For the generation of the expression plasmids, the sequences of the respective variable domains were used and sub-cloned in frame with the respective constant regions which are pre-inserted in the respective recipient mammalian expression vector. In the Fc domain, Pro329Gly, Leu234Ala and Leu235Ala mutations (PG-LALA) have been introduced in the constant region of the human IgG1 heavy chains to abrogate binding to Fc gamma receptors according to the method described in International Patent Appl. Publ. No. WO 2012/130831. For the generation of bispecific antibodies, Fc fragments contained either the "knob" (S354C/T366W mutations, numbering according to Kabat EU index) or "hole" mutations (Y349C/T366S/L368A/Y407V mutations according to Kabat EU index) to avoid mispairing of the heavy chains. In order to avoid mispairing of light chains in the bispecific antigen binding molecules, exchange of VH/VL or CH1/Ckappa domains was introduced in one binding moiety (CrossFab technology). In another binding moiety, charges were introduced into the CH1 and Ckappa domains as described in International Patent Appl. Publ. No. WO 2015/150447.

Figure 1C:
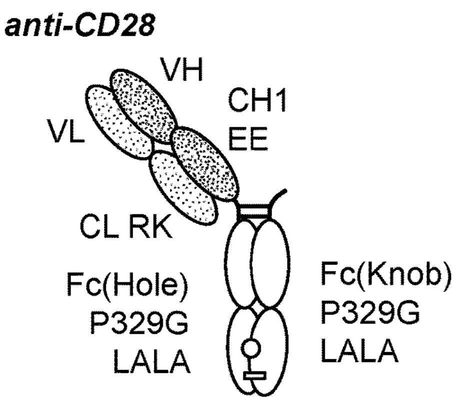

The following molecules were cloned, a schematic illustration thereof is shown in FIG. 1B to 1I:

- Molecule 1: CD28 (9.3)-CD3 (CH2527) 1+1 format, bispecific huIgG1 PG-LALA CrossFab molecule with VH/VL exchange in the CD3 (CH2527) Fab fragment (knob) and charged modifications in the CD28 (9.3) Fab fragment (hole) (FIG. 1B) comprising the heavy chain amino acid sequences of SEQ ID NOs: 89 and 91 and the light chain amino acid sequences of SEQ ID NOs: 90 and 92 (P1AD8935).
- Molecule 2: CD28 (SA)-CD3 (CH2527) 1+1 format, bispecific huIgG1 PG-LALA CrossFab molecule with VH/VL exchange in the CD3 (CH2527) Fab fragment (knob) and charged modifications in the CD28 (SA) Fab fragment (hole) (FIG. 1B) comprising the heavy chain amino acid sequences of SEQ ID NOs: 89 and 93 and the light chain amino acid sequences of SEQ ID NOs: 90 and 94 (P1AD8942).
- Molecule 3: CD28 (9.3) monospecific huIgG1 PG-LALA, monovalent anti-CD28 (9.3) huIgG1 PG-LALA construct, wherein the CD28 heavy chain is expressed as a "hole" Fc chain in combination with a Fc (knob) fragment (FIG. 1C). The molecule comprises the amino acid sequences of SEQ ID NOs: 91, 92 and 95 (P1AD8938).

Molecule 4: CD28 (SA) monospecific huIgG1 PG-LALA, monovalent anti-CD28 (SA) huIgG1 PG-LALA construct, wherein the CD28 heavy chain is expressed as a "hole" Fc chain in combination with a Fc (knob) fragment (FIG. 1C). The molecule comprises the amino acid sequences of SEQ ID NOs: 93, 94 and 95 (P1AD8944).

Figure 1D:
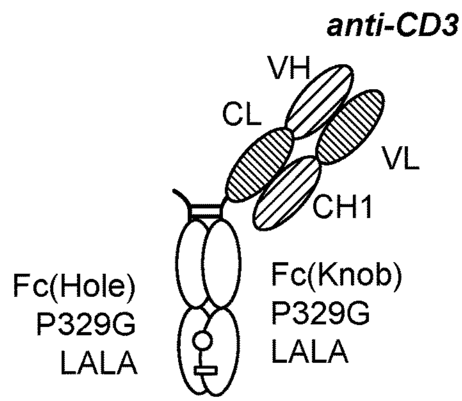

Molecule 5: CD3 (CH2527) monospecific huIgG1 PG-LALA, monovalent anti-CD3 (CH2527) huIgG1 PG-LALA construct, wherein the CD3 heavy chain is expressed as a "knob" Fc chain in combination with a Fc (hole) fragment (FIG. 1D). The molecule comprises the amino acid sequences of SEQ ID NOs: 89, 90 and 96 (P1AD8939).

Figure 1E:
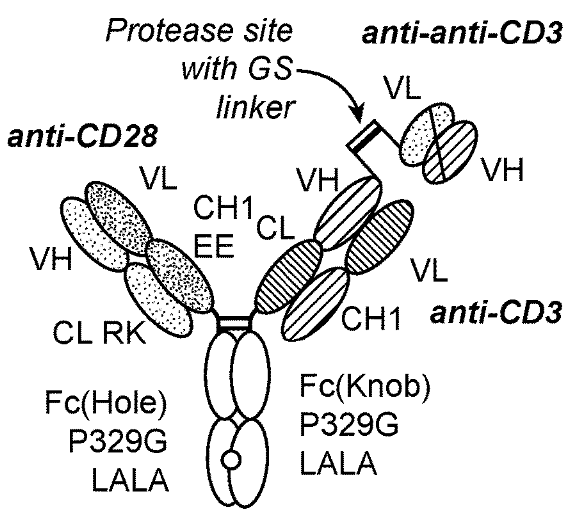

Molecule 6: masked CD28 (9.3)-CD3 (CH2527) 1+1 format, bispecific huIgG1 PG-LALA CrossFab molecule with VH/VL exchange in the CD3 (CH2527) Fab fragment (knob) and charged modifications in the CD28 (9.3) Fab fragment (hole), wherein the CD3 is masked with anti-idiotypic CD3 scFv 4.24.72 and a cleavable linker (masked 4.24.72_RQARVVNG site, MK062 Matriptase site) (FIG. 1E). The molecule comprises the heavy chain amino acid sequences of SEQ ID NOs: 98 and 97 and the light chain amino acid sequences of SEQ ID NOs: 90 and 92 (P1AD8987).

Molecule 7: masked CD28 (SA)-CD3 (CH2527) 1+1 format, bispecific huIgG1 PG-LALA CrossFab molecule with VH/VL exchange in the CD3 (CH2527) Fab fragment (knob) and charged modifications in the CD28 (SA) Fab fragment (hole), wherein the CD3 is masked with anti-idiotypic CD3 scFv 4.24.72 and a cleavable linker (masked 4.24.72_RQARVVNG site, MK062 Matriptase site) (FIG. 1E). The molecule comprises the heavy chain amino acid sequences of SEQ ID NOs: 98 and 99 and the light chain amino acid sequences of SEQ ID NOs: 90 and 94 (P1AD8990).

Figure 1F:
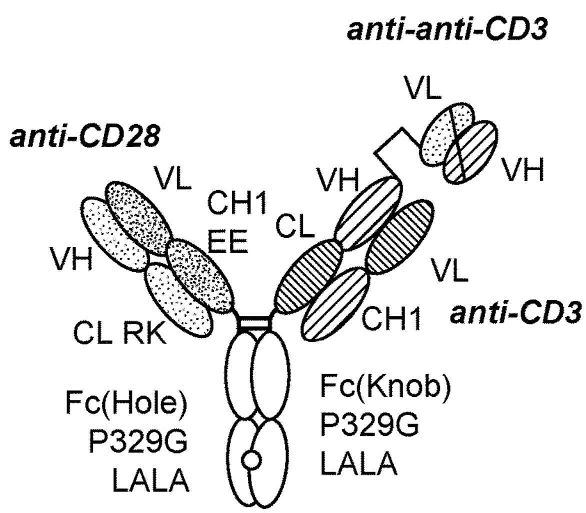
Figure 1G:
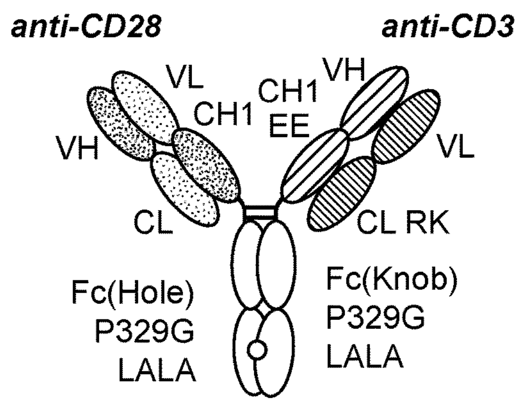

Molecule 8: masked CD28 (9.3)-CD3 (CH2527) 1+1 format, bispecific huIgG1 PG-LALA CrossFab molecule with VH/VL exchange in the CD3 (CH2527) Fab fragment (knob) and charged modifications in the CD28 (9.3) Fab fragment (hole), wherein the CD3 is masked with anti-idiotypic CD3 scFv 4.32.63 and a non-cleavable linker (masked 4.24.72_non-cleavable) (FIG. 1F). The molecule comprises the heavy chain amino acid sequences of SEQ ID NOs: 100 and 97 and the light chain amino acid sequences of SEQ ID NOs: 90 and 92 (P1AD8988).

Molecule 9: masked CD28 (SA)-CD3 (CH2527) 1+1 format, bispecific huIgG1 PG-LALA CrossFab molecule with VH/VL exchange in the CD3 (CH2527) Fab fragment (knob) and charged modifications in the CD28 (SA) Fab fragment (hole), wherein the CD3 is masked with anti-idiotypic CD3 scFv 4.32.72 and a non-cleavable linker (masked 4.24.72_non-cleavable) (FIG. 1F). The molecule comprises the heavy chain amino acid sequences of SEQ ID NOs: 100 and 99 and the light chain amino acid sequences of SEQ ID NOs: 90 and 94 (P1AD8989).

Molecule 10: CD28 (SA_variant 8)-CD3 (P035.093) 1+1, bispecific huIgG1 PG-LALA CrossFab molecule with VH/VL exchange in the CD28 (SA_Variant 8) Fab fragment (hole) and charged modifications in the CD3 (P035.093) Fab fragment (knob) (FIG. 1G) comprising the heavy chain amino acid sequences of SEQ ID NOs: 101 and 103 and the light chain amino acid sequences of SEQ ID NOs: 102 and 104 (P1AF7289).

Figure 1H:
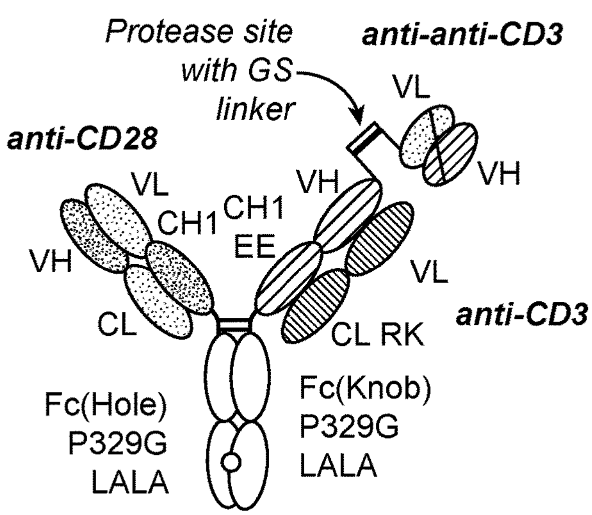

Molecule 11: masked CD28 (SA_variant 8)-CD3 (P035.093) 1+1, bispecific huIgG1 PG-LALA CrossFab molecule with VH/VL exchange in the CD28 (SA_Variant 8) Fab fragment (hole) and charged modifications in the CD3 (P035.093) Fab fragment (knob), wherein the CD3 is masked with anti-idiotypic CD3 scFv 4.24.72 and a cleavable linker (PMAKK (SEQ ID NO:162) site) (FIG. 1H). The molecule comprises the heavy chain amino acid sequences of SEQ ID NOs: 101 and 106 and the light chain amino acid sequences of SEQ ID NOs: 102 and 104 (P1AF7291).

Figure 1I:
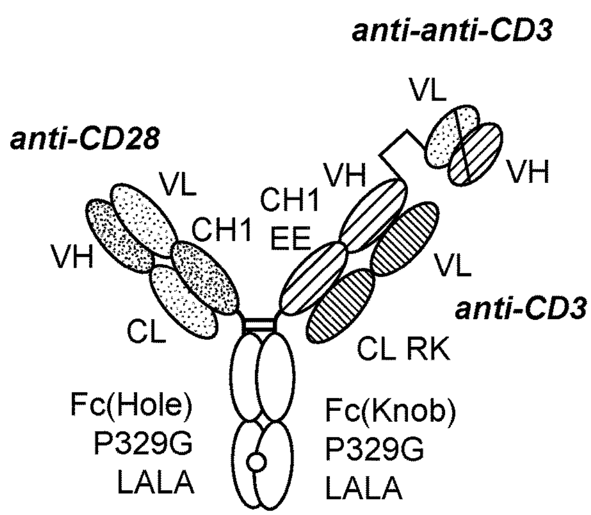

Molecule 12: masked CD28 (SA_variant 8)-CD3 (P035.093) 1+1, bispecific huIgG1 PG-LALA CrossFab molecule with VH/VL exchange in the CD28 (SA_Variant 8) Fab fragment (hole) and charged modifications in the CD3 (P035.093) Fab fragment (knob), wherein the CD3 is masked with anti-idiotypic CD3 scFv 4.32.72 and a non-cleavable linker (FIG. 1I). The molecule comprises the heavy chain amino acid sequences of SEQ ID NOs: 101 and 105 and the light chain amino acid sequences of SEQ ID NOs: 102 and 104 (P1AF7290).

1.2 Production of Bispecific Antigen Binding Molecules Targeting CD28 and CD3

Anti-idiotypic (ID) binder sequences were obtained by RACE-PCR (rapid amplification of cDNA ends) from RNA of Hybridoma cells. Hybridoma cells were obtained by immunization of mice. Single chain Fv (ScFv) sequence synthesis was ordered at Invitrogen including the necessary restriction sites for cloning. The anti-ID single chain Fv DNA sequences were subcloned in frame with the CD3 VH chain pre-inserted into the respective recipient mammalian expression vector. Protein expression is driven by an MPSV promoter and a synthetic polyA signal sequence is present at the 3' end of the CDS. In addition each vector contains an EBV OriP sequence.

The molecules were produced by co-transfecting HEK293 EXPI293® TMF (Thermo Fisher) cells growing in suspension with the mammalian expression vectors using ExpiFectamine™ Reagent. The cells were transfected with the corresponding expression vectors in a 1:1:1:1 ratio ("heavy chain hole, heavy chain knob, light chain charged, light chain crossed).

For transfection HEK293 EXPI293® TMF cells were cultivated in EXPI293® Expression Medium (Thermo Fisher) before they were transfected. On the day of transfection plasmid DNA (1 μg/mL of total transfection volume, 4 plasmids 1:1:1:1) was mixed with Opti-MEM® (5% of total transfection volume). ExpiFectamine™ Reagent (Ratio Reagent-OptiMEM 8:150) is mixed with Opti-MEM® (5% of total transfection volume) and incubated at room temperature for 5 min. DNA and reagent is mixed in a 1:1 ratio and incubated at room temperature for 30 min. Cells (for 5 ml total transfection volume $2.5 \cdot 10^6$ cells/mL are needed) are diluted with Expi medium and added to the DNA-reagent complex. Cells are incubated with complex for 16-18 hours at 37° C., 5% $CO_2$. Cells are then feeded with transfection enhancer 1 (0.5% total transfection volume) and transfection enhancer 2 (5% total transfection volume).

After 6-7 days cultivation supernatant was collected for purification by centrifugation for 20-30 min at 210×g (Sigma 8K centrifuge). The solution was sterile filtered (0.22 μm filter) and sodium azide in a final concentration of 0.01% w/v was added. The solution was kept at 4° C. until purification.

1.3 Purification of Bispecific Antigen Binding Molecules Targeting CD28 and CD3

The secreted proteins were purified from cell culture supernatants by affinity chromatography using ProteinA affinity chromatography, followed by one to two size exclusion chromatographic steps.

For affinity chromatography, supernatant was loaded on a HITRAP™ Protein A FF column (CV=5 mL, GE Healthcare) equilibrated with 25 ml 20 mM sodium phosphate, 20 mM sodium citrate, 0.5M sodium chloride pH 7.5. Unbound protein was removed by washing with at least 10 column volumes 20 mM sodium phosphate, 20 mM sodium citrate, pH 7.5 and target protein was eluted in 20 column volumes (gradient from 0%-100%) 20 mM sodium citrate, 100 mM sodium chloride, 100 mM glycine pH 3. Protein solution was neutralized by adding 1/10 of 2 M TRIS® pH 10.5. Target protein was concentrated with AMICON® Ultra-15 ULTRACEL™ 30K (Merck Millipore Ltd.) to a volume of 4 ml maximum prior loading on a HiLoad Superdex 200 column (GE Healthcare) equilibrated with 20 mM histidine, 140 mM sodium chloride, pH 6.0.

For analytics after size exclusion chromatography, the purity and molecular weight of the molecules in the single fractions were analyzed by SDS-PAGE in the absence of a reducing agent and staining with Coomassie (InstantBlue™, Expedeon). The NuPAGE® Pre-Cast gel system (4-12% bis-TRIS™, Invitrogen or 3-8% Tris-Acetate, Invitrogen) was used according to the manufacturer's instruction. The protein concentration of purified protein samples was determined by measuring the optical density (OD) at 280 nm divided by the molar extinction coefficient calculated on the basis of the amino acid sequence.

Purity and molecular weight of the molecules after the final purification step were analyzed by CE-SDS analyses in the presence and absence of a reducing agent. The Caliper LabChip GXII system (Caliper Lifescience) was used according to the manufacturer's instruction. The aggregate content of the molecules was analyzed using a TSKgel® G3000 SW XL analytical size-exclusion column (Tosoh) in 25 mM $K_2HPO_4$, 125 mM NaCl, 200 mM L-arginine monohydrocloride, 0.02% (w/v) $NaN_3$, pH 6.7 running buffer at 25° C.

The final quality of all molecules was good, with >95% (except for Molecule 9 with 84%) monomer content. A summary of the purification parameters of particular molecules is shown in Table 2.

TABLE 2

Summary of the production and purification of bispecific CD28 antigen binding molecules

| Molecule | Yield [mg/l] | Analytical SEC (HMW/Monomer/ LMW) [%] | Purity measured by CE-SDS [%] |
|---|---|---|---|
| 1 | 36.3 | 0/73.96/24.4 | 75.55 |
| 2 | 29.93 | 1.44/97.5/1.05 | 78.1 |
| 3 | 10.15 | 1.4/98.6/0 | 97.7 |
| 4 | 38.5 | 0.2/99.3/0.5 | 99.6 |
| 5 | 103.2 | 0/99.11/0.89 | 94.36 |
| 6 | 0.65 | 2/98/0 | 100 |
| 7 | 4.94 | 5/95/0 | 100 |
| 8 | 1.296 | 3.4/96.6/0 | 100 |
| 9 | 3 | 14.5/83.5/1.7 | 71.2 |
| 10 | 39.15 | 0/91.9/8.1 | 98.04 |
| 11 | 2.55 | 0/92.7/7.3 | 95.73 |
| 12 | 1.54 | 0.9/90.1/9 | 100 |

Example 2

T Cell Activation Assays Using Jurkat NFAT Reporter Cells

Jurkat-NFAT reporter assay was used to quantify T cell activation mediated by bispecific CD28-CD3 IgGs.

Jurkat-NFAT reporter cell line (Promega) is a human acute lymphatic leukemia reporter cell line with a NFAT promoter, expressing human CD3ε. Luciferase expression can be measured, if the T cell bispecific molecule binds to CD28 and the CD3ε (crosslinkage). Luminescence is measured after addition of One-Glo substrate (Promega).

Jurkat-NFAT reporter cells were harvested and viability was assessed using VI-CELL®. Cells were centrifuged at 350×g, 5 min before they were resuspended in Jurkat medium (Jurkat Medium: RPMI1640, 2 g/l Glucose, 2 g/l $NaHCO_3$, 10% FCS, 25 mM HEPES, 2 mM L-Glutamin, 1×NEAA, 1× Sodium-pyruvate). 50 μl per well (25.000 cells/well) were added in a 96-well white flat-bottom plate (Greiner, uncoated). Antibodies were diluted in Jurkat medium and 50 μl per well were added to the Jurkat cells. Plate was incubated for 5 h at 37° C. in a humidified incubator before it was taken out for Luminescence read out.

Roughly 5 hours before performing the assay, the appropriate amount of frozen aliquots of prepared ONE-Glo solution was thawed at room temperature. The assay plates were taken out of the incubator 15 min prior to addition of ONE-Glo in order to adapt them to room temperature as well. 30 μl per well of ONE-Glo solution were added and the wells were resuspended by pipetting up and down several times. The plate was incubated for roughly 10 min at room temperature in the dark and luminescence (5s) was measured.

Figure 4A:
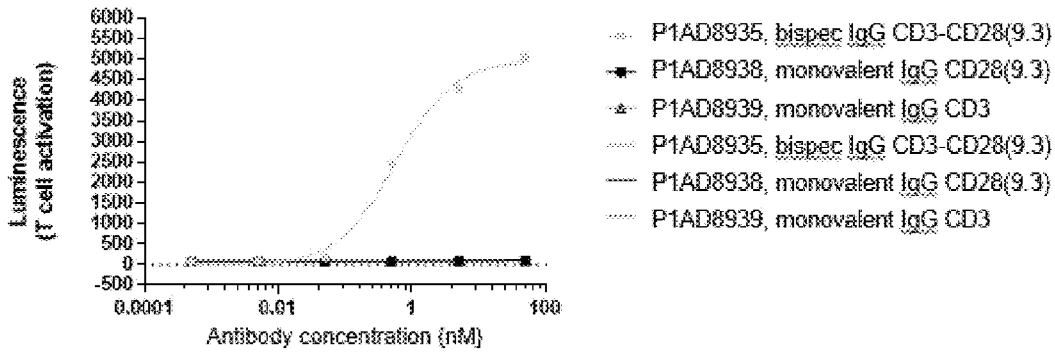
FIGS. 4A and 4B relate to the Jurkat NFAT activation assay as described in Example 2.
Figure 4B:
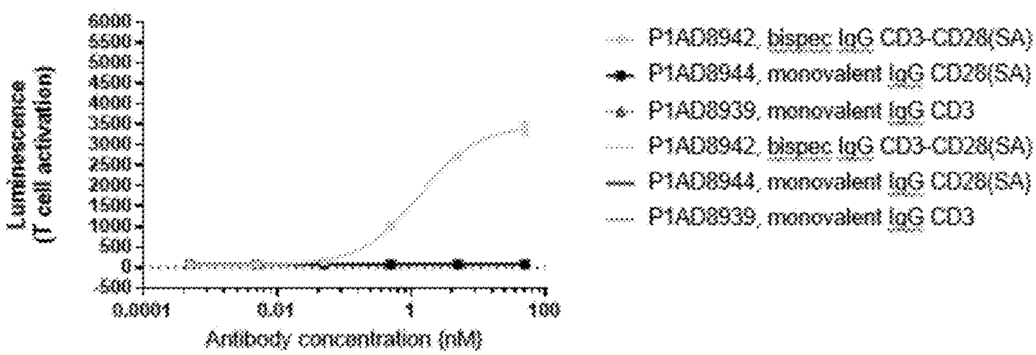

As shown in FIGS. 4A and 4B, dose-dependent Jurkat NFAT activation could be detected for the bispecific antigen binding molecules comprising both CD3 and CD28, whereas no Jurkat NFAT activation was detected for the monovalent controls, i.e. crosslinking is required for T cell activation.

Example 3

T Cell Activation Assays Using Jurkat NFAT Reporter Cells and Anti-Human Fc Coated Plates 96-well white flat-bottom plates (Greiner) were coated with 8 μg/ml anti human Fc Ab (BioLegends) in 0.025 μl/well PBS for 20 h at 4° C. DPBS was removed by aspiration.

All antibodies were diluted in Jurkat medium. For non-coated plates 50 μl/well were added, for coated plates 25 μl/well were added. Incubation for 30 min at 4° C. DPBS was removed by aspiration.

Jurkat-NFAT reporter cells were harvested and viability was assessed using VI-CELL®. Cells were centrifuged at 350×g, 5 min before they were resuspended in Jurkat medium. 50 μl per well (25.000 cells/well) were added in a 96-well white flat-bottom plate (Greiner). Plate was incubated for 5 h at 37° C. in a humidified incubator before it was taken out for Luminescence read out.

Roughly 5 hours before performing the assay, the appropriate amount of frozen aliquots of prepared ONE-Glo solution was thawed at room temperature. The assay plates were taken out of the incubator 15 min prior to addition of ONE-Glo in order to adapt them to room temperature as well. 30 μl per well of ONE-Glo solution were added and the wells were resuspended by pipetting up and down several times. The plate was incubated for roughly 10 min at room temperature in the dark and luminescence (5s) was measured.

Figure 4C:
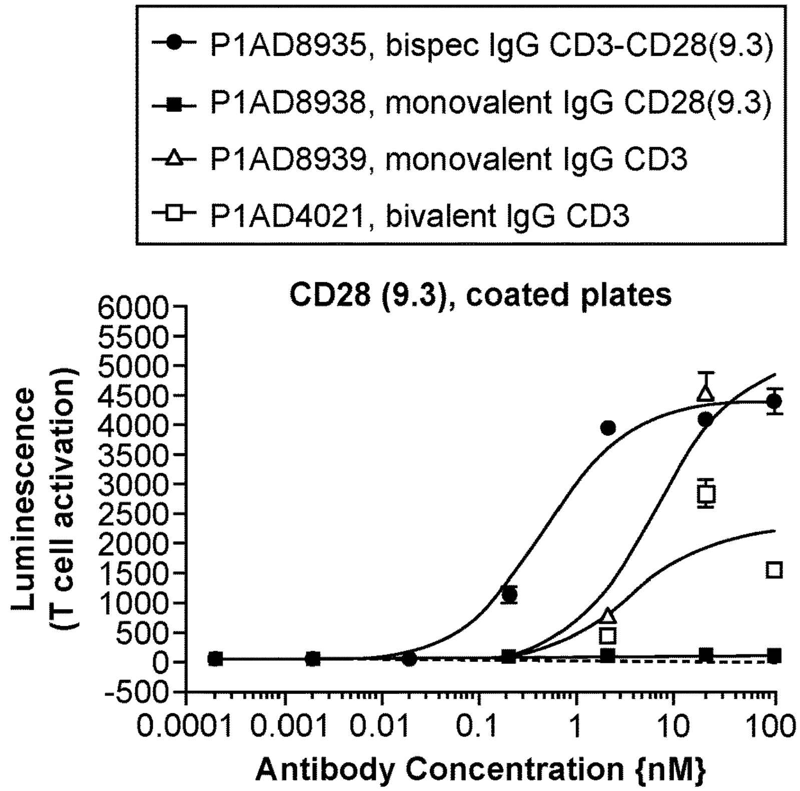
FIG. 4C shows Jurkat NFAT activation mediated by bispecific CD28 (9.3)-CD3 IgG on anti-human Fc antibody coated plate. Jurkat NFAT effector cells were incubated with bispecific CD28 (9.3)-CD3 IgG or monovalent control IgGs. Luminescence was measured after 5 h of incubation after addition of One Glo substrate. Each point represents the mean value of triplicates (n=2).
Figure 4D:
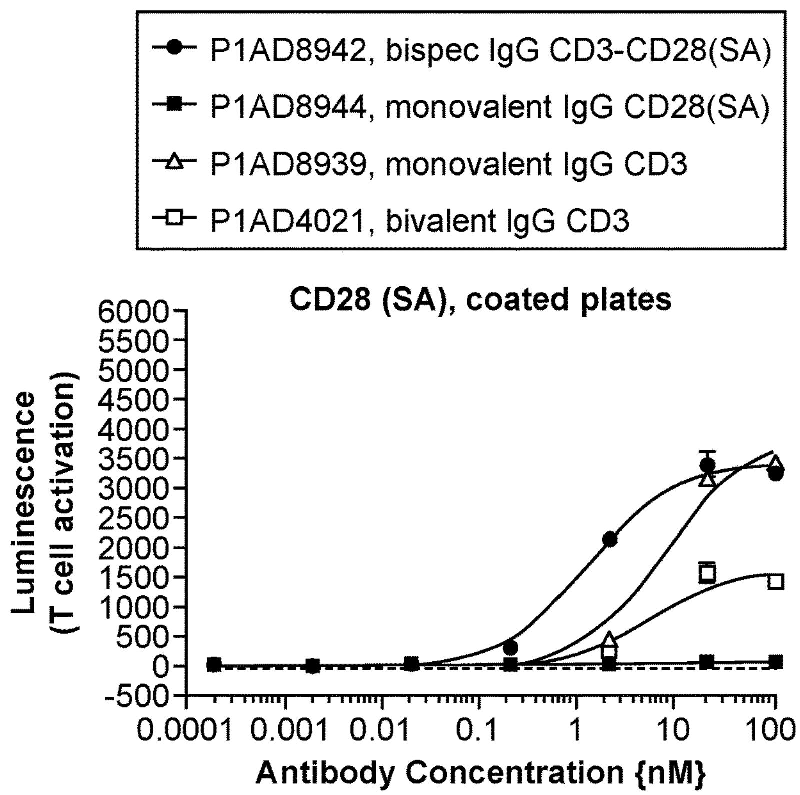
FIG. 4D shows Jurkat NFAT activation mediated by bispecific CD28 (SA)-CD3 IgG on anti-human Fc antibody coated plate. Jurkat NFAT effector cells were incubated with bispecific CD28 (SA)-CD3 IgG or monovalent control IgGs. Luminescence was measured after 5 h of incubation after addition of One Glo substrate. Each point represents the mean value of triplicates (n=2).
Figure 4E:
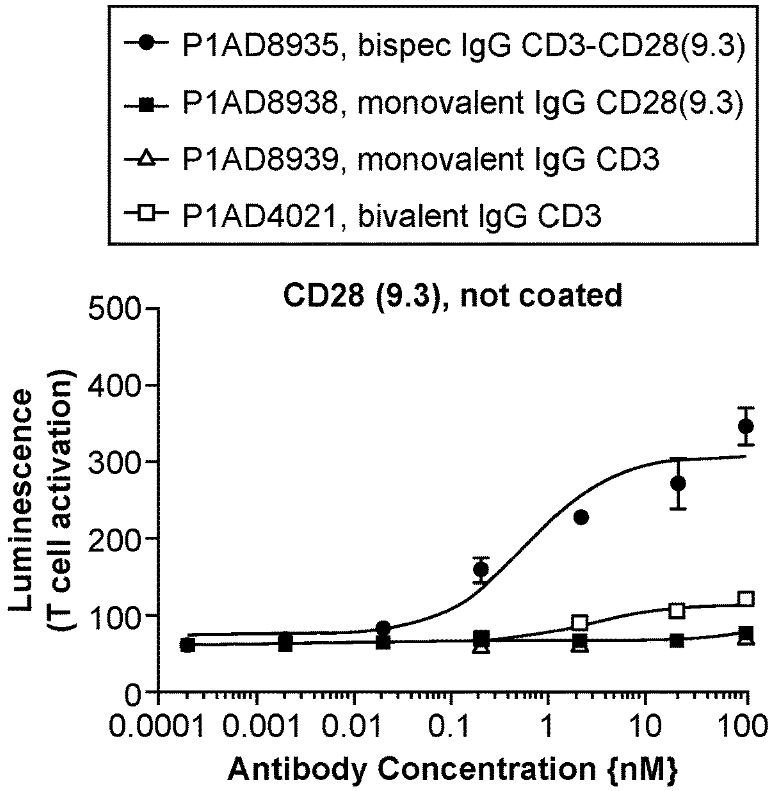
FIG. 4E shows Jurkat NFAT activation mediated by bispecific CD28 (9.3)-CD3 IgG on non-coated plate. Jurkat NFAT effector cells were incubated with bispecific CD28 (9.3)-CD3 IgG or monovalent control IgGs. Luminescence was measured after 5 h of incubation after addition of One Glo substrate. Each point represents the mean value of triplicates (n=2).
Figure 4F:
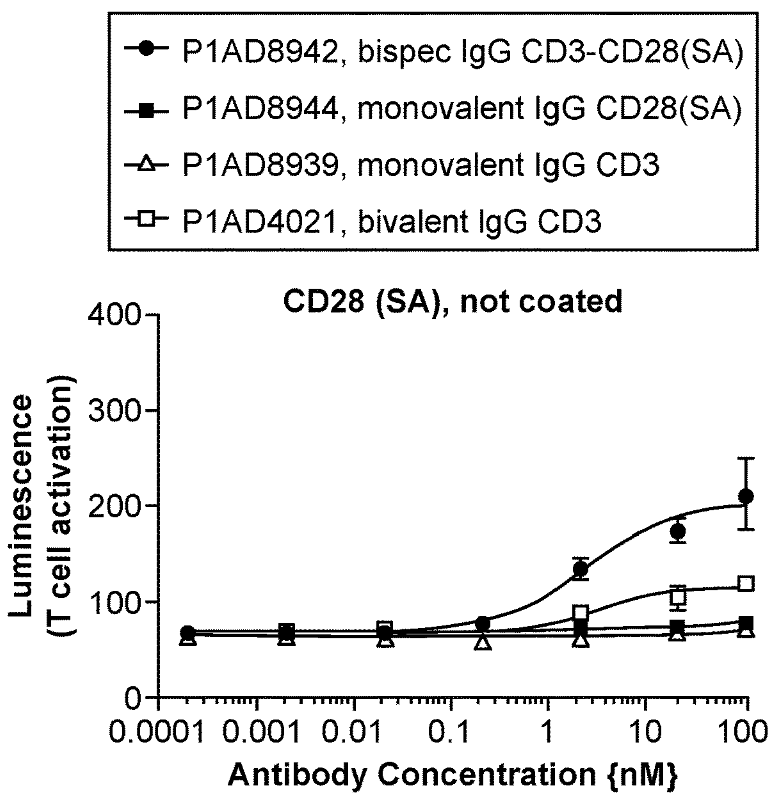
FIG. 4F shows Jurkat NFAT activation mediated by bispecific CD28 (SA)-CD3 IgG on non-coated plate. Jurkat NFAT effector cells were incubated with bispecific CD28 (SA)-CD3 IgG or monovalent control IgGs. Luminescence was measured after 5 h of incubation after addition of One Glo substrate. Each point represents the mean value of triplicates (n=2).

The results are shown in FIGS. 4C and 4D (with the anti-human Fc coated plates) and in FIGS. 4E and 4F (uncoated plates), respectively. Dose-dependent Jurkat NFAT activation could be detected for the bispecific antigen binding molecules comprising both CD3 and CD28 whereas no Jurkat NFAT activation was detected for the monovalent controls (crosslinking is required for T cell activation). The Jurkat NFAT activation for the IgGs (bispecific CD28-CD3 antibodies and bivalent CD3 IgG) was higher (<10 fold) with the anti-human Fc coated plates.

Example 4

T Cell Activation Assays Using Human PBMCs 96-well flat-bottom plates (TPP) were coated with 8 μg/ml anti human Fc Ab (BioLegends) in 0.025 μl/well PBS for 20 h at 4° C. DPBS was removed by aspiration. All antibodies were diluted in assay medium (advanced RPMI 1640 Medium (12633012, FisherScientific) completed with 2% FCS and 1× GlutaMAX™). For non-coated plate 50 μl/well were added for coated plate 25 μl/well were added. Incubation for 30 min at 4° C. DPBS was removed by aspiration.

Human PBMCs were used as effector cells and cell killing was detected at 48 h of incubation with the molecules. Human Peripheral blood mononuclear cells (PBMCs) were isolated from buffy coats obtained from healthy human donors. For enriched lymphocyte preparations (buffy coats) HISTOPAQUE®-1077 density preparation was used. Blood/buffy coat was diluted 1:1 with sterile PBS and layered over HISTOPAQUE® gradient (Sigma, #H8889). After centrifugation (450×g, 30 minutes, w/o break, room temperature), the plasma above the PBMC-containing interphase was discarded and PBMCs transferred in a new falcon tube subsequently filled with 50 ml of PBS. The mixture was centrifuged (400× g, 10 minutes, room temperature), the supernatant discarded and the PBMC pellet resuspended in 2 ml ACK buffer for Erythrocytes lysis. After incubation at 37° C. for about 2-3 minutes the tubes were filled with sterile PBS to 50 ml and centrifuged at 350×g for 10 minutes. This washing step was repeated once prior to resuspension of PBMCs in RPMI1640 medium containing 2% FCS and 1× GlutaMAX™. PBMCs were frozen over night at −80° C. in COOLCELL® boxes before they were transferred to liquid nitrogen. 24 h before assay start, PBMCs were thawed and kept in assay medium (density 2 mio/ml) at 37° C., 5% $CO_2$ in a humidified incubator.

T-cell activation was assessed after 48 h of incubation at 37° C., 5% $CO_2$ by quantification of CD25 and CD69 on CD4 positive and CD8 positive T cells and by quantification of Interferon gamma release (ELISA).

Materials Used for T Cell Activation: Quantification of CD25 and CD69 on CD4 Positive and CD8 Positive T Cells

- FACS buffer (1×PBS 0.1% BSA)
- 4% PFA Formalinsolution (Sigma) HT501320-9 51
- Brilliant Violet 421™ anti human CD4 (BioLegend, 317434)
- Brilliant Violet 421™ anti human CD25 (BioLegend, 356114)
- APC anti human CD8 (BioLegend, 344722)
- PE-anti human CD8 (BioLegend, 344706)
- FITC anti human CD4 (BioLegend, 357406)
- PE-anti human CD69 (BioLegend, 310906)

Used Compensation Controls: Only PBMCs

- Unstained
- Bv421 CD4
- APC CD8
- FITC CD4
- PE CD8

Staining:

- APC CD8 R1
- FITC CD4 B1
- PE CD69 B2
- BV421 CD25 V1

FACS Staining and Fixation:

Plates were centrifuged at 350×g for 5 min, supernatant was removed by flipping plate. 150 μl cold FACS buffer were added and plate was again centrifuged at 350×g for 4 min. Cells were resuspended by vortexing before 25 μl/well (FACS buffer with 0.8 μl/well Ab for each fluorophor) were added and plate was incubated at 4° C. for 60 min. Cells were washed twice (150 μl cold FACS buffer) before cells were resuspended in 100 μl 2% PFA (formalin solution) per well to fix cells.

Interferon Gamma Release (ELISA)

Materials used:

- Human IFN-gamma DuoSet ELISA, 15 Plate (R&D Systems)
- Immunoplates MaxiSorp™ F Boden 400 ml MaxiSorp™ (10547781, Fisher Scientific)
- TMB High Sensitivity Substrate Solution (BioLegend)
- Pierce™ TMB Substrate Kit (34021, Thermo Fisher)
- Stop Solution: Sulfuric acid solution, 1M (35276, Fluka)
- Reagent diluent: 0.01%, 0.05% TWEEN®-20 in PBS
- Wash Buffer: 0.05% TWEEN®-20 in PBS
- Block Buffer: 1% BSA in PBS
- TWEEN®-20, 10% solution (Roche)

Capture antibody was reconstituted in 500 μl PBS. 240 μg/vial, so 480 μg/ml. Final concentration should be 4 μg/ml, so diluted 1:120 in PBS (300 ul in 30 ml PBS)

Coating with Capture Antibody:

100 μl/well were plated in Microtest™ 96-well ELISA plate, clear (BD Falcon), sealed and incubated at room temperature overnight. Plate was flipped and washed with Wash Buffer, repeating the process two times for a total of three washes. Wash by filling each well with Wash Buffer (0.05% TWEEN®-20 in PBS) (400 μL). Complete removal of liquid at each step is essential for good performance. After the last wash, remove any remaining Wash Buffer by aspirating or by inverting the plate and blotting it against clean paper towels. Blocking was done by adding 300 μL of Block Buffer (1% BSA in PBS) to each well. Incubate at room temperature for a minimum of 1 hour. Washing steps repeated for 3 times.

Standard: 32.5 ng reconstituted in 0.5 ml Reagent diluent (0.01%, 0.05% TWEEN®-20 in PBS). 65 ng/ml diluted and standard dilutions prepared. 100 μL standard added per well. Plates were covered with adhesive strip and incubated for 2 hours at room temperature. Washing steps repeated for 3 times. 100 μL of the Detection Antibody (12 ug/ml >200 ng/ml diluted 1:60), diluted in Reagent Diluent, were added to each well. Cover with an adhesive strip and incubate 2 hours at room temperature. Washing steps repeated for 3 times. 100 μL of the working dilution (1:40) of Streptavidin-HRP were added to each well. Cover the plate and incubate for 20 minutes at room temperature in the darkness. Washing steps repeated for 3 times. 100 μL of Substrate Solution (TMB High Sensitivity Substrate Solution, BioLegend) solution to each well. Incubate for at room temperature in the darkness. As soon as the solution turned dark blue, 50 ul/well of stop solution was added (turn yellow). Determine the optical density of each well immediately, using a microplate reader set to 450 nm. If wavelength correction is available, set to 540 nm or 570 nm. If wavelength correction is not available, subtract readings at 540 nm or 570 nm from the readings at 450 nm. This subtraction will correct for optical imperfections in the plate. Readings made directly at 450 nm without correction may be higher and less accurate.

Figure 5A:
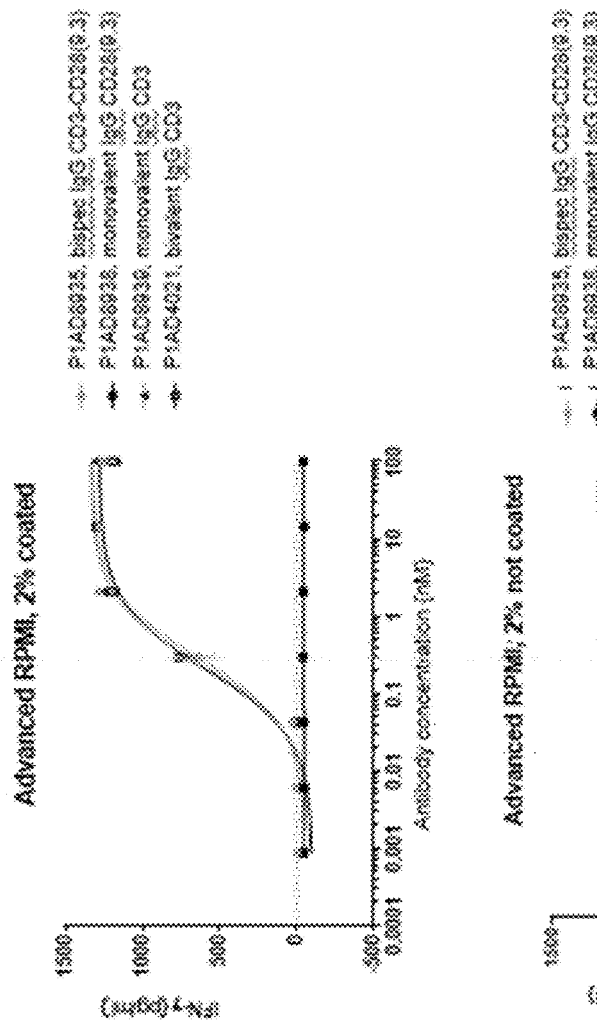
FIG. 5A to 5D show T cell activation mediated by bispecific CD3-CD28 IgGs, monovalent control IgGs at a concentration of 10 nM in human PBMCs after 48 h of incubation (see Example 4).
Figure 5B:
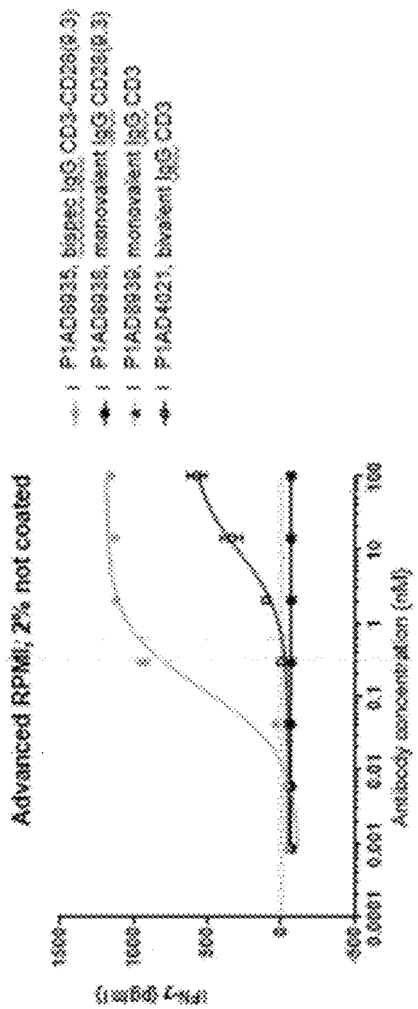

Using huFc coating for crosslinking: Dose-dependent T cell activation (measured by Interferon gamma release) could be detected for the bispecific CD3-CD28 (9.3) IgG as well as for the CD3 IgG (bivalent) and the monovalent CD3 IgG whereas no T cell activation could be detected for the monovalent CD28 mAb9.3 IgG (FIG. 5A). Without coating (crosslinking) the CD3 IgG (bivalent) induces dose-dependent T cell activation (measured by Interferon gamma release) with an $EC_{50}$~0.13 nM whereas the T cell activation induced by the CD3 IgG is reduced ($EC_{50}$~12 nM). No T cell activation could be detected without coating for the monovalent CD3 nor the monovalent CD28 (9.3) IgGs (FIG. 5B).

Figure 5C:
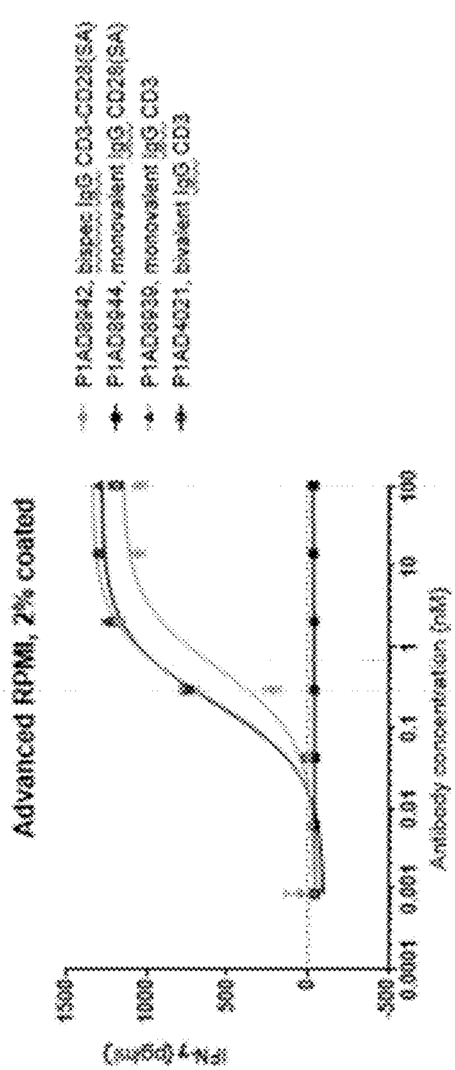
Figure 5D:
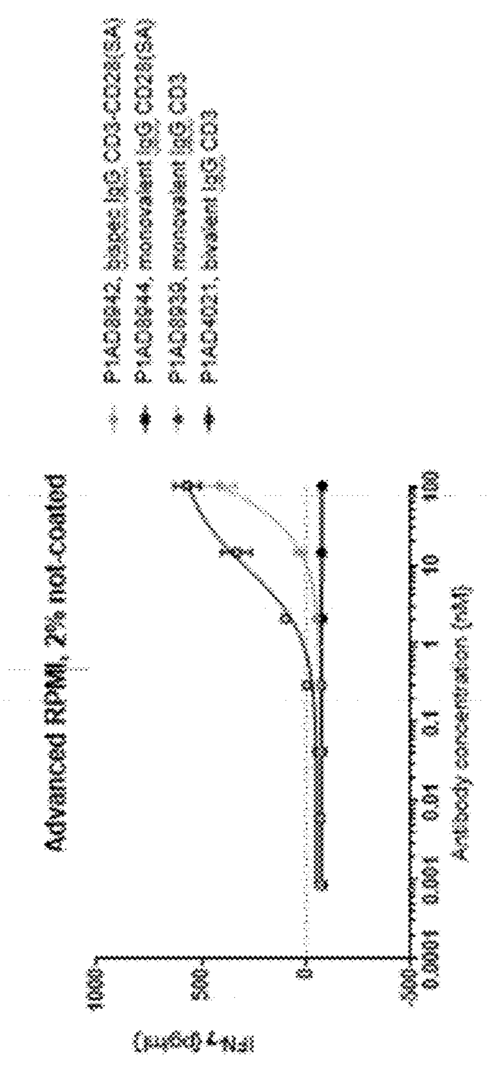

Using huFc coating for crosslinking: Dose-dependent T cell activation (measured by Interferon gamma release) could be detected for the bispecific CD3-CD28 (SA) IgG as well as for the CD3 IgG (bivalent) and the monovalent CD3 IgG whereas no T cell activation could be detected for the monovalent CD28 (SA) IgG (FIG. 5C). Without coating (crosslinking) the CD3 IgG (bivalent) induces very weak dose-dependent T cell activation (measured by Interferon gamma release) with an $EC_{50}$~9 nM. For the bispecific CD3-CD28 (SA) bispecific IgG IFNγ release could only be detected at 100 nM. No T cell activation could be detected without coating for the monovalent CD3 nor the monovalent CD28 (SA) IgGs (FIG. 5D).

Figure 6A:
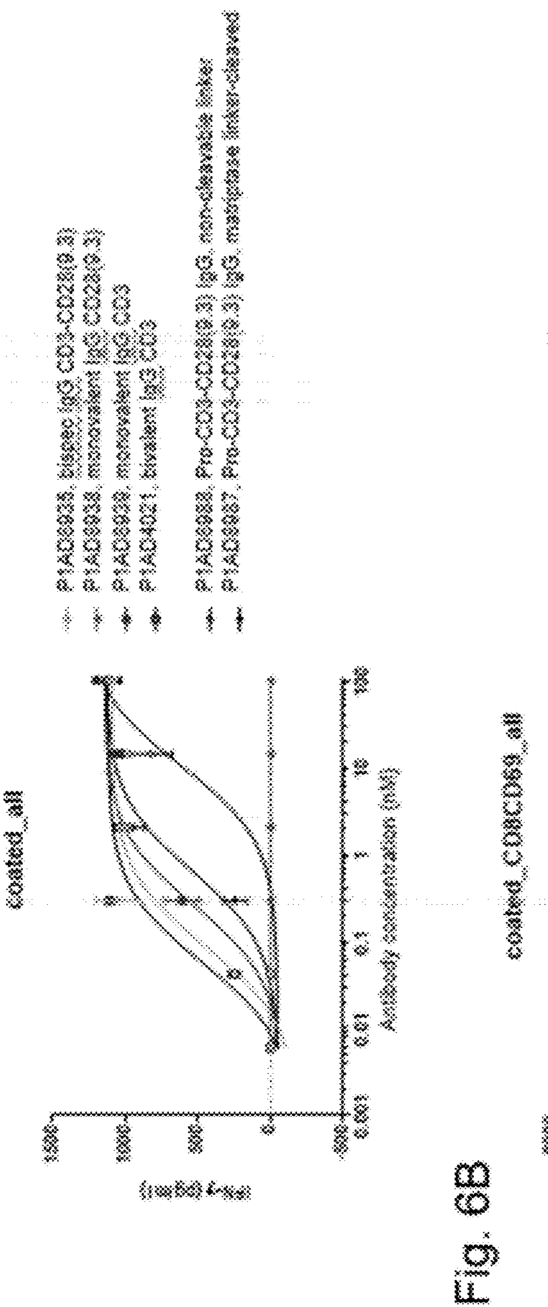
FIG. 6A to 6D show T cell activation as measured in an experiment, wherein also protease-activatable masked CD3-CD28 IgGs (Pro-CD3 masked with anti-idiotypic CD3 scFv, fused to CD3 with either cleavable or non-cleavable linker) were tested. Pre-treatment with rhMatriptase/ST14 (R&D Systems) was done for 24 h at 37° C.

Using huFc coating for crosslinking: Dose-dependent T cell activation (measured by Interferon gamma release) could be detected for the bispecific CD3-CD28 (9.3) IgG as well as for the CD3 IgG (bivalent). The monovalent CD3 IgG as well as the cleaved bispecific CD28 mAb9.3-CD3 IgG induce dose-dependent T cell activation whereas reduced T cell activation could be detected for the masked CD3-CD28 (9.3) IgG (non-cleavable) and no T cell activation could be detected for the monovalent CD28 (9.3) IgG (FIG. 6A).

Figure 6B:
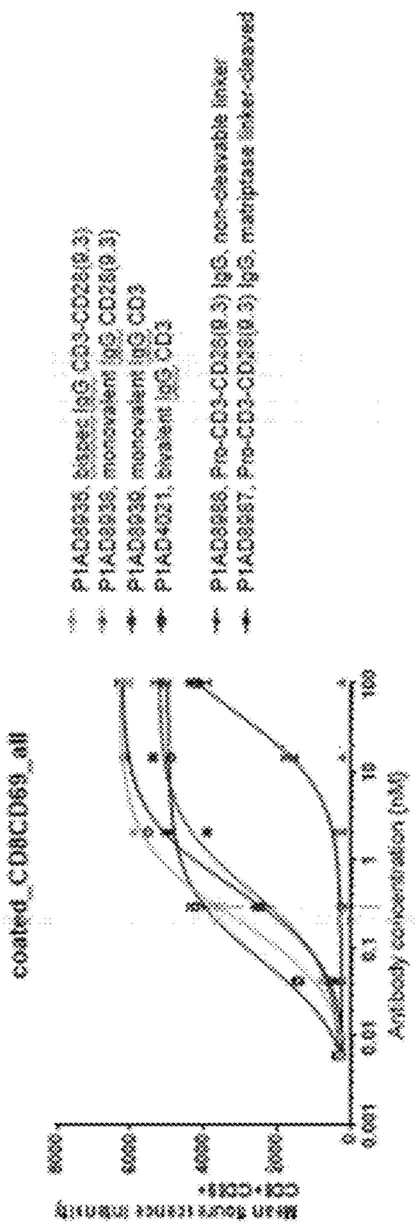

Using huFc coating for crosslinking: Dose-dependent T cell activation (measured by quantification of CD69 on CD8 positive T cells) could be detected for the bispecific CD3-CD28 (9.3) IgG as well as for the CD3 IgG (bivalent). The monovalent CD3 IgG as well as the cleaved bispecific CD3-CD28 (9.3) IgG also induce dose-dependent T cell activation whereas reduced T cell activation could be detected for the masked CD3-CD28 (9.3) IgG (non-cleavable) and no T cell activation could be detected for the monovalent CD28 (9.3) IgG (FIG. 6B).

Figure 6C:
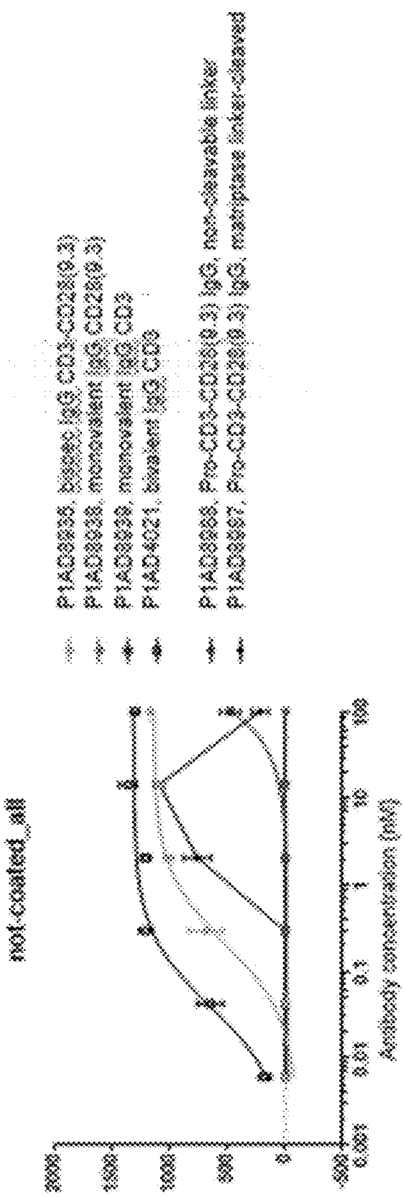

No coating: Dose-dependent T cell activation (measured by Interferone gamma release) could be detected for the bispecific CD3-CD28 (9.3) IgG as well as for the CD3 IgG (bivalent) (~5 fold lower EC50 than bispecific). The masked CD3-CD28 (9.3) (non-cleavable) IgG, the monovalent CD3 IgG as well as the monovalent CD28 (9.3) IgG do not induce T cell activation except for the monovalent CD3 IgG at the highest concentration used herein. The cleaved CD3-CD28 (9.3) IgG does induce T-cell activation with a higher EC50 compared to the bispecific CD3-CD28 (9.3) IgG without mask and a strong bell-shape (FIG. 6C).

Figure 6D:
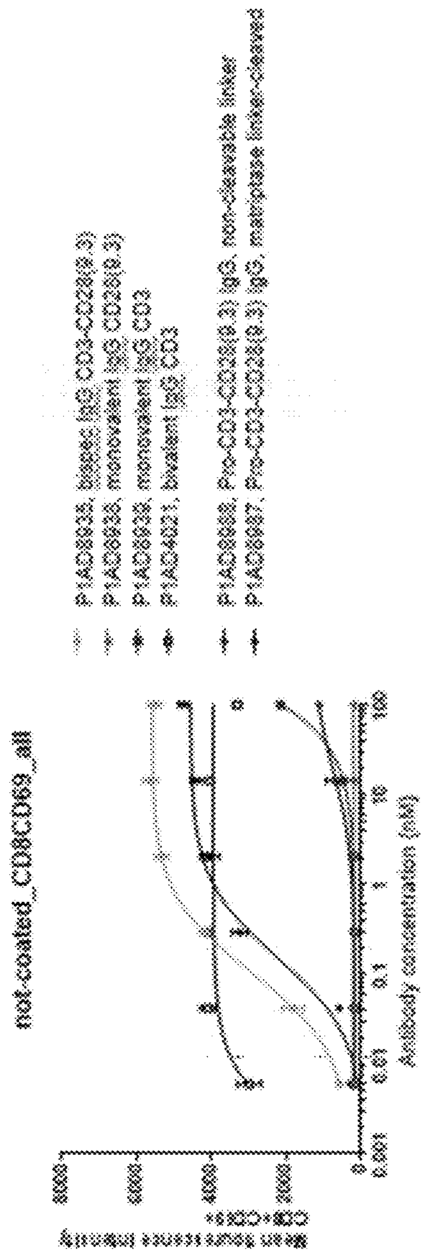

No coating: Dose-dependent T cell activation (measured by quantification of CD69 on CD8 positive T cells) could be detected for the bispecific CD3-CD28 (9.3) IgG as well as for the CD3 IgG (bivalent). The cleaved CD3-CD28 (9.3) IgG was comparable to the bispecific without mask whereas no T cell activation could be observed for the monovalent CD3 IgG, the monovalent CD28 (9.3) IgG and the masked CD3-CD28 (9.3) IgG (non-cleavable linker) (FIG. 6D).

Figure 7A:
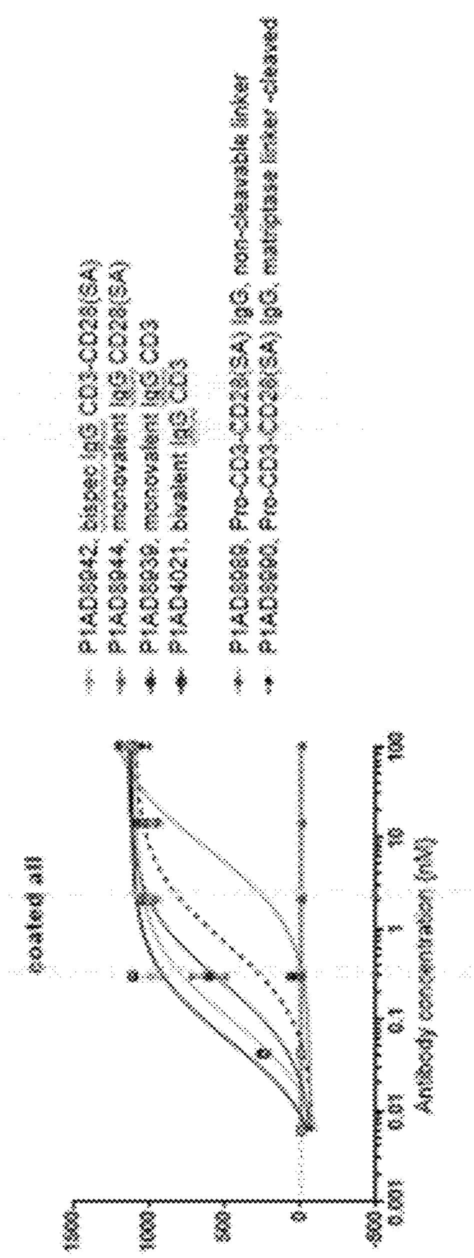
FIG. 7A to 7D show T cell activation as measured in a further experiment, wherein also protease-activatable masked CD3-CD28 (SA) IgGs (Pro-CD3 masked with anti-idiotypic CD3 scFv, fused to CD3 with either cleavable or non-cleavable linker) were included and the effect of huFc coating vs. non huFc coating was further studied.

Using huFc coating for crosslinking: Dose-dependent T cell activation (measured by Interferone gamma release) could be detected for the bispecific CD3-CD28 (SA) IgG as well as for the CD3 IgG (bivalent). The monovalent CD3 IgG as well as the cleaved bispecific CD3-CD28 (SA) IgG induce dose-dependent T cell activation whereas reduced T cell activation could be detected for the masked CD3-CD28 (SA) IgG (non-cleavable) and no T cell activation could be detected for the monovalent CD28 (SA) (FIG. 7A).

Figure 7B:
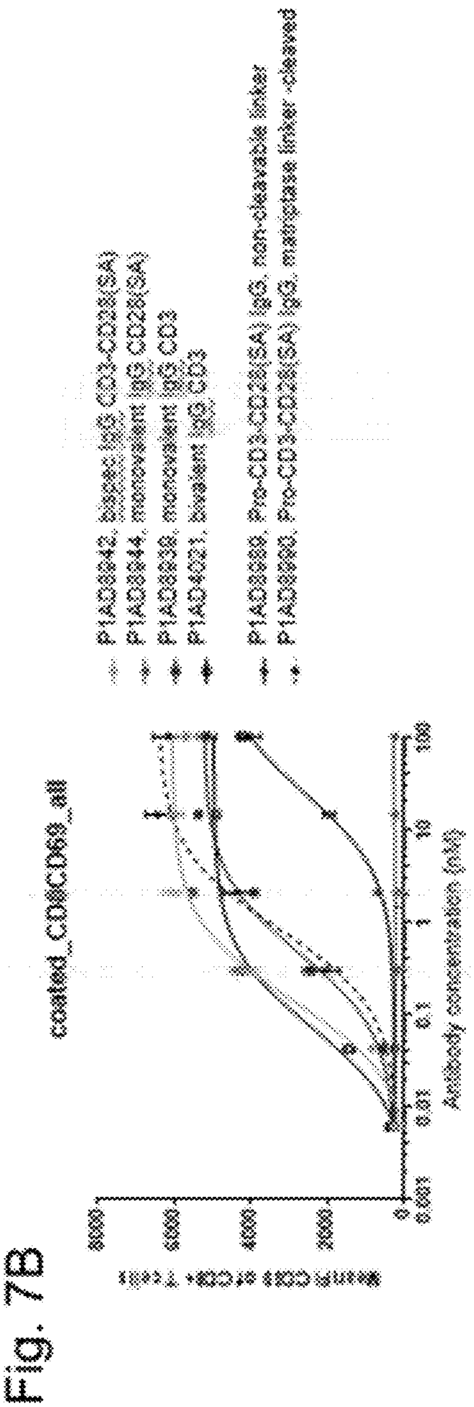

Using huFc coating for crosslinking: Dose-dependent T cell activation (measured by quantification of CD69 on CD8 positive T cells) could be detected for the bispecific CD3-CD28 (SA) IgG as well as for the CD3 IgG (bivalent). The monovalent CD3 IgG as well as the cleaved bispecific CD3-CD28 (SA) IgG also induce dose-dependent T cell activation whereas reduced T cell activation (EC50 around 240 fold higher than for bispecific CD3-CD28 (SA) IgG without mask) could be detected for the masked CD3-CD28 (SA) IgG (non-cleavable) and no T cell activation could be detected for the monovalent CD28 (SA) IgG (FIG. 7B).

Figure 7C:
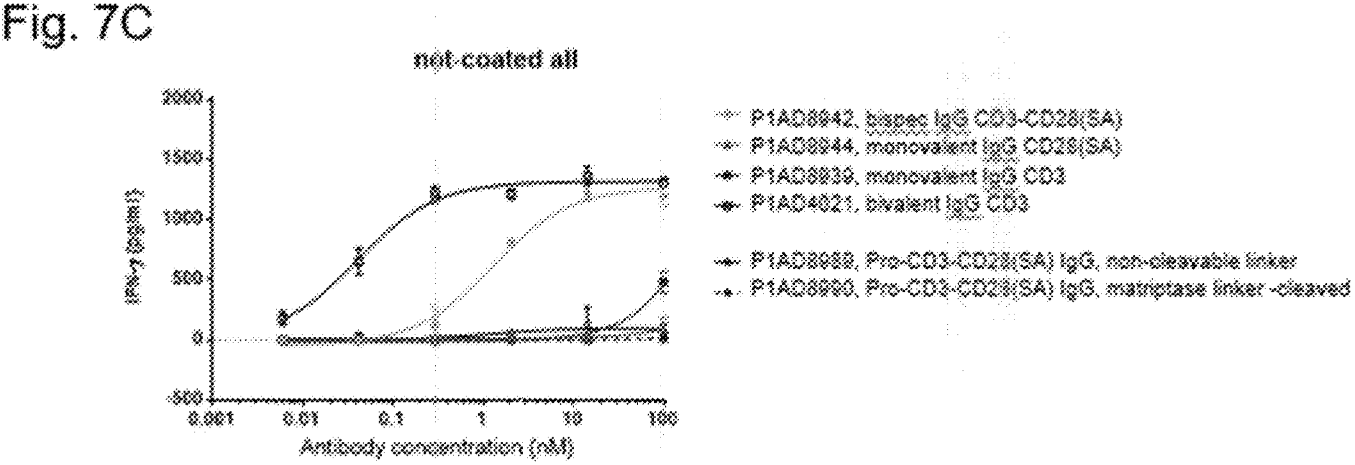

No coating: Dose-dependent T cell activation (measured by Interferone gamma release) could be detected for the bispecific CD3-CD28 (SA) IgG as well as for the CD3 IgG (bivalent) (~30 fold lower EC50 than bispecific). The masked CD3-CD28 (SA) (non-cleavable), the monovalent CD3 IgG as well as the monovalent CD28 (SA) IgG do not induce T cell activation except for the monovalent CD3 IgG at the highest concentration used herein. The cleaved CD3-CD28 (SA) IgG does not induce T cell activation (FIG. 7C).

Figure 7D:
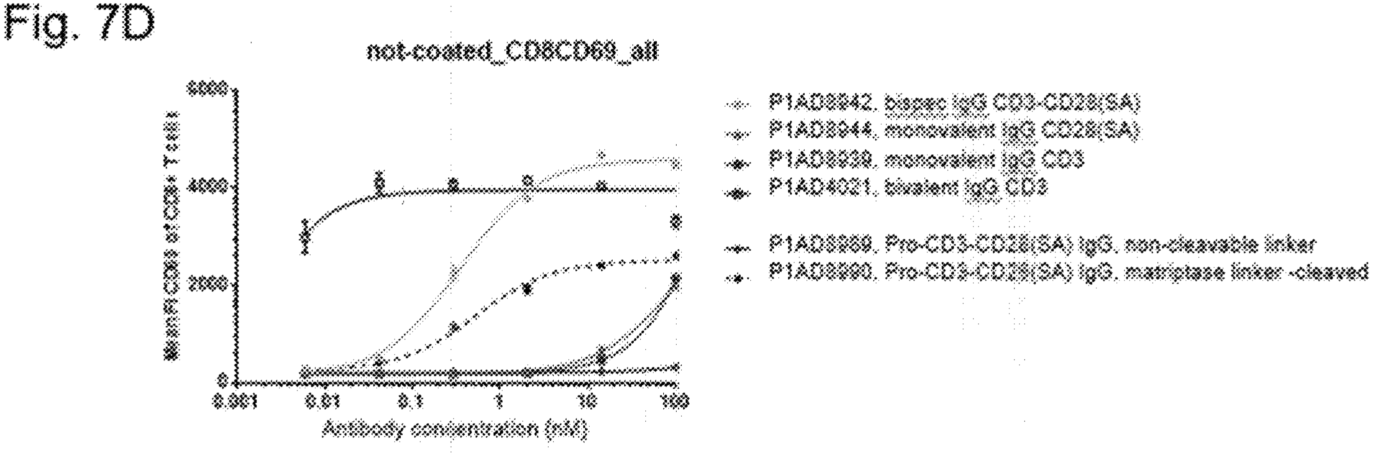

No coating: Dose-dependent T cell activation (measured by quantification of CD69 on CD8 positive T cells) could be detected for the bispecific CD3-CD28 (SA) IgG as well as for the CD3 IgG (bivalent). The cleaved CD3-CD28 (SA) IgG did also induce dose-dependent T cell activation whereas the potency was lower compared to the bispecific CD3-CD28 (SA) without mask. No T cell activation could be observed for the masked CD3-CD28 (SA) (non-cleavable). The monovalent CD3 IgG and the monovalent CD28 (SA) induced T cell activation at the highest concentration used herein (FIG. 7D).

Example 5

T Cell Activation as Measured in the Jurkat IL2 Reporter Cell Assay

The T cell activation mediated by masked CD3-CD28 bispecific antibodies was also measured using Jurkat IL2 Reporter Cell Assay. Simultaneous binding of CD3 (signal 1) and CD28 (signal 2) on Jurkat IL2 reporter cells leads to downstream activation of the Jurkat IL2 reporter cells. The activation of the IL2-Jurkat reporter cells leads to the production of IL2, which triggers the expression of an IL2-regulated Firefly Luciferase in the Jurkat IL2 reporter cells. The latter is quantified upon addition of One-Glo substrate (Promega). The amount of the determined luminescence is a direct measure of CD3- and CD28-mediated Jurkat activation.

Jurkat IL-2 reporter cells (Promega, Ca No J1651) served as effector cells. Jurkat T cell line is a human acute lymphatic leukemia reporter cell line with an IL2 promoter leading to luciferase expression upon activation via human CD3 alone, and even more, with additional activation of human CD28. The cells were grown in suspension in RPMI1640 (include. 2 g/l Glucose, 2 g/l $NaHCO_3$) plus 10% FCS, 25 mM HEPES, 1× GlutaMAX™, 1×NEAA MEM, 1× Sodium-pyruvate at 0.1-0.5 Mio cells per ml. A final concentration of 200 μg per ml Hygromycin B was added, whenever cells were passaged.

For the assay, Jurkat IL2 reporter cells in suspension were counted and viability was assessed using VI-CELL®. After centrifugation (310×g, 3 min), the medium was aspirated and cells were resuspended in fresh in Jurkat medium (Jurkat Medium: RPMI1640, 2 g/l Glucose, 2 g/l $NaHCO_3$, 10% FCS, 25 mM HEPES, 2 mM L-Glutamin, 1×NEAA, 1× Sodium-pyruvate).

Jurkat-NFAT reporter cells were harvested and viability was assessed using VI-CELL®. Cells were centrifuged at 350×g, 5 min before they were resuspended in Jurkat medium (Jurkat Medium: RPMI1640, 2 g/l Glucose, 2 g/l $NaHCO_3$, 10% FCS, 25 mM HEPES, 2 mM L-Glutamin, 1×NEAA, 1× Sodium-pyruvate). 30 μl per well (30.000 cells/well) were added in a 384-well white clear bottom plate (Corning) and Glosensor cAMP reagent (Promega) was added. Antibodies were diluted (a dilution row of 1:5 was prepared) in Jurkat medium and the required amounts (200 nM per antibody) were added to safe lock eppis and incubated for 2 h at 37° C. with or without 1 μl Rh-Matriptase (*E. coli* derived with His-tag, Enzo). Each dilution was then 4× concentrated and 10 μl per well of each concentrated antibody dilution were added to the assay plate. The assay plate was centrifuged for a few seconds to make sure all the liquid was on the bottom of the plate and then covered with medium liquid and incubated for a certain time (for example 4 h and 6 h) at 37° C. in humidified $CO_2$ before it was taken out for Luminescence read out. Luminescence (0.5 seconds per well) was directly measured using the Tecan Spark 10M.

Figure 8:
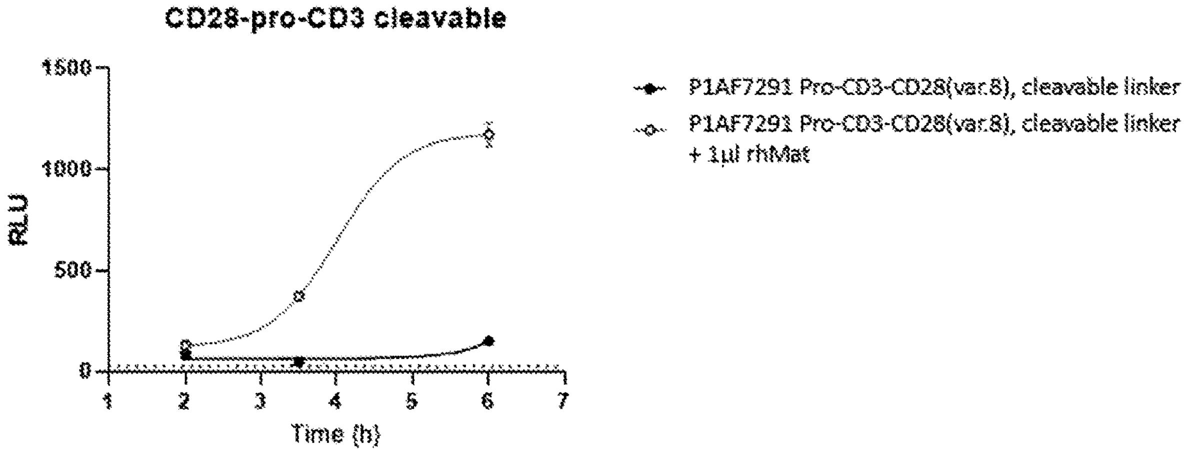
FIG. 8 shows the kinetics of protease-activatable masked CD3-CD28 (var. 8) IgGs (Pro-CD3 masked with anti-idiotypic CD3 scFv, fused to CD3 with a matriptase cleavable linker) without incubation with recombinant matriptase and in the presence of 1 μl recombinant Matriptase (rhMat).
Figure 9A:
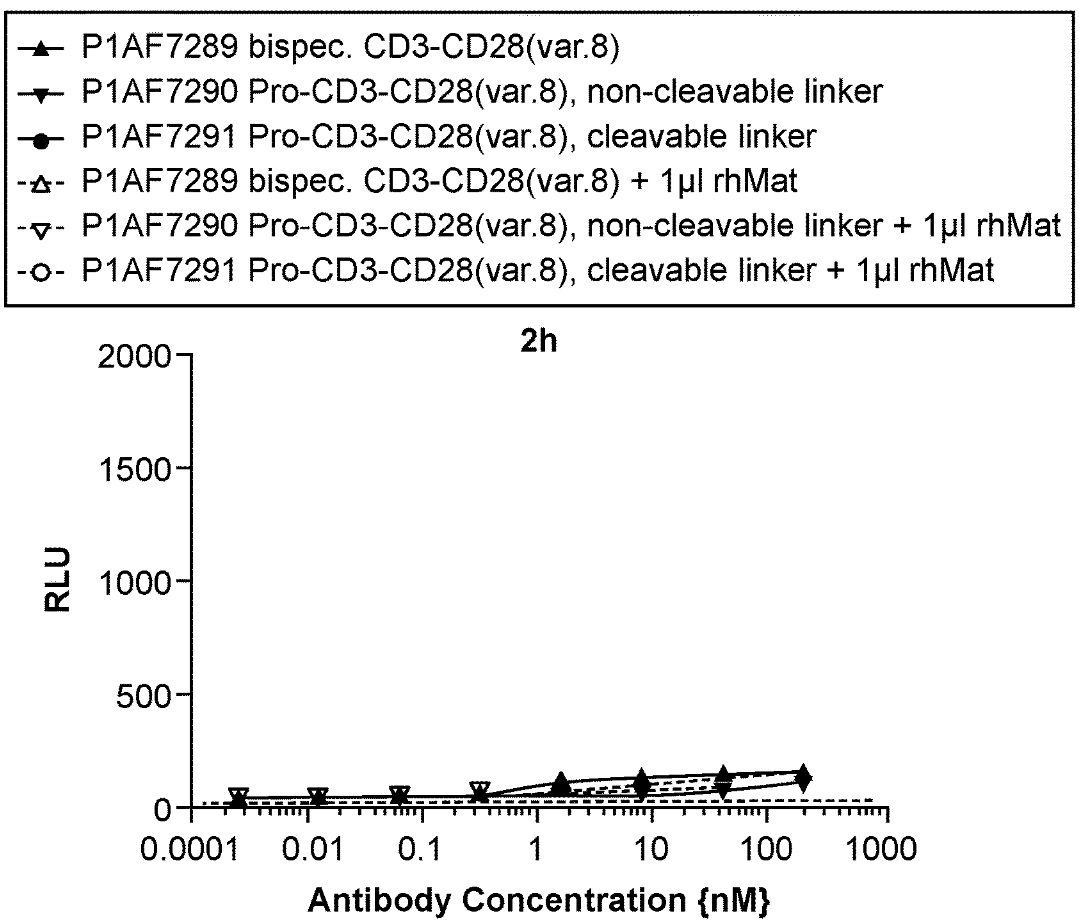
FIG. 9A to 9C show T cell activation by measuring Jurkat NFAT IL2 activation (Luminescence read out) at different timepoints, wherein the protease-activatable masked CD3-CD28 (Var. 8) IgGs (Pro-CD3 masked with anti-idiotypic CD3 scFv, fused to CD3 with either cleavable or non-cleavable linker) were compared with unmasked CD3-CD28 (Var. 8). Shown is the NFAT IL2 activation without Matriptase or with incubation of 1 μl recombinant Matriptase (rhMat) after 2 h (FIG. 9A), 3.40 h (FIG. 9B) and 6h (FIG. 9C).
Figure 9B:
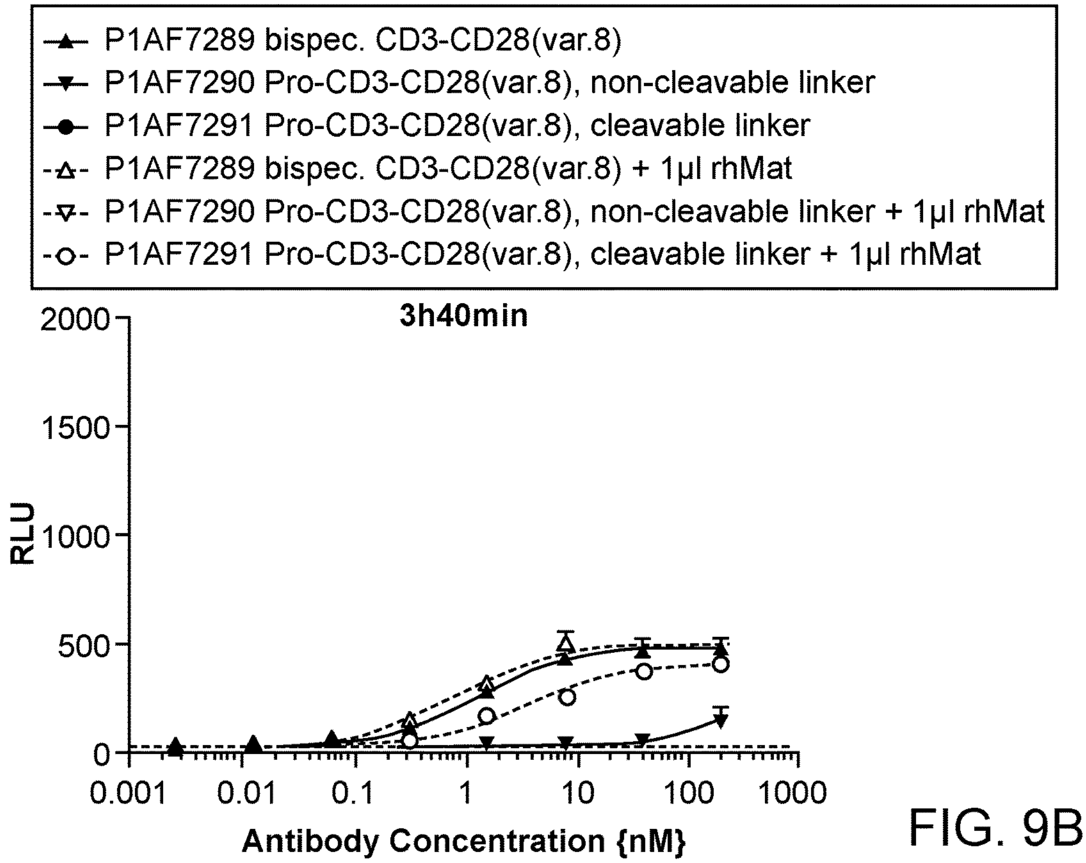
Figure 9C:
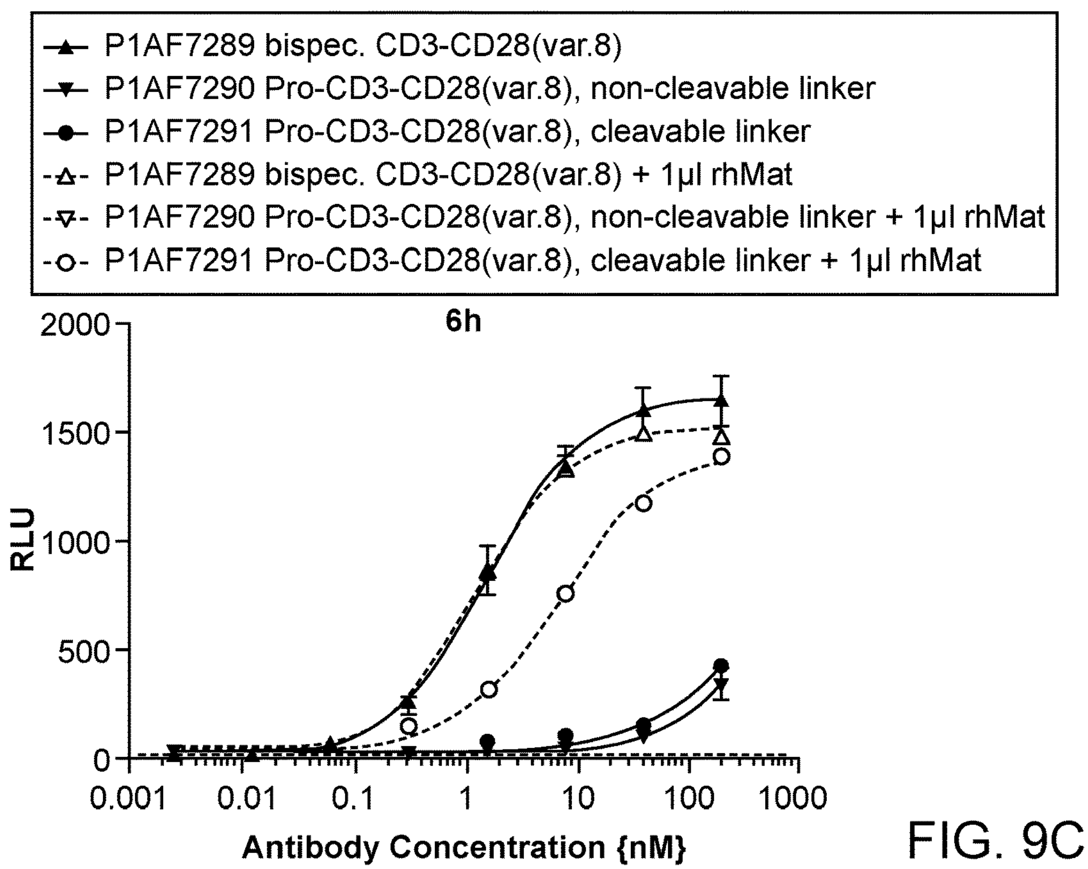

As shown in FIG. 8, for the masked CD28 (SA_variant 8)-CD3 (P035.093) 1+1 antigen binding molecule Jurkat NFAT IL2 activation could be detected after 2 to 6 hours incubation time when Rh-Matriptase had been added, whereas no Jurkat IL2 activation was detected in the absence of Matriptase. In FIG. 9A to 9C the Jurkat NFAT IL2 activation for various CD28-CD3 bispecific antibodies is shown at different time points, i.e. at 2 hours (FIG. 9A), 3 h 40 min (FIG. 9B) and 6 hours (FIG. 9C).

The bispecific CD28-CD3 IgG induces dose-dependent Jurkat NFAT IL2 activation. The incubation with recombinant human matriptase for 2 h at 37° C. does not reduce potency of CD28-CD3 IgG. The Jurkat NFAT IL2 activation of the CD28-CD3 IgG with or without matriptase incubation is the comparable. The masked CD28-Pro-CD3 IgG containing a non-cleavable linker does not induce Jurkat NFAT IL2 activation except at the highest concentration of 200 nM. The activation is significantly less compared to the unmasked molecule. The Jurkat NFAT IL2 activation of the CD28-pro-CD3 IgG with or without matriptase incubation is the same. The masked CD28-Pro-CD3 IgG containing a matriptase cleavable linker (PMAKK (SEQ ID NO: 162)) does induce dose-dependent Jurkat NFAT IL2 activation. The potency is slightly lower in terms of $EC_{50}$ compared to the CD28-CD3 IgG. Without the presence of matriptase masked CD28-Pro-CD3 IgG containing a matriptase cleavable linker (PMAKK (SEQ ID NO: 162)) is comparable to the masked CD28-Pro-CD3 IgG containing a non-cleavable linker.

REFERENCES

Acuto, O., and Michel, F. (2003). CD28-mediated co-stimulation: a quantitative support for TCR signalling. Nat Rev Immunol 3, 939-951.

Atamaniuk, J., Gleiss A., Porpazcy E., Kainz B., Grunt T. W., Raderer M., Hilgarth B., Drach J., Ludwig H., Gisslinger H., Jaeger U., Gaiger A. (2012). Overexpression of G protein-coupled receptor 5D in the bone marrow is associated with poor prognosis in patients with multiple myeloma. Eur J Clin Invest. 42 (9), 953-60.

Bahlis N. J., King A. M., Kolonias D. Carlson L. M., Liu H. Y., Hussein M. A., Terebelo H. R., Byrne G. E. Jr, Levine B. L., Boise L. H., Lee K. P. (2007). CD28-mediated regulation of multiple myeloma cell proliferation and survival. Blood 109 (11), 5002-5010.

Boomer, J. S., and Green, J. M. (2010). An enigmatic tail of CD28 signaling. Cold Spring Harb Perspect Biol 2, a002436.

Carreno, B. M., and Collins, M. (2002). The B7 family of ligands and its receptors: new pathways for costimulation and inhibition of immune responses. Annu Rev Immunol 20, 29-53.

Chen, L., and Flies, D. B. (2013). Molecular mechanisms of T cell co-stimulation and co-inhibition. Nat Rev Immunol 13, 227-242.

Engelhardt, J. J., Sullivan, T. J., and Allison, J. P. (2006). CTLA-4 overexpression inhibits T cell responses through a CD28-B7-dependent mechanism. J Immunol 177, 1052-1061.

Esensten, J. H., Helou, Y. A., Chopra, G., Weiss, A., and Bluestone, J. A. (2016). CD28 Costimulation: From Mechanism to Therapy. Immunity 44, 973-988.

Fraser, J. D., Irving, B. A., Crabtree, G. R., and Weiss, A. (1991). Regulation of interleukin-2 gene enhancer activity by the T cell accessory molecule CD28. Science 251, 313-316.

Gao Y., Wang X., Yan H., Zeng J., Ma S., Niu Y., Zhou G., Jiang Y., Chen Y. (2016). Comparative Transcriptome Analysis of Fetal Skin Reveals Key Genes Related to Hair Follicle Morphogenesis in Cashmere Goats. PLOS One 11 (3), e0151118.

Hui, E., Cheung, J., Zhu, J., Su, X., Taylor, M. J., Wallweber, H. A., Sasmal, D. K., Huang, J., Kim, J. M., Mellman, I., and Vale, R. D. (2017). T cell costimulatory receptor CD28 is a primary target for PD-1-mediated inhibition. Science 355, 1428-1433.

Hunig, T. (2012). The storm has cleared: lessons from the CD28 superagonist TGN1412 trial. Nat Rev Immunol 12, 317-318.

June, C. H., Ledbetter, J. A., Gillespie, M. M., Lindsten, T., and Thompson, C. B. (1987). T-cell proliferation involving the CD28 pathway is associated with cyclosporine-resistant interleukin 2 gene expression. Mol Cell Biol 7, 4472-4481.

Kamphorst, A. O., Wieland, A., Nasti, T., Yang, S., Zhang, R., Barber, D. L., Konieczny, B. T., Daugherty, C. Z., Koenig, L., Yu, K., et al. (2017). Rescue of exhausted CD8 T cells by PD-1-targeted therapies is CD28-dependent. Science 355, 1423-1427.

Lavin, Y., Kobayashi, S., Leader, A., Amir, E. D., Elefant, N., Bigenwald, C., Remark, R., Sweeney, R., Becker, C. D., Levine, J. H., et al. (2017). Innate Immune Landscape in Early Lung Adenocarcinoma by Paired Single-Cell Analyses. Cell 169, 750-765 e717.

Linsley, P. S., Clark, E. A., and Ledbetter, J. A. (1990). T-cell antigen CD28 mediates adhesion with B cells by interacting with activation antigen B7/BB-1. Proc Natl Acad Sci USA 87, 5031-5035.

Murray M. E., Gavile C. M., Nair J. R., Koorella C., Carlson L. M., Buac D., Utley A., Chesi M., Bergsagel P. L., Boise L. H., Lee K. P. (2014). CD28-mediated pro-survival signaling induces chemotherapeutic resistance in multiple myeloma. Blood 123 (24), 3770-3779.

Römer, P. S., Berr, S., Avota, E., Na, S. Y., Battaglia, M., ten Berge, I., Einsele, H., and Hunig, T. (2011). Preculture of PBMCs at high cell density increases sensitivity of T-cell responses, revealing cytokine release by CD28 superagonist TGN1412. Blood 118, 6772-6782.

Tai, X., Van Laethem, F., Sharpe, A. H., and Singer, A. (2007). Induction of autoimmune disease in CTLA-4−/− mice depends on a specific CD28 motif that is required for in vivo costimulation. Proc Natl Acad Sci USA 104, 13756-13761.

Thompson, C. B., Lindsten, T., Ledbetter, J. A., Kunkel, S. L., Young, H. A., Emerson, S. G., Leiden, J. M., and June, C. H. (1989). CD28 activation pathway regulates the production of multiple T-cell-derived lymphokines/cytokines. Proc Natl Acad Sci USA 86, 1333-1337.

Tirosh, I., Izar, B., Prakadan, S. M., Wadsworth, M. H., 2nd, Treacy, D., Trombetta, J. J., Rotem, A., Rodman, C., Lian, C., Murphy, G., et al. (2016). Dissecting the multicellular ecosystem of metastatic melanoma by single-cell RNA-seq. Science 352, 189-196.

Zheng, C., Zheng, L., Yoo, J. K., Guo, H., Zhang, Y., Guo, X., Kang, B., Hu, R., Huang, J. Y., Zhang, Q., et al. (2017). Landscape of Infiltrating T Cells in Liver Cancer Revealed by Single-Cell Sequencing. Cell 169, 1342-1356 e1316.

SEQUENCE LISTING

```
Sequence total quantity: 217
SEQ ID NO: 1             moltype = AA  length = 220
FEATURE                  Location/Qualifiers
source                   1..220
                         mol_type = protein
                         organism = Homo sapiens
SEQUENCE: 1
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                        220

SEQ ID NO: 2             moltype = AA  length = 5
FEATURE                  Location/Qualifiers
REGION                   1..5
                         note = CD3 (CH2527) CDR-H1
source                   1..5
                         mol_type = protein
                         organism = synthetic construct
SEQUENCE: 2
TYAMN                                                              5

SEQ ID NO: 3             moltype = AA  length = 19
FEATURE                  Location/Qualifiers
REGION                   1..19
                         note = CD3 (CH2527) CDR-H2
source                   1..19
                         mol_type = protein
                         organism = synthetic construct
SEQUENCE: 3
RIRSKYNNYA TYYADSVKG                                               19

SEQ ID NO: 4             moltype = AA  length = 14
FEATURE                  Location/Qualifiers
REGION                   1..14
                         note = CD3 (CH2527) CDR-H3
source                   1..14
                         mol_type = protein
                         organism = synthetic construct
SEQUENCE: 4
HGNFGNSYVS WFAY                                                    14

SEQ ID NO: 5             moltype = AA  length = 14
FEATURE                  Location/Qualifiers
REGION                   1..14
                         note = CD3 (CH2527) CDR-L1
source                   1..14
                         mol_type = protein
                         organism = synthetic construct
SEQUENCE: 5
GSSTGAVTTS NYAN                                                    14

SEQ ID NO: 6             moltype = AA  length = 7
FEATURE                  Location/Qualifiers
REGION                   1..7
                         note = CD3 (CH2527) CDR-L2
```

```
source                  1..7
                        mol_type = protein
                        organism = synthetic construct
SEQUENCE: 6
GTNKRAP                                                                   7

SEQ ID NO: 7            moltype = AA  length = 9
FEATURE                 Location/Qualifiers
REGION                  1..9
                        note = CD3 (CH2527) CDR-L3
source                  1..9
                        mol_type = protein
                        organism = synthetic construct
SEQUENCE: 7
ALWYSNLWV                                                                 9

SEQ ID NO: 8            moltype = AA  length = 125
FEATURE                 Location/Qualifiers
REGION                  1..125
                        note = heavy chain variable domain VH, CD3 (CH2527)
source                  1..125
                        mol_type = protein
                        organism = synthetic construct
SEQUENCE: 8
EVQLLESGGG LVQPGGSLRL SCAASGFTFS TYAMNWVRQA PGKGLEWVSR IRSKYNNYAT  60
YYADSVKGRF TISRDDSKNT LYLQMNSLRA EDTAVYYCVR HGNFGNSYVS WFAYWGQGTL  120
VTVSS                                                                     125

SEQ ID NO: 9            moltype = AA  length = 109
FEATURE                 Location/Qualifiers
REGION                  1..109
                        note = light chain variable domain VL, CD3 (CH2527)
source                  1..109
                        mol_type = protein
                        organism = synthetic construct
SEQUENCE: 9
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVL             109

SEQ ID NO: 10           moltype = AA  length = 5
FEATURE                 Location/Qualifiers
REGION                  1..5
                        note = CD3 (P035.093) CDR-H1
source                  1..5
                        mol_type = protein
                        organism = synthetic construct
SEQUENCE: 10
SYAMN                                                                     5

SEQ ID NO: 11           moltype = AA  length = 19
FEATURE                 Location/Qualifiers
REGION                  1..19
                        note = CD3 (P035.093) CDR-H2
source                  1..19
                        mol_type = protein
                        organism = synthetic construct
SEQUENCE: 11
RIRSKYNNYA TYYADSVKG                                                      19

SEQ ID NO: 12           moltype = AA  length = 14
FEATURE                 Location/Qualifiers
REGION                  1..14
                        note = CD3 (P035.093) CDR-H3
source                  1..14
                        mol_type = protein
                        organism = synthetic construct
SEQUENCE: 12
ASNFPASYVS YFAY                                                           14

SEQ ID NO: 13           moltype = AA  length = 14
FEATURE                 Location/Qualifiers
REGION                  1..14
                        note = CD3 (P035.093) CDR-L1
source                  1..14
                        mol_type = protein
                        organism = synthetic construct
SEQUENCE: 13
GSSTGAVTTS NYAN                                                           14
```

-continued

```
SEQ ID NO: 14           moltype = AA  length = 7
FEATURE                 Location/Qualifiers
REGION                  1..7
                        note = CD3 (P035.093) CDR-L2
source                  1..7
                        mol_type = protein
                        organism = synthetic construct
SEQUENCE: 14
GTNKRAP                                                           7

SEQ ID NO: 15           moltype = AA  length = 9
FEATURE                 Location/Qualifiers
REGION                  1..9
                        note = CD3 (P035.093) CDR-L3
source                  1..9
                        mol_type = protein
                        organism = synthetic construct
SEQUENCE: 15
ALWYSNLWV                                                         9

SEQ ID NO: 16           moltype = AA  length = 125
FEATURE                 Location/Qualifiers
REGION                  1..125
                        note = heavy chain variable domain VH, CD3 (P035.093)
source                  1..125
                        mol_type = protein
                        organism = synthetic construct
SEQUENCE: 16
EVQLLESGGG LVQPGGSLRL SCAASGFTFS SYAMNWVRQA PGKGLEWVSR IRSKYNNYAT  60
YYADSVKGRF TISRDDSKNT LYLQMNSLRA EDTAVYYCVR ASNFPASYVS YFAYWGQGTL  120
VTVSS                                                             125

SEQ ID NO: 17           moltype = AA  length = 109
FEATURE                 Location/Qualifiers
REGION                  1..109
                        note = light chain variable domain VL, CD3 (P035.093)
source                  1..109
                        mol_type = protein
                        organism = synthetic construct
SEQUENCE: 17
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVL             109

SEQ ID NO: 18           moltype = AA  length = 5
FEATURE                 Location/Qualifiers
REGION                  1..5
                        note = CD28(SA) CDR-H1
source                  1..5
                        mol_type = protein
                        organism = synthetic construct
SEQUENCE: 18
SYYIH                                                             5

SEQ ID NO: 19           moltype = AA  length = 17
FEATURE                 Location/Qualifiers
REGION                  1..17
                        note = CD28(SA) CDR-H2
source                  1..17
                        mol_type = protein
                        organism = synthetic construct
SEQUENCE: 19
CIYPGNVNTN YNEKFKD                                                17

SEQ ID NO: 20           moltype = AA  length = 11
FEATURE                 Location/Qualifiers
REGION                  1..11
                        note = CD28(SA) CDR-H3
source                  1..11
                        mol_type = protein
                        organism = synthetic construct
SEQUENCE: 20
SHYGLDWNFD V                                                      11

SEQ ID NO: 21           moltype = AA  length = 11
FEATURE                 Location/Qualifiers
REGION                  1..11
                        note = CD28(SA) CDR-L1
source                  1..11
                        mol_type = protein
```

```
                       organism = synthetic construct
SEQUENCE: 21
HASQNIYVWL N                                                11

SEQ ID NO: 22          moltype = AA  length = 7
FEATURE                Location/Qualifiers
REGION                 1..7
                       note = CD28(SA) CDR-L2
source                 1..7
                       mol_type = protein
                       organism = synthetic construct
SEQUENCE: 22
KASNLHT                                                     7

SEQ ID NO: 23          moltype = AA  length = 9
FEATURE                Location/Qualifiers
REGION                 1..9
                       note = CD28(SA) CDR-L3
source                 1..9
                       mol_type = protein
                       organism = synthetic construct
SEQUENCE: 23
QQGQTYPYT                                                   9

SEQ ID NO: 24          moltype = AA  length = 120
FEATURE                Location/Qualifiers
REGION                 1..120
                       note = CD28(SA) VH
source                 1..120
                       mol_type = protein
                       organism = synthetic construct
SEQUENCE: 24
QVQLVQSGAE VKKPGASVKV SCKASGYTFT SYYIHWVRQA PGQGLEWIGC IYPGNVNTNY  60
NEKFKDRATL TVDTSISTAY MELSRLRSDD TAVYFCTRSH YGLDWNFDVW GQGTTVTVSS  120

SEQ ID NO: 25          moltype = AA  length = 107
FEATURE                Location/Qualifiers
REGION                 1..107
                       note = CD28(SA) VL
source                 1..107
                       mol_type = protein
                       organism = synthetic construct
SEQUENCE: 25
DIQMTQSPSS LSASVGDRVT ITCHASQNIY VWLNWYQQKP GKAPKLLIYK ASNLHTGVPS  60
RFSGSGSGTD FTLTISSLQP EDFATYYCQQ GQTYPYTFGG GTKVEIK             107

SEQ ID NO: 26          moltype = AA  length = 5
FEATURE                Location/Qualifiers
REGION                 1..5
                       note = CD28 CDR-H1 consensus
source                 1..5
                       mol_type = protein
                       organism = synthetic construct
SEQUENCE: 26
SYYIH                                                       5

SEQ ID NO: 27          moltype = AA  length = 17
FEATURE                Location/Qualifiers
REGION                 1..17
                       note = CD28 CDR-H2 consensus
VARIANT                5
                       note = Gly or Arg
VARIANT                6
                       note = Asn or Asp
VARIANT                7
                       note = Val or Gly
VARIANT                8
                       note = Asn, Gln or Ala
source                 1..17
                       mol_type = protein
                       organism = synthetic construct
SEQUENCE: 27
SIYPXXXXTN YNEKFKD                                          17

SEQ ID NO: 28          moltype = AA  length = 11
FEATURE                Location/Qualifiers
REGION                 1..11
                       note = CD28 CDR-H3 consensus
VARIANT                5
```

-continued

```
                        note = Leu or Ala
VARIANT                 7
                        note = Trp, His, Tyr or Phe
source                  1..11
                        mol_type = protein
                        organism = synthetic construct
SEQUENCE: 28
SHYGXDXNFD V                                                   11

SEQ ID NO: 29           moltype = AA  length = 11
FEATURE                 Location/Qualifiers
REGION                  1..11
                        note = CD28 CDR-L1 consensus
VARIANT                 1
                        note = His or Arg
VARIANT                 5
                        note = Asn or Gly
VARIANT                 7
                        note = Tyr or Ser
VARIANT                 8
                        note = Val or Asn
VARIANT                 9
                        note = Trp, His, Phe or Tyr
source                  1..11
                        mol_type = protein
                        organism = synthetic construct
SEQUENCE: 29
XASQXIXXXL N                                                   11

SEQ ID NO: 30           moltype =   length =
SEQUENCE: 30
000

SEQ ID NO: 31           moltype = AA  length = 9
FEATURE                 Location/Qualifiers
REGION                  1..9
                        note = CD28 CDR-L3 consensus
VARIANT                 3
                        note = Gly or Ala
source                  1..9
                        mol_type = protein
                        organism = synthetic construct
SEQUENCE: 31
QQXQTYPYT                                                      9

SEQ ID NO: 32           moltype = AA  length = 120
FEATURE                 Location/Qualifiers
REGION                  1..120
                        note = CD28 VH variant a
source                  1..120
                        mol_type = protein
                        organism = synthetic construct
SEQUENCE: 32
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120

SEQ ID NO: 33           moltype = AA  length = 120
FEATURE                 Location/Qualifiers
REGION                  1..120
                        note = CD28 VH variant b
source                  1..120
                        mol_type = protein
                        organism = synthetic construct
SEQUENCE: 33
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGLDHNFDVW GQGTTVTVSS  120

SEQ ID NO: 34           moltype = AA  length = 120
FEATURE                 Location/Qualifiers
REGION                  1..120
                        note = CD28 VH variant c
source                  1..120
                        mol_type = protein
                        organism = synthetic construct
SEQUENCE: 34
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGADHNFDVW GQGTTVTVSS  120

SEQ ID NO: 35           moltype = AA  length = 120
```

-continued

```
FEATURE                Location/Qualifiers
REGION                 1..120
                       note = CD28 VH variant d
source                 1..120
                       mol_type = protein
                       organism = synthetic construct
SEQUENCE: 35
QVQLVQSGAE VKKPGASVKV SCKASGYTFT SYYIHWVRQA PGQGLEWIGS IYPRDGQTNY  60
NEKFKDRATL TVDTSISTAY MELSRLRSDD TAVYFCTRSH YGLDYNFDVW GQGTTVTVSS  120

SEQ ID NO: 36          moltype = AA  length = 120
FEATURE                Location/Qualifiers
REGION                 1..120
                       note = CD28 VH variant e
source                 1..120
                       mol_type = protein
                       organism = synthetic construct
SEQUENCE: 36
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGLDWNFDVW GQGTTVTVSS  120

SEQ ID NO: 37          moltype = AA  length = 120
FEATURE                Location/Qualifiers
REGION                 1..120
                       note = CD28 VH variant f
source                 1..120
                       mol_type = protein
                       organism = synthetic construct
SEQUENCE: 37
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGLDFNFDVW GQGTTVTVSS  120

SEQ ID NO: 38          moltype = AA  length = 120
FEATURE                Location/Qualifiers
REGION                 1..120
                       note = CD28 VH variant g
source                 1..120
                       mol_type = protein
                       organism = synthetic construct
SEQUENCE: 38
QVQLVQSGAE VKKPGASVKV SCKASGYTFT SYYIHWVRQA PGQGLEWIGS IYPRNVQTNY  60
NEKFKDRATL TVDTSISTAY MELSRLRSDD TAVYFCTRSH YGLDHNFDVW GQGTTVTVSS  120

SEQ ID NO: 39          moltype = AA  length = 120
FEATURE                Location/Qualifiers
REGION                 1..120
                       note = CD28 VH variant h
source                 1..120
                       mol_type = protein
                       organism = synthetic construct
SEQUENCE: 39
QVQLVQSGAE VKKPGASVKV SCKASGYTFT SYYIHWVRQA PGQGLEWIGS IYPRDVQTNY  60
NEKFKDRATL TVDTSISTAY MELSRLRSDD TAVYFCTRSH YGLDHNFDVW GQGTTVTVSS  120

SEQ ID NO: 40          moltype = AA  length = 120
FEATURE                Location/Qualifiers
REGION                 1..120
                       note = CD28 VH variant i
source                 1..120
                       mol_type = protein
                       organism = synthetic construct
SEQUENCE: 40
EVQLVESGGG LVQPGGSLRL SCAASGFTFT SYYIHWVRQA PGKGLEWVAS IYPGNVNTRY  60
ADSVKGRFTI SADTSKNTAY LQMNSLRAED TAVYYCTRSH YGLDWNFDVW GQGTTVTVSS  120

SEQ ID NO: 41          moltype = AA  length = 120
FEATURE                Location/Qualifiers
REGION                 1..120
                       note = CD28 VH variant j
source                 1..120
                       mol_type = protein
                       organism = synthetic construct
SEQUENCE: 41
EVQLVESGGG LVQPGGSLRL SCAASGFTFT SYYIHWVRQA PGKGLEWVAS IYPGNVATRY  60
ADSVKGRFTI SADTSKNTAY LQMNSLRAED TAVYYCTRSH YGLDWNFDVW GQGTTVTVSS  120

SEQ ID NO: 42          moltype = AA  length = 107
FEATURE                Location/Qualifiers
REGION                 1..107
```

```
                         note = CD28 VL variant k
source                   1..107
                         mol_type = protein
                         organism = synthetic construct
SEQUENCE: 42
DIQMTQSPSS LSASVGDRVT ITCHASQNIY VHLNWYQQKP GKAPKLLIYK ASNLHTGVPS  60
RFSGSGSGTD FTLTISSLQP EDFATYYCQQ AQTYPYTFGG GTKVEIK               107

SEQ ID NO: 43            moltype = AA  length = 107
FEATURE                  Location/Qualifiers
REGION                   1..107
                         note = CD28 VL variant l
source                   1..107
                         mol_type = protein
                         organism = synthetic construct
SEQUENCE: 43
DIQMTQSPSS LSASVGDRVT ITCHASQNIY VFLNWYQQKP GKAPKLLIYK ASNLHTGVPS  60
RFSGSGSGTD FTLTISSLQP EDFATYYCQQ GQTYPYTFGG GTKVEIK               107

SEQ ID NO: 44            moltype = AA  length = 107
FEATURE                  Location/Qualifiers
REGION                   1..107
                         note = CD28 VL variant m
source                   1..107
                         mol_type = protein
                         organism = synthetic construct
SEQUENCE: 44
DIQMTQSPSS LSASVGDRVT ITCHASQNIY VYLNWYQQKP GKAPKLLIYK ASNLHTGVPS  60
RFSGSGSGTD FTLTISSLQP EDFATYYCQQ GQTYPYTFGG GTKVEIK               107

SEQ ID NO: 45            moltype = AA  length = 107
FEATURE                  Location/Qualifiers
REGION                   1..107
                         note = CD28 VL variant n
source                   1..107
                         mol_type = protein
                         organism = synthetic construct
SEQUENCE: 45
DIQMTQSPSS LSASVGDRVT ITCHASQGIS NYLNWYQQKP GKAPKLLIYK ASNLHTGVPS  60
RFSGSGSGTD FTLTISSLQP EDFATYYCQQ GQTYPYTFGG GTKVEIK               107

SEQ ID NO: 46            moltype = AA  length = 107
FEATURE                  Location/Qualifiers
REGION                   1..107
                         note = CD28 VL variant o
source                   1..107
                         mol_type = protein
                         organism = synthetic construct
SEQUENCE: 46
DIQMTQSPSS LSASVGDRVT ITCHASQNIY VWLNWYQQKP GKAPKLLIYY TSSLHSGVPS  60
RFSGSGSGTD FTLTISSLQP EDFATYYCQQ GQTYPYTFGG GTKVEIK               107

SEQ ID NO: 47            moltype = AA  length = 107
FEATURE                  Location/Qualifiers
REGION                   1..107
                         note = CD28 VL variant p
source                   1..107
                         mol_type = protein
                         organism = synthetic construct
SEQUENCE: 47
DIQMTQSPSS LSASVGDRVT ITCHASQGIS NYLNWYQQKP GKAPKLLIYY TSSLHSGVPS  60
RFSGSGSGTD FTLTISSLQP EDFATYYCQQ GQTYPYTFGG GTKVEIK               107

SEQ ID NO: 48            moltype = AA  length = 107
FEATURE                  Location/Qualifiers
REGION                   1..107
                         note = CD28 VL variant q
source                   1..107
                         mol_type = protein
                         organism = synthetic construct
SEQUENCE: 48
DIQMTQSPSS LSASVGDRVT ITCHASQGIS NHLNWYQQKP GKAPKLLIYK ASNLHTGVPS  60
RFSGSGSGTD FTLTISSLQP EDFATYYCQQ GQTYPYTFGG GTKVEIK               107

SEQ ID NO: 49            moltype = AA  length = 107
FEATURE                  Location/Qualifiers
REGION                   1..107
                         note = CD28 VL variant r
source                   1..107
```

```
                        mol_type = protein
                        organism = synthetic construct
SEQUENCE: 49
DIQMTQSPSS LSASVGDRVT ITCHASQGIY VYLNWYQQKP GKAPKLLIYK ASNLHTGVPS  60
RFSGSGSGTD FTLTISSLQP EDFATYYCQQ GQTYPYTFGG GTKVEIK               107

SEQ ID NO: 50           moltype = AA  length = 107
FEATURE                 Location/Qualifiers
REGION                  1..107
                        note = CD28 VL variant s
source                  1..107
                        mol_type = protein
                        organism = synthetic construct
SEQUENCE: 50
DIQMTQSPSS LSASVGDRVT ITCHASQGIS VYLNWYQQKP GKAPKLLIYK ASNLHTGVPS  60
RFSGSGSGTD FTLTISSLQP EDFATYYCQQ GQTYPYTFGG GTKVEIK               107

SEQ ID NO: 51           moltype = AA  length = 107
FEATURE                 Location/Qualifiers
REGION                  1..107
                        note = CD28 VL variant t
source                  1..107
                        mol_type = protein
                        organism = synthetic construct
SEQUENCE: 51
DIQMTQSPSS LSASVGDRVT ITCRASQNIY VWLNWYQQKP GKAPKLLIYK ASNLYSGVPS  60
RFSGSRSGTD FTLTISSLQP EDFATYYCQQ GQTYPYTFGQ GTKLEIK               107

SEQ ID NO: 52           moltype = AA  length = 5
FEATURE                 Location/Qualifiers
REGION                  1..5
                        note = CD28(variant 8) CDR-H1
source                  1..5
                        mol_type = protein
                        organism = synthetic construct
SEQUENCE: 52
SYYIH                                                             5

SEQ ID NO: 53           moltype = AA  length = 17
FEATURE                 Location/Qualifiers
REGION                  1..17
                        note = CD28(variant 8) CDR-H2
source                  1..17
                        mol_type = protein
                        organism = synthetic construct
SEQUENCE: 53
SIYPGNVQTN YNEKFKD                                                17

SEQ ID NO: 54           moltype = AA  length = 11
FEATURE                 Location/Qualifiers
REGION                  1..11
                        note = CD28(variant 8) CDR-H3
source                  1..11
                        mol_type = protein
                        organism = synthetic construct
SEQUENCE: 54
SHYGLDWNFD V                                                      11

SEQ ID NO: 55           moltype = AA  length = 11
FEATURE                 Location/Qualifiers
REGION                  1..11
                        note = CD28(variant 8) CDR-L1
source                  1..11
                        mol_type = protein
                        organism = synthetic construct
SEQUENCE: 55
HASQNIYVYL N                                                      11

SEQ ID NO: 56           moltype = AA  length = 7
FEATURE                 Location/Qualifiers
REGION                  1..7
                        note = CD28(variant 8) CDR-L2
source                  1..7
                        mol_type = protein
                        organism = synthetic construct
SEQUENCE: 56
KASNLHT                                                           7

SEQ ID NO: 57           moltype = AA  length = 9
```

```
FEATURE                Location/Qualifiers
REGION                 1..9
                       note = CD28(variant 8) CDR-L3
source                 1..9
                       mol_type = protein
                       organism = synthetic construct
SEQUENCE: 57
QQGQTYPYT                                                                9

SEQ ID NO: 58          moltype = AA  length = 5
FEATURE                Location/Qualifiers
REGION                 1..5
                       note = CD28(variant 15) CDR-H1
source                 1..5
                       mol_type = protein
                       organism = synthetic construct
SEQUENCE: 58
SYYIH                                                                    5

SEQ ID NO: 59          moltype = AA  length = 17
FEATURE                Location/Qualifiers
REGION                 1..17
                       note = CD28(variant 15) CDR-H2
source                 1..17
                       mol_type = protein
                       organism = synthetic construct
SEQUENCE: 59
SIYPGNVQTN YNEKFKD                                                       17

SEQ ID NO: 60          moltype = AA  length = 11
FEATURE                Location/Qualifiers
REGION                 1..11
                       note = CD28(variant 15) CDR-H3
source                 1..11
                       mol_type = protein
                       organism = synthetic construct
SEQUENCE: 60
SHYGLDWNFD V                                                             11

SEQ ID NO: 61          moltype = AA  length = 11
FEATURE                Location/Qualifiers
REGION                 1..11
                       note = CD28(variant 15) CDR-L1
source                 1..11
                       mol_type = protein
                       organism = synthetic construct
SEQUENCE: 61
HASQNIYVFL N                                                             11

SEQ ID NO: 62          moltype = AA  length = 7
FEATURE                Location/Qualifiers
REGION                 1..7
                       note = CD28(variant 15) CDR-L2
source                 1..7
                       mol_type = protein
                       organism = synthetic construct
SEQUENCE: 62
KASNLHT                                                                  7

SEQ ID NO: 63          moltype = AA  length = 9
FEATURE                Location/Qualifiers
REGION                 1..9
                       note = CD28(variant 15) CDR-L3
source                 1..9
                       mol_type = protein
                       organism = synthetic construct
SEQUENCE: 63
QQGQTYPYT                                                                9

SEQ ID NO: 64          moltype = AA  length = 5
FEATURE                Location/Qualifiers
REGION                 1..5
                       note = CD28(variant 29) CDR-H1
source                 1..5
                       mol_type = protein
                       organism = synthetic construct
SEQUENCE: 64
SYYIH                                                                    5
```

-continued

```
SEQ ID NO: 65           moltype = AA  length = 17
FEATURE                 Location/Qualifiers
REGION                  1..17
                        note = CD28(variant 29) CDR-H2
source                  1..17
                        mol_type = protein
                        organism = synthetic construct
SEQUENCE: 65
SIYPGNVNTN YNEKFKD                                            17

SEQ ID NO: 66           moltype = AA  length = 11
FEATURE                 Location/Qualifiers
REGION                  1..11
                        note = CD28(variant 29) CDR-H3
source                  1..11
                        mol_type = protein
                        organism = synthetic construct
SEQUENCE: 66
SHYGLDWNFD V                                                  11

SEQ ID NO: 67           moltype = AA  length = 11
FEATURE                 Location/Qualifiers
REGION                  1..11
                        note = CD28(variant 29) CDR-L1
source                  1..11
                        mol_type = protein
                        organism = synthetic construct
SEQUENCE: 67
HASQNIYVWL N                                                  11

SEQ ID NO: 68           moltype = AA  length = 7
FEATURE                 Location/Qualifiers
REGION                  1..7
                        note = CD28(variant 29) CDR-L2
source                  1..7
                        mol_type = protein
                        organism = synthetic construct
SEQUENCE: 68
KASNLHT                                                       7

SEQ ID NO: 69           moltype = AA  length = 9
FEATURE                 Location/Qualifiers
REGION                  1..9
                        note = CD28(variant 29) CDR-L3
source                  1..9
                        mol_type = protein
                        organism = synthetic construct
SEQUENCE: 69
QQGQTYPYT                                                     9

SEQ ID NO: 70           moltype = AA  length = 207
FEATURE                 Location/Qualifiers
source                  1..207
                        mol_type = protein
                        organism = Homo sapiens
SEQUENCE: 70
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                 207

SEQ ID NO: 71           moltype = AA  length = 198
FEATURE                 Location/Qualifiers
source                  1..198
                        mol_type = protein
                        organism = Macaca fascicularis
SEQUENCE: 71
MQSGTRWRVL GLCLLSIGVW GQDGNEEMGS ITQTPYQVSI SGTTVILTCS QHLGSEAQWQ  60
HNGKNKEDSG DRLFLPEFSE MEQSGYYVCY PRGSNPEDAS HHLYLKARVC ENCMEMDVMA  120
VATIVIVDIC ITLGLLLLVY YWSKNRKAKA KPVTRGAGAG GRQRGQNKER PPPVPNPDYE  180
PIRKGQQDLY SGLNQRRI                                           198

SEQ ID NO: 72           moltype = AA  length = 448
FEATURE                 Location/Qualifiers
REGION                  1..448
                        note = VH (CD28 SA) CH1 (EE)- Fc knob PGLALA
source                  1..448
                        mol_type = protein
                        organism = synthetic construct
```

```
SEQUENCE: 72
QVQLVQSGAE VKKPGASVKV SCKASGYTFT SYYIHWVRQA PGQGLEWIGC IYPGNVNTNY  60
NEKFKDRATL TVDTSISTAY MELSRLRSDD TAVYFCTRSH YGLDWNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                     448

SEQ ID NO: 73          moltype = AA  length = 448
FEATURE                Location/Qualifiers
REGION                 1..448
                       note = VH (CD28 variant g) CH1- Fc knob PGLALA
source                 1..448
                       mol_type = protein
                       organism = synthetic construct
SEQUENCE: 73
QVQLVQSGAE VKKPGASVKV SCKASGYTFT SYYIHWVRQA PGQGLEWIGS IYPRNVQTNY  60
NEKFKDRATL TVDTSISTAY MELSRLRSDD TAVYFCTRSH YGLDHNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                     448

SEQ ID NO: 74          moltype = AA  length = 448
FEATURE                Location/Qualifiers
REGION                 1..448
                       note = VH (CD28 variant f) CH1- Fc knob PGLALA
source                 1..448
                       mol_type = protein
                       organism = synthetic construct
SEQUENCE: 74
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGLDFNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                     448

SEQ ID NO: 75          moltype = AA  length = 448
FEATURE                Location/Qualifiers
REGION                 1..448
                       note = VH (CD28 variant j) CH1- Fc knob PGLALA
source                 1..448
                       mol_type = protein
                       organism = synthetic construct
SEQUENCE: 75
EVQLVESGGG LVQPGGSLRL SCAASGFTFT SYYIHWVRQA PGKGLEWVAS IYPGNVATRY  60
ADSVKGRFTI SADTSKNTAY LQMNSLRAED TAVYYCTRSH YGLDWNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                     448

SEQ ID NO: 76          moltype = AA  length = 448
FEATURE                Location/Qualifiers
REGION                 1..448
                       note = VH (CD28 variant e) CH1- Fc knob PGLALA
source                 1..448
                       mol_type = protein
                       organism = synthetic construct
SEQUENCE: 76
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGLDWNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                     448

SEQ ID NO: 77          moltype = AA  length = 448
```

-continued

```
FEATURE                Location/Qualifiers
REGION                 1..448
                       note = VH (CD28 variant b) CH1- Fc knob PGLALA
source                 1..448
                       mol_type = protein
                       organism = synthetic construct
SEQUENCE: 77
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGLDHNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                   448

SEQ ID NO: 78          moltype = AA  length = 448
FEATURE                Location/Qualifiers
REGION                 1..448
                       note = VH (CD28 variant a) CH1- Fc knob PGLALA
source                 1..448
                       mol_type = protein
                       organism = synthetic construct
SEQUENCE: 78
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                   448

SEQ ID NO: 79          moltype = AA  length = 448
FEATURE                Location/Qualifiers
REGION                 1..448
                       note = VH (CD28 variant i) CH1- Fc knob PGLALA
source                 1..448
                       mol_type = protein
                       organism = synthetic construct
SEQUENCE: 79
EVQLVESGGG LVQPGGSLRL SCAASGFTFT SYYIHWVRQA PGKGLEWVAS IYPGNVNTRY  60
ADSVKGRFTI SADTSKNTAY LQMNSLRAED TAVYYCTRSH YGLDWNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VYTLPPCRDE  360
LTKNQVSLWC LVKGFYPSDI AVEWESNGQP ENNYKTTPPV LDSDGSFFLY SKLTVDKSRW  420
QQGNVFSCSV MHEALHNHYT QKSLSLSP                                   448

SEQ ID NO: 80          moltype = AA  length = 214
FEATURE                Location/Qualifiers
REGION                 1..214
                       note = VL-CD28(SA)-CL"RK"
source                 1..214
                       mol_type = protein
                       organism = synthetic construct
SEQUENCE: 80
DIQMTQSPSS LSASVGDRVT ITCHASQNIY VWLNWYQQKP GKAPKLLIYK ASNLHTGVPS  60
RFSGSGSGTD FTLTISSLQP EDFATYYCQQ GQTYPYTFGG GTKVEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 81          moltype = AA  length = 214
FEATURE                Location/Qualifiers
REGION                 1..214
                       note = VL (CD28 variant k)-CL (RK)
source                 1..214
                       mol_type = protein
                       organism = synthetic construct
SEQUENCE: 81
DIQMTQSPSS LSASVGDRVT ITCHASQNIY VHLNWYQQKP GKAPKLLIYK ASNLHTGVPS  60
RFSGSGSGTD FTLTISSLQP EDFATYYCQQ AQTYPYTFGG GTKVEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 82          moltype = AA  length = 214
FEATURE                Location/Qualifiers
REGION                 1..214
```

-continued

```
                        note = VL (CD28 variant l)-CL (RK)
source                  1..214
                        mol_type = protein
                        organism = synthetic construct
SEQUENCE: 82
DIQMTQSPSS LSASVGDRVT ITCHASQNIY VFLNWYQQKP GKAPKLLIYK ASNLHTGVPS  60
RFSGSGSGTD FTLTISSLQP EDFATYYCQQ GQTYPYTFGG GTKVEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 83           moltype = AA  length = 214
FEATURE                 Location/Qualifiers
REGION                  1..214
                        note = VL (CD28 variant m)-CL (RK)
source                  1..214
                        mol_type = protein
                        organism = synthetic construct
SEQUENCE: 83
DIQMTQSPSS LSASVGDRVT ITCHASQNIY VYLNWYQQKP GKAPKLLIYK ASNLHTGVPS  60
RFSGSGSGTD FTLTISSLQP EDFATYYCQQ GQTYPYTFGG GTKVEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 84           moltype = AA  length = 214
FEATURE                 Location/Qualifiers
REGION                  1..214
                        note = VL (CD28 variant r)-CL (RK)
source                  1..214
                        mol_type = protein
                        organism = synthetic construct
SEQUENCE: 84
DIQMTQSPSS LSASVGDRVT ITCHASQGIY VYLNWYQQKP GKAPKLLIYK ASNLHTGVPS  60
RFSGSGSGTD FTLTISSLQP EDFATYYCQQ GQTYPYTFGG GTKVEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 85           moltype = AA  length = 214
FEATURE                 Location/Qualifiers
REGION                  1..214
                        note = VL (CD28 variant s)-CL (RK)
source                  1..214
                        mol_type = protein
                        organism = synthetic construct
SEQUENCE: 85
DIQMTQSPSS LSASVGDRVT ITCHASQGIS VYLNWYQQKP GKAPKLLIYK ASNLHTGVPS  60
RFSGSGSGTD FTLTISSLQP EDFATYYCQQ GQTYPYTFGG GTKVEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 86           moltype = AA  length = 214
FEATURE                 Location/Qualifiers
REGION                  1..214
                        note = VL (CD28 variant t)-CL (RK)
source                  1..214
                        mol_type = protein
                        organism = synthetic construct
SEQUENCE: 86
DIQMTQSPSS LSASVGDRVT ITCRASQNIY VWLNWYQQKP GKAPKLLIYK ASNLYSGVPS  60
RFSGSRSGTD FTLTISSLQP EDFATYYCQQ GQTYPYTFGQ GTKLEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 87           moltype = AA  length = 225
FEATURE                 Location/Qualifiers
REGION                  1..225
                        note = Fc hole PGLALA, HYRF
source                  1..225
                        mol_type = protein
                        organism = synthetic construct
SEQUENCE: 87
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNRFTQKS LSLSP                 225

SEQ ID NO: 88           moltype = AA  length = 15
FEATURE                 Location/Qualifiers
REGION                  1..15
                        note = Avi tag
```

-continued

```
source                  1..15
                        mol_type = protein
                        organism = synthetic construct
SEQUENCE: 88
GLNDIFEAQK IEWHE                                              15

SEQ ID NO: 89           moltype = AA  length = 457
FEATURE                 Location/Qualifiers
REGION                  1..457
                        note = CD3(CH2527) VH-CL hu IgG1 Fc knob PGLALA
source                  1..457
                        mol_type = protein
                        organism = synthetic construct
SEQUENCE: 89
EVQLLESGGG LVQPGGSLRL SCAASGFTFS TYAMNWVRQA PGKGLEWVSR IRSKYNNYAT  60
YYADSVKGRF TISRDDSKNT LYLQMNSLRA EDTAVYYCVR HGNFGNSYVS WFAYWGQGTL  120
VTVSSASVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG ECDKTHTCPP  240
CPAPEAAGGP SVFLFPPKPK DTLMISRTPE VTCVVVDVSH EDPEVKFNWY VDGVEVHNAK  300
TKPREEQYNS TYRVVSVLTV LHQDWLNGKE YKCKVSNKAL GAPIEKTISK AKGQPREPQV  360
YTLPPCRDEL TKNQVSLWCL VKGFYPSDIA VEWESNGQPE NNYKTTPPVL DSDGSFFLYS  420
KLTVDKSRWQ QGNVFSCSVM HEALHNHYTQ KSLSLSP                      457

SEQ ID NO: 90           moltype = AA  length = 214
FEATURE                 Location/Qualifiers
REGION                  1..214
                        note = CD3(CH2527) VL-CH1
source                  1..214
                        mol_type = protein
                        organism = synthetic construct
SEQUENCE: 90
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVLS SASTKGPSVF  120
PLAPSSKSTS GGTAALGCLV KDYFPEPVTV SWNSGALTSG VHTFPAVLQS SGLYSLSSVV  180
TVPSSSLGTQ TYICNVNHKP SNTKVDKKVE PKSC                         214

SEQ ID NO: 91           moltype = AA  length = 448
FEATURE                 Location/Qualifiers
REGION                  1..448
                        note = CD28(9.3) VH-CH1 (EE) hu IgG1 Fc hole PGLALA
source                  1..448
                        mol_type = protein
                        organism = synthetic construct
SEQUENCE: 91
EVKLQQSGPG LVTPSQSLSI TCTVSGFSLS DYGVHWVRQS PGQGLEWLGV IWAGGGTNYN  60
SALMSRKSIS KDNSKSQVFL KMNSLQADDT AVYYCARDKG YSYYYSMDYW GQGTSVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSP                                448

SEQ ID NO: 92           moltype = AA  length = 218
FEATURE                 Location/Qualifiers
REGION                  1..218
                        note = CD28(9.3) VL-Ckappa (RK)
source                  1..218
                        mol_type = protein
                        organism = synthetic construct
SEQUENCE: 92
DIELTQSPAS LAVSLGQRAT ISCRASESVE YYVTSLMQWY QQKPGQPPKL LIFAASNVES  60
GVPARFSGSG SGTNFSLNIH PVDEDDVAMY FCQQSRKVPY TFGGGTKLEI KRTVAAPSVF  120
IFPPSDRKLK SGTASVVCLL NNFYPREAKV QWKVDNALQS GNSQESVTEQ DSKDSTYSLS  180
STLTLSKADY EKHKVYACEV THQGLSSPVT KSFNRGEC                      218

SEQ ID NO: 93           moltype = AA  length = 448
FEATURE                 Location/Qualifiers
REGION                  1..448
                        note = CD28(SA) VH-CH1 (EE) hu IgG1 Fc hole PGLALA
source                  1..448
                        mol_type = protein
                        organism = synthetic construct
SEQUENCE: 93
QVQLVQSGAE VKKPGASVKV SCKASGYTFT SYYIHWVRQA PGQGLEWIGC IYPGNVNTNY  60
NEKFKDRATL TVDTSISTAY MELSRLRSDD TAVYFCTRSH YGLDWNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
```

```
STYRVVSVLT VLHQDWLNGK EYKCKVSNKA LGAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSP                                    448

SEQ ID NO: 94          moltype = AA  length = 214
FEATURE                Location/Qualifiers
REGION                 1..214
                       note = CD28(SA) VL-Ckappa (RK)
source                 1..214
                       mol_type = protein
                       organism = synthetic construct
SEQUENCE: 94
DIQMTQSPSS LSASVGDRVT ITCHASQNIY VWLNWYQQKP GKAPKLLIYK ASNLHTGVPS  60
RFSGSGSGTD FTLTISSLQP EDFATYYCQQ GQTYPYTFGG GTKVEIKRTV AAPSVFIFPP  120
SDRKLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 95          moltype = AA  length = 225
FEATURE                Location/Qualifiers
REGION                 1..225
                       note = Fc knob PGLALA
source                 1..225
                       mol_type = protein
                       organism = synthetic construct
SEQUENCE: 95
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSP                  225

SEQ ID NO: 96          moltype = AA  length = 225
FEATURE                Location/Qualifiers
REGION                 1..225
                       note = Fc hole PGLALA
source                 1..225
                       mol_type = protein
                       organism = synthetic construct
SEQUENCE: 96
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALGA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSP                  225

SEQ ID NO: 97          moltype = AA  length = 448
FEATURE                Location/Qualifiers
REGION                 1..448
                       note = CD28(9.3) VH-CH1 (EE) hu IgG1 Fc hole PGLALA
source                 1..448
                       mol_type = protein
                       organism = synthetic construct
SEQUENCE: 97
EVKLQQSGPG LVTPSQSLSI TCTVSGFSLS DYGVHWVRQS PGQGLEWLGV IWAGGGTNYN  60
SALMSRKSIS KDNSKSQVFL KMNSLQADDT AVYYCARDKG YSYYYSMDYW GQGTSVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNRFT QKSLSLSP                                    448

SEQ ID NO: 98          moltype = AA  length = 739
FEATURE                Location/Qualifiers
REGION                 1..739
                       note = ScFv (4.24.72) VH-(G4S)4-VL-Matriptase linker- CD3
                        VH-CL hu IgG1Fc knob PGLALA
source                 1..739
                       mol_type = protein
                       organism = synthetic construct
SEQUENCE: 98
QVQLKESGPG LVAPSQSLSI TCTVSGFSLT SYGVSWVRQP PGKCLEWLGI IWGDGSTNYH  60
SALISRLSIS KDNSKSQVFL KLNSLQTDDT ATYYCAKGIT TVVDDYYAMD YWGQGTSVTV  120
SSGGGGSGGG GSGGGGSGGG GSDIQMTQSP ASLSASVGET VTITCRASEN IDSYLAWYQQ  180
KQGKSPQLLV YAATFLADDV PSRFSGSGSG TQYSLKINSL QSEDVARYYC QHYYSTPYTF  240
GCGTKLEIKG GGGSGGGGSR QARVVNGGGG GSGGGGSGGG GSEVQLLESG GGLVQPGGSL  300
RLSCAASGFT FSTYAMNWVR QAPGKGLEWV SRIRSKYNNY ATYYADSVKG RFTISRDDSK  360
NTLYLQMNSL RAEDTAVYYC VRHGNFGNSY VSWFAYWGQG TLVTVSSASV AAPSVFIFPP  420
SDEQLKSGTA SVVCLLNNFY PREAKVQWKV DNALQSGNSQ ESVTEQDSKD STYSLSSTLT  480
LSKADYEKHK VYACEVTHQG LSSPVTKSFN RGECDKTHTC PPCPAPEAAG GPSVFLFPPK  540
PKDTLMISRT PEVTCVVVDV SHEDPEVKFN WYVDGVEVHN AKTKPREEQY NSTYRVVSVL  600
```

-continued

```
TVLHQDWLNG KEYKCKVSNK ALGAPIEKTI SKAKGQPREP QVYTLPPCRD ELTKNQVSLW  660
CLVKGFYPSD IAVEWESNGQ PENNYKTTPP VLDSDGSFFL YSKLTVDKSR WQQGNVFSCS  720
VMHEALHNHY TQKSLSLSP                                                739

SEQ ID NO: 99          moltype = AA  length = 448
FEATURE                Location/Qualifiers
REGION                 1..448
                       note = CD28(SA) VH-CH1 (EE) hu IgG1 Fc hole PGLALA
source                 1..448
                       mol_type = protein
                       organism = synthetic construct
SEQUENCE: 99
QVQLVQSGAE VKKPGASVKV SCKASGYTFT SYYIHWVRQA PGQGLEWIGC IYPGNVNTNY  60
NEKFKDRATL TVDTSISTAY MELSRLRSDD TAVYFCTRSH YGLDWNFDVW GQGTTVTVSS  120
ASTKGPSVFP LAPSSKSTSG GTAALGCLVE DYFPEPVTVS WNSGALTSGV HTFPAVLQSS  180
GLYSLSSVVT VPSSSLGTQT YICNVNHKPS NTKVDEKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LGAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNRFT QKSLSLSP                                      448

SEQ ID NO: 100         moltype = AA  length = 739
FEATURE                Location/Qualifiers
REGION                 1..739
                       note = ScFv (4.24.72) VH-(G4S)4-VL-uncleavable linker- CD3
                        VH-CL hu IgG1Fc knob PGLALA
source                 1..739
                       mol_type = protein
                       organism = synthetic construct
SEQUENCE: 100
QVQLKESGPG LVAPSQSLSI TCTVSGFSLT SYGVSWVRQP PGKCLEWLGI IWGDGSTNYH  60
SALISRLSIS KDNSKSQVFL KLNSLQTDDT ATYYCAKGIT TVVDDYYAMD YWGQGTSVTV  120
SSGGGGSGGG GSGGGGSGGG GSDIQMTQSP ASLSASVGET VTITCRASEN IDSYLAWYQQ  180
KQGKSPQLLV YAATFLADDV PSRFSGSGSG TQYSLKINSL QSEDVARYYC QHYYSTPYTF  240
GCGTKLEIKG GGGSGGGGSG GGGSGGGGGG GSGGGGSGGG GSEVQLLESG GGLVQPGGSL  300
RLSCAASGFT FSTYAMNWVR QAPGKGLEWV SRIRSKYNNY ATYYADSVKG RFTISRDDSK  360
NTLYLQMNSL RAEDTAVYYC VRHGNFGNSY VSWFAYWGQG TLVTVSSASV AAPSVFIFPP  420
SDEQLKSGTA SVVCLLNNFY PREAKVQWKV DNALQSGNSQ ESVTEQDSKD STYSLSSTLT  480
LSKADYEKHK VYACEVTHQG LSSPVTKSFN RGECDKTHTC PPCPAPEAAG GPSVFLFPPK  540
PKDTLMISRT PEVTCVVVDV SHEDPEVKFN WYVDGVEVHN AKTKPREEQY NSTYRVVSVL  600
TVLHQDWLNG KEYKCKVSNK ALGAPIEKTI SKAKGQPREP QVYTLPPCRD ELTKNQVSLW  660
CLVKGFYPSD IAVEWESNGQ PENNYKTTPP VLDSDGSFFL YSKLTVDKSR WQQGNVFSCS  720
VMHEALHNHY TQKSLSLSP                                                739

SEQ ID NO: 101         moltype = AA  length = 437
FEATURE                Location/Qualifiers
REGION                 1..437
                       note = CD28(SA_variant 8) VL-CH hu IgG1 Fc hole PGLALA
source                 1..437
                       mol_type = protein
                       organism = synthetic construct
SEQUENCE: 101
DIQMTQSPSS LSASVGDRVT ITCHASQNIY VYLNWYQQKP GKAPKLLIYK ASNLHTGVPS  60
RFSGSGSGTD FTLTISSLQP EDFATYYCQQ GQTYPYTFGG GTKVEIKSSA STKGPSVFPL  120
APSSKSTSGG TAALGCLVKD YFPEPVTVSW NSGALTSGVH TFPAVLQSSG LYSLSSVVTV  180
PSSSLGTQTY ICNVNHKPSN TKVDKKVEPK SCDKTHTCPP CPAPEAAGGP SVFLFPPKPK  240
DTLMISRTPE VTCVVVDVSH EDPEVKFNWY VDGVEVHNAK TKPREEQYNS TYRVVSVLTV  300
LHQDWLNGKE YKCKVSNKAL GAPIEKTISK AKGQPREPQV CTLPPSRDEL TKNQVSLSCA  360
VKGFYPSDIA VEWESNGQPE NNYKTTPPVL DSDGSFFLVS KLTVDKSRWQ QGNVFSCSVM  420
HEALHNHYTQ KSLSLSP                                                  437

SEQ ID NO: 102         moltype = AA  length = 227
FEATURE                Location/Qualifiers
REGION                 1..227
                       note = CD28(SA_variant 8) VH-CL
source                 1..227
                       mol_type = protein
                       organism = synthetic construct
SEQUENCE: 102
QVQLVQSGAE VKKPGASVKV SCKASGYTFT SYYIHWVRQA PGQGLEWIGS IYPGNVQTNY  60
NEKFKDRATL TVDTSISTAY MELSRLRSDD TAVYFCTRSH YGLDFNFDVW GQGTTVTVSS  120
ASVAAPSVFI FPPSDEQLKS GTASVVCLLN NFYPREAKVQ WKVDNALQSG NSQESVTEQD  180
SKDSTYSLSS TLTLSKADYE KHKVYACEVT HQGLSSPVTK SFNRGEC                 227

SEQ ID NO: 103         moltype = AA  length = 453
FEATURE                Location/Qualifiers
REGION                 1..453
                       note = CD3 (P035.093) VH-CH1 (EE) Fc knob PGLALA
source                 1..453
```

```
                      mol_type = protein
                      organism = synthetic construct
SEQUENCE: 103
EVQLLESGGG LVQPGGSLRL SCAASGFTFS SYAMNWVRQA PGKGLEWVSR IRSKYNNYAT  60
YYADSVKGRF TISRDDSKNT LYLQMNSLRA EDTAVYYCVR ASNFPASYVS YFAYWGQGTL  120
VTVSSASTKG PSVFPLAPSS KSTSGGTAAL GCLVEDYFPE PVTVSWNSGA LTSGVHTFPA  180
VLQSSGLYSL SSVVTVPSSS LGTQTYICNV NHKPSNTKVD EKVEPKSCDK THTCPPCPAP  240
EAAGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALGAPI EKTISKAKGQ PREPQVYTLP  360
PCRDELTKNQ VSLWCLVKGF YPSDIAVEWE SNGQPENNYK TTPPVLDSDG SFFLYSKLTV  420
DKSRWQQGNV FSCSVMHEAL HNHYTQKSLS LSP                              453

SEQ ID NO: 104        moltype = AA  length = 215
FEATURE               Location/Qualifiers
REGION                1..215
                      note = CD3 (P035.093) VL-Ckappa
source                1..215
                      mol_type = protein
                      organism = synthetic construct
SEQUENCE: 104
QAVVTQEPSL TVSPGGTVTL TCGSSTGAVT TSNYANWVQE KPGQAFRGLI GGTNKRAPGT  60
PARFSGSLLG GKAALTLSGA QPEDEAEYYC ALWYSNLWVF GGGTKLTVLG QPKAAPSVTL  120
FPPSSKKLQA NKATLVCLIS DFYPGAVTVA WKADSSPVKA GVETTTPSKQ SNNKYAASSY  180
LSLTPEQWKS HRSYSCQVTH EGSTVEKTVA PTECS                            215

SEQ ID NO: 105        moltype = AA  length = 735
FEATURE               Location/Qualifiers
REGION                1..735
                      note = ScFv (4.24.72) VH-(G4S)4-VL-non-cleavable linker-
                       CD3 (P035.093)VH-CH1 hu IgG1 Fc knob PGLALA
source                1..735
                      mol_type = protein
                      organism = synthetic construct
SEQUENCE: 105
QIQLVQSGPE LKKPGETVKI SCKASGYTVT DYSMNWVKQA PGKCLKWMGW INTETGEPRY  60
TDDFKGRFAF SLETSASTAY LQINNLKNED SATYFCAREG DYDVFDYWGH GTTLKVSSGG  120
GGSGGGGSGG GGSGGGGSDI VLTQSPASLA VSLGQRATIS CRASKSVSTS SYSYMHWYQQ  180
KPGQPPKLLI KYVSYLESGV PARFSGSGSG TDFTLNIHPV EEEDAATYYC QHSREFPYTF  240
GCGTKLEIKG GGGSGGGGSG GGGSGGGGGG GSGGGGSGGG GSEVQLLESG GGLVQPGGSL  300
RLSCAASGFT FSSYAMNWVR QAPGKGLEWV SRIRSKYNNY ATYYADSVKG RFTISRDDSK  360
NTLYLQMNSL RAEDTAVYYC VRASNFPASY VSYFAYWGQG TLVTVSSAST KGPSVFPLAP  420
SSKSTSGGTA ALGCLVEDYF PEPVTVSWNS GALTSGVHTF PAVLQSSGLY SLSSVVTVPS  480
SSLGTQTYIC NVNHKPSNTK VDEKVEPKSC DKTHTCPPCP APEAAGGPSV FLFPPKPKDT  540
LMISRTPEVT CVVVDVSHED PEVKFNWYVD GVEVHNAKTK PREEQYNSTY RVVSVLTVLH  600
QDWLNGKEYK CKVSNKALGA PIEKTISKAK GQPREPQVYT LPPCRDELTK NQVSLWCLVK  660
GFYPSDIAVE WESNGQPENN YKTTPPVLDS DGSFFLYSKL TVDKSRWQQG NVFSCSVMHE  720
ALHNHYTQKS LSLSP                                                  735

SEQ ID NO: 106        moltype = AA  length = 735
FEATURE               Location/Qualifiers
REGION                1..735
                      note = ScFv (4.24.72) VH-(G4S)4-VL-PMAKK- CD3 (P035.093)
                       VH-CH1 hu IgG1Fc knob PGLALA
source                1..735
                      mol_type = protein
                      organism = synthetic construct
SEQUENCE: 106
QIQLVQSGPE LKKPGETVKI SCKASGYTVT DYSMNWVKQA PGKCLKWMGW INTETGEPRY  60
TDDFKGRFAF SLETSASTAY LQINNLKNED SATYFCAREG DYDVFDYWGH GTTLKVSSGG  120
GGSGGGGSGG GGSGGGGSDI VLTQSPASLA VSLGQRATIS CRASKSVSTS SYSYMHWYQQ  180
KPGQPPKLLI KYVSYLESGV PARFSGSGSG TDFTLNIHPV EEEDAATYYC QHSREFPYTF  240
GCGTKLEIKS GGGSGGGGSP MAKKGGGGSG GGGSGGGGSG GSEVQLLESG GGLVQPGGSL  300
RLSCAASGFT FSSYAMNWVR QAPGKGLEWV SRIRSKYNNY ATYYADSVKG RFTISRDDSK  360
NTLYLQMNSL RAEDTAVYYC VRASNFPASY VSYFAYWGQG TLVTVSSAST KGPSVFPLAP  420
SSKSTSGGTA ALGCLVEDYF PEPVTVSWNS GALTSGVHTF PAVLQSSGLY SLSSVVTVPS  480
SSLGTQTYIC NVNHKPSNTK VDEKVEPKSC DKTHTCPPCP APEAAGGPSV FLFPPKPKDT  540
LMISRTPEVT CVVVDVSHED PEVKFNWYVD GVEVHNAKTK PREEQYNSTY RVVSVLTVLH  600
QDWLNGKEYK CKVSNKALGA PIEKTISKAK GQPREPQVYT LPPCRDELTK NQVSLWCLVK  660
GFYPSDIAVE WESNGQPENN YKTTPPVLDS DGSFFLYSKL TVDKSRWQQG NVFSCSVMHE  720
ALHNHYTQKS LSLSP                                                  735

SEQ ID NO: 107        moltype = AA  length = 5
FEATURE               Location/Qualifiers
REGION                1..5
                      note = CD28(mAb 9.3) CDR-H1
source                1..5
                      mol_type = protein
                      organism = synthetic construct
SEQUENCE: 107
```

```
DYGVH                                                                5

SEQ ID NO: 108          moltype = AA  length = 16
FEATURE                 Location/Qualifiers
REGION                  1..16
                        note = CD28(mAb 9.3) CDR-H2
source                  1..16
                        mol_type = protein
                        organism = synthetic construct
SEQUENCE: 108
VIWAGGGTNY NSALMS                                                    16

SEQ ID NO: 109          moltype = AA  length = 12
FEATURE                 Location/Qualifiers
REGION                  1..12
                        note = CD28(mAb 9.3) CDR-H3
source                  1..12
                        mol_type = protein
                        organism = synthetic construct
SEQUENCE: 109
DKGYSYYYSM DY                                                        12

SEQ ID NO: 110          moltype = AA  length = 15
FEATURE                 Location/Qualifiers
REGION                  1..15
                        note = CD28(mAb 9.3) CDR-L1
source                  1..15
                        mol_type = protein
                        organism = synthetic construct
SEQUENCE: 110
RASESVEYYV TSLMQ                                                     15

SEQ ID NO: 111          moltype = AA  length = 7
FEATURE                 Location/Qualifiers
REGION                  1..7
                        note = CD28(mAb 9.3) CDR-L2
source                  1..7
                        mol_type = protein
                        organism = synthetic construct
SEQUENCE: 111
AASNVES                                                              7

SEQ ID NO: 112          moltype = AA  length = 9
FEATURE                 Location/Qualifiers
REGION                  1..9
                        note = CD28(mAb 9.3) CDR-L3
source                  1..9
                        mol_type = protein
                        organism = synthetic construct
SEQUENCE: 112
QQSRKVPYT                                                            9

SEQ ID NO: 113          moltype = AA  length = 120
FEATURE                 Location/Qualifiers
REGION                  1..120
                        note = CD28(mAb 9.3) VH
source                  1..120
                        mol_type = protein
                        organism = synthetic construct
SEQUENCE: 113
EVKLQQSGPG LVTPSQSLSI TCTVSGFSLS DYGVHWVRQS PGQGLEWLGV IWAGGGTNYN  60
SALMSRKSIS KDNSKSQVFL KMNSLQADDT AVYYCARDKG YSYYYSMDYW GQGTSVTVSS  120

SEQ ID NO: 114          moltype = AA  length = 111
FEATURE                 Location/Qualifiers
REGION                  1..111
                        note = CD28(mAb 9.3) VL
source                  1..111
                        mol_type = protein
                        organism = synthetic construct
SEQUENCE: 114
DIELTQSPAS LAVSLGQRAT ISCRASESVE YYVTSLMQWY QQKPGQPPKL LIFAASNVES  60
GVPARFSGSG SGTNFSLNIH PVDEDDVAMY FCQQSRKVPY TFGGGTKLEI K           111

SEQ ID NO: 115          moltype = AA  length = 5
FEATURE                 Location/Qualifiers
REGION                  1..5
                        note = CDR-H1 (ID_4.32.63)
source                  1..5
```

```
                        mol_type = protein
                        organism = synthetic construct
SEQUENCE: 115
SYGVS                                                                   5

SEQ ID NO: 116          moltype = AA  length = 16
FEATURE                 Location/Qualifiers
REGION                  1..16
                        note = CDR-H2 (ID_4.32.63)
source                  1..16
                        mol_type = protein
                        organism = synthetic construct
SEQUENCE: 116
IIWGDGSTNY HSALIS                                                       16

SEQ ID NO: 117          moltype = AA  length = 14
FEATURE                 Location/Qualifiers
REGION                  1..14
                        note = CDR-H3 (ID_4.32.63)
source                  1..14
                        mol_type = protein
                        organism = synthetic construct
SEQUENCE: 117
GITTVVDDYY AMDY                                                         14

SEQ ID NO: 118          moltype = AA  length = 11
FEATURE                 Location/Qualifiers
REGION                  1..11
                        note = CDR-L1 (ID_4.32.63)
source                  1..11
                        mol_type = protein
                        organism = synthetic construct
SEQUENCE: 118
RASENIDSYL A                                                            11

SEQ ID NO: 119          moltype = AA  length = 7
FEATURE                 Location/Qualifiers
REGION                  1..7
                        note = CDR-L2 (ID_4.32.63)
source                  1..7
                        mol_type = protein
                        organism = synthetic construct
SEQUENCE: 119
AATFLAD                                                                 7

SEQ ID NO: 120          moltype = AA  length = 9
FEATURE                 Location/Qualifiers
REGION                  1..9
                        note = CDR-L3 (ID_4.32.63)
source                  1..9
                        mol_type = protein
                        organism = synthetic construct
SEQUENCE: 120
QHYYSTPYT                                                               9

SEQ ID NO: 121          moltype = AA  length = 122
FEATURE                 Location/Qualifiers
REGION                  1..122
                        note = VH (ID_4.32.63)
source                  1..122
                        mol_type = protein
                        organism = synthetic construct
SEQUENCE: 121
QVQLKESGPG LVAPSQSLSI TCTVSGFSLT SYGVSWVRQP PGKCLEWLGI IWGDGSTNYH  60
SALISRLSIS KDNSKSQVFL KLNSLQTDDT ATYYCAKGIT TVVDDYYAMD YWGQGTSVTV  120
SS                                                                  122

SEQ ID NO: 122          moltype = AA  length = 107
FEATURE                 Location/Qualifiers
REGION                  1..107
                        note = VL (ID_4.32.63)
source                  1..107
                        mol_type = protein
                        organism = synthetic construct
SEQUENCE: 122
DIQMTQSPAS LSASVGETVT ITCRASENID SYLAWYQQKQ GKSPQLLVYA ATFLADDVPS  60
RFSGSGSGTQ YSLKINSLQS EDVARYYCQH YYSTPYTFGC GTKLEIK                107

SEQ ID NO: 123          moltype = AA  length = 5
```

-continued

```
FEATURE                Location/Qualifiers
REGION                 1..5
                       note = CDR-H1 (ID_4.24.72, H1L1, H1L2, H2L2, H3L2, H3L3)
source                 1..5
                       mol_type = protein
                       organism = synthetic construct
SEQUENCE: 123
DYSMN                                                                5

SEQ ID NO: 124         moltype = AA  length = 17
FEATURE                Location/Qualifiers
REGION                 1..17
                       note = CDR-H2 (ID_4.24.72, H1L1, H1L2)
source                 1..17
                       mol_type = protein
                       organism = synthetic construct
SEQUENCE: 124
WINTETGEPR YTDDFKG                                                   17

SEQ ID NO: 125         moltype = AA  length = 9
FEATURE                Location/Qualifiers
REGION                 1..9
                       note = CDR-H3 (ID_4.24.72, H1L1, H1L2, H2L2, H3L2, H3L3)
source                 1..9
                       mol_type = protein
                       organism = synthetic construct
SEQUENCE: 125
EGDYDVFDY                                                            9

SEQ ID NO: 126         moltype = AA  length = 15
FEATURE                Location/Qualifiers
REGION                 1..15
                       note = CDR-L1 (ID_4.24.72, H1L1)
source                 1..15
                       mol_type = protein
                       organism = synthetic construct
SEQUENCE: 126
RASKSVSTSS YSYMH                                                     15

SEQ ID NO: 127         moltype = AA  length = 7
FEATURE                Location/Qualifiers
REGION                 1..7
                       note = CDR-L2 (ID_4.24.72, H1L1, H1L2, H2L2, H3L2, H3L3)
source                 1..7
                       mol_type = protein
                       organism = synthetic construct
SEQUENCE: 127
YVSYLES                                                              7

SEQ ID NO: 128         moltype = AA  length = 9
FEATURE                Location/Qualifiers
REGION                 1..9
                       note = CDR-L3 (ID_4.24.72, H1L1, H1L2, H2L2, H3L2)
source                 1..9
                       mol_type = protein
                       organism = synthetic construct
SEQUENCE: 128
QHSREFPYT                                                            9

SEQ ID NO: 129         moltype = AA  length = 15
FEATURE                Location/Qualifiers
REGION                 1..15
                       note = CDR-L1 (H1L2, H2L2, H3L3)
source                 1..15
                       mol_type = protein
                       organism = synthetic construct
SEQUENCE: 129
KSSKSVSTSS YSYMH                                                     15

SEQ ID NO: 130         moltype = AA  length = 17
FEATURE                Location/Qualifiers
REGION                 1..17
                       note = CDR-H2 (H2L2)
source                 1..17
                       mol_type = protein
                       organism = synthetic construct
SEQUENCE: 130
WINTETGEPR YTDDFTG                                                   17
```

-continued

```
SEQ ID NO: 131          moltype = AA  length = 17
FEATURE                 Location/Qualifiers
REGION                  1..17
                        note = CDR-H2 (H3L2)
source                  1..17
                        mol_type = protein
                        organism = synthetic construct
SEQUENCE: 131
WINTETGEPR YTQGFKG                                                17

SEQ ID NO: 132          moltype = AA  length = 9
FEATURE                 Location/Qualifiers
REGION                  1..9
                        note = CDR-L3 (H3L3)
source                  1..9
                        mol_type = protein
                        organism = synthetic construct
SEQUENCE: 132
QQSREFPYT                                                         9

SEQ ID NO: 133          moltype = AA  length = 118
FEATURE                 Location/Qualifiers
REGION                  1..118
                        note = ID_4.24.72 VH
source                  1..118
                        mol_type = protein
                        organism = synthetic construct
SEQUENCE: 133
QIQLVQSGPE LKKPGETVKI SCKASGYTVT DYSMNWVKQA PGKCLKWMGW INTETGEPRY  60
TDDFKGRFAF SLETSASTAY LQINNLKNED SATYFCAREG DYDVFDYWGH GTTLKVSS    118

SEQ ID NO: 134          moltype = AA  length = 111
FEATURE                 Location/Qualifiers
REGION                  1..111
                        note = ID_4.24.72 VL
source                  1..111
                        mol_type = protein
                        organism = synthetic construct
SEQUENCE: 134
DIVLTQSPAS LAVSLGQRAT ISCRASKSVS TSSYSYMHWY QQKPGQPPKL LIKYVSYLES  60
GVPARFSGSG SGTDFTLNIH PVEEEDAATY YCQHSREFPY TFGCGTKLEI K           111

SEQ ID NO: 135          moltype = AA  length = 118
FEATURE                 Location/Qualifiers
REGION                  1..118
                        note = H1L1, H1L2 VH
source                  1..118
                        mol_type = protein
                        organism = synthetic construct
SEQUENCE: 135
QVQLVQSGSE LKKPGASVKV SCKASGYTVT DYSMNWVRQA PGQGLEWMGW INTETGEPRY  60
TDDFKGRFVF SLDTSVSTAY LQISSLKAED TAVYYCAREG DYDVFDYWGQ GTLVTVSS    118

SEQ ID NO: 136          moltype = AA  length = 111
FEATURE                 Location/Qualifiers
REGION                  1..111
                        note = H1L1 VL
source                  1..111
                        mol_type = protein
                        organism = synthetic construct
SEQUENCE: 136
DIVMTQSPDS LAVSLGERAT INCRASKSVS TSSYSYMHWY QQKPGQPPKL LIKYVSYLES  60
GVPDRFSGSG SGTDFTLTIS SLQAEDVAVY YCQHSREFPY TFGQGTKLEI K           111

SEQ ID NO: 137          moltype = AA  length = 111
FEATURE                 Location/Qualifiers
REGION                  1..111
                        note = H1L2, H2L2 VL
source                  1..111
                        mol_type = protein
                        organism = synthetic construct
SEQUENCE: 137
DIVMTQSPDS LAVSLGERAT INCKSSKSVS TSSYSYMHWY QQKPGQPPKL LIKYVSYLES  60
GVPDRFSGSG SGTDFTLTIS SLQAEDVAVY YCQHSREFPY TFGQGTKLEI K           111

SEQ ID NO: 138          moltype = AA  length = 118
FEATURE                 Location/Qualifiers
REGION                  1..118
                        note = H2L2 VH
```

-continued

```
source                  1..118
                        mol_type = protein
                        organism = synthetic construct
SEQUENCE: 138
QVQLVQSGSE LKKPGASVKV SCKASGYTVT DYSMNWVRQA PGQGLEWMGW INTETGEPRY  60
TDDFTGRFVF SLDTSVSTAY LQISSLKAED TAVYYCAREG DYDVFDYWGQ GTLVTVSS    118

SEQ ID NO: 139          moltype = AA  length = 118
FEATURE                 Location/Qualifiers
REGION                  1..118
                        note = H3L3 VH
source                  1..118
                        mol_type = protein
                        organism = synthetic construct
SEQUENCE: 139
QVQLVQSGSE LKKPGASVKV SCKASGYTVT DYSMNWVRQA PGQGLEWMGW INTETGEPRY  60
TQGFKGRFVF SLDTSVSTAY LQISSLKAED TAVYYCAREG DYDVFDYWGQ GTLVTVSS    118

SEQ ID NO: 140          moltype = AA  length = 111
FEATURE                 Location/Qualifiers
REGION                  1..111
                        note = H3L3 VL
source                  1..111
                        mol_type = protein
                        organism = synthetic construct
SEQUENCE: 140
DIVMTQSPDS LAVSLGERAT INCRASKSVS TSSYSYMHWY QQKPGQPPKL LIKYVSYLES  60
GVPDRFSGSG SGTDFTLTIS SLQAEDVAVY YCQQSREFPY TFGQGTKLEI K           111

SEQ ID NO: 141          moltype = AA  length = 118
FEATURE                 Location/Qualifiers
REGION                  1..118
                        note = H7L5 VH
source                  1..118
                        mol_type = protein
                        organism = synthetic construct
SEQUENCE: 141
QVQLVQSGAE VKKPGASVKV SCKASGYTVT DYSMNWVRQA PGQGLEWMGW INTETGEPRY  60
TDDFKGRVTM TRDTSISTAY MELSRLRSDD TAVYYCAREG DYDVFDYWGQ GTLVTVSS    118

SEQ ID NO: 142          moltype = AA  length = 111
FEATURE                 Location/Qualifiers
REGION                  1..111
                        note = H7L5 VL
source                  1..111
                        mol_type = protein
                        organism = synthetic construct
SEQUENCE: 142
DIVMTQSPDS LAVSLGERAT INCRASKSVS TSSYSYMHWY QQKPGQPPKL LIYYVSYLES  60
GVPDRFSGSG SGTDFTLTIS SLQAEDVAVY YCQHSREFPY TFGQGTKLEI K           111

SEQ ID NO: 143          moltype = AA  length = 249
FEATURE                 Location/Qualifiers
REGION                  1..249
                        note = H1L1 scFv
source                  1..249
                        mol_type = protein
                        organism = synthetic construct
SEQUENCE: 143
QVQLVQSGSE LKKPGASVKV SCKASGYTVT DYSMNWVRQA PGQCLEWMGW INTETGEPRY  60
TDDFKGRFVF SLDTSVSTAY LQISSLKAED TAVYYCAREG DYDVFDYWGQ GTLVTVSSGG  120
GGSGGGGSGG GGSGGGGSDI VMTQSPDSLA VSLGERATIN CRASKSVSTS SYSYMHWYQQ  180
KPGQPPKLLI KYVSYLESGV PDRFSGSGSG TDFTLTISSL QAEDVAVYYC QHSREFPYTF  240
GCGTKLEIK                                                          249

SEQ ID NO: 144          moltype = AA  length = 249
FEATURE                 Location/Qualifiers
REGION                  1..249
                        note = H1L2 scFv
source                  1..249
                        mol_type = protein
                        organism = synthetic construct
SEQUENCE: 144
QVQLVQSGSE LKKPGASVKV SCKASGYTVT DYSMNWVRQA PGQCLEWMGW INTETGEPRY  60
TDDFKGRFVF SLDTSVSTAY LQISSLKAED TAVYYCAREG DYDVFDYWGQ GTLVTVSSGG  120
GGSGGGGSGG GGSGGGGSDI VMTQSPDSLA VSLGERATIN CKSSKSVSTS SYSYMHWYQQ  180
KPGQPPKLLI KYVSYLESGV PDRFSGSGSG TDFTLTISSL QAEDVAVYYC QHSREFPYTF  240
GCGTKLEIK                                                          249
```

```
SEQ ID NO: 145          moltype = AA  length = 249
FEATURE                 Location/Qualifiers
REGION                  1..249
                        note = H2L2 scFv
source                  1..249
                        mol_type = protein
                        organism = synthetic construct
SEQUENCE: 145
QVQLVQSGSE LKKPGASVKV SCKASGYTVT DYSMNWVRQA PGQCLEWMGW INTETGEPRY  60
TDDFTGRFVF SLDTSVSTAY LQISSLKAED TAVYYCAREG DYDVFDYWGQ GTLVTVSSGG  120
GGSGGGGSGG GGSGGGGSDI VMTQSPDSLA VSLGERATIN CKSSKSVSTS SYSYMHWYQQ  180
KPGQPPKLLI KYVSYLESGV PDRFSGSGSG TDFTLTISSL QAEDVAVYYC QHSREFPYTF  240
GCGTKLEIK                                                          249

SEQ ID NO: 146          moltype = AA  length = 249
FEATURE                 Location/Qualifiers
REGION                  1..249
                        note = H3L2 scFv
source                  1..249
                        mol_type = protein
                        organism = synthetic construct
SEQUENCE: 146
QVQLVQSGSE LKKPGASVKV SCKASGYTVT DYSMNWVRQA PGQCLEWMGW INTETGEPRY  60
TQGFKGRFVF SLDTSVSTAY LQISSLKAED TAVYYCAREG DYDVFDYWGQ GTLVTVSSGG  120
GGSGGGGSGG GGSGGGGSDI VMTQSPDSLA VSLGERATIN CKSSKSVSTS SYSYMHWYQQ  180
KPGQPPKLLI KYVSYLESGV PDRFSGSGSG TDFTLTISSL QAEDVAVYYC QHSREFPYTF  240
GCGTKLEIK                                                          249

SEQ ID NO: 147          moltype = AA  length = 249
FEATURE                 Location/Qualifiers
REGION                  1..249
                        note = 4.32.63 scFv
source                  1..249
                        mol_type = protein
                        organism = synthetic construct
SEQUENCE: 147
QVQLKESGPG LVAPSQSLSI TCTVSGFSLT SYGVSWVRQP PGKCLEWLGI IWGDGSTNYH  60
SALISRLSIS KDNSKSQVFL KLNSLQTDDT ATYYCAKGIT TVVDDYYAMD YWGQGTSVTV  120
SSGGGGSGGG GSGGGGSGGG GSDIQMTQSP ASLSASVGET VTITCRASEN IDSYLAWYQQ  180
KQGKSPQLLV YAATFLADDV PSRFSGSGSG TQYSLKINSL QSEDVARYYC QHYYSTPYTF  240
GCGTKLEIK                                                          249

SEQ ID NO: 148          moltype = AA  length = 8
FEATURE                 Location/Qualifiers
REGION                  1..8
                        note = Protease recognition site 1
source                  1..8
                        mol_type = protein
                        organism = synthetic construct
SEQUENCE: 148
RQARVVNG                                                           8

SEQ ID NO: 149          moltype = AA  length = 18
FEATURE                 Location/Qualifiers
REGION                  1..18
                        note = Protease recognition site 2
source                  1..18
                        mol_type = protein
                        organism = synthetic construct
SEQUENCE: 149
VHMPLGFLGP GRSRGSFP                                                18

SEQ ID NO: 150          moltype = AA  length = 21
FEATURE                 Location/Qualifiers
REGION                  1..21
                        note = Protease recognition site 3
REGION                  9..13
                        note = misc_feature - Xaa can be any naturally occurring
                         amino acid
source                  1..21
                        mol_type = protein
                        organism = synthetic construct
SEQUENCE: 150
RQARVVNGXX XXXVPLSLYS G                                            21

SEQ ID NO: 151          moltype = AA  length = 16
FEATURE                 Location/Qualifiers
REGION                  1..16
                        note = Protease recognition site 4
```

```
source                  1..16
                        mol_type = protein
                        organism = synthetic construct
SEQUENCE: 151
RQARVVNGVP LSLYSG                                                  16

SEQ ID NO: 152          moltype = AA  length = 7
FEATURE                 Location/Qualifiers
REGION                  1..7
                        note = Protease recognition site 5
source                  1..7
                        mol_type = protein
                        organism = synthetic construct
SEQUENCE: 152
PLGLWSQ                                                            7

SEQ ID NO: 153          moltype = AA  length = 18
FEATURE                 Location/Qualifiers
REGION                  1..18
                        note = Protease recognition site 6
source                  1..18
                        mol_type = protein
                        organism = synthetic construct
SEQUENCE: 153
VHMPLGFLGP RQARVVNG                                                18

SEQ ID NO: 154          moltype = AA  length = 6
FEATURE                 Location/Qualifiers
REGION                  1..6
                        note = Protease recognition site 7
source                  1..6
                        mol_type = protein
                        organism = synthetic construct
SEQUENCE: 154
FVGGTG                                                             6

SEQ ID NO: 155          moltype = AA  length = 8
FEATURE                 Location/Qualifiers
REGION                  1..8
                        note = Protease recognition site 8
source                  1..8
                        mol_type = protein
                        organism = synthetic construct
SEQUENCE: 155
KKAAPVNG                                                           8

SEQ ID NO: 156          moltype = AA  length = 8
FEATURE                 Location/Qualifiers
REGION                  1..8
                        note = Protease recognition site 9
source                  1..8
                        mol_type = protein
                        organism = synthetic construct
SEQUENCE: 156
PMAKKVNG                                                           8

SEQ ID NO: 157          moltype = AA  length = 8
FEATURE                 Location/Qualifiers
REGION                  1..8
                        note = Protease recognition site 10
source                  1..8
                        mol_type = protein
                        organism = synthetic construct
SEQUENCE: 157
QARAKVNG                                                           8

SEQ ID NO: 158          moltype = AA  length = 10
FEATURE                 Location/Qualifiers
REGION                  1..10
                        note = Protease recognition site 11
source                  1..10
                        mol_type = protein
                        organism = synthetic construct
SEQUENCE: 158
VHMPLGFLGP                                                         10

SEQ ID NO: 159          moltype = AA  length = 5
FEATURE                 Location/Qualifiers
REGION                  1..5
```

```
                        note = Protease recognition site 12
source                  1..5
                        mol_type = protein
                        organism = synthetic construct
SEQUENCE: 159
QARAK                                                            5

SEQ ID NO: 160          moltype = AA  length = 15
FEATURE                 Location/Qualifiers
REGION                  1..15
                        note = Protease recognition site 13
source                  1..15
                        mol_type = protein
                        organism = synthetic construct
SEQUENCE: 160
VHMPLGFLGP PMAKK                                                 15

SEQ ID NO: 161          moltype = AA  length = 5
FEATURE                 Location/Qualifiers
REGION                  1..5
                        note = Protease recognition site 14
source                  1..5
                        mol_type = protein
                        organism = synthetic construct
SEQUENCE: 161
KKAAP                                                            5

SEQ ID NO: 162          moltype = AA  length = 5
FEATURE                 Location/Qualifiers
REGION                  1..5
                        note = Protease recognition site 15
source                  1..5
                        mol_type = protein
                        organism = synthetic construct
SEQUENCE: 162
PMAKK                                                            5

SEQ ID NO: 163          moltype = AA  length = 33
FEATURE                 Location/Qualifiers
REGION                  1..33
                        note = non-cleavable linker
source                  1..33
                        mol_type = protein
                        organism = synthetic construct
SEQUENCE: 163
GGGGSGGGGS GGGGSGGGGG GGSGGGGSGG GGS                             33

SEQ ID NO: 164          moltype = AA  length = 855
FEATURE                 Location/Qualifiers
source                  1..855
                        mol_type = protein
                        organism = Homo sapiens
SEQUENCE: 164
MGSDRARKGG GGPKDFGAGL KYNSRHEKVN GLEEGVEFLP VNNVKKVEKH GPGRWVVLAA  60
VLIGLLLVLL GIGFLVWHLQ YRDVRVQKVF NGYMRITNEN FVDAYENSNS TEFVSLASKV  120
KDALKLLYSG VPFLGPYHKE SAVTAFSEGS VIAYYWSEFS IPQHLVEEAE RVMAEERVVM  180
LPPRARSLKS FVVTSVVAFP TDSKTVQRTQ DNSCSFGLHA RGVELMRFTT PGFPDSPYPA  240
HARCQWALRG DADSVLSLTF RSFDLASCDE RGSDLVTVYN TLSPMEPHAL VQLCGTYPPS  300
YNLTFHSSQN VLLITLITNT ERRHPGFEAT FFQLPRMSSC GGRLRKAQGT FNSPYYPGHY  360
PPNIDCTWNI EVPNNQHVKV RFKFFYLLEP GVPAGTCPKD YVEINGEKYC GERSQFVVTS  420
NSNKITVRFH SDQSYTDTGF LAEYLSYDSS DPCPGQFTCR TGRCIRKELR CDGWADCTDH  480
SDELNCSCDA GHQFTCKNKF CKPLFWVCDS VNDCGDNSDE QGCSCPAQTF RCSNGKCLSK  540
SQQCNGKDDC GDGSDEASCP KVNVVTCTKH TYRCLNGLCL SKGNPECDGK EDCSDGSDEK  600
DCDCGLRSFT RQARVVGGTD ADEGEWPWQV SLHALGQGHI CGASLISPNW LVSAAHCYID  660
DRGFRYSDPT QWTAFLGLHD QSQRSAPGVQ ERRLKRIISH PFFNDFTFDY DIALLELEKP  720
AEYSSMVRPI CLPDASHVFP AGKAIWVTGW GHTQYGGTGA LILQKGEIRV INQTTCENLL  780
PQQITPRMMC VGFLSGGVDS CQGDSGGPLS SVEADGRIFQ AGVVSWGDGC AQRNKPGVYT  840
RLPLFRDWIK ENTGV                                                 855

SEQ ID NO: 165          moltype = AA  length = 98
FEATURE                 Location/Qualifiers
source                  1..98
                        mol_type = protein
                        organism = Homo sapiens
SEQUENCE: 165
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKV                        98

SEQ ID NO: 166          moltype = AA  length = 107
```

```
FEATURE                Location/Qualifiers
source                 1..107
                       mol_type = protein
                       organism = Homo sapiens
SEQUENCE: 166
APELLGGPSV FLFPPKPKDT LMISRTPEVT CVWDVSHEDP EVKFNWYVDG VEVHNAKTKP  60
REEQESTYRW SVLTVLHQDW LNGKEYKCKV SNKALPAPIE KTISKAK                107

SEQ ID NO: 167         moltype = AA  length = 106
FEATURE                Location/Qualifiers
source                 1..106
                       mol_type = protein
                       organism = Homo sapiens
SEQUENCE: 167
GQPREPQVYT LPPSRDELTK NQVSLTCLVK GFYPSDIAVE WESNGQPENN YKTTPPVLDS  60
DGSFFLYSKL TVDKSRWQQG NVFSCSVMHE ALHNHYTQKS LSLSPG                 106

SEQ ID NO: 168         moltype = AA  length = 5
FEATURE                Location/Qualifiers
source                 1..5
                       mol_type = protein
                       organism = Homo sapiens
SEQUENCE: 168
EPKSC                                                              5

SEQ ID NO: 169         moltype = AA  length = 10
FEATURE                Location/Qualifiers
SITE                   8
                       note = MISC_FEATURE - X is S or P
source                 1..10
                       mol_type = protein
                       organism = Homo sapiens
SEQUENCE: 169
DKTHTCPXCP                                                         10

SEQ ID NO: 170         moltype = AA  length = 7
FEATURE                Location/Qualifiers
SITE                   5
                       note = MISC_FEATURE - X is S or P
source                 1..7
                       mol_type = protein
                       organism = Homo sapiens
SEQUENCE: 170
HTCPXCP                                                            7

SEQ ID NO: 171         moltype = AA  length = 5
FEATURE                Location/Qualifiers
SITE                   3
                       note = MISC_FEATURE - X is S or P
source                 1..5
                       mol_type = protein
                       organism = Homo sapiens
SEQUENCE: 171
CPXCP                                                              5

SEQ ID NO: 172         moltype = AA  length = 330
FEATURE                Location/Qualifiers
source                 1..330
                       mol_type = protein
                       organism = Homo sapiens
SEQUENCE: 172
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 173         moltype = AA  length = 330
FEATURE                Location/Qualifiers
source                 1..330
                       mol_type = protein
                       organism = Homo sapiens
SEQUENCE: 173
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
```

-continued

```
QQGNVFSCSV MHEALHNHYT QKSLSLSPGK                                  330

SEQ ID NO: 174           moltype = AA  length = 326
FEATURE                  Location/Qualifiers
source                   1..326
                         mol_type = protein
                         organism = Homo sapiens
SEQUENCE: 174
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                      326

SEQ ID NO: 175           moltype = AA  length = 377
FEATURE                  Location/Qualifiers
source                   1..377
                         mol_type = protein
                         organism = Homo sapiens
SEQUENCE: 175
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                377

SEQ ID NO: 176           moltype = AA  length = 327
FEATURE                  Location/Qualifiers
source                   1..327
                         mol_type = protein
                         organism = Homo sapiens
SEQUENCE: 176
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 177           moltype = AA  length = 254
FEATURE                  Location/Qualifiers
source                   1..254
                         mol_type = protein
                         organism = Homo sapiens
SEQUENCE: 177
MWQLLLPTAL LLLVSAGMRT EDLPKAVVFL EPQWYRVLEK DSVTLKCQGA YSPEDNSTQW  60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLFGSKN  180
VSSETVNITI TQGLAVSTIS SFFPPGYQVS FCLVMVLLFA VDTGLYFSVK TNIRSSTRDW  240
KDHKFKWRKD PQDK                                                   254

SEQ ID NO: 178           moltype = AA  length = 5
FEATURE                  Location/Qualifiers
REGION                   1..5
                         note = Peptide linker G4S
source                   1..5
                         mol_type = protein
                         organism = synthetic construct
SEQUENCE: 178
GGGGS                                                             5

SEQ ID NO: 179           moltype = AA  length = 10
FEATURE                  Location/Qualifiers
REGION                   1..10
                         note = Peptide linker (G4S)2
source                   1..10
                         mol_type = protein
                         organism = synthetic construct
SEQUENCE: 179
GGGGSGGGGS                                                        10

SEQ ID NO: 180           moltype = AA  length = 10
FEATURE                  Location/Qualifiers
REGION                   1..10
                         note = Peptide linker (SG4)2
source                   1..10
```

-continued

```
                         mol_type = protein
                         organism = synthetic construct
SEQUENCE: 180
SGGGGSGGGG                                                            10

SEQ ID NO: 181           moltype = AA  length = 14
FEATURE                  Location/Qualifiers
REGION                   1..14
                         note = Peptide linker G4(SG4)2
source                   1..14
                         mol_type = protein
                         organism = synthetic construct
SEQUENCE: 181
GGGGSGGGGS GGGG                                                       14

SEQ ID NO: 182           moltype = AA  length = 10
FEATURE                  Location/Qualifiers
REGION                   1..10
                         note = Peptide linker
source                   1..10
                         mol_type = protein
                         organism = synthetic construct
SEQUENCE: 182
GSPGSSSSGS                                                            10

SEQ ID NO: 183           moltype = AA  length = 15
FEATURE                  Location/Qualifiers
REGION                   1..15
                         note = Peptide linker (G4S)3
source                   1..15
                         mol_type = protein
                         organism = synthetic construct
SEQUENCE: 183
GGGGSGGGGS GGGGS                                                      15

SEQ ID NO: 184           moltype = AA  length = 20
FEATURE                  Location/Qualifiers
REGION                   1..20
                         note = Peptide linker (G4S)4
source                   1..20
                         mol_type = protein
                         organism = synthetic construct
SEQUENCE: 184
GGGGSGGGGS GGGGSGGGGS                                                 20

SEQ ID NO: 185           moltype = AA  length = 8
FEATURE                  Location/Qualifiers
REGION                   1..8
                         note = Peptide linker
source                   1..8
                         mol_type = protein
                         organism = synthetic construct
SEQUENCE: 185
GSGSGSGS                                                              8

SEQ ID NO: 186           moltype = AA  length = 8
FEATURE                  Location/Qualifiers
REGION                   1..8
                         note = Peptide linker
source                   1..8
                         mol_type = protein
                         organism = synthetic construct
SEQUENCE: 186
GSGSGNGS                                                              8

SEQ ID NO: 187           moltype = AA  length = 8
FEATURE                  Location/Qualifiers
REGION                   1..8
                         note = Peptide linker
source                   1..8
                         mol_type = protein
                         organism = synthetic construct
SEQUENCE: 187
GGSGSGSG                                                              8

SEQ ID NO: 188           moltype = AA  length = 6
FEATURE                  Location/Qualifiers
REGION                   1..6
                         note = Peptide linker
```

-continued

```
source                  1..6
                        mol_type = protein
                        organism = synthetic construct
SEQUENCE: 188
GGSGSG                                                                      6

SEQ ID NO: 189          moltype = AA  length = 4
FEATURE                 Location/Qualifiers
REGION                  1..4
                        note = Peptide linker
source                  1..4
                        mol_type = protein
                        organism = synthetic construct
SEQUENCE: 189
GGSG                                                                        4

SEQ ID NO: 190          moltype = AA  length = 8
FEATURE                 Location/Qualifiers
REGION                  1..8
                        note = Peptide linker
source                  1..8
                        mol_type = protein
                        organism = synthetic construct
SEQUENCE: 190
GGSGNGSG                                                                    8

SEQ ID NO: 191          moltype = AA  length = 8
FEATURE                 Location/Qualifiers
REGION                  1..8
                        note = Peptide linker
source                  1..8
                        mol_type = protein
                        organism = synthetic construct
SEQUENCE: 191
GGNGSGSG                                                                    8

SEQ ID NO: 192          moltype = AA  length = 6
FEATURE                 Location/Qualifiers
REGION                  1..6
                        note = Peptide linker
source                  1..6
                        mol_type = protein
                        organism = synthetic construct
SEQUENCE: 192
GGNGSG                                                                      6

SEQ ID NO: 193          moltype = AA  length = 15
FEATURE                 Location/Qualifiers
REGION                  1..15
                        note = Peptide linker EPKSCGGGGSGGGGS
source                  1..15
                        mol_type = protein
                        organism = synthetic construct
SEQUENCE: 193
EPKSCGGGGS GGGGS                                                            15

SEQ ID NO: 194          moltype = AA  length = 16
FEATURE                 Location/Qualifiers
REGION                  1..16
                        note = Peptide linker EPKSCDGGGGSGGGGS
source                  1..16
                        mol_type = protein
                        organism = synthetic construct
SEQUENCE: 194
EPKSCDGGGG SGGGGS                                                           16

SEQ ID NO: 195          moltype = AA  length = 33
FEATURE                 Location/Qualifiers
REGION                  1..33
                        note = Matriptase linker
source                  1..33
                        mol_type = protein
                        organism = synthetic construct
SEQUENCE: 195
SGGGSGGGGS PMAKKGGGGS GGGGSGGGGS GGS                                        33

SEQ ID NO: 196          moltype = AA  length = 33
FEATURE                 Location/Qualifiers
REGION                  1..33
```

```
                       note = Linker 2
source                 1..33
                       mol_type = protein
                       organism = synthetic construct
SEQUENCE: 196
GGGGSVHMPL GFLGPRQARV VNGGGGGSGG GGS                              33

SEQ ID NO: 197         moltype = AA  length = 33
FEATURE                Location/Qualifiers
REGION                 1..33
                       note = Linker 3
source                 1..33
                       mol_type = protein
                       organism = synthetic construct
SEQUENCE: 197
GGGGSGGGGS RQARVVNGGG GGSGGGGSGG GGS                              33

SEQ ID NO: 198         moltype = AA  length = 35
FEATURE                Location/Qualifiers
REGION                 1..35
                       note = MMP Protease linker
source                 1..35
                       mol_type = protein
                       organism = synthetic construct
SEQUENCE: 198
GGGGSGGGGS GPLGLWSQGG GGSGGGGSGG GGSGG                            35

SEQ ID NO: 199         moltype = AA  length = 33
FEATURE                Location/Qualifiers
REGION                 1..33
                       note = Combined MMP9 MK062, 33 AA for CD3
source                 1..33
                       mol_type = protein
                       organism = synthetic construct
SEQUENCE: 199
GGGGSVHMPL GFLGPRQARV VNGGGGGSGG GGS                              33

SEQ ID NO: 200         moltype = AA  length = 33
FEATURE                Location/Qualifiers
REGION                 1..33
                       note = Cathepsin S/B
source                 1..33
                       mol_type = protein
                       organism = synthetic construct
SEQUENCE: 200
GGGGSGGGGS GGGGSFVGGT GGGGSGGGGS GGS                              33

SEQ ID NO: 201         moltype = AA  length = 33
FEATURE                Location/Qualifiers
REGION                 1..33
                       note = KKAAPVNG
source                 1..33
                       mol_type = protein
                       organism = synthetic construct
SEQUENCE: 201
GGGGSGGGGS KKAAPVNGGG GGSGGGGSGG GGS                              33

SEQ ID NO: 202         moltype = AA  length = 33
FEATURE                Location/Qualifiers
REGION                 1..33
                       note = PMAKKVNG
source                 1..33
                       mol_type = protein
                       organism = synthetic construct
SEQUENCE: 202
GGGGSGGGGS PMAKKVNGGG GGSGGGGSGG GGS                              33

SEQ ID NO: 203         moltype = AA  length = 33
FEATURE                Location/Qualifiers
REGION                 1..33
                       note = QARAKVNG
source                 1..33
                       mol_type = protein
                       organism = synthetic construct
SEQUENCE: 203
GGGGSGGGGS QARAKVNGGG GGSGGGGSGG GGS                              33

SEQ ID NO: 204         moltype = AA  length = 33
FEATURE                Location/Qualifiers
```

-continued

```
REGION                1..33
                      note = MMP9
source                1..33
                      mol_type = protein
                      organism = synthetic construct
SEQUENCE: 204
GGGGSGGGGS VHMPLGFLGP GGGGSGGGGS GGS                                  33

SEQ ID NO: 205        moltype = AA  length = 33
FEATURE               Location/Qualifiers
REGION                1..33
                      note = QARAK
source                1..33
                      mol_type = protein
                      organism = synthetic construct
SEQUENCE: 205
GGGGSGGGGS QARAKGGGGS GGGGSGGGGS GGS                                  33

SEQ ID NO: 206        moltype = AA  length = 33
FEATURE               Location/Qualifiers
REGION                1..33
                      note = MMP9-PMAKK
source                1..33
                      mol_type = protein
                      organism = synthetic construct
SEQUENCE: 206
GGGGSVHMPL GFLGPPMAKK GGGGSGGGGS GGS                                  33

SEQ ID NO: 207        moltype = AA  length = 33
FEATURE               Location/Qualifiers
REGION                1..33
                      note = KKAAP
source                1..33
                      mol_type = protein
                      organism = synthetic construct
SEQUENCE: 207
GGGGSGGGGS KKAAPGGGGS GGGGSGGGGS GGS                                  33

SEQ ID NO: 208        moltype = AA  length = 33
FEATURE               Location/Qualifiers
REGION                1..33
                      note = PMAKK
source                1..33
                      mol_type = protein
                      organism = synthetic construct
SEQUENCE: 208
GGGGSGGGGS PMAKKGGGGS GGGGSGGGGS GGS                                  33

SEQ ID NO: 209        moltype = AA  length = 28
FEATURE               Location/Qualifiers
REGION                1..28
                      note = Combined NF9/Mat5 linker
source                1..28
                      mol_type = protein
                      organism = synthetic construct
SEQUENCE: 209
GGGGSVHMPL GFLGPGRSRG SFPGGGGS                                        28

SEQ ID NO: 210        moltype = AA  length = 41
FEATURE               Location/Qualifiers
REGION                1..41
                      note = Combined MK062 MMP9
source                1..41
                      mol_type = protein
                      organism = synthetic construct
SEQUENCE: 210
GGGGSGGGGS RQARVVNGGG GGSVPLSLYS GGGGGSGGGG S                         41

SEQ ID NO: 211        moltype = AA  length = 36
FEATURE               Location/Qualifiers
REGION                1..36
                      note = Combined MK062-MMP9
source                1..36
                      mol_type = protein
                      organism = synthetic construct
SEQUENCE: 211
GGGGSGGGGS RQARVVNGVP LSLYSGGGGG SGGGGS                               36

SEQ ID NO: 212        moltype = AA  length = 249
```

-continued

```
FEATURE                 Location/Qualifiers
REGION                  1..249
                        note = 4.24.72 scFv
source                  1..249
                        mol_type = protein
                        organism = synthetic construct
SEQUENCE: 212
QIQLVQSGPE LKKPGETVKI SCKASGYTVT DYSMNWVKQA PGKCLKWMGW INTETGEPRY  60
TDDFKGRFAF SLETSASTAY LQINNLKNED SATYFCAREG DYDVFDYWGH GTTLKVSSGG  120
GGSGGGGSGG GGSGGGGSDI VLTQSPASLA VSLGQRATIS CRASKSVSTS SYSYMHWYQQ  180
KPGQPPKLLI KYVSYLESGV PARFSGSGSG TDFTLNIHPV EEEDAATYYC QHSREFPYTF  240
GCGTKLEIK                                                         249

SEQ ID NO: 213          moltype = AA  length = 5
FEATURE                 Location/Qualifiers
source                  1..5
                        mol_type = protein
                        note = G4S repeated n times
                        organism = synthetic construct
SEQUENCE: 213
GGGGS                                                             5

SEQ ID NO: 214          moltype = AA  length = 5
FEATURE                 Location/Qualifiers
source                  1..5
                        mol_type = protein
                        note = SG4 repeated n times
                        organism = synthetic construct
SEQUENCE: 214
SGGGG                                                             5

SEQ ID NO: 215          moltype = AA  length = 9
FEATURE                 Location/Qualifiers
source                  1..9
                        mol_type = protein
                        note = G4SG4 repeated n times
                        organism = synthetic construct
SEQUENCE: 215
GGGGSGGGG                                                         9

SEQ ID NO: 216          moltype = AA  length = 4
FEATURE                 Location/Qualifiers
source                  1..4
                        mol_type = protein
                        organism = synthetic construct
SEQUENCE: 216
YMNM                                                              4

SEQ ID NO: 217          moltype = AA  length = 4
FEATURE                 Location/Qualifiers
source                  1..4
                        mol_type = protein
                        organism = synthetic construct
SEQUENCE: 217
PYAP                                                              4
```

The invention claimed is:

1. A bispecific agonistic CD28 antigen binding molecule characterized by monovalent binding to CD28, comprising (a) a first antigen binding domain that specifically binds to CD28, wherein the first antigen binding domain that specifically binds to CD28 comprises a heavy chain variable region ($V_H$CD28) comprising an amino acid sequence selected from the group consisting of SEQ ID NO: 24, SEQ ID NO:32, SEQ ID NO:33, SEQ ID NO: 34, SEQ ID NO:35, SEQ ID NO:36, SEQ ID NO:37, SEQ ID NO:38, SEQ ID NO: 39, SEQ ID NO:40 and SEQ ID NO:41, and a light chain variable region ($V_L$CD28) comprising an amino acid sequence selected from the group consisting of SEQ ID NO:25, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:51;

(b) a second antigen binding domain that specifically binds to CD3, and (c) a Fc domain composed of a first and a second subunit that stably associate with each other, comprising one or more amino acid substitution that reduces the binding affinity of the antigen binding molecule to an Fc receptor and/or effector function, wherein said second antigen binding domain that specifically binds to CD3 comprises (i) a heavy chain variable region ($V_H$CD3) comprising a heavy chain complementarity determining region CDR-H1 of SEQ ID NO: 2, a CDR-H2 of SEQ ID NO: 3, and a CDR-H3 of SEQ ID NO: 4, and a light chain variable region ($V_L$CD3) comprising a light chain complementarity determining region CDR-L1 of SEQ ID NO: 5, a CDR-L2 of SEQ ID NO: 6 and a CDR-L3 of SEQ ID NO: 7; or (ii) a heavy chain variable region ($V_H$CD3) comprising a heavy chain complementarity determining region CDR-H1 of SEQ ID NO: 10, a CDR-H2 of SEQ ID NO: 11, and a CDR-H3 of SEQ ID NO: 12, and a light chain variable region ($V_L$CD3) comprising a light chain complementarity determining region CDR-L1 of SEQ ID NO: 13, a CDR-L2 of SEQ ID NO: 14 and a CDR-L3 of SEQ ID NO: 15;

wherein the Fc domain is of human IgG1 subclass and comprises the amino acid mutations L234A, L235A and P329G, in each case as numbered according to the Kabat EU index.

2. The bispecific agonistic CD28 antigen binding molecule of claim 1, wherein the first antigen binding domain that specifically binds to CD28 comprises (a) a heavy chain variable region ($V_H$CD28) comprising the amino acid sequence of SEQ ID NO: 37 and a light chain variable region ($V_L$CD28) comprising the amino acid sequence of SEQ ID NO:44, or (b) a heavy chain variable region ($V_H$CD28) comprising the amino acid sequence of SEQ ID NO: 37 and a light chain variable region ($V_L$CD28) comprising the amino acid sequence of SEQ ID NO:25, or (c) a heavy chain variable region ($V_H$CD28) comprising the amino acid sequence of SEQ ID NO: 41 and a light chain variable region ($V_L$CD28) comprising the amino acid sequence of SEQ ID NO:51, or (d) a heavy chain variable region ($V_H$CD28) comprising the amino acid sequence of SEQ ID NO: 36 and a light chain variable region ($V_L$CD28) comprising the amino acid sequence of SEQ ID NO:43, or (e) a heavy chain variable region ($V_H$CD28) comprising the amino acid sequence of SEQ ID NO: 36 and a light chain variable region ($V_L$CD28) comprising the amino acid sequence of SEQ ID NO:44, or (f) a heavy chain variable region ($V_H$CD28) comprising the amino acid sequence of SEQ ID NO: 36 and a light chain variable region ($V_L$CD28) comprising the amino acid sequence of SEQ ID NO:49, or (g) a heavy chain variable region ($V_H$CD28) comprising the amino acid sequence of SEQ ID NO: 36 and a light chain variable region ($V_L$CD28) comprising the amino acid sequence of SEQ ID NO:25, or (h) a heavy chain variable region ($V_H$CD28) comprising the amino acid sequence of SEQ ID NO: 33 and a light chain variable region ($V_L$CD28) comprising the amino acid sequence of SEQ ID NO:25, or (i) a heavy chain variable region ($V_H$CD28) comprising the amino acid sequence of SEQ ID NO: 32 and a light chain variable region ($V_L$CD28) comprising the amino acid sequence of SEQ ID NO:43, or (j) a heavy chain variable region ($V_H$CD28) comprising the amino acid sequence of SEQ ID NO: 32 and a light chain variable region ($V_L$CD28) comprising the amino acid sequence of SEQ ID NO:49, or (k) a heavy chain variable region ($V_H$CD28) comprising the amino acid sequence of SEQ ID NO: 32 and a light chain variable region ($V_L$CD28) comprising the amino acid sequence of SEQ ID NO:25.

3. The bispecific agonistic CD28 antigen binding molecule of claim 1, wherein the first antigen binding domain that specifically binds to CD28 comprises a heavy chain variable region ($V_H$CD28) comprising a heavy chain complementarity determining region CDR-H1 of SEQ ID NO: 52, a CDR-H2 of SEQ ID NO: 53, and a CDR-H3 of SEQ ID NO: 54, and a light chain variable region ($V_L$CD28) comprising a light chain complementarity determining region CDR-L1 of SEQ ID NO: 55, a CDR-L2 of SEQ ID NO: 56 and a CDR-L3 of SEQ ID NO: 57.

4. The bispecific agonistic CD28 antigen binding molecule of claim 1, wherein the first antigen binding domain that specifically binds to CD28 comprises the CDRs of the heavy chain variable region ($V_H$CD28) comprising the amino acid sequence of SEQ ID NO: 37 and the CDRs of the light chain variable region ($V_L$CD28) comprising the amino acid sequence of SEQ ID NO:44.

5. The bispecific agonistic CD28 antigen binding molecule of claim 1, wherein the antigen binding domain that specifically binds to CD3 comprises the CDRs of the heavy chain variable region ($V_H$CD3) comprising the amino acid sequence of SEQ ID NO: 16 and the CDRs of the light chain variable region ($V_L$CD3) comprising the amino acid sequence of SEQ ID NO:17.

6. The bispecific agonistic CD28 antigen binding molecule of claim 1, wherein the antigen binding domain that specifically binds to CD3 comprises a heavy chain variable region ($V_H$CD3) comprising the amino acid sequence of SEQ ID NO:16, and a light chain variable region ($V_L$CD3) comprising the amino acid sequence of SEQ ID NO:17.

7. The bispecific agonistic CD28 antigen binding molecule of claim 1, wherein the antigen binding domain that specifically binds to CD3 comprises the CDRs of the heavy chain variable region ($V_H$CD3) comprising the amino acid sequence of SEQ ID NO: 8 and the CDRs of the light chain variable region ($V_L$CD3) comprising the amino acid sequence of SEQ ID NO:9.

8. The bispecific agonistic CD28 antigen binding molecule of claim 1, wherein the antigen binding domain that specifically binds to CD3 comprises a heavy chain variable region ($V_H$CD3) comprising the amino acid sequence of SEQ ID NO:8, and a light chain variable region ($V_L$CD3) comprising the amino acid sequence of SEQ ID NO:9.

9. The bispecific agonistic CD28 antigen binding molecule of claim 1, wherein the second antigen binding domain that specifically binds to CD3 is a conventional Fab molecule, and wherein the conventional Fab molecule is a Fab molecule wherein in the constant domain CL the amino acid at position 123 is substituted by an amino acid selected from lysine (K), arginine (R) or histidine (H) and the amino acid at position 124 is substituted independently by lysine (K), arginine (R) or histidine (H), and wherein in the constant domain CH1 the amino acid at position 147 is substituted independently by glutamic acid (E) or aspartic acid (D) and the amino acid at position 213 is substituted independently by glutamic acid (E), or aspartic acid (D), in each case as numbered according to Kabat EU index.

10. The bispecific agonistic CD28 antigen binding molecule of claim 1, further comprising (d) a masking moiety covalently attached to the bispecific agonistic CD28 antigen binding molecule through a protease-cleavable linker, wherein the masking moiety binds to an idiotype of the second antigen binding domain that specifically binds to CD3 thereby reversibly concealing the antigen binding domain that specifically binds to CD3, wherein the masking moiety comprises (i) a heavy chain variable region (VH) comprising a CDR-H1 amino acid sequence of DYSMN (SEQ ID NO:123), a CDR H2 amino acid sequence selected from the group consisting of WINTETGEPRYTDDFKG (SEQ ID NO:124), WINTETGEPRYTDDFTG (SEQ ID NO:130) and WINTETGEPRYTQGFKG (SEQ ID NO:131), and a CDR H3 amino acid sequence of EGDYDVFDY (SEQ ID NO:125), and a light chain variable region (VL) comprising a light chain complementarity determining region CDR-L1 amino acid sequence selected from the group consisting of RASKSVSTSSYSYMH (SEQ ID NO: 126) and KSSKSVSTSSYSYMH (SEQ ID NO:129), a CDR-L2 amino acid sequence of YVSYLES (SEQ ID NO:127) and a CDR-L3 amino acid sequence selected from the group consisting of QHSREFPYT (SEQ ID NO:128) and QQSREFPYT (SEQ ID NO: 132); or (ii) a heavy chain variable region (VH) comprising a CDR-H1 amino acid sequence of DYSMN (SEQ ID NO:123), a CDR-H2 amino acid sequence of WINTETGEPRYTDDFKG (SEQ ID NO:124), and a CDR-H3 amino acid sequence of EGDYDVFDY (SEQ ID NO:125), and a light chain variable region (VL) comprising a CDR-L1 amino acid sequence of RASKSVSTSSYSYMH (SEQ ID NO:126), a CDR-L2 amino acid sequence of YVSYLES (SEQ ID NO:127) and a CDR-L3 amino acid sequence of QHSREFPYT (SEQ ID NO:128), or (iii) a heavy chain variable region (VH) comprising a CDR-H1 amino acid sequence of SYGVS (SEQ ID NO:123), a CDR-H2 amino acid sequence of IIWGDGSTNYHSALIS (SEQ ID NO:124), and a CDR-H3 amino acid sequence of GITTVVDDYYAMDY (SEQ ID NO: 125), and a light chain variable region (VL) comprising a CDR-L1 amino acid sequence of KSSKSVSTSSYSYMH (SEQ ID NO:129), a CDR-L2 amino acid sequence of AATFLAD (SEQ ID NO:127) and a CDR-L3 amino acid sequence of QHYYSTPYT (SEQ ID NO:128), or (iv) a heavy chain variable region (VH) comprising a CDR-H1 amino acid sequence of SYGVS (SEQ ID NO:123), a CDR-H2 amino acid sequence of WINTETGEPRYTDDFTG (SEQ ID NO:130), and a CDR-H3 amino acid sequence of GITTVVDDYYAMDY (SEQ ID NO:125), and a light chain variable region (VL) comprising a CDR-L1 amino acid sequence of KSSKSVSTSSYSYMH (SEQ ID NO: 129), a CDR-L2 amino acid sequence of AATFLAD (SEQ ID NO:127) and a CDR-L3 amino acid sequence of QHYYSTPYT (SEQ ID NO:128), or (v) a heavy chain variable region (VH) comprising a CDR-H1 amino acid sequence of SYGVS (SEQ ID NO:123), a CDR-H2 amino acid sequence of WINTETGEPRYTQGFKG (SEQ ID NO:131), and a CDR-H3 amino acid sequence of GITTVVDDYYAMDY (SEQ ID NO:125), and a light chain variable region (VL) comprising a CDR-L1 amino acid sequence of KSSKSVSTSSYSYMH (SEQ ID NO: 129), a CDR-L2 amino acid sequence of AATFLAD (SEQ ID NO:127) and a CDR-L3 amino acid sequence of QHYYSTPYT (SEQ ID NO:128); or (vii) a heavy chain variable region (VH) comprising a CDR-H1 amino acid sequence of SYGVS (SEQ ID NO:115), a CDR-H2 amino acid sequence of IIWGDGSTNYHSALIS (SEQ ID NO:116), and a CDR-H3 amino acid sequence of GITTVVDDYYAMDY (SEQ ID NO: 117), and a light chain variable region (VL) comprising a CDR-L1 amino acid sequence of RASENIDSYLA (SEQ ID NO:118), a CDR-L2 amino acid sequence of AATFLAD (SEQ ID NO:119) and a CDR-L3 amino acid sequence of QHYYSTPYT (SEQ ID NO:120).

11. The bispecific agonistic CD28 antigen binding molecule of claim 10, wherein the masking moiety is covalently attached to the heavy chain variable region ($V_H$CD3) of the second antigen binding domain that specifically binds to CD3.

12. The bispecific agonistic CD28 antigen binding molecule of claim 10, wherein the masking moiety is a scFv.

13. One or more isolated polynucleotide(s) encoding the bispecific agonistic CD28 antigen binding molecule of claim 1.

14. One or more vector(s) comprising the polynucleotide (s) of claim 13.

15. A host cell comprising the polynucleotide(s) of claim 13.

16. A method of producing a bispecific agonistic CD28 antigen binding molecule, comprising the steps of a) culturing the host cell of claim 15 under conditions for the expression of the bispecific agonistic CD28 antigen binding molecule and b) optionally recovering the bispecific agonistic CD28 antigen binding molecule.

17. A method of treating an epithelial cancer in an individual in need thereof, comprising administering to said individual a therapeutically effective amount of a composition comprising the bispecific agonistic CD28 antigen binding molecule of claim 1.

18. A host cell comprising the vector(s) of claim 14.

19. A method of producing a bispecific agonistic CD28 antigen binding molecule, comprising the steps of a) culturing the host cell of claim 18 under conditions for the expression of the bispecific agonistic CD28 antigen binding molecule and b) optionally recovering the bispecific agonistic CD28 antigen binding molecule.

20. A method of treating a squamous cell carcinoma in an individual in need thereof, comprising administering to said individual a therapeutically effective amount of a composition comprising the bispecific agonistic CD28 antigen binding molecule of claim 1.

21. A method of treating cancer in an individual in need thereof, comprising administering to said individual a therapeutically effective amount of a composition comprising the bispecific agonistic CD28 antigen binding molecule of claim 1, wherein said cancer is breast cancer, lung cancer, stomach cancer, prostate cancer, ovarian cancer, colorectal cancer, colon cancer, esophageal cancer, tracheal cancer, gastric cancer, bladder cancer, uterine cancer, rectal cancer, pancreatic cancer, or cancer of the small intestine.

* * * * *